US012257318B2

(12) United States Patent
Hennig et al.

(10) Patent No.: US 12,257,318 B2
(45) Date of Patent: *Mar. 25, 2025

(54) POLYNUCLEOTIDE COMPOSITIONS, RELATED FORMULATIONS, AND METHODS OF USE THEREOF

(71) Applicant: ReCode Therapeutics, Inc., Menlo Park, CA (US)

(72) Inventors: Mirko Hennig, Mountain View, CA (US); Daniella Ishimaru, Menlo Park, CA (US); David J. Lockhart, Menlo Park, CA (US); Michael Torres, Menlo Park, CA (US); Jackson Eby, Menlo Park, CA (US); Dmitri Boudko, Menlo Park, CA (US); Brandon A. Wustman, San Diego, CA (US)

(73) Assignee: ReCode Therapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/431,504

(22) Filed: Feb. 2, 2024

(65) Prior Publication Data

US 2024/0269325 A1 Aug. 15, 2024

Related U.S. Application Data

(63) Continuation of application No. 18/283,523, filed as application No. PCT/US2022/021526 on Mar. 23, 2022.

(60) Provisional application No. 63/274,912, filed on Nov. 2, 2021, provisional application No. 63/208,966, filed on Jun. 9, 2021, provisional application No. 63/164,573, filed on Mar. 23, 2021.

(51) Int. Cl.

| | |
|---|---|
| ***A61K 48/00*** | (2006.01) |
| ***A61K 9/00*** | (2006.01) |
| ***A61K 9/12*** | (2006.01) |
| ***A61K 9/127*** | (2006.01) |
| ***A61K 9/1271*** | (2025.01) |
| ***A61K 9/51*** | (2006.01) |
| ***A61K 38/17*** | (2006.01) |

(52) U.S. Cl.

CPC .......... *A61K 48/005* (2013.01); *A61K 9/0078* (2013.01); *A61K 9/12* (2013.01); *A61K 9/1271* (2013.01); *A61K 9/5123* (2013.01); *A61K 38/1709* (2013.01); *A61K 48/0075* (2013.01)

(58) Field of Classification Search

None

See application file for complete search history.

(56) References Cited

U.S. PATENT DOCUMENTS

| | | | |
|---|---|---|---|
| 5,820,873 | A | 10/1998 | Choi et al. |
| 8,450,298 | B2 | 5/2013 | Mahon et al. |
| 10,717,982 | B2 | 7/2020 | Eberle et al. |
| 10,898,574 | B2 | 1/2021 | De Fougerolles et al. |
| 11,090,264 | B2 | 8/2021 | Heartlein et al. |
| 11,135,312 | B2 | 10/2021 | Von Der Mulbe et al. |
| 11,173,190 | B2 | 11/2021 | Heartlein et al. |
| 11,498,944 | B2 | 11/2022 | Langedijk et al. |
| 2019/0167811 | A1 | 6/2019 | Benenato et al. |

FOREIGN PATENT DOCUMENTS

| | | | |
|---|---|---|---|
| WO | 2010141069 | A2 | 12/2010 |
| WO | 2010144740 | A1 | 12/2010 |
| WO | 2011068810 | A1 | 6/2011 |
| WO | 2012045075 | A1 | 4/2012 |
| WO | 2012170930 | A1 | 12/2012 |
| WO | 2013063468 | A1 | 5/2013 |
| WO | 2013086354 | A1 | 6/2013 |
| WO | 2013086373 | A1 | 6/2013 |
| WO | 2013149140 | A1 | 10/2013 |
| WO | 2013151663 | A1 | 10/2013 |
| WO | 2013151664 | A1 | 10/2013 |
| WO | 2013151665 | A2 | 10/2013 |
| WO | 2013151667 | A1 | 10/2013 |
| WO | 2013151736 | A2 | 10/2013 |
| WO | 2014153052 | A2 | 9/2014 |
| WO | 2015095340 | A1 | 6/2015 |
| WO | 2015184256 | A2 | 12/2015 |
| WO | 2015199952 | A1 | 12/2015 |
| WO | 2016004202 | A1 | 1/2016 |
| WO | 2016094342 | A1 | 6/2016 |

(Continued)

OTHER PUBLICATIONS

Alabi et al. (Aug. 6, 2013) "Multiparametric Approach for the Evaluation of Lipid Nanoparticles For siRNA delivery", Proceedings of the National Academy of Sciences of the United States of America, 110(32):12881-12886.

(Continued)

*Primary Examiner* — Christopher M Babic
*Assistant Examiner* — Kimberly A Aron
(74) *Attorney, Agent, or Firm* — Mintz Levin Cohn Ferris Glovsky and Popeo, P.C.

(57) ABSTRACT

Compositions of polynucleotide(s), pharmaceutical compositions thereof, and methods of use thereof are disclosed. A polynucleotide may encode for a cystic fibrosis transmembrane conductance regulator (CFTR) protein or a functional fragment thereof. The polynucleotide may be assembled with a lipid composition for targeted delivery to a cell or an organ, such as a lung cell or a lung of a subject. Methods for enhancing an expression or activity of CFTR protein in a cell are provided. Methods for treating a subject having or suspected of having a CFTR-associated condition are also provided.

30 Claims, 25 Drawing Sheets

Specification includes a Sequence Listing.

(56) References Cited

FOREIGN PATENT DOCUMENTS

| | | | |
|---|---|---|---|
| WO | 2016118724 | A1 | 7/2016 |
| WO | 2016118725 | A1 | 7/2016 |
| WO | 2016205691 | A1 | 12/2016 |
| WO | 2017004143 | A1 | 1/2017 |
| WO | 2017048789 | A1 | 3/2017 |
| WO | 2017049245 | A2 | 3/2017 |
| WO | 2017075531 | A1 | 5/2017 |
| WO | 2017117528 | A1 | 7/2017 |
| WO | 2017173054 | A1 | 10/2017 |
| WO | 2017201076 | A1 | 11/2017 |
| WO | 2017201091 | A1 | 11/2017 |
| WO | 2017205767 | A1 | 11/2017 |
| WO | 2018157154 | A2 | 8/2018 |
| WO | 2018213476 | A1 | 11/2018 |
| WO | 2019246203 | A1 | 12/2019 |
| WO | 2020051220 | A1 | 3/2020 |
| WO | 2020051223 | A1 | 3/2020 |
| WO | 2020106946 | A1 | 5/2020 |
| WO | 2021155274 | A1 | 8/2021 |
| WO | 2021222801 | A2 | 11/2021 |
| WO | 2022032154 | A2 | 2/2022 |
| WO | 2022040641 | A2 | 2/2022 |
| WO | 2022169508 | A1 | 8/2022 |
| WO | 2022198099 | A1 | 9/2022 |
| WO | 2022204053 | A1 | 9/2022 |
| WO | 2022204215 | A1 | 9/2022 |
| WO | 2022204219 | A1 | 9/2022 |
| WO | 2022204270 | A1 | 9/2022 |

OTHER PUBLICATIONS

Allen et al. (Jan. 2013) "Liposomal Drug Delivery Systems: From Concept to Clinical Applications", Advanced Drug Delivery Reviews, 65(1):36-48.

Arteta et al. (Mar. 27, 2018) "Successful Reprogramming of Cellular Protein Production Through mRNA Delivered by Functionalized Lipid Nanoparticles", Proceedings of the National Academy of Sciences of the United States of America, 115(15):E3351-E3360.

Battaglia et al. (Jan. 15, 2019) "Lipid Nano- and Microparticles: An Overview of Patent-Related Research", Journal of Nanomaterials, 2:1-22.

Chahal et al. (Jul. 19, 2016) "Dendrimer-RNA Nanoparticles Generate Protective Immunity Against Lethal Ebola, H1N1 Influenza, and Toxoplasma Gondii Challenges With a Single Dose", Proceedings of the National Academy of Sciences of the United States of America, 113(29):E4133-4142.

Chang et al. (Oct. 6, 2021) "Lipid Nanoparticles for The Inhalation of mRNA", Nature Biomedical Engineering, 5(9):949-950.

Cheng et al. (Dec. 2018) "Dendrimer-Based Lipid Nanoparticles Deliver Therapeutic FAH mRNA to Normalize Liver Function and Extend Survival in a Mouse Model of Hepatorenal Tyrosinemia Type I", Advanced Materials, 30(52):e1805308 (10 pages).

Chow et al. (Oct. 2020) "Inhaled RNA Therapy: From Promise to Reality", Trends in Pharmacological Sciences, 41(10):715-729.

Zhou et al. (Jan. 19, 2016) "Modular Degradable Dendrimers Enable Small Rnas to Extend Survival in an Aggressive Liver Cancer Model", Proceedings of the National Academy of Sciences of the United States of America, 113(3):520-525.

Gary et al. (Aug. 2013) "The Effect of N/P Ratio on the In Vitro and In Vivo Interaction Properties of PEGylated Poly(2-(dimethylamino)ethyl methacrylate)-Based siRNA Complexes", Macromolecular Bioscience, 13(8):1059-1071.

Guevara et al. (Oct. 23, 2020) "Advances in Lipid Nanoparticles for mRNA-Based Cancer Immunotherapy", Frontiers in Chemistry, 8(589959):17 pages.

Haque et al. (Nov. 13, 2018) "Chemically Modified hCFTR mRNAs Recuperate Lung Function in A Mouse Model of Cystic Fibrosis", Scientific reports, 8(1):1-14.

Jayaraman et al. (Aug. 20, 2012) "Maximizing the Potency of siRNA Lipid Nanoparticles for Hepatic Gene Silencing in Vivot", Angewandte Chemie International Edition, 51(34):8529-8533.

Khan et al. (May 13, 2015) "Dendrimer-Inspired Nanomaterials for the in Vivo Delivery of siRNA to Lung Vasculature", Nano Letters, 15(5):1-24.

Khan et al. (Dec. 22, 2014) "Ionizable Amphiphilic Dendrimer-based Nanomaterials with Alkyl-chain-substituted Amines for Tunable siRNA delivery to the Liver Endothelium in Vivo", Angewandte Chemie, 53(52):14397-14401.

Liu et al. (May 25, 2021) "Membrane-Destabilizing Ionizable Phospholipids for Organ-Selective mRNA Delivery and CRISPR-Cas Gene Editing", Nature Materials, 20(5):701-710.

McClellan et al. (Apr. 16, 2010) "Genetic Heterogeneity in Human Disease", Cell, 141(2):210-217.

Micklefield, Jason (Aug. 2001) "Backbone Modification of Nucleic Acids: Synthesis, Structure and Therapeutic Applications", Current Medicinal Chemistry, 8(10):1157-1179.

Miller et al. (Jan. 19, 2017) "Non-Viral CRISPR/Cas Gene Editing In Vitro and In Vivo Enabled by Synthetic Nanoparticle Co-Delivery of Cas9 mRNA and sgRNA", Angewandte Chemie, 56(4):1059-1063.

Pardi et al. (Nov. 10, 2015) "Expression Kinetics of Nucleoside-modified mRNA Delivered in Lipid Nanoparticles to Mice by Various Routes", Journal of Controlled Release, 217:345-351.

Pei et al. (Mar. 2022) "Synthesis and Bioactivity of Readily Hydrolysable Novel Cationic Lipids for Potential Lung Delivery Application of mRNAs", Chemistry and Physics of Lipids, 243:105178 (11 pages).

Samaridou et al. (2020) "Lipid Nanoparticles for Nucleic Acid Delivery: Current Perspectives", Advanced Drug Delivery Reviews, 154-155:37-63.

Shaffer et al. (Oct. 5, 2020) "Mist Begins to Clear for Lung Delivery of RNA", Nature Biotechnology, 38(10):1110-1112.

Uner et al. (Sep. 2007) "Importance of Solid Lipid Nanoparticles (SLN) in Various Administration Routes and Future Perspectives", International Journal of Nanomedicine, 2(3):289-300.

Whitehead et al. (Jun. 27, 2014) "Degradable Lipid Nanoparticles with Predictable in Vivo Sirna Delivery Activity", Nature Communications, 5:4277 (10 pages).

DOTAP

DODAP

EPC

4A3-SC6

4A1-SC5

4A3-SC7

5A4-SC6

5A4-SC5

5A4-SC8

4A3-SC8

4A1-SC8

5A2-SC8

| Ciliated | acetylated-tubulin (AC-Tubulin) |
|---|---|
| Club | Secretoglobin Family 1A Member 1 (SCGB1A1) |
| Goblet | Mucin 5AC (MUC5AC) |
| Basal | Cytokeratin 5 (CK5) |
| Ciliated | acetylated-tubulin (AC-Tubulin) |

Examples

| Indication / Inclusion criteria | Phase 1/2 Study* | Primary Outcome Measures |
| --- | --- | --- |
| **CF Lead tRNA Program**<br>- Adults<br>- CFTR mutation R553X, R1162X, or G542X<br>- FEV1 between 40% and 90% | SAD • MAD (3 mo.) • OLE (9 mo.)<br>Placebo<br>Low Dose<br>High Dose | - Safety and tolerability<br>- Absolute change in percent predicted FEV1 |

FIG. 19

SEQUENCE LISTING

```
Sequence total quantity: 23
SEQ ID NO: 1              moltype = DNA  length = 4479
FEATURE                   Location/Qualifiers
source                    1..4479
                          mol_type = other DNA
                          organism = synthetic construct
SEQUENCE: 1
atgcagagaa gccctctgga aaaggccagc gtggtgagca agctgttctt cagctggacc  60
cggcccatcc tgcggaaggg ctacagacag agactggaac tgagcgacat ctatcagatc  120
cccagcgtgg acagcgccga caacctgtct gagaagctgg aaagagagtg ggacagagag  180
ctggccagca agaagaaccc caagctgatc aacgccctgc ggcggtgctt cttctggcgg  240
ttcatgttct acggcatctt cctgtacctg ggcgaagtga ccaaagccgt gcagcctctg  300
ctgctgggca gaatcatcgc cagctacgac cccgacaaca aagaggaacg gagcatcgcc  360
atctacctcg gcatcggcct gtgcctgctg ttcatcgtca gaaccctgct gctgcacccc  420
gccatcttcg gactgcacca catcggcatg cagatgcgga tcgccatgtt cagcctgatc  480
tacaagaaaa ccctgaagct gagcagcaga gtgctggaca agatcagcat cggacagctg  540
gtgagcctgc tgagcaacaa cctgaacaag ttcgacgaag gcctggctct ggcccacttc  600
gtgtggatcg ctcctctgca agtggccctg ctgatgggcc tgatctggga actgctgcag  660
gccagcgcct tctgcggact gggattcctg atcgtgctgg ccctgttcca ggccggactg  720
gggagaatga tgatgaagta ccgggaccag agagccggca agatcagcga gagactggtc  780
atcaccagcg agatgatcga gaacatccag agcgtgaagg cctactgctg ggaagaggcc  840
atggaaaaga tgatcgagaa tctgcggcag accgagctga agctgacaag aaaggccgcc  900
tacgtgcgct acttcaacag cagcgccttc ttcttcagcg gcttcttcgt ggtgttcctg  960
agcgtgctgc cctacgctct gatcaagggc atcatcctga gaaagatctt caccaccatc  1020
agcttctgca tcgtgctgcg gatggccgtg accagacagt tcccctgggc tgtgcagacc  1080
tggtacgaca gcctgggcgc catcaacaag atccaggact tcctgcagaa gcaagagtac  1140
aagaccctcg agtacaacct gaccaccacc gaggtggtca tggaaaacgt gaccgccttc  1200
tgggaggaag gcttcggcga gctgttcgag aaggccaagc agaacaacaa caaccgcaag  1260
accagcaacg gcgacgacag cctgttcttc agcaacttca gcctgctggg gacccctgtg  1320
ctgaaggaca tcaacttcaa gatcgagcgg ggacagctgc tggccgtggc tggaagcaca  1380
ggcgccggaa aaaccagcct gctcatggtc atcatgggcg agctggaacc cagcgagggc  1440
aagatcaagc acagcggcag gatcagcttc tgcagccagt tcagctggat catgcccggc  1500
accatcaaag agaacatcat cttcggcgtg agctacgacg agtacagata ccgcagcgtg  1560
atcaaggcct gccagctgga agaggacatc agcaagttcg ccgagaagga caacatcgtg  1620
ctcggcgaag gcggcatcac actgtctggc ggacagaggg ccagaatctc tctggccaga  1680
gccgtgtaca aggacgccga tctgtacctg ctggacagcc ccttcggcta cctggatgtg  1740
ctgaccgaga aagagatctt cgagagctgc gtgtgcaagc tgatggccaa caagacccgg  1800
atcctggtca ccagcaagat ggaacacctg aagaaggccg acaagatcct gatcctgcac  1860
gagggcagca gctacttcta cggcaccttc agcgagctgc agaacctgca gcctgacttc  1920
agcagcaaac tgatgggctg cgacagcttc gaccagttca gcgccgagcg gagaaacagc  1980
atcctgacag agacactgca ccggttcagc ctggaaggcg acgctcctgt gagctggacc  2040
gagacaaaga agcagagctt caagcagacc ggcgagttcg gcgagaagcg gaagaacagc  2100
atcctgaacc ccatcaacag catccggaag ttcagcatcg tccagaaaac ccctctgcag  2160
atgaacggca tcgaagagga cagcgacgag cccctggaaa gacggctgtc tctggtgcct  2220
gacagcgaac agggcgaagc catcctgcct cggatcagcg tgatcagcac aggccccaca  2280
ctgcaggctc ggagaaggca gagtgtgctg aacctgatga cccacagcgt gaaccaggga  2340
cagaacatcc acagaaagac caccgccagc acacggaaag tgagcctggc ccctcaggcc  2400
aacctgactg agctggacat ctacagcaga cggctgagcc aagagacagg cctggaaatc  2460
agcgaggaaa tcaacgaaga ggacctgaaa gagtgcttct tcgacgacat ggaaagcatc  2520
cccgccgtga caacctggaa cacctacctg cggtacatca ccgtgcacaa gagcctgatc  2580
ttcgtgctga tctggtgtct cgtgatcttc ctggccgaag tggccgcctc tctggtggtg  2640
ctgtggctgc tcggaaacac cccactgcag gacaagggca acagcaccca cagccggaac  2700
aacagctacg ccgtgatcat caccagcacc agcagctact acgtgttcta catctacgtg  2760
ggcgtcgccg acactctgct cgccatgggc ttcttcagag gactgcccct ggtgcacacc  2820
ctgatcaccg tgagcaagat cctgcaccac aagatgctgc acagcgtcct gcaggccccc  2880
atgagcacac tgaacaccct gaaagccggc ggaatcctga acagattcag caaggacatc  2940
gccatcctgg acgacctgct gcctctgacc atcttcgact tcatccagct gctgctgatc  3000
gtgatcggcg ccatcgctgt ggtggctgtg ctgcagccct acatcttcgt ggccaccgtg  3060
cctgtgatcg tggccttcat catgctgcgg gcctacttcc tgcagacctc tcagcagctg  3120
aagcagctcg agtctgaggg cagaagcccc atcttcaccc acctcgtgac cagcctgaaa  3180
ggcctgtgga ccctgagagc cttcggcaga cagccctact tcgagacact gttccacaag  3240
gccctgaacc tgcacaccgc caactggttc ctgtatctga gcaccctgcg gtggttccag  3300
atgaggatcg agatgatctt cgtcatcttc ttcatcgccg tgaccttcat cagcatcctc  3360
accactggcg aaggcgaggg cagagtggga atcatcctga ccctggccat gaacatcatg  3420
agcacactcc agtgggccgt gaacagcagc atcgatgtgg acagcctgat gcggagcgtg  3480
agccgggtgt tcaagttcat cgacatgccc acagagggca agcccaccaa gagcaccaag  3540
ccctacaaga acggccagct gagcaaagtc atgatcatcg agaacagcca cgtcaagaag  3600
gacgacatct ggcccagcgg aggccagatg accgtgaagg atctgaccgc caagtacacc  3660
```

```
gaaggcggaa acgccatcct ggaaaacatc agcttcagca tcagccctgg ccagcgcgtg  3720
ggactcctgg gaagaaccgg aagcggcaag agcactctgc tgagcgcctt cctgagactg  3780
ctgaacaccg agggcgagat ccagatcgat ggggtgagct gggacagcat caccctgcaa  3840
caatggcgga aggccttcgg cgtgatccct cagaaggtgt tcatcttcag cggcacgttc  3900
cggaagaatc tggacccccta cgagcagtgg agcgaccaag agatctggaa ggtggccgat  3960
gaagtgggac tgagaagcgt gatcgagcag ttccccggca agctggactt cgtgctggtg  4020
gatggcggct gtgtgctgtc tcacggacac aagcagctga tgtgcctggc cagaagcgtg  4080
ctgagcaagg ccaagatcct gctgctcgac gagcccagcg ctcacctgga tcctgtgacc  4140
taccagatca tccggcggac actgaagcag gccttcgccg actgcaccgt gatcctgtgc  4200
gagcacagaa tcgaggccat gctggaatgc cagcagttcc tggtgatcga agagaacaaa  4260
gtgcggcagt acgacagcat ccagaagctg ctgaacgagc ggagcctgtt cagacaggcc  4320
atctctccca gcgacagagt gaagctgttc cctcaccgga acagcagcaa gtgcaagagc  4380
aagcctcaga tcgccgctct gaaagaagaa accgaggaag aggtgcagga cacacggctg  4440
gcggccgttt acccatacga tgttcctgac tatgcgtga                         4479

SEQ ID NO: 2           moltype = DNA  length = 4443
FEATURE                Location/Qualifiers
source                 1..4443
                       mol_type = other DNA
                       organism = synthetic construct
SEQUENCE: 2
atgcagagaa gccctctgga aaaggccagc gtggtgagca agctgttctt cagctggacc  60
cggcccatcc tgcggaaggg ctacagacag agactggaac tgagcgacat ctatcagatc  120
cccagcgtgg acagcgccga caacctgtct gagaagctgg aaagagagtg ggacagagag  180
ctggccagca agaagaaccc caagctgatc aacgccctgc ggcggtgctt cttctggcgg  240
ttcatgttct acggcatctt cctgtacctg ggcgaagtga ccaaagccgt gcagcctctg  300
ctgctgggca gaatcatcgc cagctacgac cccgacaaca aagaggaacg gagcatcgcc  360
atctacctcg gcatcggcct gtgcctgctg ttcatcgtca gaaccctgct gctgcacccc  420
gccatcttcg gactgcacca catcggcatg cagatgcgga tcgccatgtt cagcctgatc  480
tacaagaaaa ccctgaagct gagcagcaga gtgctggaca agatcagcat cggacagctg  540
gtgagcctgc tgagcaacaa cctgaacaag ttcgacgaag gcctggctct ggcccacttc  600
gtgtggatcg ctcctctgca agtggccctg ctgatgggcc tgatctggga actgctgcag  660
gccagcgcct tctgcggact gggattcctg atcgtgctgg ccctgttcca ggccggactg  720
gggagaatga tgatgaagta ccgggaccag agagccggca agatcagcga gagactggtc  780
atcaccagcg agatgatcga gaacatccag agcgtgaagg cctactgctg ggaagaggcc  840
atggaaaaga tgatcgagaa tctgcggcag accgagctga agctgacaag aaaggccgcc  900
tacgtgcgct acttcaacag cagcgccttc ttcttcagcg gcttcttcgt ggtgttcctg  960
agcgtgctgc cctacgctct gatcaagggc atcatcctga gaaagatctt caccaccatc  1020
agcttctgca tcgtgctgcg gatggccgtg accagacagt tcccctgggc tgtgcagacc  1080
tggtacgaca gcctgggcgc catcaacaag atccaggact tcctgcagaa gcaagagtac  1140
aagaccctcg agtacaacct gaccaccacc gaggtggtca tggaaaacgt gaccgccttc  1200
tgggaggaag gcttcggcga gctgttcgag aaggccaagc agaacaacaa caaccgcaag  1260
accagcaacg gcgacgacag cctgttcttc agcaacttca gcctgctggg gacccctgtg  1320
ctgaaggaca tcaacttcaa gatcgagcgg ggacagctgc tggccgtggc tggaagcaca  1380
ggcgccggaa aaaccagcct gctcatggtc atcatgggcg agctggaacc cagcgagggc  1440
aagatcaagc acagcggcag gatcagcttc tgcagccagt tcagctggat catgcccggc  1500
accatcaaag agaacatcat cttcggcgtg agctacgacg agtacagata ccgcagcgtg  1560
atcaaggcct gccagctgga agaggacatc agcaagttcg ccgagaagga caacatcgtg  1620
ctcggcgaag gcggcatcac actgtctggc ggacagaggg ccagaatctc tctggccaga  1680
gccgtgtaca aggacgccga tctgtacctg ctggacagcc ccttcggcta cctggatgtg  1740
ctgaccgaga aagagatctt cgagagctgc gtgtgcaagc tgatggccaa caagacccgg  1800
atcctggtca ccagcaagat ggaacacctg aagaaggccg acaagatcct gatcctgcac  1860
gagggcagca gctacttcta cggcaccttc agcgagctgc agaacctgca gcctgacttc  1920
agcagcaaac tgatgggctg cgacagcttc gaccagttca gcgccgagcg gagaaacagc  1980
atcctgacag agacactgca ccggttcagc ctggaaggcg acgctcctgt gagctggacc  2040
gagacaaaga agcagagctt caagcagacc ggcgagttcg gcgagaagcg gaagaacagc  2100
atcctgaacc ccatcaacag catccggaag ttcagcatcg tccagaaaac ccctctgcag  2160
atgaacggca tcgaagagga cagcgacgag cccctggaaa gacggctgtc tctggtgcct  2220
gacagcgaac agggcgaagc catcctgcct cggatcagcg tgatcagcac aggccccaca  2280
ctgcaggctc ggagaaggca gagtgtgctg aacctgatga cccacagcgt gaaccaggga  2340
cagaacatcc acagaaagac caccgccagc acacggaaag tgagcctggc ccctcaggcc  2400
aacctgactg agctggacat ctacagcaga cggctgagcc aagagacagg cctggaaatc  2460
agcgaggaaa tcaacgaaga ggacctgaaa gagtgcttct tcgacgacat ggaaagcatc  2520
cccgccgtga caacctggaa cacctacctg cggtacatca ccgtgcacaa gagcctgatc  2580
ttcgtgctga tctggtgtct cgtgatcttc ctggccgaag tggccgcctc tctggtggtg  2640
ctgtggctgc tcggaaacac ccactgcag gacaagggca acagcaccca cagccggaac  2700
aacagctacg ccgtgatcat caccagcacc agcagctact acgtgttcta catctacgtg  2760
ggcgtcgccg acactctgct cgccatgggc ttcttcagag gactgcccct ggtgcacacc  2820
ctgatcaccg tgagcaagat cctgcaccac aagatgctgc acagcgtcct gcaggccccc  2880
atgagcacac tgaacaccct gaaagccggc ggaatcctga acagattcag caaggacatc  2940
gccatcctgg acgacctgct gcctctgacc atcttcgact tcatccagct gctgctgatc  3000
gtgatcggcg ccatcgctgt ggtggctgtg ctgcagccct acatcttcgt ggccaccgtg  3060
cctgtgatcg tggccttcat catgctgcgg gcctacttcc tgcagacctc tcagcagctg  3120
aagcagctcg agtctgaggg cagaagcccc atcttcaccc acctcgtgac cagcctgaaa  3180
ggcctgtgga ccctgagagc cttcggcaga cagccctact tcgagacact gttccacaag  3240
gccctgaacc tgcacaccgc caactggttc ctgtatctga gcaccctgcg gtggttccag  3300
atgaggatcg agatgatctt cgtcatcttc ttcatcgccg tgaccttcat cagcatcctc  3360
accactggcg aaggcgaggg cagagtggga atcatcctga ccctggccat gaacatcatg  3420
agcacactcc agtgggccgt gaacagcagc atcgatgtgg acagcctgat gcggagcgtg  3480
```

-continued

```
agccgggtgt tcaagttcat cgacatgccc acagagggca agcccaccaa gagcaccaag  3540
ccctacaaga acggccagct gagcaaagtc atgatcatcg agaacagcca cgtcaagaag  3600
gacgacatct ggcccagcgg aggccagatg accgtgaagg atctgaccgc caagtacacc  3660
gaaggcggaa acgccatcct ggaaaacatc agcttcagca tcagccctgg ccagcgcgtg  3720
ggactcctgg gaagaaccgg aagcggcaag agcactctgc tgagcgcctt cctgagactg  3780
ctgaacaccg agggcgagat ccagatcgat ggggtgagct gggacagcat caccctgcaa  3840
caatggcgga aggccttcgg cgtgatccct cagaaggtgt tcatcttcag cggcacgttc  3900
cggaagaatc tggaccccta cgagcagtgg agcgaccaag agatctggaa ggtggccgat  3960
gaagtgggac tgagaagcgt gatcgagcag ttccccggca agctggactt cgtgctggtg  4020
gatggcggct gtgtgctgtc tcacggacac aagcagctga tgtgcctggc cagaagcgtg  4080
ctgagcaagg ccaagatcct gctgctcgac gagcccagcg ctcacctgga tcctgtgacc  4140
taccagatca tccggcggac actgaagcag gccttcgccg actgcaccgt gatcctgtgc  4200
gagcacagaa tcgaggccat gctggaatgc cagcagttcc tggtgatcga agagaacaaa  4260
gtgcggcagt acgacagcat ccagaagctg ctgaacgagc ggagcctgtt cagacaggcc  4320
atctctccca gcgacagagt gaagctgttc cctcaccgga acagcagcaa gtgcaagagc  4380
aagcctcaga tcgccgctct gaaagaagaa accgaggaag aggtgcagga cacacggctg  4440
tga                                                                4443
```

```
SEQ ID NO: 3            moltype = DNA  length = 4479
FEATURE                 Location/Qualifiers
source                  1..4479
                        mol_type = other DNA
                        organism = synthetic construct
SEQUENCE: 3
atgcagagaa gcccccctgga aaaggccagc gtggtgagca agctgttctt cagctggacc  60
cggcccatcc tgcggaaggg ctacagacag agactggaac tgagcgacat ctaccagatc  120
cccagcgtgg acagcgccga caacctgagc gagaagctgg aaagagagtg ggacagagag  180
ctggccagca agaagaaccc caagctgatc aacgccctgc ggcggtgctt cttctggcgg  240
ttcatgttct acggcatctt cctgtacctg ggcgaagtga ccaaagccgt gcagcccctg  300
ctgctgggca gaatcatcgc cagctacgac cccgacaaca aagaggaacg gagcatcgcc  360
atctacctcg gcatcggcct gtgcctgctg ttcatcgtca gaaccctgct gctgcacccc  420
gccatcttcg gactgcacca catcggcatg cagatgcgga tcgccatgtt cagcctgatc  480
tacaagaaaa ccctgaagct gagcagcaga gtgctggaca agatcagcat cggacagctg  540
gtgagcctgc tgagcaacaa cctgaacaag ttcgacgaag gcctggccct ggcccacttc  600
gtgtggatcg cccccctgca agtggccctg ctgatgggcc tgatctggga actgctgcag  660
gccagcgcct tctgcggact gggattcctg atcgtgctgg ccctgttcca ggccggactg  720
gggagaatga tgatgaagta ccgggaccag agagccggca agatcagcga gagactggtc  780
atcaccagcg agatgatcga gaacatccag agcgtgaagg cctactgctg ggaagaggcc  840
atggaaaaga tgatcgagaa cctgcggcag accgagctga agctgacaag aaaggccgcc  900
tacgtgcgct acttcaacag cagcgccttc ttcttcagcg gcttcttcgt ggtgttcctg  960
agcgtgctgc cctacgccct gatcaagggc atcatcctga gaaagatctt caccaccatc  1020
agcttctgca tcgtgctgcg gatggccgtg accagacagt tcccctgggc cgtgcagacc  1080
tggtacgaca gcctgggcgc catcaacaag atccaggact tcctgcagaa gcaagagtac  1140
aagaccctcg agtacaacct gaccaccacc gaggtggtca tggaaaacgt gaccgccttc  1200
tgggaggaag gcttcggcga gctgttcgag aaggccaagc agaacaacaa caaccgcaag  1260
accagcaacg gcgacgacag cctgttcttc agcaacttca gcctgctggg gacccccgtg  1320
ctgaaggaca tcaacttcaa gatcgagcgg ggacagctgc tggccgtggc cggaagcaca  1380
ggcgccggaa aaaccagcct gctcatggtc atcatgggcg agctggaacc cagcgagggc  1440
aagatcaagc acagcggcag gatcagcttc tgcagccagt tcagctggat catgcccggc  1500
accatcaaag agaacatcat cttcggcgtg agctacgacg agtacagata ccgcagcgtg  1560
atcaaggcct gccagctgga agaggacatc agcaagttcg ccgagaagga caacatcgtg  1620
ctcggcgaag gcggcatcac actgagcggc ggacagaggg ccagaatcag cctggccaga  1680
gccgtgtaca aggacgccga cctgtacctg ctggacagcc ccttcggcta cctggacgtg  1740
ctgaccgaga aagagatctt cgagagctgc gtgtgcaagc tgatggccaa caagacccgg  1800
atcctggtca ccagcaagat ggaacacctg aagaaggccg acaagatcct gatcctgcac  1860
gagggcagca gctacttcta cggcaccttc agcgagctgc agaacctgca gcccgacttc  1920
agcagcaaac tgatgggctg cgacagcttc gaccagttca gcgccgagcg gagaaacagc  1980
atcctgacag agacactgca ccggttcagc ctggaaggcg acgcccccgt gagctggacc  2040
gagacaaaga agcagagctt caagcagacc ggcgagttcg gcgagaagcg gaagaacagc  2100
atcctgaacc ccatcaacag catccggaag ttcagcatcg tccagaaaac cccccctgcag  2160
atgaacggca tcgaagagga cagcgacgag cccctggaaa gacggctgag cctggtgccc  2220
gacagcgaac agggcgaagc catcctgccc cggatcagcg tgatcagcac aggccccaca  2280
ctgcaggccc ggagaaggca gagcgtgctg aacctgatga cccacagcgt gaaccaggga  2340
cagaacatcc acagaaagac caccgccagc acacggaaag tgagcctggc cccccaggcc  2400
aacctgactg agctggacat ctacagcaga cggctgagcc aagagacagg cctggaaatc  2460
agcgaggaaa tcaacgaaga ggacctgaaa gagtgcttct tcgacgacat ggaaagcatc  2520
cccgccgtga caacctggaa cacctacctg cggtacatca ccgtgcacaa gagcctgatc  2580
ttcgtgctga tctggtgcct cgtgatcttc ctggccgaag tggccgccag cctggtggtg  2640
ctgtggctgc tcggaaacac cccactgcag gacaagggca acagcaccca cagccggaac  2700
aacagctacg ccgtgatcat caccagcacc agcagctact acgtgttcta catctacgtg  2760
ggcgtcgccg acactctgct cgccatgggc ttcttcagag gactgcccct ggtgcacacc  2820
ctgatcaccg tgagcaagat cctgcaccac aagatgctgc acagcgtcct gcaggccccc  2880
atgagcacac tgaacaccct gaaagccggc ggaatcctga acagattcag caaggacatc  2940
gccatcctgg acgacctgct gcccctgacc atcttcgact tcatccagct gctgctgatc  3000
gtgatcggcg ccatcgccgt ggtggccgtg ctgcagccct acatcttcgt ggccaccgtg  3060
cccgtgatcg tggccttcat catgctgcgg gcctacttcc tgcagaccag ccagcagctg  3120
aagcagctcg agagcgaggg cagaagcccc atcttcaccc acctcgtgac cagcctgaaa  3180
ggcctgtgga ccctgagagc cttcggcaga cagccctact tcgagacact gttccacaag  3240
gccctgaacc tgcacaccgc caactggttc ctgtacctga gcaccctgcg gtggttccag  3300
```

```
atgaggatcg agatgatctt cgtcatcttc ttcatcgccg tgaccttcat cagcatcctc  3360
accactggcg aaggcgaggg cagagtggga atcatcctga ccctggccat gaacatcatg  3420
agcacactcc agtgggccgt gaacagcagc atcgacgtgg acagcctgat gcggagcgtg  3480
agccgggtgt tcaagttcat cgacatgccc acagagggca agcccaccaa gagcaccaag  3540
ccctacaaga acggccagct gagcaaagtc atgatcatcg agaacagcca cgtcaagaag  3600
gacgacatct ggcccagcgg aggccagatg accgtgaagg acctgaccgc caagtacacc  3660
gaaggcggaa acgccatcct ggaaaacatc agcttcagca tcagccccgg ccagcgcgtg  3720
ggactcctgg gaagaaccgg aagcggcaag agcactctgc tgagcgcctt cctgagactg  3780
ctgaacaccg agggcgagat ccagatcgac ggggtgagct gggacagcat caccctgcaa  3840
caatggcgga aggccttcgg cgtgatcccc cagaaggtgt tcatcttcag cggcacgttc  3900
cggaagaacc tggaccccta cgagcagtgg agcgaccaag agatctggaa ggtggccgac  3960
gaagtgggac tgagaagcgt gatcgagcag ttccccggca agctggactt cgtgctggtg  4020
gacggcggct gcgtgctgag ccacggacac aagcagctga tgtgcctggc cagaagcgtg  4080
ctgagcaagg ccaagatcct gctgctcgac gagcccagcg cccacctgga ccccgtgacc  4140
taccagatca tccggcggac actgaagcag gccttcgccg actgcaccgt gatcctgtgc  4200
gagcacagaa tcgaggccat gctggaatgc cagcagttcc tggtgatcga agagaacaaa  4260
gtgcggcagt acgacagcat ccagaagctg ctgaacgagc ggagcctgtt cagacaggcc  4320
atcagcccca gcgacagagt gaagctgttc ccccaccgga acagcagcaa gtgcaagagc  4380
aagccccaga tcgccgccct gaaagaagaa accgaggaag aggtgcagga cacacggctg  4440
gcggccgttt acccatacga tgttcctgac tatgcgtga                         4479

SEQ ID NO: 4            moltype = DNA  length = 4443
FEATURE                 Location/Qualifiers
source                  1..4443
                        mol_type = other DNA
                        organism = synthetic construct
SEQUENCE: 4
atgcagagaa gcccccctgga aaaggccagc gtggtgagca agctgttctt cagctggacc  60
cggcccatcc tgcggaaggg ctacagacag agactggaac tgagcgacat ctaccagatc  120
cccagcgtgg acagcgccga caacctgagc gagaagctgg aaagagagtg ggacagagag  180
ctggccagca agaagaaccc caagctgatc aacgccctgc ggcggtgctt cttctggcgg  240
ttcatgttct acggcatctt cctgtacctg ggcgaagtga ccaaagccgt gcagcccctg  300
ctgctgggca gaatcatcgc cagctacgac cccgacaaca aagaggaacg gagcatcgcc  360
atctacctcg gcatcggcct gtgcctgctg ttcatcgtca gaaccctgct gctgcacccc  420
gccatcttcg gactgcacca catcggcatg cagatgcgga tcgccatgtt cagcctgatc  480
tacaagaaaa ccctgaagct gagcagcaga gtgctggaca agatcagcat cggacagctg  540
gtgagcctgc tgagcaacaa cctgaacaag ttcgacgaag gcctggccct ggcccacttc  600
gtgtggatcg ccccccctgca agtggccctg ctgatgggcc tgatctggga actgctgcag  660
gccagcgcct tctgcggact gggattcctg atcgtgctgg ccctgttcca ggccggactg  720
gggagaatga tgatgaagta ccgggaccag agagccggca agatcagcga gagactggtc  780
atcaccagcg agatgatcga gaacatccag agcgtgaagg cctactgctg ggaagaggcc  840
atggaaaaga tgatcgagaa cctgcggcag accgagctga agctgacaag aaaggccgcc  900
tacgtgcgct acttcaacag cagcgccttc ttcttcagcg gcttcttcgt ggtgttcctg  960
agcgtgctgc cctacgccct gatcaagggc atcatcctga gaaagatctt caccaccatc  1020
agcttctgca tcgtgctgcg gatggccgtg accagacagt tcccctgggc cgtgcagacc  1080
tggtacgaca gcctgggcgc catcaacaag atccaggact tcctgcagaa gcaagagtac  1140
aagaccctcg agtacaacct gaccaccacc gaggtggtca tggaaaacgt gaccgccttc  1200
tgggaggaag gcttcggcga gctgttcgag aaggccaagc agaacaacaa caaccgcaag  1260
accagcaacg gcgacgacag cctgttcttc agcaacttca gcctgctggg gaccccccgtg  1320
ctgaaggaca tcaacttcaa gatcgagcgg ggacagctgc tggccgtggc cggaagcaca  1380
ggcgccggaa aaaccagcct gctcatggtc atcatgggcg agctggaacc cagcgagggc  1440
aagatcaagc acagcggcag gatcagcttc tgcagccagt tcagctggat catgcccggc  1500
accatcaaag agaacatcat cttcggcgtg agctacgacg agtacagata ccgcagcgtg  1560
atcaaggcct gccagctgga agaggacatc agcaagttcg ccgagaagga caacatcgtg  1620
ctcggcgaag gcggcatcac actgagcggc ggacagaggg ccagaatcag cctggccaga  1680
gccgtgtaca aggacgccga cctgtacctg ctggacagcc ccttcggcta cctggacgtg  1740
ctgaccgaga aagagatctt cgagagctgc gtgtgcaagc tgatggccaa caagacccgg  1800
atcctggtca ccagcaagat ggaacacctg aagaaggccg acaagatcct gatcctgcac  1860
gagggcagca gctacttcta cggcaccttc agcgagctgc agaacctgca gcccgacttc  1920
agcagcaaac tgatgggctg cgacagcttc gaccagttca gcgccgagcg gagaaacagc  1980
atcctgacag agacactgca ccggttcagc ctggaaggcg acgccccccgt gagctggacc  2040
gagacaaaga agcagagctt caagcagacc ggcgagttcg gcgagaagcg gaagaacagc  2100
atcctgaacc ccatcaacag catccggaag ttcagcatcg tccagaaaac cccccctgcag  2160
atgaacggca tcgaagagga cagcgacgag cccctggaaa gacggctgag cctggtgccc  2220
gacagcgaac agggcgaagc catcctgccc cggatcagcg tgatcagcac aggccccaca  2280
ctgcaggccc ggagaaggca gagcgtgctg aacctgatga cccacagcgt gaaccaggga  2340
cagaacatcc acagaaagac caccgccagc acacggaaag tgagcctggc cccccaggcc  2400
aacctgactg agctggacat ctacagcaga cggctgagcc aagagacagg cctggaaatc  2460
agcgaggaaa tcaacgaaga ggacctgaaa gagtgcttct tcgacgacat ggaaagcatc  2520
cccgccgtga caacctggaa cacctacctg cggtacatca ccgtgcacaa gagcctgatc  2580
ttcgtgctga tctggtgcct cgtgatcttc ctggccgaag tggccgccag cctggtggtg  2640
ctgtggctgc tcggaaacac ccccactgcag gacaagggca acagcaccca cagccggaac  2700
aacagctacg ccgtgatcat caccagcacc agcagctact acgtgttcta catctacgtg  2760
ggcgtcgccg acactctgct cgccatgggc ttcttcagag gactgcccct ggtgcacacc  2820
ctgatcaccg tgagcaagat cctgcaccac aagatgctgc acagcgtcct gcaggccccc  2880
atgagcacac tgaacaccct gaaagccggc ggaatcctga acagattcag caaggacatc  2940
gccatcctgg acgacctgct gcccctgacc atcttcgact tcatccagct gctgctgatc  3000
gtgatcggcg ccatcgccgt ggtggccgtg ctgcagccct acatcttcgt ggccaccgtg  3060
cccgtgatcg tggccttcat catgctgcgg gcctacttcc tgcagaccag ccagcagctg  3120
```

-continued

```
aagcagctcg agagcgaggg cagaagcccc atcttcaccc acctcgtgac cagcctgaaa  3180
ggcctgtgga ccctgagagc cttcggcaga cagccctact tcgagacact gttccacaag  3240
gccctgaacc tgcacaccgc caactggttc ctgtacctga gcaccctgcg gtggttccag  3300
atgaggatcg agatgatctt cgtcatcttc ttcatcgccg tgaccttcat cagcatcctc  3360
accactggcg aaggcgaggg cagagtggga atcatcctga ccctggccat gaacatcatg  3420
agcacactcc agtgggccgt gaacagcagc atcgacgtgg acagcctgat gcggagcgtg  3480
agccgggtgt tcaagttcat cgacatgccc acagagggca agcccaccaa gagcaccaag  3540
ccctacaaga acggccagct gagcaaagtc atgatcatcg agaacagcca cgtcaagaag  3600
gacgacatct ggcccagcgg aggccagatg accgtgaagg acctgaccgc caagtacacc  3660
gaaggcggaa acgccatcct ggaaaacatc agcttcagca tcagccccgg ccagcgcgtg  3720
ggactcctgg gaagaaccgg aagcggcaag agcactctgc tgagcgcctt cctgagactg  3780
ctgaacaccg agggcgagat ccagatcgac ggggtgagct gggacagcat caccctgcaa  3840
caatggcgga aggccttcgg cgtgatcccc cagaaggtgt tcatcttcag cggcacgttc  3900
cggaagaacc tggaccccta cgagcagtgg agcgaccaag agatctggaa ggtggccgac  3960
gaagtgggac tgagaagcgt gatcgagcag ttccccggca agctggactt cgtgctggtg  4020
gacggcggct gcgtgctgag ccacggacac aagcagctga tgtgcctggc cagaagcgtg  4080
ctgagcaagg ccaagatcct gctgctcgac gagcccagcg cccacctgga ccccgtgacc  4140
taccagatca tccggcggac actgaagcag gccttcgccg actgcaccgt gatcctgtgc  4200
gagcacagaa tcgaggccat gctggaatgc cagcagttcc tggtgatcga agagaacaaa  4260
gtgcggcagt acgacagcat ccagaagctg ctgaacgagc ggagcctgtt cagacaggcc  4320
atcagcccca gcgacagagt gaagctgttc cccccaccgga acagcagcaa gtgcaagagc  4380
aagccccaga tcgccgccct gaaagaagaa accgaggaag aggtgcagga cacacggctg  4440
tga                                                                4443

SEQ ID NO: 5              moltype = DNA  length = 4443
FEATURE                   Location/Qualifiers
source                    1..4443
                          mol_type = other DNA
                          organism = unidentified
SEQUENCE: 5
atgcagaggt cgcctctgga aaaggccagc gttgtctcca aactttttt cagctggacc  60
agaccaattt tgaggaaagg atacagacag cgcctggaat tgtcagacat ataccaaatc  120
ccttctgttg attctgctga caatctatct gaaaaattgg aaagagaatg ggatagagag  180
ctggcttcaa agaaaaatcc taaactcatt aatgcccttc ggcgatgttt tttctggaga  240
tttatgttct atggaatctt tttatattta ggggaagtca ccaaagcagt acagcctctc  300
ttactgggaa gaatcatagc ttcctatgac ccggataaca aggaggaacg ctctatcgcg  360
atttatctag gcataggctt atgccttctc tttattgtga ggacactgct cctacaccca  420
gccatttttg gccttcatca cattggaatg cagatgagaa tagctatgtt tagtttgatt  480
tataagaaga ctttaaagct gtcaagccgt gttctagata aaataagtat tggacaactt  540
gttagtctcc tttccaacaa cctgaacaaa tttgatgaag gacttgcatt ggcacatttc  600
gtgtggatcg ctcctttgca agtggcactc ctcatggggc taatctggga gttgttacag  660
gcgtctgcct tctgtggact tggtttcctg atagtccttg ccctttttca ggctgggcta  720
gggagaatga tgatgaagta cagagatcag agagctggga agatcagtga aagacttgtg  780
attacctcag aaatgattga aaatatccaa tctgttaagg catactgctg ggaagaagca  840
atggaaaaaa tgattgaaaa cttaagacaa acagaactga aactgactcg gaaggcagcc  900
tatgtgagat acttcaatag ctcagccttc ttcttctcag ggttctttgt ggtgttttta  960
tctgtgcttc cctatgcact aatcaaagga atcatcctcc ggaaaatatt caccaccatc  1020
tcattctgca ttgttctgcg catggcggtc actcggcaat ttccctgggc tgtacaaaca  1080
tggtatgact ctcttggagc aataaacaaa atacaggatt tcttacaaaa gcaagaatat  1140
aagacattgg aatataactt aacgactaca gaagtagtga tggagaatgt aacagccttc  1200
tgggaggagg gatttgggga attatttgag aaagcaaaac aaaacaataa caatagaaaa  1260
acttctaatg gtgatgacag cctcttcttc agtaatttct cacttcttgg tactcctgtc  1320
ctgaaagata ttaatttcaa gatagaaaga ggacagttgt tggcggttgc tggatccact  1380
ggagcaggca agacttcact tctaatgatg attatgggag aactggagcc ttcagagggt  1440
aaaattaagc acagtggaag aatttcattc tgttctcagt tttcctggat tatgcctggc  1500
accattaaag aaaatatcat ctttggtgtt tcctatgatg aatatagata cagaagcgtc  1560
atcaaagcat gccaactaga agaggacatc tccaagtttg cagagaaaga caatatagtt  1620
cttggagaag gtggaatcac actgagtgga ggtcaacgag caagaatttc tttagcaaga  1680
gcagtataca aagatgctga tttgtattta ttagactctc cttttggata cctagatgtt  1740
ttaacagaaa aagaaatatt tgaaagctgt gtctgtaaac tgatggctaa caaaactagg  1800
attttggtca cttctaaaat ggaacattta aagaaagctg acaaaatatt aattttgaat  1860
gaaggtagca gctattttta tgggacattt tcagaactcc aaaatctaca gccagacttt  1920
agctcaaaac tcatgggatg tgattctttc gaccaattta gtgcagaaag aagaaattca  1980
atcctaactg agaccttaca ccgtttctca ttagaaggag atgctcctgt ctcctggaca  2040
gaaacaaaaa aacaatcttt taaacagact ggagagtttg ggaaaaaaag gaagaattct  2100
attctcaatc caatcaactc tatacgaaaa ttttccattg tgcaaaagac tcccttacaa  2160
atgaatggca tcgaagagga ttctgatgag cctttagaga gaaggctgtc cttagtacca  2220
gattctgagc agggagaggc gatactgcct cgcatcagcg tgatcagcac tggccccacg  2280
cttcaggcac gaaggaggca gtctgtcctg aacctgatga cacactcagt taaccaaggt  2340
cagaacattc accgaaagac aacagcatcc acacgaaaag tgtcactggc ccctcaggca  2400
aacttgactg aactggatat atattcaaga aggttatctc aagaaactgg cttggaaata  2460
agtgaagaaa ttaacgaaga agacttaaag gagtgccttt ttgatgatat ggagagcata  2520
ccagcagtga ctacatggaa cacatacctt cgatatatta ctgtccacaa gagcttaatt  2580
tttgtgctaa tttggtgctt agtaattttt ctggcagagg tggctgcttc tttggttgtg  2640
ctgtggctcc ttggaaacac tcctcttcaa gacaaaggga atagtactca tagtagaaat  2700
aacagctatg cagtgattat caccagcacc agttcgtatt atgtgtttta catttacgtg  2760
ggagtagccg acactttgct tgctatggga ttcttcagag gtctaccact ggtgcatact  2820
ctaatcacag tgtcgaaaat tttacaccac aaaatgttac attctgttct tcaagcacct  2880
atgtcaaccc tcaacacgtt gaaagcaggt gggattctta atagattctc caaagatata  2940
```

```
gcaattttgg atgaccttct gcctcttacc atatttgact tcatccagtt gttattaatt  3000
gtgattggag ctatagcagt tgtcgcagtt ttacaaccct acatctttgt tgcaacagtg  3060
ccagtgatag tggcttttat tatgttgaga gcatatttcc tccaaacctc acagcaactc  3120
aaacaactgg aatctgaagg caggagtcca attttcactc atcttgttac aagcttaaaa  3180
ggactatgga cacttcgtgc cttcggacgg cagccttact ttgaaactct gttccacaaa  3240
gctctgaatt tacatactgc caactggttc ttgtacctgt caacactgcg ctggttccaa  3300
atgagaatag aaatgatttt tgtcatcttc ttcattgctg ttaccttcat ttccatttta  3360
acaacaggag aaggagaagg aagagttggt attatcctga ctttagccat gaatatcatg  3420
agtacattgc agtgggctgt aaactccagc atagatgtgg atagcttgat gcgatctgtg  3480
agccgagtct ttaagttcat tgacatgcca acagaaggta aacctaccaa gtcaaccaaa  3540
ccatacaaga atggccaact ctcgaaagtt atgattattg agaattcaca cgtgaagaaa  3600
gatgacatct ggccctcagg gggccaaatg actgtcaaag atctcacagc aaaatacaca  3660
gaaggtggaa atgccatatt agagaacatt tccttctcaa taagtcctgg ccagagggtg  3720
ggcctcttgg gaagaactgg atcagggaag agtactttgt tatcagcttt tttgagacta  3780
ctgaacactg aaggagaaat ccagatcgat ggtgtgtctt gggattcaat aactttgcaa  3840
cagtggagga aagcctttgg agtgatacca cagaaagtat ttatttttc tggaacattt  3900
agaaaaaact tggatcccta tgaacagtgg agtgatcaag aaatatggaa agttgcagat  3960
gaggttgggc tcagatctgt gatagaacag tttcctggga agcttgactt tgtccttgtg  4020
gatgggggct gtgtcctaag ccatggccac aagcagttga tgtgcttggc tagatctgtt  4080
ctcagtaagg cgaagatctt gctgcttgat gaacccagtg ctcatttgga tccagtaaca  4140
taccaaataa ttagaagaac tctaaaacaa gcatttgctg attgcacagt aattctctgt  4200
gaacacagga tagaagcaat gctggaatgc caacaatttt tggtcataga agagaacaaa  4260
gtgcggcagt acgattccat ccagaaactg ctgaacgaga ggagcctctt ccggcaagcc  4320
atcagcccct ccgacagggt gaagctcttt ccccaccgga actcaagcaa gtgcaagtct  4380
aagccccaga ttgctgctct gaaagaggag acagaagaag aggtgcaaga tacaaggctt  4440
tag                                                                4443

SEQ ID NO: 6           moltype = DNA  length = 66
FEATURE                Location/Qualifiers
source                 1..66
                       mol_type = other DNA
                       organism = synthetic construct
SEQUENCE: 6
gggagaccca agctggctag cgtttaaact tcagcttggc aatccggtac tgttggtaaa  60
gccacc                                                            66

SEQ ID NO: 7           moltype = DNA  length = 147
FEATURE                Location/Qualifiers
source                 1..147
                       mol_type = other DNA
                       organism = synthetic construct
SEQUENCE: 7
gaattctgca gaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaattcg                                     147

SEQ ID NO: 8           moltype = DNA  length = 146
FEATURE                Location/Qualifiers
source                 1..146
                       mol_type = other DNA
                       organism = synthetic construct
SEQUENCE: 8
gaattctgca gaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaatt                                      146

SEQ ID NO: 9           moltype = DNA  length = 72
FEATURE                Location/Qualifiers
source                 1..72
                       mol_type = other DNA
                       organism = synthetic construct
SEQUENCE: 9
gggagacata aaccctggcg cgctcgcggc ccggcactct tctggtcccc acagactcag  60
agagaagcca cc                                                     72

SEQ ID NO: 10          moltype = DNA  length = 72
FEATURE                Location/Qualifiers
source                 1..72
                       mol_type = other DNA
                       organism = synthetic construct
SEQUENCE: 10
gggagacata aaccctggcg cgctcgcggg ccggcactct tctggtcccc acagactcag  60
agagaagcca cc                                                     72

SEQ ID NO: 11          moltype = DNA  length = 43
FEATURE                Location/Qualifiers
source                 1..43
                       mol_type = other DNA
                       organism = synthetic construct
```

```
SEQUENCE: 11
gggagactct tctggtcccc acagactcag agagaacgcc acc                   43

SEQ ID NO: 12           moltype = DNA  length = 511
FEATURE                 Location/Qualifiers
source                  1..511
                        mol_type = other DNA
                        organism = synthetic construct
SEQUENCE: 12
gttattttcc accatattgc cgtcttttgg caatgtgagg gcccggaaac ctggccctgt  60
cttcttgacg agcattccta ggggtctttc ccctctcgcc aaaggaatgc aaggtctgtt  120
gaatgtcgtg aaggaagcag ttcctctgga agcttcttga agacaaacaa cgtctgtagc  180
gaccctttgc aggcagcgga acccccacc tggcgacagg tgcctctgcg gccaaaagcc  240
acgtgtataa gatacacctg caaaggcggc acaaccccag tgccacgttg tgagttggat  300
agttgtggaa agagtcaaat ggctctcctc aagcgtattc aacaaggggc tgaaggatgc  360
ccagaaggta ccccattgta tgggatctga tctggggcct cggtgcacat gctttacgtg  420
tgtttagtcg aggttaaaaa acgtctaggc cccccgaacc acggggacgt ggttttcctt  480
tgaaaaacac gatgataata tggccacaac c                                 511

SEQ ID NO: 13           moltype = DNA  length = 143
FEATURE                 Location/Qualifiers
source                  1..143
                        mol_type = other DNA
                        organism = synthetic construct
SEQUENCE: 13
aaataacaaa tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gca                                          143

SEQ ID NO: 14           moltype = DNA  length = 47
FEATURE                 Location/Qualifiers
source                  1..47
                        mol_type = other DNA
                        organism = synthetic construct
SEQUENCE: 14
gggagacaag agagaaaaga agagcaagaa gaaatataag agccacc                47

SEQ ID NO: 15           moltype = DNA  length = 66
FEATURE                 Location/Qualifiers
source                  1..66
                        mol_type = other DNA
                        organism = synthetic construct
SEQUENCE: 15
gggagaccca agctggctag cgtttaaact taagcttggc aatccggtac tgttggtaaa  60
gccacc                                                             66

SEQ ID NO: 16           moltype = DNA  length = 70
FEATURE                 Location/Qualifiers
source                  1..70
                        mol_type = other DNA
                        organism = synthetic construct
SEQUENCE: 16
gtagtaggtc tttggcatta ggagcttgag cccagacggc cctagcaggg accccagcgc  60
ccgagagacc                                                         70

SEQ ID NO: 17           moltype = DNA  length = 186
FEATURE                 Location/Qualifiers
source                  1..186
                        mol_type = other DNA
                        organism = synthetic construct
SEQUENCE: 17
ggattgtgtc cgtaatcaca cgtggtgcgt acgataacgc atagtgtttt tccctccact  60
taaatcgaag ggttgtgtct tggatcgcgc gggtcaaatg tatatggttc atatacatcc  120
gcaggcacgt aataaagcga ggggttcgaa tccccccgtt acccccggta ggggcccatt  180
gtcttc                                                             186

SEQ ID NO: 18           moltype = DNA  length = 114
FEATURE                 Location/Qualifiers
source                  1..114
                        mol_type = other DNA
                        organism = synthetic construct
SEQUENCE: 18
tcagtagggt catgaaggtt tttcttttcc tgagaaaaca acacgtattg ttttctcagg  60
ttttgctttt tggccttttt ctagcttaaa aaaaaaaaaa gcaaaattgt cttc        114

SEQ ID NO: 19           moltype = DNA  length = 112
FEATURE                 Location/Qualifiers
source                  1..112
                        mol_type = other DNA
```

```
                         organism = synthetic construct
SEQUENCE: 19
tcagtagggt tgtaaaggtt tttcttttcc tgagaaaaca accttttgtt ttctcaggtt  60
ttgctttttg gcctttccct agctttaaaa aaaaaaaagc aaaattgtct tc          112

SEQ ID NO: 20            moltype = DNA  length = 68
FEATURE                  Location/Qualifiers
source                   1..68
                         mol_type = other DNA
                         organism = synthetic construct
SEQUENCE: 20
gaagtggcgg ttcggccgga ggttccatcg tatccaaaag gctcttttca gagccaccca  60
ttgtcttc                                                           68

SEQ ID NO: 21            moltype = DNA  length = 1557
FEATURE                  Location/Qualifiers
source                   1..1557
                         mol_type = other DNA
                         organism = synthetic construct
SEQUENCE: 21
agagcagcat aaatgttgac atgggacatt tgctcatgga attggagctc gtgggacagt  60
cacctcatgg aattggagct cgtggaacag ttacctctgc ctcagaaaac aaggatgaat  120
taagtttttt tttaaaaaag aaacatttgg taaggggaat tgaggacact gatatgggtc  180
ttgataaatg gcttcctggc aatagtcaaa ttgtgtgaaa ggtacttcaa atccttgaag  240
atttaccact tgtgttttgc aagccagatt ttcctgaaaa cccttgccat gtgctagtaa  300
ttggaaaggc agctctaaat gtcaatcagc ctagttgatc agcttattgt ctagtgaaac  360
tcgttaattt gtagtgttgg agaagaactg aaatcatact tcttagggtt atgattaagt  420
aatgataact ggaaacttca gcggtttata taagcttgta ttccttttc tctcctctcc   480
ccatgatgtt tagaaacaca actatattgt ttgctaagca ttccaactat ctcatttcca  540
agcaagtatt agaataccac aggaaccaca agactgcaca tcaaaatatg ccccattcaa  600
catctagtga gcagtcagga aagagaactt ccagatcctg gaaatcaggg ttagtattgt  660
ccaggtctac caaaaatctc aatatttcag ataatcacaa tacatccctt acctgggaaa  720
gggctgttat aatctttcac aggggacagg atggttccct tgatgaagaa gttgatatgc  780
cttttcccaa ctccagaaag tgacaagctc acagaccttt gaactagagt ttagctggaa  840
aagtatgtta gtgcaaattg tcacaggaca gcccttcttt ccacagaagc tccaggtaga  900
gggtgtgtaa gtagataggc catgggcact gtgggtagac acacatgaag tccaagcatt  960
tagatgtata ggttgatggt ggtatgtttt caggctagat gtatgtactt catgctgtct  1020
acactaagag agaatgagag acacactgaa gaagcaccaa tcatgaatta gttttatatg  1080
cttctgtttt ataattttgt gaagcaaaat tttttctcta ggaaatattt attttaataa  1140
tgtttcaaac atatataaca atgctgtatt ttaaaagaat gattatgaat tacatttgta  1200
taaaataatt tttatatttg aaatattgac tttttatggc actagtattt ctatgaaata  1260
ttatgttaaa actgggacag gggagaacct agggtgatat taaccagggg ccatgaatca  1320
ccttttggtc tggagggaag ccttggggct gatgcagttg ttgcccacag ctgtatgatt  1380
cccagccagc acagcctctt agatgcagtt ctgaagaaga tggtaccacc agtctgactg  1440
tttccatcaa gggtacactg ccttctcaac tccaaactga ctcttaagaa gactgcatta  1500
tatttattac tgtaagaaaa tatcacttgt caataaaatc catacatttg tgtgaaa     1557

SEQ ID NO: 22            moltype = DNA  length = 66
FEATURE                  Location/Qualifiers
source                   1..66
                         mol_type = other DNA
                         organism = synthetic construct
SEQUENCE: 22
gggagaccca agctggctag cgtttaaact tcagcttggc aatccggtac tgttggtaaa  60
gccacc                                                             66

SEQ ID NO: 23            moltype = DNA  length = 4482
FEATURE                  Location/Qualifiers
source                   1..4482
                         mol_type = other DNA
                         organism = synthetic construct
SEQUENCE: 23
atgtacccat acgatgttcc tgactatgcg gcggccgtta tgcagagaag ccccctggaa  60
aaggccagcg tggtgagcaa gctgttcttc agctggaccc ggcccatcct gcggaagggc  120
tacagacaga gactggaact gagcgacatc taccagatcc ccagcgtgga cagcgccgac  180
aacctgagcg agaagctgga aagagagtgg gacagagagc tggccagcaa gaagaacccc  240
aagctgatca acgccctgcg gcggtgcttc ttctggcggt tcatgttcta cggcatcttc  300
ctgtacctgg gcgaagtgac caaagccgtg cagcccctgc tgctgggcag aatcatcgcc  360
agctacgacc ccgacaacaa agaggaacgg agcatcgcca tctacctcgg catcggcctg  420
tgcctgctgt tcatcgtcag aaccctgctg ctgcaccccg ccatcttcgg actgcaccac  480
atcggcatgc agatgcggat cgccatgttc agcctgatct acaagaaaac cctgaagctg  540
agcagcagag tgctggacaa gatcagcatc ggacagctgg tgagcctgct gagcaacaac  600
ctgaacaagt tcgacgaagg cctggccctg gcccacttcg tgtggatcgc ccccctgcaa  660
gtggccctgc tgatgggcct gatctgggaa ctgctgcagg ccagcgcctt ctgcggactg  720
ggattcctga tcgtgctggc cctgttccag gccggactgg ggagaatgat gatgaagtac  780
cgggaccaga gagccggcaa gatcagcgag agactggtca tcaccagcga gatgatcgag  840
aacatccaga gcgtgaaggc ctactgctgg gaagaggcca tggaaaagat gatcgagaac  900
ctgcggcaga ccgagctgaa gctgacaaga aaggccgcct acgtgcgcta cttcaacagc  960
agcgccttct tcttcagcgg cttcttcgtg gtgttcctga gcgtgctgcc ctacgccctg  1020
```

-continued

```
atcaagggca tcatcctgag aaagatcttc accaccatca gcttctgcat cgtgctgcgg  1080
atggccgtga ccagacagtt cccctgggcc gtgcagacct ggtacgacag cctgggcgcc  1140
atcaacaaga tccaggactt cctgcagaag caagagtaca agaccctcga gtacaacctg  1200
accaccaccg aggtggtcat ggaaaacgtg accgccttct gggaggaagg cttcggcgag  1260
ctgttcgaga aggccaagca gaacaacaac aaccgcaaga ccagcaacgg cgacgacagc  1320
ctgttcttca gcaacttcag cctgctgggg acccccgtgc tgaaggacat caacttcaag  1380
atcgagcggg gacagctgct ggccgtggcc ggaagcacag gcgccggaaa aaccagcctg  1440
ctcatggtca tcatgggcga gctggaaccc agcgagggca agatcaagca cagcggcagg  1500
atcagcttct gcagccagtt cagctggatc atgcccggca ccatcaaaga gaacatcatc  1560
ttcggcgtga gctacgacga gtacagatac cgcagcgtga tcaaggcctg ccagctggaa  1620
gaggacatca gcaagttcgc cgagaaggac aacatcgtgc tcggcgaagg cggcatcaca  1680
ctgagcggcg gacagagggc cagaatcagc ctggccagag ccgtgtacaa ggacgccgac  1740
ctgtacctgc tggacagccc cttcggctac ctggacgtgc tgaccgagaa agagatcttc  1800
gagagctgcg tgtgcaagct gatggccaac aagacccgga tcctggtcac cagcaagatg  1860
gaacacctga agaaggccga caagatcctg atcctgcacg agggcagcag ctacttctac  1920
ggcaccttca gcgagctgca gaacctgcag cccgacttca gcagcaaact gatgggctgc  1980
gacagcttcg accagttcag cgccgagcgg agaaacagca tcctgacaga gacactgcac  2040
cggttcagcc tggaaggcga cgcccccgtg agctggaccg agacaaagaa gcagagcttc  2100
aagcagaccg gcgagttcgg cgagaagcgg aagaacagca tcctgaaccc catcaacagc  2160
atccggaagt tcagcatcgt ccagaaaacc cccctgcaga tgaacggcat cgaagaggac  2220
agcgacgagc ccctggaaag acggctgagc ctggtgcccg acagcgaaca gggcgaagcc  2280
atcctgcccc ggatcagcgt gatcagcaca ggccccacac tgcaggcccg gagaaggcag  2340
agcgtgctga acctgatgac ccacagcgtg aaccagggac agaacatcca cagaaagacc  2400
accgccagca cacggaaagt gagcctggcc ccccaggcca acctgactga gctggacatc  2460
tacagcagac ggctgagcca agagacaggc ctggaaatca gcgaggaaat caacgaagag  2520
gacctgaaag agtgcttctt cgacgacatg gaaagcatcc ccgccgtgac aacctggaac  2580
acctacctgc ggtacatcac cgtgcacaag agcctgatct tcgtgctgat ctggtgcctc  2640
gtgatcttcc tggccgaagt ggccgccagc ctggtggtgc tgtggctgct cggaaacacc  2700
ccactgcagg acaagggcaa cagcacccac agccggaaca acagctacgc cgtgatcatc  2760
accagcacca gcagctacta cgtgttctac atctacgtgg gcgtcgccga cactctgctc  2820
gccatgggct tcttcagagg actgcccctg gtgcacaccc tgatcaccgt gagcaagatc  2880
ctgcaccaca agatgctgca cagcgtcctg caggccccca tgagcacact gaacaccctg  2940
aaagccggcg gaatcctgaa cagattcagc aaggacatcg ccatcctgga cgacctgctg  3000
cccctgacca tcttcgactt catccagctg ctgctgatcg tgatcggcgc catcgccgtg  3060
gtggccgtgc tgcagcccta catcttcgtg gccaccgtgc ccgtgatcgt ggccttcatc  3120
atgctgcggg cctacttcct gcagaccagc cagcagctga agcagctcga gagcgagggc  3180
agaagcccca tcttcaccca cctcgtgacc agcctgaaag gcctgtggac cctgagagcc  3240
ttcggcagac agccctactt cgagacactg ttccacaagg ccctgaacct gcacaccgcc  3300
aactggttcc tgtacctgag caccctgcgg tggttccaga tgaggatcga gatgatcttc  3360
gtcatcttct tcatcgccgt gaccttcatc agcatcctca ccactggcga aggcgagggc  3420
agagtgggaa tcatcctgac cctggccatg aacatcatga gcacactcca gtgggccgtg  3480
aacagcagca tcgacgtgga cagcctgatg cggagcgtga gccgggtgtt caagttcatc  3540
gacatgccca cagagggcaa gcccaccaag agcaccaagc cctacaagaa cggccagctg  3600
agcaaagtca tgatcatcga gaacagccac gtcaagaagg acgacatctg gcccagcgga  3660
ggccagatga ccgtgaagga cctgaccgcc aagtacaccg aaggcggaaa cgccatcctg  3720
gaaaacatca gcttcagcat cagccccggc cagcgcgtgg gactcctggg aagaaccgga  3780
agcggcaaga gcactctgct gagcgccttc ctgagactgc tgaacaccga gggcgagatc  3840
cagatcgacg gggtgagctg ggacagcatc accctgcaac aatggcggaa ggccttcggc  3900
gtgatccccc agaaggtgtt catcttcagc ggcacgttcc ggaagaacct ggacccctac  3960
gagcagtgga gcgaccaaga gatctggaag gtggccgacg aagtgggact gagaagcgtg  4020
atcgagcagt tccccggcaa gctggacttc gtgctggtgg acggcggctg cgtgctgagc  4080
cacggacaca agcagctgat gtgcctggcc agaagcgtgc tgagcaaggc caagatcctg  4140
ctgctcgacg agcccagcgc ccacctggac cccgtgacct accagatcat ccggcggaca  4200
ctgaagcagg ccttcgccga ctgcaccgtg atcctgtgcg agcacagaat cgaggccatg  4260
ctggaatgcc agcagttcct ggtgatcgaa gagaacaaag tgcggcagta cgacagcatc  4320
cagaagctgc tgaacgagcg gagcctgttc agacaggcca tcagccccag cgacagagtg  4380
aagctgttcc cccaccggaa cagcagcaag tgcaagagca agccccagat cgccgccctg  4440
aaagaagaaa ccgaggaaga ggtgcaggac acacggctgt ga                    4482
```

POLYNUCLEOTIDE COMPOSITIONS, RELATED FORMULATIONS, AND METHODS OF USE THEREOF

CROSS-REFERENCE

This application is a continuation of and claims priority to U.S. patent application Ser. No. 18/283,523 filed Sep. 22, 2023, which is the U.S. national stage application under 35 U.S.C. 371 of International Patent Application No. PCT/US2022/021526 filed on Mar. 23, 2022, which claims the benefits of U.S. Provisional Application No. 63/164,573 filed Mar. 23, 2021, U.S. Provisional Application No. 63/208,966 filed Jun. 9, 2021, and U.S. Provisional Application No. 63/274,912 filed Nov. 2, 2021, each of which is hereby incorporated by reference herein in its entirety.

BACKGROUND

Nucleic acids, such as messenger ribonucleic acid(s) (mRNA(s)) may be used by cells to express proteins and polypeptides. Some cells may be deficient in a certain protein or nucleic acid and result in disease states. A cell can also take up and translate exogenous ribonucleic acid(s) (RNA(s)), but many factors influence efficient uptake and translation. For instance, the immune system recognizes many exogenous RNAs as foreign and triggers a response that is aimed at inactivating the RNAs.

SEQUENCE LISTING

This application contains a Sequence Listing, which has been submitted electronically in XML format and is hereby incorporated by reference in its entirety. Said XML copy, created on Jan. 19, 2024, is named 061529-719C01US_SeqList_ST26.xml and is 50 kb in size.

SUMMARY

Provided here are composition and methods for delivery of nucleic acids. Nucleic acids may be used as a therapeutic. In particular, mRNA may be delivered to a cell of a subject. Upon delivery of a nucleic acid to a cell, the nucleic acid may be used to synthesize a polypeptide. In the case of a cell or subject with a disease or disorder, the nucleic acid may be effective at acting as a therapeutic by increasing the expression of a polypeptide. In cases, where a disorder or disease is caused or correlated to aberrant expression or activity of polypeptide, the increased in expression of the polypeptide may be beneficial. However, the cells may have limited uptake of exogenous nucleic acids and the delivery of the nucleic acids may benefit from compositions that allow for increase uptake of a nucleic acid.

Additionally, therapeutics may benefit from organ specific delivery. Many different types of compounds such as chemotherapeutic agents exhibit significant cytotoxicity. If these compounds were better directed towards delivery to the desired organs, then fewer off target effects will be seen.

In an aspect, the present disclosure provides a synthetic polynucleotide encoding a cystic fibrosis transmembrane conductance regulator (CFTR) protein, wherein said synthetic polynucleotide comprises one or more nucleoside analogue(s). In some embodiments, the synthetic polynucleotide comprises 1-methylpseudouridine.

In an aspect, the present disclosure provides A synthetic polynucleotide encoding a cystic fibrosis transmembrane conductance regulator (CFTR) protein, wherein said synthetic polynucleotide comprises a nucleic acid sequence (e.g., an open reading frame (ORF) sequence) having at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100, 300, 500, 700, 900, or 1,000 bases of a sequence selected from SEQ ID NOs: 1-4 and 23. In some embodiments, the said nucleic acid sequence comprises fewer than about 115, 110, 105, 100, 95, or 90 UU or TT dinucleotide. In some embodiments, the nucleic acid sequence comprises at least two synonymous codons encoding arginine. In some embodiments, the nucleic acid sequence comprises at least three synonymous codons encoding arginine. In some embodiments, no more than about 70%, 65%, 60%, 55%, or 50% of all arginine encoding codons of said nucleic acid sequence is AGA codon. In some embodiments, the nucleic acid sequence encodes a polypeptide that comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100, 300, 500, 700, 900, or 1,000 contiguous amino acid residues to SEQ ID NO: 5. In some embodiments, the synthetic polynucleotide is a messenger ribonucleic acid (mRNA). In some embodiments, the synthetic polynucleotide further comprises a 3'- or 5'-noncoding region. In some embodiments, the 3'- or 5'-noncoding region enhances an expression or activity of said CFTR protein encoded by said synthetic polynucleotide within a cell. In some embodiments, the synthetic polynucleotide further comprises a 5' cap structure. In some embodiments, the 3' noncoding region comprises a poly adenosine tail. In some embodiments, the poly adenosine tail comprises at most 200 adenosines. In some embodiments, the poly adenosine tail improves a pharmacokinetic characteristic of said synthetic polynucleotide in a cell. In some embodiments, the poly adenosine tail improves a prolonged half-life of said synthetic polynucleotide in a cell.

In an aspect, the present disclosure provides a pharmaceutical composition comprising a synthetic polynucleotide assembled with a lipid composition, which synthetic polynucleotide encodes a cystic fibrosis transmembrane conductance regulator (CFTR) protein, wherein said lipid composition comprises: an ionizable cationic lipid; and a selective organ targeting (SORT) lipid separate from said ionizable cationic lipid.

In some embodiments, the lipid composition comprises said ionizable cationic lipid at a molar percentage of about 5% to about 30% In some embodiments, a (e.g., mass or weight) ratio of said ionizable cationic lipid to said synthetic polynucleotide is of no more than about 50:1, 40:1, 30:1, 20:1, 15:1 or 10:1. In some embodiments, the SORT lipid is a permanently cationic lipid. In some embodiments, the SORT lipid is a second ionizable cationic lipid. In some embodiments, the lipid composition comprises said SORT lipid at a molar percentage of about 5% to about 65%. In some embodiments, the lipid composition comprises said SORT lipid at a molar percentage of about 5% to about 30%. In some embodiments, the lipid composition further comprises a zwitterionic lipid (e.g., a phospholipid). In some embodiments, the lipid composition comprises said zwitterionic lipid at a molar percentage of about 5% to about 25%. In some embodiments, a (e.g., mass or weight) ratio of said zwitterionic lipid to said synthetic polynucleotide is of no more than about 50:1, 40:1, 30:1, or 20:1. In some embodiments, the lipid composition further comprises a steroid or steroid derivative. In some embodiments, the lipid composition comprises said steroid or steroid derivative at a molar percentage of about 15% to about 46%. In some embodiments, the lipid composition further comprises a polymer-conjugated lipid (e.g., poly(ethylene glycol) (PEG)-conjugated lipid). In some embodiments, the lipid composition comprises said polymer-conjugated lipid at a molar percentage of about 0.5% to about 10% In some embodiments, a molar ratio of nitrogen in said lipid composition to phosphate in said synthetic polynucleotide (N/P ratio) is of no more than about 50:1, 40:1, 30:1, or 20:1 In some embodiments, the N/P ratio is from about 5:1 to about 30:1. In some embodiments, the a (e.g., mass or weight) ratio of said synthetic polynucleotide to total lipids of said lipid composition is no more than about 1:20, 1:50, or 1:100. In some embodiments, the SORT lipid comprises a permanently positively charged moiety (e.g., a quaternary ammonium ion). In some embodiments, the SORT lipid comprises a counterion. In some embodiments, the SORT lipid is a phosphocholine lipid (e.g., saturated or unsaturated). In some embodiments, the SORT lipid is an ethylphosphocholine. In some embodiments, the SORT lipid comprises a headgroup having a structural formula:

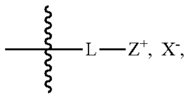

wherein L is a (e.g., biodegradable) linker; $Z^+$ is positively charged moiety (e.g., a quaternary ammonium ion); and $X^-$ is a counterion. In some embodiments, the SORT lipid has a structural formula:

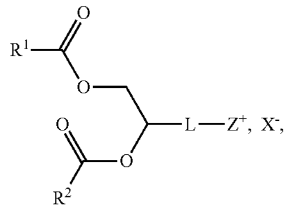

wherein $R^1$ and $R^2$ are each independently an optionally substituted $C_6$-$C_{24}$ alkyl, or an optionally substituted $C_6$-$C_{24}$ alkenyl. In some embodiments, the SORT lipid has a structural formula:

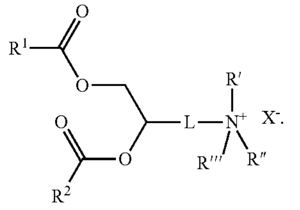

In some embodiments, L is

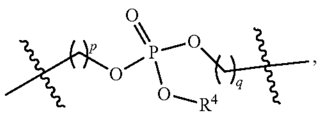

wherein:

p and q are each independently 1, 2, or 3; and $R^4$ is an optionally substituted $C_1$-$C_6$ alkyl. In some embodiments, the SORT lipid has a structural formula:

(IA)

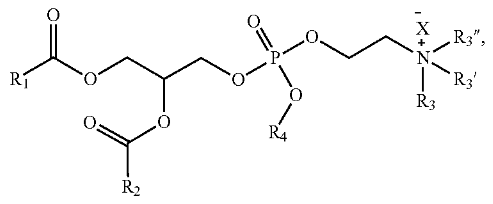

wherein:

$R_1$ and $R_2$ are each independently alkyl$_{(C8-C24)}$, alkenyl$_{(C8-C24)}$, or a substituted version of either group;

$R_3$, $R_{3'}$, and $R_3''$ are each independently alkyl$_{(C\leq6)}$ or substituted alkyl$_{(C\leq6)}$;

$R_4$ is alkyl$_{(C\leq6)}$ or substituted alkyl$_{(C\leq6)}$; and

X is a monovalent anion.

In some embodiments, the SORT lipid has a structural formula:

(S-I')

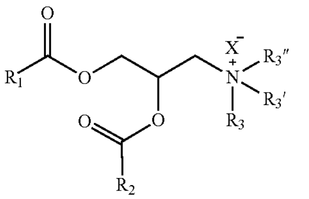

wherein:

$R_1$ and $R_2$ are each independently alkyl$_{(C8-C24)}$, alkenyl$_{(C8-C24)}$, or a substituted version of either group;

$R_3$, $R_{3'}$, and $R_3''$ are each independently alkyl$_{(C\leq6)}$ or substituted alkyl$_{(C\leq6)}$;

$X^-$ is a monovalent anion.

In some embodiments, the SORT lipid has a structural formula:

(S-II')

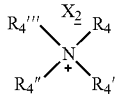

wherein:

$R_4$ and $R_{4'}$ are each independently alkyl$_{(C6-C24)}$, alkenyl$_{(C6-C24)}$, or a substituted version of either group;

$R_4''$ is alkyl$_{(C\leq24)}$, alkenyl$_{(C\leq24)}$, or a substituted version of either group;

$R_{4'''}$ is alkyl$_{(C1-C8)}$, alkenyl$_{(C2-C8)}$, or a substituted version of either group; and $X_2$ is a monovalent anion.

In some embodiments, the pharmaceutical composition is an aerosol composition. In some embodiments, the aerosol composition has a droplet size from 0.5 micron (μm) to 10 μm. In some embodiments, the aerosol composition has a median droplet size from 0.5 μm to 10 μm. In some embodiments, the aerosol composition has an average droplet size from 0.5 μm to 10 μm. In some embodiments, the pharmaceutical composition is formulated for aerosol administration. In some embodiments, the pharmaceutical composition is formulated for apical delivery. In some embodiments, the pharmaceutical composition is formulated for nebulization.

In another aspect, the present disclosure provides a method for enhancing an expression or activity of cystic fibrosis transmembrane conductance regulator (CFTR) protein in a cell, the method comprising: contacting said cell with a composition comprising a synthetic polynucleotide assembled with a lipid composition, wherein said synthetic polynucleotide encodes a CFTR protein; and wherein said lipid composition comprises: an ionizable cationic lipid; and a selective organ targeting (SORT) lipid separate from said ionizable cationic lipid, thereby yielding a therapeutically effective amount or activity of a functional variant of CFTR protein in said cell at least 24 hours after contacting, optionally wherein said therapeutically effective activity of said functional variant of CFTR protein is determined by measuring a change in a transepithelial ion transport characteristic of a plurality of cells comprising said cell as compared to that of a reference plurality of cells in absence of said contacting. In some embodiments, the contacting is repeated In some embodiments, the contacting is at least once a week. In some embodiments, the contacting is at least twice a week. In some embodiments, the method yields a therapeutically effective amount or activity of a functional variant of CFTR protein in said cell at least 24 hours after each contacting. In some embodiments, the contacting is a first contacting, and wherein the method comprises a second contacting, optionally, performed at least 1, 2, or 3 day(s) after said first contacting. In some embodiments, the method further comprises a third contacting, optionally wherein said third contacting is performed at least 1, 2, or 3 day(s) after said second contacting. In some embodiments, the method yields a therapeutically effective amount or activity of a functional variant of CFTR protein in said cell at least 24 hours after said second contacting. In some embodiments, the method yields a therapeutically effective amount or activity of a functional variant of CFTR protein in said cell at least 24 hours after said third contacting. In some embodiments, the contacting comprises administering to a subject said composition comprising said synthetic polynucleotide assembled with said lipid composition. In some embodiments, the subject is a mammal. In some embodiments, the subject is a human. In some embodiments, the administering comprises inhalation by nebulization. In some embodiments, the composition in each contacting is identical. In some embodiments, the cell is a lung airway cell. In some embodiments, the cell is a lung secretory cell or a lung basal cell. The lung basal cell may be a lung basal stem cell. In some embodiments, the cell is a bronchial epithelial cell In some embodiments, the cell is undifferentiated. In some embodiments, the cell is differentiated. In some embodiments, the cell is derived from said subject. In some embodiments, the contacting is in vivo. In some embodiments, the contacting is in vitro. In some embodiments, the contacting is ex vivo. In some embodiments, the functional variant of CFTR protein is a wild-type CFTR protein. In some embodiments, the functional variant of CFTR protein is a full-length CFTR protein. In some embodiments, the therapeutically effective activity of said functional variant of CFTR protein corresponds to a transepithelial current of at least about 5 micro-Ampere (μA), e.g., as determined in an in vitro assay. In some embodiments, the therapeutically effective activity of said functional variant of CFTR protein corresponds to a transepithelial current from about 5 micro-Ampere (μA) to about 30 μA. In some embodiments, the therapeutically effective activity of said functional variant of CFTR protein corresponds to a transepithelial current of at least about 2 micro-Ampere (μA) per squared centimeter per minute ($\mu A \cdot cm^{-2} \cdot min^{-1}$), e.g., as determined in an in vitro assay. In some embodiments, the therapeutically effective activity of said functional variant of CFTR protein corresponds to a transepithelial current from about 2 micro-Ampere (μA) per squared centimeter per minute ($\mu A \cdot cm^{-2} \cdot min^{-1}$) to about 20 $\mu A \cdot cm^{-2} \cdot min^{-1}$. In some embodiments, the method increases an amount or activity of said functional variant of CFTR protein in said cell (e.g., by at least about 1.1-fold) relative to a corresponding control (e.g., that of a corresponding cell absent said contacting). In some embodiments, the method enhances (e.g., chloride) ion transport in said cell (e.g., by at least about 1.1-fold) relative to a corresponding control (e.g., that of a corresponding cell absent said contacting). In some embodiments, the subject exhibits or is determined to exhibit a mutation in a cystic fibrosis transmembrane conductance regulator (CFTR) gene. In some embodiments, the mutation is a loss-of-function mutation. In some embodiments, the mutation is a nonsense or frameshift mutation. In some embodiments, the mutation is in one or more of exons 11-27 of CFTR gene. In some embodiments, the mutation is R553X, G542X or F508del, or a combination thereof. In some embodiments, the mutation is R1162X. In some embodiments, the mutation is R553X, G542X, F508del, or R1162X, or a combination thereof.

In another aspect the present disclosure provides a method for targeted pulmonary delivery, such as lung secretory cell or lung basal cell delivery (alternatively, lung secretory and/or basal cell delivery), comprising administering to a subject a composition comprising a synthetic polynucleotide assembled with a lipid composition, which synthetic polynucleotide encodes a cystic fibrosis transmembrane conductance regulator (CFTR) protein, wherein said lipid composition comprises: an ionizable cationic lipid; and a selective organ targeting (SORT) lipid separate from said ionizable cationic lipid, thereby yielding a therapeutically effective amount or activity of said synthetic polynucleotide in a lung secretory cell or lung basal cell of said subject, optionally wherein said therapeutically effective activity of said synthetic polynucleotide is determined by measuring a change in a transepithelial ion transport characteristic of a lung comprising said lung secretory cell or lung basal cell as compared to that of a reference lung in absence of said contacting. The lung basal cell may be a lung basal stem cell.

In another aspect, the present disclosure provides a method for targeted pulmonary delivery, such as lung secretory cell or lung basal cell delivery (alternatively, lung secretory and/or basal cell delivery), comprising administering to a subject a composition comprising a synthetic polynucleotide assembled with a lipid composition, which synthetic polynucleotide encodes a cystic fibrosis transmembrane conductance regulator (CFTR) protein, wherein said lipid composition comprises: an ionizable cationic lipid; and a selective organ targeting (SORT) lipid separate from said ionizable cationic lipid, thereby yielding a greater therapeutic amount or activity of said synthetic polynucleotide in a lung secretory cell or lung basal cell of said subject as compared to that in a lung non-secretory cell or lung non-basal cell of said subject. In some embodiments of the method for targeted pulmonary delivery, such as lung secretory cell or lung basal cell delivery (alternatively, lung secretory and/or basal cell delivery), at least about 50%, 55%, or 60% of (e.g., pulmonary) expression of said synthetic polynucleotide is detected or observed in lung secretory cells, lung basal cells, or a combination thereof, e.g., as determined by measuring an amount or activity of the corresponding polypeptide encoded by the synthetic polynucleotide. In some embodiments of the method for targeted pulmonary delivery, such as lung secretory cell or lung basal cell delivery (alternatively, lung secretory and/or basal cell delivery), no more than about 50%, 45%, or 40% of (e.g., pulmonary) expression of said synthetic polynucleotide is detected or observed in lung non-secretory cells, lung non-basal cells, or a combination thereof, e.g., as determined by measuring an amount or activity of the corresponding polypeptide encoded by the synthetic polynucleotide. In some embodiments of the method for targeted pulmonary delivery, such as lung secretory cell or lung basal cell delivery (alternatively, lung secretory and/or basal cell delivery), no more than about 50%, 45%, or 40% of (e.g., pulmonary) expression of said synthetic polynucleotide is in lung ciliated cells, e.g., as determined by measuring an amount or activity of the corresponding polypeptide encoded by the synthetic polynucleotide. In some embodiments, the method for lung secretory cell or lung basal cell delivery yields an amount or activity of said synthetic polynucleotide in lung secretory cell(s) or lung basal cell(s) that is at least 1.1-, 1.5-, or 2-fold greater than that in reference cell(s), which reference cell(s) are neither lung secretory cell(s) nor lung basal cell(s). The reference cell(s) may be lung ciliated cell(s). In some embodiments, the lung non-secretory cell or lung non-basal cell is a lung ciliated cell. In some embodiments, the lung non-secretory cell is a lung basal cell. The (e.g., lung) basal cell may be a (e.g., lung) basal stem cell.

In another aspect, the present disclosure provides a method for targeted pulmonary delivery, such as lung secretory cell or lung basal cell delivery (alternatively, lung secretory and/or basal cell delivery), comprising administering to a subject a composition comprising a synthetic polynucleotide assembled with a lipid composition, which synthetic polynucleotide encodes a cystic fibrosis transmembrane conductance regulator (CFTR) protein, wherein said lipid composition comprises: an ionizable cationic lipid; and a selective organ targeting (SORT) lipid separate from said ionizable cationic lipid, thereby yielding a therapeutic amount or activity of said synthetic polynucleotide in at least 5% of lung secretory cells or lung basal cells of said subject. In some embodiments, the administering comprises administering to a lung of said subject said composition comprising said synthetic polynucleotide assembled with said lipid composition. In some embodiments, the lung secretory cell is a club cell or a goblet cell. The (e.g., lung) basal cell may be a (e.g., lung) basal stem cell.

In another aspect, the present disclosure provides a method for treating a subject having or suspected of having a cystic fibrosis transmembrane conductance regulator (CFTR)-associated condition, the method comprising administering to said subject a pharmaceutical composition disclosed elsewhere herein. In some embodiments, the CFTR-associated condition is cystic fibrosis, hereditary emphysema, or chronic obstructive pulmonary disease (COPD). In some embodiments, the administering comprises local administration. In some embodiments, the administering comprises nebulization.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 11B shows that 5 day-old confluent FRT cells grown on TransWell® permeable support were transfected with ReCode-optimized mRNAs using Lipofectamine 2000. MTECC24 assay of the transepithelial conductance was performed 1 day after transfection with one dose of the CFTR mRNA described herein. FIG. 11C shows mRNA dose dependent transepithelial conductance (Gt) responses: bars were Gt area under the curve (AUC) per min between forskolin addition and Inhibitor-172 addition time points.

FIG. 16A shows representative traces of Forskolin-induced G542X/F508 hBE cells using CFTR mRNA formulation of the present application after single dosing.

FIG. 17A and FIG. 17B show that each dose was able to generate improved CFTR function over a negative control.

FIG. 19 shows an overview of a clinical trial in human subjects for treating cystic fibrosis with compositions disclosed herein.

DETAILED DESCRIPTION

Figure 1:
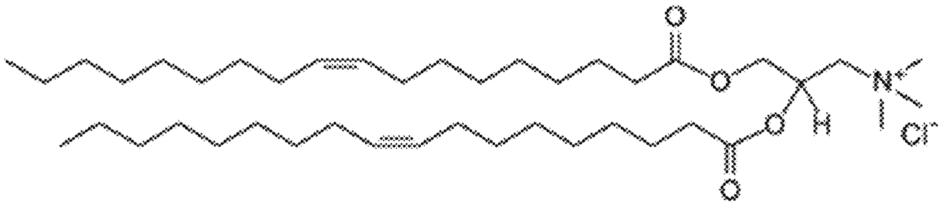
FIG. 1 shows the chemical structures of example lipids.
Figure 1:
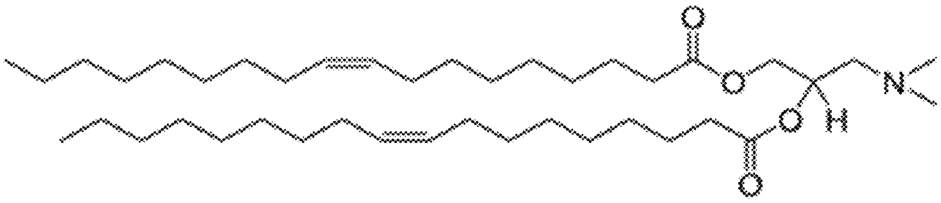
Figure 1:
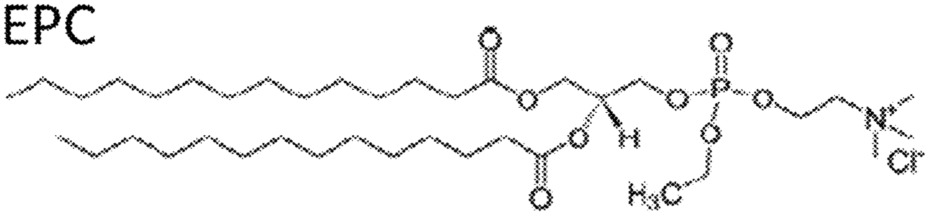

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "polynucleotide" or "nucleic acid" as used herein generally refers to a polymeric form of nucleotides of any length, either ribonucleotides or deoxyribonucleotides, that comprise purine and pyrimidine bases, purine and pyrimidine analogues, chemically or biochemically modified, natural or non-natural, or derivatized nucleotide bases. Polynucleotides include sequences of deoxyribonucleic acid (DNA), ribonucleic acid (RNA), or DNA copies of ribonucleic acid (cDNA), all of which can be recombinantly produced, artificially synthesized, or isolated and purified from natural sources. The polynucleotides and nucleic acids may exist as single-stranded or double-stranded. The backbone of the polynucleotide can comprise sugars and phosphate groups, as may typically be found in RNA or DNA, or analogues or substituted sugar or phosphate groups. A polynucleotide may comprise naturally occurring or non-naturally occurring nucleotides, such as methylated nucleotides and nucleotide analogues (or analogs).

The term "polyribonucleotide," as used herein, generally refers to polynucleotide polymers that comprise ribonucleic acids. The term also refers to polynucleotide polymers that comprise chemically modified ribonucleotides. A polyribonucleotide can be formed of D-ribose sugars, which can be found in nature.

The term "polypeptides," as used herein, generally refers to polymer chains comprised of amino acid residue monomers which are joined together through amide bonds (peptide bonds). A polypeptide can be a chain of at least three amino acids, a protein, a recombinant protein, an antigen, an epitope, an enzyme, a receptor, or a structure analogue or combinations thereof. As used herein, the abbreviations for the L-enantiomeric amino acids that form a polypeptide are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). X or Xaa can indicate any amino acid.

The term "engineered," as used herein, generally refers to polynucleotides, vectors, and nucleic acid constructs that have been genetically designed and manipulated to provide a polynucleotide intracellularly. An engineered polynucleotide can be partially or fully synthesized in vitro. An engineered polynucleotide can also be cloned. An engineered polyribonucleotide can contain one or more base or sugar analogues, such as ribonucleotides not naturally-found in messenger RNAs. An engineered polyribonucleotide can contain nucleotide analogues that exist in transfer RNAs (tRNAs), ribosomal RNAs (rRNAs), guide RNAs (gRNAs), small nuclear RNA (snRNA), small nucleolar RNA (snoRNA), SmY RNA, spliced leader RNA (SL RNA), CRISPR RNA, long untranslated RNA (lncRNA), microRNA (miRNA), or another suitable RNA.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate (e.g., non-human primate). In certain embodiments, the patient or subject is a human. Non-limiting examples of human subjects are adults, juveniles, infants and fetuses.

The term "assemble" or "assembled," as used herein, in context of delivery of a payload to target cell(s) generally refers to covalent or non-covalent interaction(s) or association(s), for example, such that a therapeutic or prophylactic agent be complexed with or encapsulated in a lipid composition.

As used herein, the term "lipid composition" generally refers to a composition comprising lipid compound(s), including but not limited to, a lipoplex, a liposome, a lipid particle. Example of lipid compositions include suspensions, emulsions, and vesicular compositions.

As used herein, the term "detectable" refers to an occurrence of, or a change in, a signal that is directly or indirectly detectable either by observation or by instrumentation. Typically, a detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

Unless otherwise indicated, all numbers expressing quantities, ranges, conditions, and so forth used in the specification and claims are to be understood as being modified in all instances by the term "about." Accordingly, unless indicated to the contrary, the numerical parameters set forth in the present specification and attached claims are approximations that can vary depending upon the desired properties sought to be obtained by the present application. Generally the term "about", as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed method.

As used herein, the term "ratio" generally refers to the relative amount of one or more molecules to another molecule(s), Non-limiting examples of the ratio(s) include molar ratio(s), weight ratio(s), or mass ratio(s).

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means =NH; "cyano" means —CN; "isocyanate" means —N=C=O; "azido" means —$N_3$; in a monovalent context "phosphate" means —OP(O)$(OH)_2$ or a deprotonated form thereof, in a divalent context "phosphate" means —OP(O)(OH)O— or a deprotonated form thereof, "mercapto" means —SH; and "thio" means =S; "sulfonyl" means —$S(O)_2$—; "hydroxysulfonyl" means —$S(O)_2$OH; "sulfonamide" means —$S(O)_2NH_2$; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "=̲=" represents a single bond or a double bond. Thus, for example, the formula

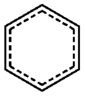

includes

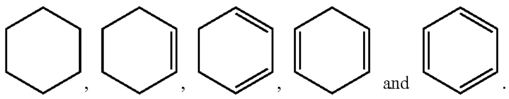

, , , and .

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "~", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "" means a single bond where the group attached to the thick end of the wedge is "out of the page." The symbol "" means a single bond where the group attached to the thick end of the wedge is "into the page". The symbol "~" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

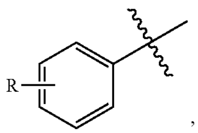

, then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

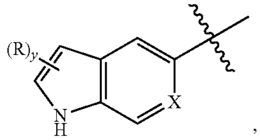

, then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —$CH_3$ (Me), —$CH_2CH_3$ (Et), —$CH_2CH_2CH_3$ (n-Pr or propyl), —$CH(CH_3)_2$ (i-Pr, $^i$Pr or isopropyl), —$CH_2CH_2CH_2CH_3$ (n-Bu), —$CH(CH_3)CH_2CH_3$ (sec-butyl), —$CH_2CH(CH_3)_2$ (isobutyl), —$C(CH_3)_3$ (tert-butyl, t-butyl, t-Bu or $^t$Bu), and —$CH_2C(CH_3)_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —$CH_2$— (methylene), —$CH_2CH_2$—, —$CH_2C(CH_3)_2CH_2$—, and —$CH_2CH_2CH_2$— are non-limiting examples of alkanediyl groups. An "alkane" refers to the class of compounds having the formula H-R, wherein R is alkyl as this term is defined above. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$. The following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —$CH(CH_2)_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

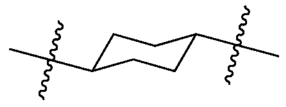 [SMILES: *C1CCC(*)CC1]

is a non-limiting example of cycloalkanediyl group. A "cycloalkane" refers to the class of compounds having the formula H-R, wherein R is cycloalkyl as this term is defined above. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH═$CH_2$ (vinyl), —CH═$CHCH_3$, —CH═$CHCH_2CH_3$, —$CH_2CH$═$CH_2$ (allyl), —$CH_2CH$═$CHCH_3$, and —CH═CHCH═$CH_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups $—CH{=}CH—$, $—CH{=}C(CH_3)CH_2—$, $—CH{=}CHCH_2—$, and $—CH_2CH{=}CHCH_2—$ are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H-R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$. The groups $—CH{=}CHF$, $—CH{=}CHCl$ and $—CH{=}CHBr$ are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups $—C{\equiv}CH$, $—C{\equiv}CCH_3$, and $—CH_2C{\equiv}CCH_3$ are non-limiting examples of alkynyl groups. An "alkyne" refers to the class of compounds having the formula H-R, wherein R is alkynyl. When any of these terms are used with the "substituted" modifier one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, $—C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

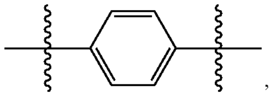,
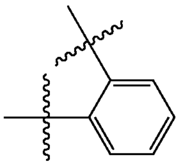,
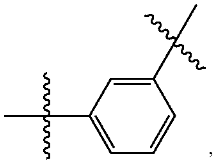,
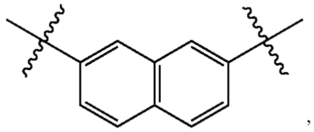,
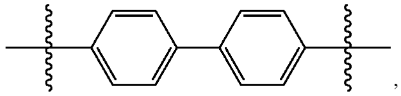,
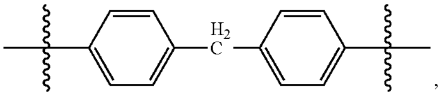, and
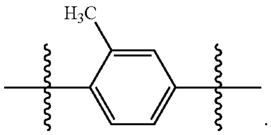.

An "arene" refers to the class of compounds having the formula H-R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Heteroaryl rings may contain 1, 2, 3, or 4 ring atoms selected from are nitrogen, oxygen, and sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

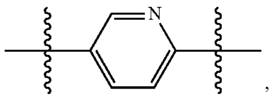
,
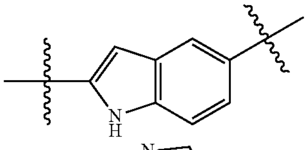
and
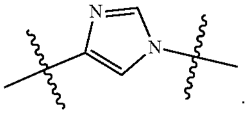
.

A "heteroarene" refers to the class of compounds having the formula H-R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —$S(O)_2OH$, or —$S(O)_2NH_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. Heterocycloalkyl rings may contain 1, 2, 3, or 4 ring atoms selected from nitrogen, oxygen, or sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

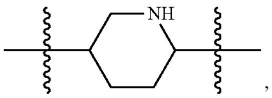
,
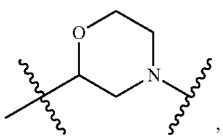
, and
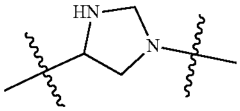
.

When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —$S(O)_2OH$, or —$S(O)_2NH_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)$CH_3$ (acetyl, Ac), —C(O)$CH_2CH_3$, —C(O)$CH_2CH_2CH_3$, —C(O)$CH(CH_3)_2$, —C(O)$CH(CH_2)_2$, —C(O)$C_6H_5$, —C(O)$C_6H_4CH_3$, —C(O)$CH_2C_6H_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$. The groups, $—C(O)CH_2CF_3$, $—CO_2H$ (carboxyl), $—CO_2CH_3$ (methylcarboxyl), $—CO_2CH_2CH_3$, $—C(O)NH_2$ (carbamoyl), and $—CON(CH_3)_2$, are non-limiting examples of substituted acyl groups.

The term “alkoxy” when used without the “substituted” modifier refers to the group —OR, in which R is an alkyl, as that term is defined above. Non-limiting examples include: $—OCH_3$ (methoxy), $—OCH_2CH_3$ (ethoxy), $—OCH_2CH_2CH_3$, $—OCH(CH_3)_2$ (isopropoxy), $—OC(CH_3)_3$ (tert-butoxy), $—OCH(CH_2)_2$, —O-cyclopentyl, and —O-cyclohexyl. The terms “cycloalkoxy”, “alkenyloxy”, “alkynyloxy”, “aryloxy”, “aralkoxy”, “heteroaryloxy”, “heterocycloalkoxy”, and “acyloxy”, when used without the “substituted” modifier, refers to groups, defined as —OR, in which R is cycloalkyl, alkenyl, alkynyl, aryl, aralkyl, heteroaryl, heterocycloalkyl, and acyl, respectively. The term “alkoxydiyl” refers to the divalent group —O-alkanediyl-, —O-alkanediyl-O—, or -alkanediyl-O-alkanediyl-. The term “alkylthio” and “acylthio” when used without the “substituted” modifier refers to the group —SR, in which R is an alkyl and acyl, respectively. The term “alcohol” corresponds to an alkane, as defined above, wherein at least one of the hydrogen atoms has been replaced with a hydroxy group. The term “ether” corresponds to an alkane, as defined above, wherein at least one of the hydrogen atoms has been replaced with an alkoxy group. When any of these terms is used with the “substituted” modifier one or more hydrogen atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$.

The term “alkylamino” when used without the “substituted” modifier refers to the group —NHR, in which R is an alkyl, as that term is defined above. Non-limiting examples include: $—NHCH_3$ and $—NHCH_2CH_3$. The term “dialkylamino” when used without the “substituted” modifier refers to the group —NRR', in which R and R' can be the same or different alkyl groups, or R and R' can be taken together to represent an alkanediyl. Non-limiting examples of dialkylamino groups include: $—N(CH_3)_2$ and $—N(CH_3)(CH_2CH_3)$. The terms “cycloalkylamino”, “alkenylamino”, “alkynylamino”, “arylamino”, “aralkylamino”, “heteroarylamino”, “heterocycloalkylamino”, “alkoxyamino”, and “alkylsulfonylamino” when used without the “substituted” modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is $—NHC_6H_5$. The term “alkylaminodiyl” refers to the divalent group —NH-alkanediyl-, —NH-alkanediyl-NH—, or -alkanediyl-NH-alkanediyl-. The term “amido” (acylamino), when used without the “substituted” modifier, refers to the group —NHR, in which R is acyl, as that term is defined above. A non-limiting example of an amido group is $—NHC(O)CH_3$. The term “alkylimino” when used without the “substituted” modifier refers to the divalent group =NR, in which R is an alkyl, as that term is defined above. When any of these terms is used with the “substituted” modifier one or more hydrogen atom attached to a carbon atom has been independently replaced by —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—C(O)NHCH_3$, $—C(O)N(CH_3)_2$, $—OC(O)CH_3$, $—NHC(O)CH_3$, $—S(O)_2OH$, or $—S(O)_2NH_2$. The groups $—NHC(O)OCH_3$ and $—NHC(O)NHCH_3$ are non-limiting examples of substituted amido groups.

The use of the word “a” or “an,” when used in conjunction with the term “comprising” in the claims and/or the specification may mean “one,” but it is also consistent with the meaning of “one or more,” “at least one,” and “one or more than one.”

As used in this application, the term “average molecular weight” refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

The terms “comprise,” “have” and “include” are open-ended linking verbs. Any forms or tenses of one or more of these verbs, such as “comprises,” “comprising,” “has,” “having,” “includes” and “including,” are also open-ended. For example, any method that “comprises,” “has” or “includes” one or more steps is not limited to possessing only those one or more steps and also covers other unlisted steps.

The term “effective,” as that term is used in the specification and/or claims, means adequate to accomplish a desired, expected, or intended result. “Effective amount,” “Therapeutically effective amount” or “pharmaceutically effective amount” when used in the context of treating a patient or subject with a compound means that amount of the compound which, when administered to a subject or patient for treating a disease, is sufficient to effect such treatment for the disease.

As used herein, the term “$IC_{50}$” refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An “isomer” of a first compound is a separate compound in which each molecule contains the same constituent atoms as the first compound, but where the configuration of those atoms in three dimensions differs.

As used herein, the term “patient” or “subject” refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein “pharmaceutically acceptable” refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $-[-CH_2CH_2-]_n-$, the repeat unit is $-CH_2CH_2-$. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc. Within the context of the dendrimer, the repeating unit may also be described as the branching unit, interior layers, or generations. Similarly, the terminating group may also be described as the surface group.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The term "molar percentage" or "molar %" as used herein in connection with lipid composition(s) generally refers to the molar proportion of that component lipid relative to compared to all lipids formulated or present in the lipid composition.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

The present disclosure provides, in some embodiments, compositions and methods for the treatment of conditions associated with cilia maintenance and function, with nucleic acids encoding a protein or protein fragment(s). Numerous eukaryotic cells carry appendages, which are often referred to as cilia or flagella, whose inner core comprises a cytoskeletal structure called the axoneme. The axoneme can function as the skeleton of cellular cytoskeletal structures, both giving support to the structure and, In some embodiments, causing it to bend. Usually, the internal structure of the axoneme is common to both cilia and flagella. Cilia are often found in the linings of the airway, the reproductive system, and other organs and tissues. Flagella are tail-like structures that, similarly to cilia, can propel cells forward, such as sperm cells.

Without properly functioning cilia in the airway, bacteria can remain in the respiratory tract and cause infection. In the respiratory tract, cilia move back and forth in a coordinated way to move mucus towards the throat. This movement of mucus helps to eliminate fluid, bacteria, and particles from the lungs. Many infants afflicted with cilia and flagella malfunction experience breathing problems at birth, which suggests that cilia play an important role in clearing fetal fluid from the lungs. Beginning in early childhood, subjects afflicted with cilia malfunction can develop frequent respiratory tract infections.

Cystic Fibrosis Transmembrane Conductance Regulator (CFTR)

Cystic fibrosis transmembrane conductance regulator (CFTR) is a membrane protein and chloride channel in vertebrates encoded by the CFTR gene. CFTR gene is on the long arm of chromosome 7, at position q31.2. Mutations of the CFTR gene affecting chloride ion channel function led to dysregulation of epithelial fluid transport in the lung, pancreas and other organs, resulting in cystic fibrosis (CF).

Cystic fibrosis (CF) affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease. Complications of cystic fibrosis include thickened mucus in the lungs with frequent respiratory infections, and pancreatic insufficiency giving rise to malnutrition and diabetes. These conditions lead to chronic disability and reduced life expectancy. In male patients, the progressive obstruction and destruction of the developing vas deferens (spermatic cord) and epididymis appear to result from abnormal intraluminal secretions, causing congenital absence of the vas deferens and male infertility.

So far, nearly 1000 cystic fibrosis-causing mutations have been described. Many mutations are infrequent. The distribution and frequency of mutations varies among different populations. Mutations consist of replacements, duplications, deletions, or shortenings in the CFTR gene. This may result in dysfunctional proteins which have less activity, are more quickly degraded or present in inadequate numbers. The most common mutation, DeltaF508 (ΔF508) results from a deletion (Δ) of three nucleotides which results in a loss of the amino acid phenylalanine (F) at the 508th position on the protein. As a result, the protein does not fold normally and is more quickly degraded.

Compositions

In some embodiments, the present disclosure provides a (e.g., pharmaceutical) composition comprising a (e.g., synthetic) polynucleotide encoding CFTR protein as described herein. In some embodiments of the composition, the polynucleotide is assembled with a lipid composition (such as described herein).

Polynucleotides

In some embodiments, the synthetic polynucleotide encodes a cystic fibrosis transmembrane conductance regulator (CFTR) protein. In some embodiments, the synthetic polynucleotide is a ribonucleic acid (RNA), e.g., a messenger ribonucleic acid (mRNA), encoding a CFTR protein. In some embodiments, the synthetic polynucleotide is a deoxyribonucleic acid (DNA) encoding a CFTR protein.

In some embodiments of various aspects, the nucleic acid sequence encodes a polypeptide that comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100, 300, 500, 700, 900, or 1,000 contiguous amino acid residues to SEQ ID NO: 5. In some embodiments of various aspects, the nucleic acid sequence encodes a polypeptide substantially identical to SEQ ID NO: 5. In some embodiments, said nucleic acid sequence encodes a polypeptide substantially identical over at least 1,000 contiguous amino acid residues to SEQ ID NO. 5. In some embodiments, said nucleic acid sequence encodes a polypeptide substantially identical to SEQ ID NO. 5. In some embodiments, said nucleic acid sequence encodes a polypeptide that comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100, 300, 500, 700, 900, or 1,000 contiguous amino acid residues to SEQ ID NO: 5. In some embodiments, said nucleic acid sequence encodes a polypeptide substantially identical to SEQ ID NO. 5.

Hydrolysis Hot Spots

Altered nucleotide usage schemes aiming to reduce the number of more reactive 5'-U(U/A)-3' dinucleotides within codons as well as across codons of modified mRNAs partially alleviate limitations imposed by the inherent chemical instability of RNA. At the same time, lowering the U-content in RNA transcripts renders them less immunogenic. The present disclosure relates to RNA transcripts comprising altered open reading frames (ORF). For example, the codon optimized or altered nucleotide usage may comprise a substantial reduction of 5'-U(U/A)-3' dinucleotides within protein coding regions leading to stabilized therapeutic mRNAs. The codon optimized polynucleotide may comprise a codon coding for a particular amino acid to be substituted or replaced of a with a synonymous codon. The codon optimized polynucleotide may encode a same or identical polypeptide as a corresponding wild type polynucleotide, with the polynucleotide comprising a different sequence of polynucleotide than the corresponding wild type. Multiple codons may encode for a same amino acid, however the qualities of a given codon are differ between even those that code for a same amino acid. Because multiple different codons may code for a same amino acid, a particular polynucleotide may encode for a same polypeptide and have advantageous features over another polynucleotide that codes for the same polypeptide. For example, a codon optimized polynucleotides may be translated faster, may comprise a higher stability (in vivo or in vitro), may result in increased expression yield or full length or functional polypeptides, or may result in an increase of soluble polypeptide and a decrease in polypeptide aggregates. Without being limited to a specific mechanism, the advantageous features of a codon optimized polynucleotides may be for example, a result of improved protein folding of the expressed product based on ribosomal interactions with the polynucleotides or may be result of decreased hydrolysis of reactive bonds in solution. For example, the codon optimization may alter or improve characteristics relating to ribosomal binding sites, Shine-Dalgarno sequences, or ribosomal or translational pausing. The advantageous features may be a result of decreased usage of "rare codons" which may have a lower concentration of cognate tRNAs, allowing for an improved translation reaction. The advantageous features may be a result of decreased usage of "rare codons" which may have a lower concentration of cognate tRNAs, allowing for an improved translation reaction. The advantageous features may be a result of decreasing degradation via enzymatic reaction. For example, hydrolysis of oligonucleotides suggests that the reactivity of the phosphodiester bond linking two ribonucleotides in single-stranded (ss)RNA depends on the nature of those nucleotides. At pH 8.5, dinucleotide cleavage susceptibility when embedded in ssRNA dodecamers may vary by an order of magnitude. Under near physiological conditions, hydrolysis of RNA usually involves an $S_N2$-type attack by the 2'-oxygen nucleophile on the adjacent phosphorus target center on the opposing side of the 5'-oxyanion leaving group, yielding two RNA fragments with 2',3'-cyclic phosphate and 5'-hydroxyl termini. More reactive scissile phosphodiester bonds may include 5'-UpA-3' ($R_1=U_1$, $R_2=A$) and 5'-CpA-3' ($R_1=C$, $R_2=A$) because the backbone at these steps can most easily adopt the "in-line" conformation that is required for $S_N2$-type nucleophilic attack by the 2'-OH on the adjacent phosphodiester linkage. In addition, interferon-regulated dsRNA-activated antiviral pathways produce 2'-5' oligoadenylates which bind to ankyrin repeats leading to activation of RNase L endoribonuclease. RNase L cleaves ssRNA efficiently at UA and UU dinucleotides. Lastly, U-rich sequences are potent activators of RNA sensors including Toll-like receptor 7 and 8 and RIG-I making global uridine content reduction a potentially attractive approach to reduce immunogenicity of therapeutic mRNAs.

In some cases, the number or percent of UU and UA sequences in the polynucleotide are below a certain threshold. For example, the percent of dinucleotide sequences comprising UU and UA may be less than 30%, 25%, 20%, 15%, 10%, 5% or less in the polynucleotides. In some case the number of UU or UA in a sequence may be less than 50, 45, 40, 35, 30, 25, 20, 15, 10, 9, 8, 7, 6, 5, 4, 3, 2, 1, or less in the polynucleotide.

In some embodiments of the synthetic polynucleotide, the polynucleotide comprises fewer than about 115 UU or TT dinucleotide. In some embodiments of the synthetic polynucleotide, the polynucleotide comprises fewer than about 110 UU or TT dinucleotide. In some embodiments of the synthetic polynucleotide, the polynucleotide comprises fewer than about 105 UU or TT dinucleotide. In some embodiments of the synthetic polynucleotide, the polynucleotide comprises fewer than about 100 UU or TT dinucleotide. In some embodiments of the synthetic polynucleotide, the polynucleotide comprises fewer than about 95 UU or TT dinucleotide. In some embodiments of the synthetic polynucleotide, the polynucleotide comprises fewer than about 90 UU or TT dinucleotide. In some embodiments of the synthetic polynucleotide, the polynucleotide comprises fewer than about 85 UU or TT dinucleotide. In some embodiments of the synthetic polynucleotide, the polynucleotide comprises fewer than about 80 UU or TT dinucleotide. In some embodiments of the synthetic polynucleotide, the polynucleotide comprises fewer than about 75 UU or TT dinucleotide. In some embodiments of the synthetic polynucleotide, the polynucleotide comprises fewer than about 70 UU or TT dinucleotide. In some embodiments of the synthetic polynucleotide, the polynucleotide comprises fewer than about 65 UU or TT dinucleotide. In some embodiments of the synthetic polynucleotide, the polynucleotide comprises fewer than about 60 UU or TT dinucleotide. In some embodiments of the synthetic polynucleotide, the polynucleotide comprises fewer than about 55 UU or TT dinucleotide. In some embodiments of the synthetic polynucleotide, the polynucleotide comprises fewer than about 50 UU or TT dinucleotide. In some embodiments of the synthetic polynucleotide, the polynucleotide comprises fewer than about 45 UU or TT dinucleotide. In some embodiments of the synthetic polynucleotide, the polynucleotide comprises fewer than about 40 UU or TT dinucleotide. In some embodiments of the synthetic polynucleotide, the polynucleotide comprises fewer than about 35 UU or TT dinucleotide. In some embodiments of the synthetic polynucleotide, the polynucleotide comprises fewer than about 45 UU or TT dinucleotide. In some embodiments of the synthetic polynucleotide, the polynucleotide comprises fewer than about 30 UU or TT dinucleotide.

In some embodiments of the synthetic polynucleotide, the polynucleotide comprises fewer than about 115 UA or TA dinucleotide. In some embodiments of the synthetic polynucleotide, the polynucleotide comprises fewer than about 110 UA or TA dinucleotide. In some embodiments of the synthetic polynucleotide, the polynucleotide comprises fewer than about 105 UA or TA dinucleotide. In some embodiments of the synthetic polynucleotide, the polynucleotide comprises fewer than about 100 UA or TA dinucleotide. In some embodiments of the synthetic polynucleotide, the polynucleotide comprises fewer than about 95 UA or TA dinucleotide. In some embodiments of the synthetic polynucleotide, the polynucleotide comprises fewer than about 90 UA or TA dinucleotide. In some embodiments of the synthetic polynucleotide, the polynucleotide comprises fewer than about 85 UA or TA dinucleotide. In some embodiments of the synthetic polynucleotide, the polynucleotide comprises fewer than about 80 UA or TA dinucleotide. In some embodiments of the synthetic polynucleotide, the polynucleotide comprises fewer than about 75 UA or TA dinucleotide. In some embodiments of the synthetic polynucleotide, the polynucleotide comprises fewer than about 70 UA or TA dinucleotide. In some embodiments of the synthetic polynucleotide, the polynucleotide comprises fewer than about 65 UA or TA dinucleotide. In some embodiments of the synthetic polynucleotide, the polynucleotide comprises fewer than about 60 UA or TA dinucleotide. In some embodiments of the synthetic polynucleotide, the polynucleotide comprises fewer than about 55 UA or TA dinucleotide. In some embodiments of the synthetic polynucleotide, the polynucleotide comprises fewer than about 50 UA or TA dinucleotide. In some embodiments of the synthetic polynucleotide, the polynucleotide comprises fewer than about 45 UA or TA dinucleotide. In some embodiments of the synthetic polynucleotide, the polynucleotide comprises fewer than about 40 UA or TA dinucleotide. In some embodiments of the synthetic polynucleotide, the polynucleotide comprises fewer than about 35 UA or TA dinucleotide. In some embodiments of the synthetic polynucleotide, the polynucleotide comprises fewer than about 30 UA or TA dinucleotide.

In some embodiments of the synthetic polynucleotide, the polynucleotide comprises fewer than about 200 of UU and UA. In some embodiments of the synthetic polynucleotide, the polynucleotide comprises fewer than about 195 of UU and UA. In some embodiments of the synthetic polynucleotide, the polynucleotide comprises fewer than about 190 of UU and UA. In some embodiments of the synthetic polynucleotide, the polynucleotide comprises fewer than about 185 of UU and UA. In some embodiments of the synthetic polynucleotide, the polynucleotide comprises fewer than about 180 of UU and UA. In some embodiments of the synthetic polynucleotide, the polynucleotide comprises fewer than about 175 of UU and UA. In some embodiments of the synthetic polynucleotide, the polynucleotide comprises fewer than about 170 of UU and UA. In some embodiments of the synthetic polynucleotide, the polynucleotide comprises fewer than about 165 of UU and UA. In some embodiments of the synthetic polynucleotide, the polynucleotide comprises fewer than about 160 of UU and UA. In some embodiments of the synthetic polynucleotide, the polynucleotide comprises fewer than about 155 of UU and UA. In some embodiments of the synthetic polynucleotide, the polynucleotide comprises fewer than about 150 of UU and UA. In some embodiments of the synthetic polynucleotide, the polynucleotide comprises fewer than about 145 of UU and UA. In some embodiments of the synthetic polynucleotide, the polynucleotide comprises fewer than about 140 of UU and UA. In some embodiments of the synthetic polynucleotide, the polynucleotide comprises fewer than about 135 of UU and UA. In some embodiments of the synthetic polynucleotide, the polynucleotide comprises fewer than about 130 of UU and UA. In some embodiments of the synthetic polynucleotide, the polynucleotide comprises fewer than about 125 of UU and UA. In some embodiments of the synthetic polynucleotide, the polynucleotide comprises fewer than about 120 of UU and UA. In some embodiments of the synthetic polynucleotide, the polynucleotide comprises fewer than about 115 of UU and UA. In some embodiments of the synthetic polynucleotide, the polynucleotide comprises fewer than about 110 of UU and UA. In some embodiments of the synthetic polynucleotide, the polynucleotide comprises fewer than about 105 of UU and UA. In some embodiments of the synthetic polynucleotide, the polynucleotide comprises fewer than about 100 of UU and UA. In some embodiments of the synthetic polynucleotide, the polynucleotide comprises fewer than about 95 of UU and UA. In some embodiments of the synthetic polynucleotide, the polynucleotide comprises fewer than about 90 of UU and UA. In some embodiments of the synthetic polynucleotide, the polynucleotide comprises fewer than about 85 of UU and UA. In some embodiments of the synthetic polynucleotide, the polynucleotide comprises fewer than about 80 of UU and UA.

In some embodiments of the synthetic polynucleotide, the polynucleotide comprises fewer than about 200 of TT and TA. In some embodiments of the synthetic polynucleotide, the polynucleotide comprises fewer than about 195 of TT and TA. In some embodiments of the synthetic polynucleotide, the polynucleotide comprises fewer than about 190 of TT and TA. In some embodiments of the synthetic polynucleotide, the polynucleotide comprises fewer than about 185 of TT and TA. In some embodiments of the synthetic polynucleotide, the polynucleotide comprises fewer than about 180 of TT and TA. In some embodiments of the synthetic polynucleotide, the polynucleotide comprises fewer than about 175 of TT and TA. In some embodiments of the synthetic polynucleotide, the polynucleotide comprises fewer than about 170 of TT and TA. In some embodiments of the synthetic polynucleotide, the polynucleotide comprises fewer than about 165 of TT and TA. In some embodiments of the synthetic polynucleotide, the polynucleotide comprises fewer than about 160 of TT and TA. In some embodiments of the synthetic polynucleotide, the polynucleotide comprises fewer than about 155 of TT and TA. In some embodiments of the synthetic polynucleotide, the polynucleotide comprises fewer than about 150 of TT and TA. In some embodiments of the synthetic polynucleotide, the polynucleotide comprises fewer than about 145 of TT and TA. In some embodiments of the synthetic polynucleotide, the polynucleotide comprises fewer than about 140 of TT and TA. In some embodiments of the synthetic polynucleotide, the polynucleotide comprises fewer than about 135 of TT and TA. In some embodiments of the synthetic polynucleotide, the polynucleotide comprises fewer than about 130 of TT and TA. In some embodiments of the synthetic polynucleotide, the polynucleotide comprises fewer than about 125 of TT and TA. In some embodiments of the synthetic polynucleotide, the polynucleotide comprises fewer than about 120 of TT and TA. In some embodiments of the synthetic polynucleotide, the polynucleotide comprises fewer than about 115 of TT and TA. In some embodiments of the synthetic polynucleotide, the polynucleotide comprises fewer than about 110 of TT and TA. In some embodiments of the synthetic polynucleotide, the polynucleotide comprises fewer than about 105 of TT and TA. In some embodiments of the synthetic polynucleotide, the polynucleotide comprises fewer than about 100 of TT and TA. In some embodiments of the synthetic polynucleotide, the polynucleotide comprises fewer than about 95 of TT and TA. In some embodiments of the synthetic polynucleotide, the polynucleotide comprises fewer than about 90 of TT and TA. In some embodiments of the synthetic polynucleotide, the polynucleotide comprises fewer than about 85 of TT and TA. In some embodiments of the synthetic polynucleotide, the polynucleotide comprises fewer than about 80 of TT and TA.

Codon Usage

In some embodiments of the synthetic polynucleotide, the polynucleotide comprises at least two synonymous codons encoding arginine. In some embodiments of the synthetic polynucleotide, the polynucleotide comprises at least two synonymous codons encoding arginine, and said codon is selected from the group consisting of AGG, AGA, CGG, CGA, CGT and CGC. In some embodiments of the synthetic polynucleotide, the polynucleotide comprises at least three synonymous codons encoding arginine, and said codon is selected from the group consisting of AGG, AGA, CGG, CGA, CGT and CGC. In some embodiments of the synthetic polynucleotide, the polynucleotide comprises at least four synonymous codons encoding arginine, and said codon is selected from the group consisting of AGG, AGA, CGG, CGA, CGT and CGC. In some embodiments of the synthetic polynucleotide, the polynucleotide comprises at least five synonymous codons encoding arginine, and said codon is selected from the group consisting of AGG, AGA, CGG, CGA, CGT and CGC. In some embodiments of the synthetic polynucleotide, the polynucleotide comprises four synonymous codons encoding arginine, and said codon is selected from the group consisting of AGG, AGA, CGG and CGC.

In some embodiments of the synthetic polynucleotide, no more than about 70% of all arginine encoding codons of said nucleic acid sequence is AGG codon. In some embodiments of the synthetic polynucleotide, no more than about 65% of all arginine encoding codons of said nucleic acid sequence is AGG codon. In some embodiments of the synthetic polynucleotide, no more than about 60% of all arginine encoding codons of said nucleic acid sequence is AGG codon. In some embodiments of the synthetic polynucleotide, no more than about 55% of all arginine encoding codons of said nucleic acid sequence is AGG codon. In some embodiments of the synthetic polynucleotide, no more than about 50% of all arginine encoding codons of said nucleic acid sequence is AGG codon. In some embodiments of the synthetic polynucleotide, no more than about 55% of all arginine encoding codons of said nucleic acid sequence is AGG codon. In some embodiments of the synthetic polynucleotide, no more than about 50% of all arginine encoding codons of said nucleic acid sequence is AGG codon.

In some embodiments of the synthetic polynucleotide, no more than about 70% of all arginine encoding codons of said nucleic acid sequence is AGA codon. In some embodiments of the synthetic polynucleotide, no more than about 65% of all arginine encoding codons of said nucleic acid sequence is AGA codon. In some embodiments of the synthetic polynucleotide, no more than about 60% of all arginine encoding codons of said nucleic acid sequence is AGA codon. In some embodiments of the synthetic polynucleotide, no more than about 55% of all arginine encoding codons of said nucleic acid sequence is AGA codon. In some embodiments of the synthetic polynucleotide, no more than about 50% of all arginine encoding codons of said nucleic acid sequence is AGA codon. In some embodiments of the synthetic polynucleotide, no more than about 55% of all arginine encoding codons of said nucleic acid sequence is AGA codon. In some embodiments of the synthetic polynucleotide, no more than about 50% of all arginine encoding codons of said nucleic acid sequence is AGA codon.

In some embodiments of the synthetic polynucleotide, no more than about 70% of all arginine encoding codons of said nucleic acid sequence is CGG codon. In some embodiments of the synthetic polynucleotide, no more than about 65% of all arginine encoding codons of said nucleic acid sequence is CGG codon. In some embodiments of the synthetic polynucleotide, no more than about 60% of all arginine encoding codons of said nucleic acid sequence is CGG codon. In some embodiments of the synthetic polynucleotide, no more than about 55% of all arginine encoding codons of said nucleic acid sequence is CGG codon. In some embodiments of the synthetic polynucleotide, no more than about 50% of all arginine encoding codons of said nucleic acid sequence is CGG codon. In some embodiments of the synthetic polynucleotide, no more than about 55% of all arginine encoding codons of said nucleic acid sequence is CGG codon. In some embodiments of the synthetic polynucleotide, no more than about 50% of all arginine encoding codons of said nucleic acid sequence is CGG codon.

In some embodiments of the synthetic polynucleotide, no more than about 70% of all arginine encoding codons of said nucleic acid sequence is CGA codon. In some embodiments of the synthetic polynucleotide, no more than about 65% of all arginine encoding codons of said nucleic acid sequence is CGA codon. In some embodiments of the synthetic polynucleotide, no more than about 60% of all arginine encoding codons of said nucleic acid sequence is CGA codon. In some embodiments of the synthetic polynucleotide, no more than about 55% of all arginine encoding codons of said nucleic acid sequence is CGA codon. In some embodiments of the synthetic polynucleotide, no more than about 50% of all arginine encoding codons of said nucleic acid sequence is CGA codon. In some embodiments of the synthetic polynucleotide, no more than about 55% of all arginine encoding codons of said nucleic acid sequence is CGA codon. In some embodiments of the synthetic polynucleotide, no more than about 50% of all arginine encoding codons of said nucleic acid sequence is CGA codon.

In some embodiments of the synthetic polynucleotide, no more than about 70% of all arginine encoding codons of said nucleic acid sequence is CGT (or CGU) codon. In some embodiments of the synthetic polynucleotide, no more than about 65% of all arginine encoding codons of said nucleic acid sequence is CGT (or CGU) codon. In some embodiments of the synthetic polynucleotide, no more than about 60% of all arginine encoding codons of said nucleic acid sequence is CGT (or CGU) codon. In some embodiments of the synthetic polynucleotide, no more than about 55% of all arginine encoding codons of said nucleic acid sequence is CGT (or CGU) codon. In some embodiments of the synthetic polynucleotide, no more than about 50% of all arginine encoding codons of said nucleic acid sequence is CGT (or CGU) codon. In some embodiments of the synthetic polynucleotide, no more than about 55% of all arginine encoding codons of said nucleic acid sequence is CGT (or CGU) codon. In some embodiments of the synthetic polynucleotide, no more than about 50% of all arginine encoding codons of said nucleic acid sequence is CGT (or CGU) codon.

In some embodiments of the synthetic polynucleotide, no more than about 70% of all arginine encoding codons of said nucleic acid sequence is CGC codon. In some embodiments of the synthetic polynucleotide, no more than about 65% of all arginine encoding codons of said nucleic acid sequence is CGC codon. In some embodiments of the synthetic polynucleotide, no more than about 60% of all arginine encoding codons of said nucleic acid sequence is CGC codon. In some embodiments of the synthetic polynucleotide, no more than about 55% of all arginine encoding codons of said nucleic acid sequence is CGC codon. In some embodiments of the synthetic polynucleotide, no more than about 50% of all arginine encoding codons of said nucleic acid sequence is CGC codon. In some embodiments of the synthetic polynucleotide, no more than about 55% of all arginine encoding codons of said nucleic acid sequence is CGC codon. In some embodiments of the synthetic polynucleotide, no more than about 50% of all arginine encoding codons of said nucleic acid sequence is CGC codon.

In some embodiments of the synthetic polynucleotide as described herein, the polynucleotides may comprise an open reading frame (ORF) sequence. The ORF sequence may be characterized by a codon usage profile comprising: (1) a total number of codons, (2) a species number of codons (e.g. a total number of different codon types), (3) a number of each (unique) codon, and (4) a (usage) frequency of each codon among all synonymous codons (if present). The codon usage profile may be altered or compared to a corresponding wild type sequence. For example, the frequency or number of particular codons may be reduced or increased compared to a wild type sequence. The change in codon frequency of the polynucleotide may provide benefits over the wild type sequence. For example, the altered codon frequency may result in a less immunogenic polynucleotide. The polynucleotide with an altered codon frequency may result in a polynucleotide that is more quickly expressed or results in a greater amount of expression product. The polynucleotide with an altered codon frequency may have increase stability, such as increased half-life in sera, or may be less susceptible to hydrolysis or other reactions that may result in the degradation of the polynucleotide.

In some embodiments, the polynucleotide comprises an altered nucleotide usage as compared to a corresponding wild type sequence. The altered nucleotide usage may also be referred to as a "codon optimized" sequence or be generated by way of "codon optimization".

In some cases, a codon coding for a particular amino acid in the polypeptide may be substituted or replaced with a synonymous codon. For example, a codon coding for leucine may be substituted for another codon coding for leucine. In this way, the resulting translation products may be identical with the polynucleotide differing in sequence. At least one type of an isoleucine-encoding codons in said corresponding wild-type sequence may be substituted with a synonymous codon type in said nucleic acid sequence. At least one type of a valine-encoding codons in said corresponding wild-type sequence may be substituted with a synonymous codon type in said nucleic acid sequence. At least one type of an alanine-encoding codons in said corresponding wild-type sequence may be substituted with a synonymous codon type in said nucleic acid sequence. At least one type of a glycine-encoding codons in said corresponding wild-type sequence may be substituted with a synonymous codon type in said nucleic acid sequence. At least one type of a proline-encoding codons in said corresponding wild-type sequence may be substituted with a synonymous codon type in said nucleic acid sequence. At least one type of a threonine-encoding codons in said corresponding wild-type sequence may be substituted with a synonymous codon type in said nucleic acid sequence. At least one type of a leucine-encoding codons in said corresponding wild-type sequence may be substituted with a synonymous codon type in said nucleic acid sequence. At least one type of an arginine-encoding codons in said corresponding wild-type sequence is substituted with a synonymous codon type in said nucleic acid sequence. At least one type of a serine-encoding codons in said corresponding wild-type sequence may be substituted with a synonymous codon type in said nucleic acid sequence.

In some embodiments, a particular codon of a particular amino acid comprises a percentage or amount of the total number of codons for that particular amino acid the polynucleotide. This may be referred to a "codon frequency". For example, at least 50% of the total codons encoding a particular amino acid in the polynucleotide may be encoded by a first codon sequence. For example, at least 55% of the total codons encoding a particular amino acid in the polynucleotide may be encoded by a first codon sequence. At least 5%, 10%, 20%, 30%, 40%, 50%, 55%, 60%, 65%, 70%, 75%, 80%, 85%, 90%, 95%, or more of the total codons encoding a particular amino in the polynucleotide may be encoded by a first codon sequence. In some cases, no more than 5%, 10%, 20%, 30%, 40%, 50%, 55%, 60%, 65%, 70%, 75%, 80%, 85%, 90%, 95%, or less of the total codons encoding a particular amino in the polynucleotide are encoded by a first codon sequence. At least about 90% phenylalanine-encoding codons of said synthetic polynucleotide may be TTC (as opposed to TTT). At least about 60% cysteine-encoding codons of said synthetic polynucleotide may be TGC (as opposed to TGT). At least about 70% aspartic acid-encoding codons of said synthetic polynucleotide may be GAC (as opposed to GAT). At least about 50% glutamic acid-encoding codons of said synthetic polynucleotide may be GAG (as opposed to GAA). At least about 60% histidine-encoding codons of said synthetic polynucleotide may be CAC (as opposed to CAT). At least about 60% lysine-encoding codons of said synthetic polynucleotide may be AAG (as opposed to AAA). At least about 60% asparagine-encoding codons of said synthetic polynucleotide may be AAC (as opposed to AAT). At least about 70% glutamine-encoding codons of said synthetic polynucleotide may be CAG (as opposed to CAA). At least about 80% tyrosine-encoding codons of said synthetic polynucleotide may be TAC (as opposed to TAT). At least about 90% isoleucine-encoding codons of said synthetic polynucleotide may be ATC.

In some embodiments, a particular amino acid the polynucleotide may be encoded by a number of different codon sequences. For example, a particular amino acid in the polynucleotide may be encoded by no more than 2 different codon sequences. In some cases, the polynucleotide comprises no more than 2 types of isoleucine-encoding codons.

In some embodiments, a particular amino acid in the polynucleotide may be encoded by no more than 3 different codon sequences. The polynucleotide may comprise no more than 3 types of alanine (Ala)-encoding codons. The polynucleotide may comprise no more than 3 types of glycine (Gly)-encoding codons. The polynucleotide may comprise no more than 3 types of proline (Pro)-encoding codons. The polynucleotide may comprise no more than 3 types of threonine (Thr)-encoding codons.

In some embodiments, a particular amino acid in the polynucleotide may be encoded by no more than 4 different codon sequences. The polynucleotide may comprise no more than 4 types of arginine (Arg)-encoding codons. The polynucleotide may comprise no more than 4 types of serine (Ser)-encoding codons. In some embodiments, a particular amino acid in the polynucleotide may be encoded by no more than 5 different codon sequences. The polynucleotide may comprise no more than 5 types of arginine (Arg)-encoding codons. The polynucleotide may comprise no more than 5 types of serine (Ser)-encoding codons. In some embodiments, a particular amino acid in the polynucleotide may be encoded by no more than 6 different codon sequences. In some embodiments, a particular amino acid in the polynucleotide may be encoded by 1 or more different codon sequences. In some embodiments, a particular amino acid in the polynucleotide may be encoded by 2 or more different codon sequences. In some embodiments, a particular amino acid in the polynucleotide may be encoded by 3 or more different codon sequences. In some embodiments, a particular amino acid in the polynucleotide may be encoded by 4 or more different codon sequences. In some embodiments, a particular amino acid in the polynucleotide may be encoded by 5 or more different codon sequences. In some embodiments, a particular amino acid in the polynucleotide may be encoded by 6 or more different codon sequences.

In some cases, a frequency of a first codon sequence of a is higher, lower or the same as a frequency of a second codon sequence encoding for a particular amino acid in the polynucleotide. For example, a frequency of a first codon is higher than a frequency of second codon for a particular amino acid in the polynucleotide. The frequency of GCC codon may be higher than a frequency of GCT codon. The frequency of GCT codon may be lower than a frequency of GCA codon. The frequency of GCT codon may be higher than a frequency of GCA codon.

In some embodiments, the codon usage for alanine-encoding codons in the polynucleotide may have a particular parameter. For example, a frequency of GCG codon may be no more than about 10% or 5%. A frequency of GCA codon may be no more than about 20%. A frequency of GCT codon may be at least about 1%, 5%, 10%, 15%, 20%, or 25%. A frequency of GCT codon may be no more than about 30%, 25%, 20%, 15%, 10%, or 5%. A frequency of GCC codon may be at least about 60%, 70%, 80%, or 90%. A frequency of GCC codon is no more than about 95%, 90%, 85%, 80%, or 75%. The frequency of GCC codon may be higher than a frequency of GCT codon. The frequency of GCT codon may be lower than a frequency of GCA codon. The frequency of GCT codon may be higher than a frequency of GCA codon.

In some embodiments, the codon usage for glycine-encoding codons the polynucleotide may have a particular parameter. For example, a frequency of GGC codon may be lower than a frequency of GGA codon. For example, a frequency of GGC codon may be higher than a frequency of GGA codon. A frequency of GGG codon may be no more than about 10% or 5%. A frequency of GGG codon may be least about 1%. A frequency of GGA codon may be no more than about 30% or 20%. A frequency of GGA codon may be at least about 10% or 20%. A frequency of GGT codon may be more than about 10% or 5%. A frequency of GGC codon may be no more than about 90%, 80%, or 70%. A frequency of GGC codon may be at least about 60%, 70%, or 80%.

In some embodiments, the codon usage for proline-encoding codons the polynucleotide may have a particular parameter. For example, a frequency of CCC codon may be lower than a frequency of CCT codon. A frequency of CCC codon may be higher than a frequency of CCT codon. A frequency of CCC codon may be lower than a frequency of CCA codon. A frequency of CCC codon may be higher than a frequency of CCA codon. A frequency of CCT codon may be lower than a frequency of CCA codon. A frequency of CCT codon may be higher than a frequency of CCA codon. A frequency of CCG codon may be no more than about 10% or 5%, frequency of CCA codon may be no more than about 30%, 20%, or 10%. A frequency of CCA codon may be at least about 5%, 10%, 15%, 20%, or 25%. A frequency of CCT codon may be no more than about 60%, 50%, 40%, or 30%. A frequency of CCT codon may be at least about 20%, 30%, 40%, or 50%. A frequency of CCC codon may be no more than about 60%, 50%, or 40%. A frequency of CCC codon may be at least about 30%, 40%, 50%, 60%, or 70%.

In some embodiments, the codon usage for threonine-encoding codons the polynucleotide may have a particular parameter. For example, a frequency of ACA codon is higher than a frequency of ACT codon. A frequency of ACC codon may be higher than a frequency of ACT codon. A frequency of ACC codon may be lower than a frequency of ACA codon. A frequency of ACC codon may be higher than a frequency of ACA codon. A frequency of ACG codon may be no more than about 10% or 5%. A frequency of ACA codon may be no more than about 60%, 50%, 40%, or 30%. A frequency of ACA codon may be at least about 10%, 20%, 30%, 40%, or 50%. A frequency of ACT codon may be no more than about 10% or 5%. A frequency of ACC codon may be no more than about 90%, 80%, 70%, 60%, or 50%. A frequency of ACC codon is at least about 40%, 50%, 60%, 70%, or 80%.

In some embodiments, the codon usage for arginine-encoding codons the polynucleotide may have a particular parameter. For example, a frequency of AGA codon may be lower than a frequency of AGG codon. A frequency of AGA codon may be higher than a frequency of AGG codon. A frequency of AGA codon may be lower than a frequency of CGG codon. A frequency of AGA codon may be higher than a frequency of CGG codon. A frequency of CGG codon may be higher than a frequency of CGA codon. A frequency of CGG codon is higher than a frequency of CGC codon. A frequency of AGG codon may be no more than about 10%. A frequency of AGG codon may be less than about 10%. A frequency of AGA codon may be no more than about 70%, 60%, or 50%. A frequency of AGA codon may be at least about 40%, 50%, 60%, or 70%. A frequency of CGG codon may be no more than about 50%, 40%, or 30%. A frequency of CGG codon may be at least about 20%, 30%, or 40%. A frequency of CGA codon may be at least about 1%. A frequency of CGA codon may be no more than about 10% or 5%. A frequency of CGT codon may be no more about 10% or 5%. A frequency of CGC codon may be no more than about 20%, 10%, or 5%. A frequency of CGC codon may be at least about 1%, 2%, 3%, 4%, or 5%.

In some embodiments, the codon usage for serine-encoding codons the polynucleotide may have a particular parameter. For example, a frequency of AGC codon may be higher than a frequency of TCT codon. A frequency of TCT codon may be higher than a frequency of TCG codon. A frequency of TCT codon may be higher than a frequency of TCA codon. A frequency of TCT codon may be higher than a frequency of TCC codon. A frequency of AGT codon may be no more than about 10%. A frequency of AGT codon may be at least about 1%. A frequency of AGC codon may be no more about 95%, 90%, 85%, or 80%. A frequency of AGC codon may be at least about 70%, 80%, or 90%. A frequency of TCG codon may be no more than about 10% or 5%. A frequency of TCA codon may be no more than about 10% or 5%. A frequency of TCT codon may be no more than about 30%, 20%, or 10%. A frequency of TCT codon may be at least about 10%, or 20%. A frequency of TCC codon may be no more than about 10% or 5%.

Example CFTR-Encoding Polynucleotides

In some embodiments of the synthetic polynucleotide, the synthetic polynucleotide is mRNA encoding a cystic fibrosis transmembrane conductance regulator (CFTR) protein. In some embodiments, said synthetic polynucleotide comprises a nucleic acid sequence (e.g., an open reading frame (ORF) sequence) having at least about 70% sequence identity over at least 100 bases of a sequence selected from SEQ ID NOs: 1-4 and 23. In some embodiments, said synthetic polynucleotide comprises a nucleic acid sequence (e.g., an open reading frame (ORF) sequence) having at least about 75% sequence identity over at least 100 bases of a sequence selected from SEQ ID NOs: 1-4 and 23. In some embodiments, said synthetic polynucleotide comprises a nucleic acid sequence (e.g., an open reading frame (ORF) sequence) having at least about 80%, at least about 80%, at least about 80%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity over at least 100 bases of a sequence selected from SEQ ID NOs: 1-4 and 23.

In some embodiments of the synthetic polynucleotide, the synthetic polynucleotide is mRNA encoding a cystic fibrosis transmembrane conductance regulator (CFTR) protein. In some embodiments, said synthetic polynucleotide comprises a nucleic acid sequence (e.g., an open reading frame (ORF) sequence) having at least about 70% sequence identity over at least 200 bases of a sequence selected from SEQ ID NOs: 1-4 and 23. In some embodiments, said synthetic polynucleotide comprises a nucleic acid sequence (e.g., an open reading frame (ORF) sequence) having at least about 75% sequence identity over at least 200 bases of a sequence selected from SEQ ID NOs: 1-4 and 23. In some embodiments, said synthetic polynucleotide comprises a nucleic acid sequence (e.g., an open reading frame (ORF) sequence) having at least about 80%, at least about 80%, at least about 80%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity over at least 200 bases of a sequence selected from SEQ ID NOs: 1-4 and 23.

In some embodiments of the synthetic polynucleotide, the synthetic polynucleotide is mRNA encoding a cystic fibrosis transmembrane conductance regulator (CFTR) protein. In some embodiments, said synthetic polynucleotide comprises a nucleic acid sequence (e.g., an open reading frame (ORF) sequence) having at least about 70% sequence identity with a sequence selected from SEQ ID NOs: 1-4 and 23. In some embodiments, said synthetic polynucleotide comprises a nucleic acid sequence (e.g., an open reading frame (ORF) sequence) having at least about 75% sequence identity with a sequence selected from SEQ ID NOs: 1-4 and 23. In some embodiments, said synthetic polynucleotide comprises a nucleic acid sequence (e.g., an open reading frame (ORF) sequence) having at least about 80%, at least about 80%, at least about 80%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity with a sequence selected from SEQ ID NOs: 1-4 and 23. In some embodiments, said synthetic polynucleotide comprises a nucleic acid sequence (e.g., an open reading frame (ORF) sequence) selected from SEQ ID NOs: 1-4 and 23.

In some embodiments of the synthetic polynucleotide, the synthetic polynucleotide is mRNA encoding a cystic fibrosis transmembrane conductance regulator (CFTR) protein. In some embodiments, said synthetic polynucleotide comprises a nucleic acid sequence (e.g., an open reading frame (ORF) sequence) having at least about 70% sequence identity over at least 100 bases of a sequence selected from SEQ ID NOs: 1-4 and 23. In some embodiments, said synthetic polynucleotide comprises a nucleic acid sequence (e.g., an open reading frame (ORF) sequence) having at least about 75% sequence identity over at least 100 bases of a sequence selected from SEQ ID NOs: 1-4 and 23. In some embodiments, said synthetic polynucleotide comprises a nucleic acid sequence (e.g., an open reading frame (ORF) sequence) having at least about 80%, at least about 80%, at least about 80%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity over at least 100 bases of a sequence selected from SEQ ID NOs: 1-4 and 23.

In some embodiments of the synthetic polynucleotide, the synthetic polynucleotide is mRNA encoding a cystic fibrosis transmembrane conductance regulator (CFTR) protein. In some embodiments, said synthetic polynucleotide comprises a nucleic acid sequence (e.g., an open reading frame (ORF) sequence) having at least about 70% sequence identity over at least 200 bases of a sequence selected from SEQ ID NOs: 1-4 and 23. In some embodiments, said synthetic polynucleotide comprises a nucleic acid sequence (e.g., an open reading frame (ORF) sequence) having at least about 75% sequence identity over at least 200 bases of a sequence selected from SEQ ID NOs: 1-4 and 23. In some embodiments, said synthetic polynucleotide comprises a nucleic acid sequence (e.g., an open reading frame (ORF) sequence) having at least about 80%, at least about 80%, at least about 80%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity over at least 200 bases of a sequence selected from SEQ ID NOs: 1-4 and 23.

In some embodiments of the synthetic polynucleotide, the synthetic polynucleotide is mRNA encoding a cystic fibrosis transmembrane conductance regulator (CFTR) protein. In some embodiments, said synthetic polynucleotide comprises a nucleic acid sequence (e.g., an open reading frame (ORF) sequence) having at least about 70% sequence identity with a sequence selected from SEQ ID NOs: 1-4 and 23. In some embodiments, said synthetic polynucleotide comprises a nucleic acid sequence (e.g., an open reading frame (ORF) sequence) having at least about 75% sequence identity with a sequence selected from SEQ ID NOs: 1-4 and 23. In some embodiments, said synthetic polynucleotide comprises a nucleic acid sequence (e.g., an open reading frame (ORF) sequence) having at least about 80%, at least about 80%, at least about 80%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity with a sequence selected from SEQ ID NOs: 1-4 and 23. In some embodiments, said synthetic polynucleotide comprises a nucleic acid sequence (e.g., an open reading frame (ORF) sequence) selected from SEQ ID NOs: 1-4 and 23.

TABLE 1

Example CFTR ORF sequences

| Construct | DNA sequence (from 5' to 3') | SEQ ID NO. |
|---|---|---|
| CFTR-001 | ATGCAGAGAAGCCCTCTGGAAAAGGCCAGCGTGGTGAGCAAGCTGTTCTTCAGCTGGAC<br>CCGGCCCATCCTGCGGAAGGGCTACAGACAGAGACTGGAACTGAGCGACATCTATCAGA<br>TCCCCAGCGTGGACAGCGCCGACAACCTGTCTGAGAAGCTGGAAAGAGAGTGGGACAGA<br>GAGCTGGCCAGCAAGAAGAACCCCAAGCTGATCAACGCCCTGCGGCGGTGCTTCTTCTG<br>GCGGTTCATGTTCTACGGCATCTTCCTGTACCTGGGCGAAGTGACCAAAGCCGTGCAGC<br>CTCTGCTGCTGGGCAGAATCATCGCCAGCTACGACCCCGACAACAAAGAGGAACGGAGC<br>ATCGCCATCTACCTCGGCATCGGCCTGTGCCTGCTGTTCATCGTCAGAACCCTGCTGCT<br>GCACCCCGCCATCTTCGGACTGCACCACATCGGCATGCAGATGCGGATCGCCATGTTCA | 1 |

TABLE 1-continued

| Example CFTR ORF sequences | | |
|---|---|---|
| Construct | DNA sequence (from 5' to 3') | SEQ ID NO. |
| | GCCTGATCTACAAGAAAACCCTGAAGCTGAGCAGCAGAGTGCTGGACAAGATCAGCATC<br>GGACAGCTGGTGAGCCTGCTGAGCAACAACCTGAACAAGTTCGACGAAGGCCTGGCTCT<br>GGCCCACTTCGTGTGGATCGCTCCTCTGCAAGTGGCCCTGCTGATGGGCCTGATCTGGG<br>AACTGCTGCAGGCCAGCGCCTTCTGCGGACTGGGATTCCTGATCGTGCTGGCCCTGTTC<br>CAGGCCGGACTGGGGAGAATGATGATGAAGTACCGGGACCAGAGAGCCGGCAAGATCAG<br>CGAGAGACTGGTCATCACCAGCGAGATGATCGAGAACATCCAGAGCGTGAAGGCCTACT<br>GCTGGGAAGAGGCCATGGAAAAGATGATCGAGAATCTGCGGCAGACCGAGCTGAAGCTG<br>ACAAGAAAGGCCGCCTACGTGCGCTACTTCAACAGCAGCGCCTTCTTCTTCAGCGGCTT<br>CTTCGTGGTGTTCCTGAGCGTGCTGCCCTACGCTCTGATCAAGGGCATCATCCTGAGAA<br>AGATCTTCACCACCATCAGCTTCTGCATCGTGCTGCGGATGGCCGTGACCAGACAGTTC<br>CCCTGGGCTGTGCAGACCTGGTACGACAGCCTGGGCGCCATCAACAAGATCCAGGACTT<br>CCTGCAGAAGCAAGAGTACAAGACCCTCGAGTACAACCTGACCACCACCGAGGTGGTCA<br>TGGAAAACGTGACCGCCTTCTGGGAGGAAGGCTTCGGCGAGCTGTTCGAGAAGGCCAAG<br>CAGAACAACAACAACCGCAAGACCAGCAACGGCGACGACAGCCTGTTCTTCAGCAACTT<br>CAGCCTGCTGGGGACCCCTGTGCTGAAGGACATCAACTTCAAGATCGAGCGGGGACAGC<br>TGCTGGCCGTGGCTGGAAGCACAGGCGCCGGAAAAACCAGCCTGCTCATGGTCATCATG<br>GGCGAGCTGGAACCCAGCGAGGGCAAGATCAAGCACAGCGGCAGGATCAGCTTCTGCAG<br>CCAGTTCAGCTGGATCATGCCCGGCACCATCAAAGAGAACATCATCTTCGGCGTGAGCT<br>ACGACGAGTACAGATACCGCAGCGTGATCAAGGCCTGCCAGCTGGAAGAGGACATCAGC<br>AAGTTCGCCGAGAAGGACAACATCGTGCTCGGCGAAGGCGGCATCACACTGTCTGGCGG<br>ACAGAGGGCCAGAATCTCTCTGGCCAGAGCCGTGTACAAGGACGCCGATCTGTACCTGC<br>TGGACAGCCCCTTCGGCTACCTGGATGTGCTGACCGAGAAAGAGATCTTCGAGAGCTGC<br>GTGTGCAAGCTGATGGCCAACAAGACCCGGATCCTGGTCACCAGCAAGATGGAACACCT<br>GAAGAAGGCCGACAAGATCCTGATCCTGCACGAGGGCAGCAGCTACTTCTACGGCACCT<br>TCAGCGAGCTGCAGAACCTGCAGCCTGACTTCAGCAGCAAACTGATGGGCTGCGACAGC<br>TTCGACCAGTTCAGCGCCGAGCGGAGAAACAGCATCCTGACAGAGACACTGCACCGGTT<br>CAGCCTGGAAGGCGACGCTCCTGTGAGCTGGACCGAGACAAAGAAGCAGAGCTTCAAGC<br>AGACCGGCGAGTTCGGCGAGAAGCGGAAGAACAGCATCCTGAACCCCATCAACAGCATC<br>CGGAAGTTCAGCATCGTCCAGAAAACCCCTCTGCAGATGAACGGCATCGAAGAGGACAG<br>CGACGAGCCCCTGGAAAGACGGCTGTCTCTGGTGCCTGACAGCGAACAGGGCGAAGCCA<br>TCCTGCCTCGGATCAGCGTGATCAGCACAGGCCCCACACTGCAGGCTCGGAGAAGGCAG<br>AGTGTGCTGAACCTGATGACCCACAGCGTGAACCAGGGACAGAACATCCACAGAAAGAC<br>CACCGCCAGCACACGGAAAGTGAGCCTGGCCCCTCAGGCCAACCTGACTGAGCTGGACA<br>TCTACAGCAGACGGCTGAGCCAAGAGACAGGCCTGGAAATCAGCGAGGAAATCAACGAA<br>GAGGACCTGAAAGAGTGCTTCTTCGACGACATGGAAAGCATCCCCGCCGTGACAACCTG<br>GAACACCTACCTGCGGTACATCACCGTGCACAAGAGCCTGATCTTCGTGCTGATCTGGT<br>GTCTCGTGATCTTCCTGGCCGAAGTGGCCGCCTCTCTGGTGGTGCTGTGGCTGCTCGGA<br>AACACCCCACTGCAGGACAAGGGCAACAGCACCCACAGCCGGAACAACAGCTACGCCGT<br>GATCATCACCAGCACCAGCAGCTACTACGTGTTCTACATCTACGTGGGCGTCGCCGACA<br>CTCTGCTCGCCATGGGCTTCTTCAGAGGACTGCCCCTGGTGCACACCCTGATCACCGTG<br>AGCAAGATCCTGCACCACAAGATGCTGCACAGCGTCCTGCAGGCCCCCATGAGCACACT<br>GAACACCCTGAAAGCCGGCGGAATCCTGAACAGATTCAGCAAGGACATCGCCATCCTGG<br>ACGACCTGCTGCCTCTGACCATCTTCGACTTCATCCAGCTGCTGCTGATCGTGATCGGC<br>GCCATCGCTGTGGTGGCTGTGCTGCAGCCCTACATCTTCGTGGCCACCGTGCCTGTGAT<br>CGTGGCCTTCATCATGCTGCGGGCCTACTTCCTGCAGACCTCTCAGCAGCTGAAGCAGC<br>TCGAGTCTGAGGGCAGAAGCCCCATCTTCACCCACCTCGTGACCAGCCTGAAAGGCCTG<br>TGGACCCTGAGAGCCTTCGGCAGACAGCCCTACTTCGAGACACTGTTCCACAAGGCCCT<br>GAACCTGCACACCGCCAACTGGTTCCTGTATCTGAGCACCCTGCGGTGGTTCCAGATGA<br>GGATCGAGATGATCTTCGTCATCTTCTTCATCGCCGTGACCTTCATCAGCATCCTCACC<br>ACTGGCGAAGGCGAGGGCAGAGTGGGAATCATCCTGACCCTGGCCATGAACATCATGAG<br>CACACTCCAGTGGGCCGTGAACAGCAGCATCGATGTGGACAGCCTGATGCGGAGCGTGA<br>GCCGGGTGTTCAAGTTCATCGACATGCCCACAGAGGGCAAGCCCACCAAGAGCACCAAG<br>CCCTACAAGAACGGCCAGCTGAGCAAAGTCATGATCATCGAGAACAGCCACGTCAAGAA<br>GGACGACATCTGGCCCAGCGGAGGCCAGATGACCGTGAAGGATCTGACCGCCAAGTACA<br>CCGAAGGCGGAAACGCCATCCTGGAAAACATCAGCTTCAGCATCAGCCCTGGCCAGCGC<br>GTGGGACTCCTGGGAAGAACCGGAAGCGGCAAGAGCACTCTGCTGAGCGCCTTCCTGAG<br>ACTGCTGAACACCGAGGGCGAGATCCAGATCGATGGGGTGAGCTGGGACAGCATCACCC<br>TGCAACAATGGCGGAAGGCCTTCGGCGTGATCCCTCAGAAGGTGTTCATCTTCAGCGGC<br>ACGTTCCGGAAGAATCTGGACCCCTACGAGCAGTGGAGCGACCAAGAGATCTGGAAGGT<br>GGCCGATGAAGTGGGACTGAGAAGCGTGATCGAGCAGTTCCCCGGCAAGCTGGACTTCG<br>TGCTGGTGGATGGCGGCTGTGTGCTGTCTCACGGACACAAGCAGCTGATGTGCCTGGCC<br>AGAAGCGTGCTGAGCAAGGCCAAGATCCTGCTGCTCGACGAGCCCAGCGCTCACCTGGA<br>TCCTGTGACCTACCAGATCATCCGGCGGACACTGAAGCAGGCCTTCGCCGACTGCACCG<br>TGATCCTGTGCGAGCACAGAATCGAGGCCATGCTGGAATGCCAGCAGTTCCTGGTGATC<br>GAAGAGAACAAAGTGCGGCAGTACGACAGCATCCAGAAGCTGCTGAACGAGCGGAGCCT<br>GTTCAGACAGGCCATCTCTCCCAGCGACAGAGTGAAGCTGTTCCCTCACCGGAACAGCA<br>GCAAGTGCAAGAGCAAGCCTCAGATCGCCGCTCTGAAAGAAGAAACCGAGGAAGAGGTG<br>CAGGACACACGGCTGGCGGCCGTTTACCCATACGATGTTCCTGACTATGCGTGA | |
| CFTR-003 | ATGCAGAGAAGCCCTCTGGAAAAGGCCAGCGTGGTGAGCAAGCTGTTCTTCAGCTGGAC<br>CCGGCCCATCCTGCGGAAGGGCTACAGACAGAGACTGGAACTGAGCGACATCTATCAGA<br>TCCCCAGCGTGGACAGCGCCGACAACCTGTCTGAGAAGCTGGAAAGAGAGTGGGACAGA<br>GAGCTGGCCAGCAAGAAGAACCCCAAGCTGATCAACGCCCTGCGGCGGTGCTTCTTCTG<br>GCGGTTCATGTTCTACGGCATCTTCCTGTACCTGGGCGAAGTGACCAAAGCCGTGCAGC<br>CTCTGCTGCTGGGCAGAATCATCGCCAGCTACGACCCCGACAACAAAGAGGAACGGAGC | 2 |

TABLE 1-continued

Example CFTR ORF sequences

| Construct | DNA sequence (from 5' to 3') | SEQ ID NO. |
|---|---|---|
| | ATCGCCATCTACCTCGGCATCGGCCTGTGCCTGCTGTTCATCGTCAGAACCCTGCTGCT<br>GCACCCCGCCATCTTCGGACTGCACCACATCGGCATGCAGATGCGGATCGCCATGTTCA<br>GCCTGATCTACAAGAAAACCCTGAAGCTGAGCAGCAGAGTGCTGGACAAGATCAGCATC<br>GGACAGCTGGTGAGCCTGCTGAGCAACAACCTGAACAAGTTCGACGAAGGCCTGGCTCT<br>GGCCCACTTCGTGTGGATCGCTCCTCTGCAAGTGGCCCTGCTGATGGGCCTGATCTGGG<br>AACTGCTGCAGGCCAGCGCCTTCTGCGGACTGGGATTCCTGATCGTGCTGGCCCTGTTC<br>CAGGCCGGACTGGGGAGAATGATGATGAAGTACCGGGACCAGAGAGCCGGCAAGATCAG<br>CGAGAGACTGGTCATCACCAGCGAGATGATCGAGAACATCCAGAGCGTGAAGGCCTACT<br>GCTGGGAAGAGGCCATGGAAAAGATGATCGAGAATCTGCGGCAGACCGAGCTGAAGCTG<br>ACAAGAAAGGCCGCCTACGTGCGCTACTTCAACAGCAGCGCCTTCTTCTTCAGCGGCTT<br>CTTCGTGGTGTTCCTGAGCGTGCTGCCCTACGCTCTGATCAAGGGCATCATCCTGAGAA<br>AGATCTTCACCACCATCAGCTTCTGCATCGTGCTGCGGATGGCCGTGACCAGACAGTTC<br>CCCTGGGCTGTGCAGACCTGGTACGACAGCCTGGGCGCCATCAACAAGATCCAGGACTT<br>CCTGCAGAAGCAAGAGTACAAGACCCTCGAGTACAACCTGACCACCACCGAGGTGGTCA<br>TGGAAAACGTGACCGCCTTCTGGGAGGAAGGCTTCGGCGAGCTGTTCGAGAAGGCCAAG<br>CAGAACAACAACAACCGCAAGACCAGCAACGGCGACGACAGCCTGTTCTTCAGCAACTT<br>CAGCCTGCTGGGGACCCCTGTGCTGAAGGACATCAACTTCAAGATCGAGCGGGGACAGC<br>TGCTGGCCGTGGCTGGAAGCACAGGCGCCGGAAAAACCAGCCTGCTCATG**GTC**ATCATG<br>GGCGAGCTGGAACCCAGCGAGGGCAAGATCAAGCACAGCGGCAGGATCAGCTTCTGCAG<br>CCAGTTCAGCTGGATCATGCCCGGCACCATCAAAGAGAACATCATCTTCGGCGTGAGCT<br>ACGACGAGTACAGATACCGCAGCGTGATCAAGGCCTGCCAGCTGGAAGAGGACATCAGC<br>AAGTTCGCCGAGAAGGACAACATCGTGCTCGGCGAAGGCGGCATCACACTGTCTGGCGG<br>ACAGAGGGCCAGAATCTCTCTGGCCAGAGCCGTGTACAAGGACGCCGATCTGTACCTGC<br>TGGACAGCCCCTTCGGCTACCTGGATGTGCTGACCGAGAAAGAGATCTTCGAGAGCTGC<br>GTGTGCAAGCTGATGGCCAACAAGACCCGGATCCTGGTCACCAGCAAGATGGAACACCT<br>GAAGAAGGCCGACAAGATCCTGATCCTGCACGAGGGCAGCAGCTACTTCTACGGCACCT<br>TCAGCGAGCTGCAGAACCTGCAGCCTGACTTCAGCAGCAAACTGATGGGCTGCGACAGC<br>TTCGACCAGTTCAGCGCCGAGCGGAGAAACAGCATCCTGACAGAGACACTGCACCGGTT<br>CAGCCTGGAAGGCGACGCTCCTGTGAGCTGGACCGAGACAAAGAAGCAGAGCTTCAAGC<br>AGACCGGCGAGTTCGGCGAGAAGCGGAAGAACAGCATCCTGAACCCCATCAACAGCATC<br>CGGAAGTTCAGCATCGTCCAGAAAACCCCTCTGCAGATGAACGGCATCGAAGAGGACAG<br>CGACGAGCCCCTGGAAAGACGGCTGTCTCTGGTGCCTGACAGCGAACAGGGCGAAGCCA<br>TCCTGCCTCGGATCAGCGTGATCAGCACAGGCCCCACACTGCAGGCTCGGAGAAGGCAG<br>AGTGTGCTGAACCTGATGACCCACAGCGTGAACCAGGGACAGAACATCCACAGAAAGAC<br>CACCGCCAGCACACGGAAAGTGAGCCTGGCCCCTCAGGCCAACCTGACTGAGCTGGACA<br>TCTACAGCAGACGGCTGAGCCAAGAGACAGGCCTGGAAATCAGCGAGGAAATCAACGAA<br>GAGGACCTGAAAGAGTGCTTCTTCGACGACATGGAAAGCATCCCCGCCGTGACAACCTG<br>GAACACCTACCTGCGGTACATCACCGTGCACAAGAGCCTGATCTTCGTGCTGATCTGGT<br>GTCTCGTGATCTTCCTGGCCGAAGTGGCCGCCTCTCTGGTGGTGCTGTGGCTGCTCGGA<br>AACACCCCACTGCAGGACAAGGGCAACAGCACCCACAGCCGGAACAACAGCTACGCCGT<br>GATCATCACCAGCACCAGCAGCTACTACGTGTTCTACATCTACGTGGGCGTCGCCGACA<br>CTCTGCTCGCCATGGGCTTCTTCAGAGGACTGCCCCTGGTGCACACCCTGATCACCGTG<br>AGCAAGATCCTGCACCACAAGATGCTGCACAGCGTCCTGCAGGCCCCCATGAGCACACT<br>GAACACCCTGAAAGCCGGCGGAATCCTGAACAGATTCAGCAAGGACATCGCCATCCTGG<br>ACGACCTGCTGCCTCTGACCATCTTCGACTTCATCCAGCTGCTGCTGATCGTGATCGGC<br>GCCATCGCTGTGGTGGCTGTGCTGCAGCCCTACATCTTCGTGGCCACCGTGCCTGTGAT<br>CGTGGCCTTCATCATGCTGCGGGCCTACTTCCTGCAGACCTCTCAGCAGCTGAAGCAGC<br>TCGAGTCTGAGGGCAGAAGCCCCATCTTCACCCACCTCGTGACCAGCCTGAAAGGCCTG<br>TGGACCCTGAGAGCCTTCGGCAGACAGCCCTACTTCGAGACACTGTTCCACAAGGCCCT<br>GAACCTGCACACCGCCAACTGGTTCCTGTATCTGAGCACCCTGCGGTGGTTCCAGATGA<br>GGATCGAGATGATCTTCGTCATCTTCTTCATCGCCGTGACCTTCATCAGCATCCTCACC<br>ACTGGCGAAGGCGAGGGCAGAGTGGGAATCATCCTGACCCTGGCCATGAACATCATGAG<br>CACACTCCAGTGGGCCGTGAACAGCAGCATCGATGTGGACAGCCTGATGCGGAGCGTGA<br>GCCGGGTGTTCAAGTTCATCGACATGCCCACAGAGGGCAAGCCCACCAAGAGCACCAAG<br>CCCTACAAGAACGGCCAGCTGAGCAAAGTCATGATCATCGAGAACAGCCACGTCAAGAA<br>GGACGACATCTGGCCCAGCGGAGGCCAGATGACCGTGAAGGATCTGACCGCCAAGTACA<br>CCGAAGGCGGAAACGCCATCCTGGAAAACATCAGCTTCAGCATCAGCCCTGGCCAGCGC<br>GTGGGACTCCTGGGAAGAACCGGAAGCGGCAAGAGCACTCTGCTGAGCGCCTTCCTGAG<br>ACTGCTGAACACCGAGGGCGAGATCCAGATCGATGGGGTGAGCTGGGACAGCATCACCC<br>TGCAACAATGGCGGAAGGCCTTCGGCGTGATCCCTCAGAAGGTGTTCATCTTCAGCGGC<br>ACGTTCCGGAAGAATCTGGACCCCTACGAGCAGTGGAGCGACCAAGAGATCTGGAAGGT<br>GGCCGATGAAGTGGGACTGAGAAGCGTGATCGAGCAGTTCCCCGGCAAGCTGGACTTCG<br>TGCTGGTGGATGGCGGCTGTGTGCTGTCTCACGGACACAAGCAGCTGATGTGCCTGGCC<br>AGAAGCGTGCTGAGCAAGGCCAAGATCCTGCTGCTCGACGAGCCCAGCGCTCACCTGGA<br>TCCTGTGACCTACCAGATCATCCGGCGGACACTGAAGCAGGCCTTCGCCGACTGCACCG<br>TGATCCTGTGCGAGCACAGAATCGAGGCCATGCTGGAATGCCAGCAGTTCCTGGTGATC<br>GAAGAGAACAAAGTGCGGCAGTACGACAGCATCCAGAAGCTGCTGAACGAGCGGAGCCT<br>GTTCAGACAGGCCATCTCTCCCAGCGACAGAGTGAAGCTGTTCCCTCACCGGAACAGCA<br>GCAAGTGCAAGAGCAAGCCTCAGATCGCCGCTCTGAAAGAAGAAACCGAGGAAGAGGTG<br>CAGGACACACGGCTGTGA | |
| CFTR-004 | ATGCAGAGAAGCCCCCTGGAAAAGGCCAGCGTGGTGAGCAAGCTGTTCTTCAGCTGGAC<br>CCGGCCCATCCTGCGGAAGGGCTACAGACAGAGACTGGAACTGAGCGACATCTACCAGA<br>TCCCCAGCGTGGACAGCGCCGACAACCTGAGCGAGAAGCTGGAAAGAGAGTGGGACAGA<br>GAGCTGGCCAGCAAGAAGAACCCCAAGCTGATCAACGCCCTGCGGCGGTGCTTCTTCTG | 3 |

TABLE 1-continued

Example CFTR ORF sequences

| Construct | DNA sequence (from 5' to 3') | SEQ ID NO. |
|---|---|---|
| | GCGGTTCATGTTCTACGGCATCTTCCTGTACCTGGGCGAAGTGACCAAAGCCGTGCAGC | |
| | CCCTGCTGCTGGGCAGAATCATCGCCAGCTACGACCCCGACAACAAAGAGGAACGGAGC | |
| | ATCGCCATCTACCTCGGCATCGGCCTGTGCCTGCTGTTCATCGTCAGAACCCTGCTGCT | |
| | GCACCCCGCCATCTTCGGACTGCACCACATCGGCATGCAGATGCGGATCGCCATGTTCA | |
| | GCCTGATCTACAAGAAAACCCTGAAGCTGAGCAGCAGAGTGCTGGACAAGATCAGCATC | |
| | GGACAGCTGGTGAGCCTGCTGAGCAACAACCTGAACAAGTTCGACGAAGGCCTGGCCCT | |
| | GGCCCACTTCGTGTGGATCGCCCCCCTGCAAGTGGCCCTGCTGATGGGCCTGATCTGGG | |
| | AACTGCTGCAGGCCAGCGCCTTCTGCGGACTGGGATTCCTGATCGTGCTGGCCCTGTTC | |
| | CAGGCCGGACTGGGGAGAATGATGATGAAGTACCGGGACCAGAGAGCCGGCAAGATCAG | |
| | CGAGAGACTGGTCATCACCAGCGAGATGATCGAGAACATCCAGAGCGTGAAGGCCTACT | |
| | GCTGGGAAGAGGCCATGGAAAAGATGATCGAGAACCTGCGGCAGACCGAGCTGAAGCTG | |
| | ACAAGAAAGGCCGCCTACGTGCGCTACTTCAACAGCAGCGCCTTCTTCTTCAGCGGCTT | |
| | CTTCGTGGTGTTCCTGAGCGTGCTGCCCTACGCCCTGATCAAGGGCATCATCCTGAGAA | |
| | AGATCTTCACCACCATCAGCTTCTGCATCGTGCTGCGGATGGCCGTGACCAGACAGTTC | |
| | CCCTGGGCCGTGCAGACCTGGTACGACAGCCTGGGCGCCATCAACAAGATCCAGGACTT | |
| | CCTGCAGAAGCAAGAGTACAAGACCCTCGAGTACAACCTGACCACCACCGAGGTGGTCA | |
| | TGGAAAACGTGACCGCCTTCTGGGAGGAAGGCTTCGGCGAGCTGTTCGAGAAGGCCAAG | |
| | CAGAACAACAACAACCGCAAGACCAGCAACGGCGACGACAGCCTGTTCTTCAGCAACTT | |
| | CAGCCTGCTGGGGACCCCCGTGCTGAAGGACATCAACTTCAAGATCGAGCGGGGACAGC | |
| | TGCTGGCCGTGGCCGGAAGCACAGGCGCCGGAAAAACCAGCCTGCTCATGGTCATCATG | |
| | GGCGAGCTGGAACCCAGCGAGGGCAAGATCAAGCACAGCGGCAGGATCAGCTTCTGCAG | |
| | CCAGTTCAGCTGGATCATGCCCGGCACCATCAAAGAGAACATCATCTTCGGCGTGAGCT | |
| | ACGACGAGTACAGATACCGCAGCGTGATCAAGGCCTGCCAGCTGGAAGAGGACATCAGC | |
| | AAGTTCGCCGAGAAGGACAACATCGTGCTCGGCGAAGGCGGCATCACACTGAGCGGCGG | |
| | ACAGAGGGCCAGAATCAGCCTGGCCAGAGCCGTGTACAAGGACGCCGACCTGTACCTGC | |
| | TGGACAGCCCCTTCGGCTACCTGGACGTGCTGACCGAGAAAGAGATCTTCGAGAGCTGC | |
| | GTGTGCAAGCTGATGGCCAACAAGACCCGGATCCTGGTCACCAGCAAGATGGAACACCT | |
| | GAAGAAGGCCGACAAGATCCTGATCCTGCACGAGGGCAGCAGCTACTTCTACGGCACCT | |
| | TCAGCGAGCTGCAGAACCTGCAGCCCGACTTCAGCAGCAAACTGATGGGCTGCGACAGC | |
| | TTCGACCAGTTCAGCGCCGAGCGGAGAAACAGCATCCTGACAGAGACACTGCACCGGTT | |
| | CAGCCTGGAAGGCGACGCCCCCGTGAGCTGGACCGAGACAAAGAAGCAGAGCTTCAAGC | |
| | AGACCGGCGAGTTCGGCGAGAAGCGGAAGAACAGCATCCTGAACCCCATCAACAGCATC | |
| | CGGAAGTTCAGCATCGTCCAGAAAACCCCCCTGCAGATGAACGGCATCGAAGAGGACAG | |
| | CGACGAGCCCCTGGAAAGACGGCTGAGCCTGGTGCCCGACAGCGAACAGGGCGAAGCCA | |
| | TCCTGCCCCGGATCAGCGTGATCAGCACAGGCCCCACACTGCAGGCCCGGAGAAGGCAG | |
| | AGCGTGCTGAACCTGATGACCCACAGCGTGAACCAGGGACAGAACATCCACAGAAAGAC | |
| | CACCGCCAGCACACGGAAAGTGAGCCTGGCCCCCCAGGCCAACCTGACTGAGCTGGACA | |
| | TCTACAGCAGACGGCTGAGCCAAGAGACAGGCCTGGAAATCAGCGAGGAAATCAACGAA | |
| | GAGGACCTGAAAGAGTGCTTCTTCGACGACATGGAAAGCATCCCCGCCGTGACAACCTG | |
| | GAACACCTACCTGCGGTACATCACCGTGCACAAGAGCCTGATCTTCGTGCTGATCTGGT | |
| | GCCTCGTGATCTTCCTGGCCGAAGTGGCCGCCAGCCTGGTGGTGCTGTGGCTGCTCGGA | |
| | AACACCCCACTGCAGGACAAGGGCAACAGCACCCACAGCCGGAACAACAGCTACGCCGT | |
| | GATCATCACCAGCACCAGCAGCTACTACGTGTTCTACATCTACGTGGGCGTCGCCGACA | |
| | CTCTGCTCGCCATGGGCTTCTTCAGAGGACTGCCCCTGGTGCACACCCTGATCACCGTG | |
| | AGCAAGATCCTGCACCACAAGATGCTGCACAGCGTCCTGCAGGCCCCCATGAGCACACT | |
| | GAACACCCTGAAAGCCGGCGGAATCCTGAACAGATTCAGCAAGGACATCGCCATCCTGG | |
| | ACGACCTGCTGCCCCTGACCATCTTCGACTTCATCCAGCTGCTGCTGATCGTGATCGGC | |
| | GCCATCGCCGTGGTGGCCGTGCTGCAGCCCTACATCTTCGTGGCCACCGTGCCCGTGAT | |
| | CGTGGCCTTCATCATGCTGCGGGCCTACTTCCTGCAGACCAGCCAGCAGCTGAAGCAGC | |
| | TCGAGAGCGAGGGCAGAAGCCCCATCTTCACCCACCTCGTGACCAGCCTGAAAGGCCTG | |
| | TGGACCCTGAGAGCCTTCGGCAGACAGCCCTACTTCGAGACACTGTTCCACAAGGCCCT | |
| | GAACCTGCACACCGCCAACTGGTTCCTGTACCTGAGCACCCTGCGGTGGTTCCAGATGA | |
| | GGATCGAGATGATCTTCGTCATCTTCTTCATCGCCGTGACCTTCATCAGCATCCTCACC | |
| | ACTGGCGAAGGCGAGGGCAGAGTGGGAATCATCCTGACCCTGGCCATGAACATCATGAG | |
| | CACACTCCAGTGGGCCGTGAACAGCAGCATCGACGTGGACAGCCTGATGCGGAGCGTGA | |
| | GCCGGGTGTTCAAGTTCATCGACATGCCCACAGAGGGCAAGCCCACCAAGAGCACCAAG | |
| | CCCTACAAGAACGGCCAGCTGAGCAAAGTCATGATCATCGAGAACAGCCACGTCAAGAA | |
| | GGACGACATCTGGCCCAGCGGAGGCCAGATGACCGTGAAGGACCTGACCGCCAAGTACA | |
| | CCGAAGGCGGAAACGCCATCCTGGAAAACATCAGCTTCAGCATCAGCCCCGGCCAGCGC | |
| | GTGGGACTCCTGGGAAGAACCGGAAGCGGCAAGAGCACTCTGCTGAGCGCCTTCCTGAG | |
| | ACTGCTGAACACCGAGGGCGAGATCCAGATCGACGGGGTGAGCTGGGACAGCATCACCC | |
| | TGCAACAATGGCGGAAGGCCTTCGGCGTGATCCCCCAGAAGGTGTTCATCTTCAGCGGC | |
| | ACGTTCCGGAAGAACCTGGACCCCTACGAGCAGTGGAGCGACCAAGAGATCTGGAAGGT | |
| | GGCCGACGAAGTGGGACTGAGAAGCGTGATCGAGCAGTTCCCCGGCAAGCTGGACTTCG | |
| | TGCTGGTGGACGGCGGCTGCGTGCTGAGCCACGGACACAAGCAGCTGATGTGCCTGGCC | |
| | AGAAGCGTGCTGAGCAAGGCCAAGATCCTGCTGCTCGACGAGCCCAGCGCCCACCTGGA | |
| | CCCCGTGACCTACCAGATCATCCGGCGGACACTGAAGCAGGCCTTCGCCGACTGCACCG | |
| | TGATCCTGTGCGAGCACAGAATCGAGGCCATGCTGGAATGCCAGCAGTTCCTGGTGATC | |
| | GAAGAGAACAAAGTGCGGCAGTACGACAGCATCCAGAAGCTGCTGAACGAGCGGAGCCT | |
| | GTTCAGACAGGCCATCAGCCCCAGCGACAGAGTGAAGCTGTTCCCCCACCGGAACAGCA | |
| | GCAAGTGCAAGAGCAAGCCCCAGATCGCCGCCCTGAAAGAAGAAACCGAGGAAGAGGTG | |
| | CAGGACACACGGCTGGCGGCCGTTTACCCATACGATGTTCCTGACTATGCGTGA | |
| CFTR-005 | ATGCAGAGAAGCCCCCTGGAAAAGGCCAGCGTGGTGAGCAAGCTGTTCTTCAGCTGGAC | 4 |
| | CCGGCCCATCCTGCGGAAGGGCTACAGACAGAGACTGGAACTGAGCGACATCTACCAGA | |

TABLE 1-continued

Example CFTR ORF sequences

| Construct | DNA sequence (from 5' to 3') | SEQ ID NO. |
|---|---|---|
| | TCCCCAGCGTGGACAGCGCCGACAACCTGAGCGAGAAGCTGGAAAGAGAGTGGGACAGA | |
| | GAGCTGGCCAGCAAGAAGAACCCCAAGCTGATCAACGCCCTGCGGCGGTGCTTCTTCTG | |
| | GCGGTTCATGTTCTACGGCATCTTCCTGTACCTGGGCGAAGTGACCAAAGCCGTGCAGC | |
| | CCCTGCTGCTGGGCAGAATCATCGCCAGCTACGACCCCGACAACAAAGAGGAACGGAGC | |
| | ATCGCCATCTACCTCGGCATCGGCCTGTGCCTGCTGTTCATCGTCAGAACCCTGCTGCT | |
| | GCACCCCGCCATCTTCGGACTGCACCACATCGGCATGCAGATGCGGATCGCCATGTTCA | |
| | GCCTGATCTACAAGAAAACCCTGAAGCTGAGCAGCAGAGTGCTGGACAAGATCAGCATC | |
| | GGACAGCTGGTGAGCCTGCTGAGCAACAACCTGAACAAGTTCGACGAAGGCCTGGCCCT | |
| | GGCCCACTTCGTGTGGATCGCCCCCCTGCAAGTGGCCCTGCTGATGGGCCTGATCTGGG | |
| | AACTGCTGCAGGCCAGCGCCTTCTGCGGACTGGGATTCCTGATCGTGCTGGCCCTGTTC | |
| | CAGGCCGGACTGGGGAGAATGATGATGAAGTACCGGGACCAGAGAGCCGGCAAGATCAG | |
| | CGAGAGACTGGTCATCACCAGCGAGATGATCGAGAACATCCAGAGCGTGAAGGCCTACT | |
| | GCTGGGAAGAGGCCATGGAAAAGATGATCGAGAACCTGCGGCAGACCGAGCTGAAGCTG | |
| | ACAAGAAAGGCCGCCTACGTGCGCTACTTCAACAGCAGCGCCTTCTTCTTCAGCGGCTT | |
| | CTTCGTGGTGTTCCTGAGCGTGCTGCCCTACGCCCTGATCAAGGGCATCATCCTGAGAA | |
| | AGATCTTCACCACCATCAGCTTCTGCATCGTGCTGCGGATGGCCGTGACCAGACAGTTC | |
| | CCCTGGGCCGTGCAGACCTGGTACGACAGCCTGGGCGCCATCAACAAGATCCAGGACTT | |
| | CCTGCAGAAGCAAGAGTACAAGACCCTCGAGTACAACCTGACCACCACCGAGGTGGTCA | |
| | TGGAAAACGTGACCGCCTTCTGGGAGGAAGGCTTCGGCGAGCTGTTCGAGAAGGCCAAG | |
| | CAGAACAACAACAACCGCAAGACCAGCAACGGCGACGACAGCCTGTTCTTCAGCAACTT | |
| | CAGCCTGCTGGGGACCCCCGTGCTGAAGGACATCAACTTCAAGATCGAGCGGGGACAGC | |
| | TGCTGGCCGTGGCCGGAAGCACAGGCGCCGGAAAAACCAGCCTGCTCATGGTCATCATG | |
| | GGCGAGCTGGAACCCAGCGAGGGCAAGATCAAGCACAGCGGCAGGATCAGCTTCTGCAG | |
| | CCAGTTCAGCTGGATCATGCCCGGCACCATCAAAGAGAACATCATCTTCGGCGTGAGCT | |
| | ACGACGAGTACAGATACCGCAGCGTGATCAAGGCCTGCCAGCTGGAAGAGGACATCAGC | |
| | AAGTTCGCCGAGAAGGACAACATCGTGCTCGGCGAAGGCGGCATCACACTGAGCGGCGG | |
| | ACAGAGGGCCAGAATCAGCCTGGCCAGAGCCGTGTACAAGGACGCCGACCTGTACCTGC | |
| | TGGACAGCCCCTTCGGCTACCTGGACGTGCTGACCGAGAAAGAGATCTTCGAGAGCTGC | |
| | GTGTGCAAGCTGATGGCCAACAAGACCCGGATCCTGGTCACCAGCAAGATGGAACACCT | |
| | GAAGAAGGCCGACAAGATCCTGATCCTGCACGAGGGCAGCAGCTACTTCTACGGCACCT | |
| | TCAGCGAGCTGCAGAACCTGCAGCCCGACTTCAGCAGCAAACTGATGGGCTGCGACAGC | |
| | TTCGACCAGTTCAGCGCCGAGCGGAGAAACAGCATCCTGACAGAGACACTGCACCGGTT | |
| | CAGCCTGGAAGGCGACGCCCCCGTGAGCTGGACCGAGACAAAGAAGCAGAGCTTCAAGC | |
| | AGACCGGCGAGTTCGGCGAGAAGCGGAAGAACAGCATCCTGAACCCCATCAACAGCATC | |
| | CGGAAGTTCAGCATCGTCCAGAAAACCCCCCTGCAGATGAACGGCATCGAAGAGGACAG | |
| | CGACGAGCCCCTGGAAAGACGGCTGAGCCTGGTGCCCGACAGCGAACAGGGCGAAGCCA | |
| | TCCTGCCCCGGATCAGCGTGATCAGCACAGGCCCCACACTGCAGGCCCGGAGAAGGCAG | |
| | AGCGTGCTGAACCTGATGACCCACAGCGTGAACCAGGGACAGAACATCCACAGAAAGAC | |
| | CACCGCCAGCACACGGAAAGTGAGCCTGGCCCCCCAGGCCAACCTGACTGAGCTGGACA | |
| | TCTACAGCAGACGGCTGAGCCAAGAGACAGGCCTGGAAATCAGCGAGGAAATCAACGAA | |
| | GAGGACCTGAAAGAGTGCTTCTTCGACGACATGGAAAGCATCCCCGCCGTGACAACCTG | |
| | GAACACCTACCTGCGGTACATCACCGTGCACAAGAGCCTGATCTTCGTGCTGATCTGGT | |
| | GCCTCGTGATCTTCCTGGCCGAAGTGGCCGCCAGCCTGGTGGTGCTGTGGCTGCTCGGA | |
| | AACACCCCACTGCAGGACAAGGGCAACAGCACCCACAGCCGGAACAACAGCTACGCCGT | |
| | GATCATCACCAGCACCAGCAGCTACTACGTGTTCTACATCTACGTGGGCGTCGCCGACA | |
| | CTCTGCTCGCCATGGGCTTCTTCAGAGGACTGCCCCTGGTGCACACCCTGATCACCGTG | |
| | AGCAAGATCCTGCACCACAAGATGCTGCACAGCGTCCTGCAGGCCCCCATGAGCACACT | |
| | GAACACCCTGAAAGCCGGCGGAATCCTGAACAGATTCAGCAAGGACATCGCCATCCTGG | |
| | ACGACCTGCTGCCCCTGACCATCTTCGACTTCATCCAGCTGCTGCTGATCGTGATCGGC | |
| | GCCATCGCCGTGGTGGCCGTGCTGCAGCCCTACATCTTCGTGGCCACCGTGCCCGTGAT | |
| | CGTGGCCTTCATCATGCTGCGGGCCTACTTCCTGCAGACCAGCCAGCAGCTGAAGCAGC | |
| | TCGAGAGCGAGGGCAGAAGCCCCATCTTCACCCACCTCGTGACCAGCCTGAAAGGCCTG | |
| | TGGACCCTGAGAGCCTTCGGCAGACAGCCCTACTTCGAGACACTGTTCCACAAGGCCCT | |
| | GAACCTGCACACCGCCAACTGGTTCCTGTACCTGAGCACCCTGCGGTGGTTCCAGATGA | |
| | GGATCGAGATGATCTTCGTCATCTTCTTCATCGCCGTGACCTTCATCAGCATCCTCACC | |
| | ACTGGCGAAGGCGAGGGCAGAGTGGGAATCATCCTGACCCTGGCCATGAACATCATGAG | |
| | CACACTCCAGTGGGCCGTGAACAGCAGCATCGACGTGGACAGCCTGATGCGGAGCGTGA | |
| | GCCGGGTGTTCAAGTTCATCGACATGCCCACAGAGGGCAAGCCCACCAAGAGCACCAAG | |
| | CCCTACAAGAACGGCCAGCTGAGCAAAGTCATGATCATCGAGAACAGCCACGTCAAGAA | |
| | GGACGACATCTGGCCCAGCGGAGGCCAGATGACCGTGAAGGACCTGACCGCCAAGTACA | |
| | CCGAAGGCGGAAACGCCATCCTGGAAAACATCAGCTTCAGCATCAGCCCCGGCCAGCGC | |
| | GTGGGACTCCTGGGAAGAACCGGAAGCGGCAAGAGCACTCTGCTGAGCGCCTTCCTGAG | |
| | ACTGCTGAACACCGAGGGCGAGATCCAGATCGACGGGGTGAGCTGGGACAGCATCACCC | |
| | TGCAACAATGGCGGAAGGCCTTCGGCGTGATCCCCCAGAAGGTGTTCATCTTCAGCGGC | |
| | ACGTTCCGGAAGAACCTGGACCCCTACGAGCAGTGGAGCGACCAAGAGATCTGGAAGGT | |
| | GGCCGACGAAGTGGGACTGAGAAGCGTGATCGAGCAGTTCCCCGGCAAGCTGGACTTCG | |
| | TGCTGGTGGACGGCGGCTGCGTGCTGAGCCACGGACACAAGCAGCTGATGTGCCTGGCC | |
| | AGAAGCGTGCTGAGCAAGGCCAAGATCCTGCTGCTCGACGAGCCCAGCGCCCACCTGGA | |
| | CCCCGTGACCTACCAGATCATCCGGCGGACACTGAAGCAGGCCTTCGCCGACTGCACCG | |
| | TGATCCTGTGCGAGCACAGAATCGAGGCCATGCTGGAATGCCAGCAGTTCCTGGTGATC | |
| | GAAGAGAACAAAGTGCGGCAGTACGACAGCATCCAGAAGCTGCTGAACGAGCGGAGCCT | |
| | GTTCAGACAGGCCATCAGCCCCAGCGACAGAGTGAAGCTGTTCCCCCACCGGAACAGCA | |
| | GCAAGTGCAAGAGCAAGCCCCAGATCGCCGCCCTGAAAGAAGAAACCGAGGAAGAGGTG | |
| | CAGGACACACGGCTGTGA | |

TABLE 1-continued

| Example CFTR ORF sequences | | |
|---|---|---|
| Construct | DNA sequence (from 5' to 3') | SEQ ID NO. |
| Wild Type CFTR | ATGCAGAGGTCGCCTCTGGAAAAGGCCAGCGTTGTCTCCAAACTTTTTTTCAGCTGGAC<br>CAGACCAATTTTGAGGAAAGGATACAGACAGCGCCTGGAATTGTCAGACATATACCAAA<br>TCCCTTCTGTTGATTCTGCTGACAATCTATCTGAAAAATTGGAAAGAGAATGGGATAGA<br>GAGCTGGCTTCAAAGAAAAATCCTAAACTCATTAATGCCCTTCGGCGATGTTTTTTCTG<br>GAGATTTATGTTCTATGGAATCTTTTTATATTTAGGGGAAGTCACCAAAGCAGTACAGC<br>CTCTCTTACTGGGAAGAATCATAGCTTCCTATGACCCGGATAACAAGGAGGAACGCTCT<br>ATCGCGATTTATCTAGGCATAGGCTTATGCCTTCTCTTTATTGTGAGGACACTGCTCCT<br>ACACCCAGCCATTTTTGGCCTTCATCACATTGGAATGCAGATGAGAATAGCTATGTTTA<br>GTTTGATTTATAAGAAGACTTTAAAGCTGTCAAGCCGTGTTCTAGATAAAATAAGTATT<br>GGACAACTTGTTAGTCTCCTTTCCAACAACCTGAACAAATTTGATGAAGGACTTGCATT<br>GGCACATTTCGTGTGGATCGCTCCTTTGCAAGTGGCACTCCTCATGGGGCTAATCTGGG<br>AGTTGTTACAGGCGTCTGCCTTCTGTGGACTTGGTTTCCTGATAGTCCTTGCCCTTTTT<br>CAGGCTGGGCTAGGGAGAATGATGATGAAGTACAGAGATCAGAGAGCTGGGAAGATCAG<br>TGAAAGACTTGTGATTACCTCAGAAATGATTGAAAATATCCAATCTGTTAAGGCATACT<br>GCTGGGAAGAAGCAATGGAAAAAATGATTGAAAACTTAAGACAAACAGAACTGAAACTG<br>ACTCGGAAGGCAGCCTATGTGAGATACTTCAATAGCTCAGCCTTCTTCTTCTCAGGGTT<br>CTTTGTGGTGTTTTTATCTGTGCTTCCCTATGCACTAATCAAAGGAATCATCCTCCGGA<br>AAATATTCACCACCATCTCATTCTGCATTGTTCTGCGCATGGCGGTCACTCGGCAATTT<br>CCCTGGGCTGTACAAACATGGTATGACTCTCTTGGAGCAATAAACAAAATACAGGATTT<br>CTTACAAAAGCAAGAATATAAGACATTGGAATATAACTTAACGACTACAGAAGTAGTGA<br>TGGAGAATGTAACAGCCTTCTGGGAGGAGGGATTTGGGGAATTATTTGAGAAAGCAAAA<br>CAAAACAATAACAATAGAAAAACTTCTAATGGTGATGACAGCCTCTTCTTCAGTAATTT<br>CTCACTTCTTGGTACTCCTGTCCTGAAAGATATTAATTTCAAGATAGAAAGAGGACAGT<br>TGTTGGCGGTTGCTGGATCCACTGGAGCAGGCAAGACTTCACTTCTAATGATGATTATG<br>GGAGAACTGGAGCCTTCAGAGGGTAAAATTAAGCACAGTGGAAGAATTTCATTCTGTTC<br>TCAGTTTTCCTGGATTATGCCTGGCACCATTAAAGAAAATATCATCTTTGGTGTTTCCT<br>ATGATGAATATAGATACAGAAGCGTCATCAAAGCATGCCAACTAGAAGAGGACATCTCC<br>AAGTTTGCAGAGAAAGACAATATAGTTCTTGGAGAAGGTGGAATCACACTGAGTGGAGG<br>TCAACGAGCAAGAATTTCTTTAGCAAGAGCAGTATACAAAGATGCTGATTTGTATTTAT<br>TAGACTCTCCTTTTGGATACCTAGATGTTTTAACAGAAAAAGAAATATTTGAAAGCTGT<br>GTCTGTAAACTGATGGCTAACAAAACTAGGATTTTGGTCACTTCTAAAATGGAACATTT<br>AAAGAAAGCTGACAAAATATTAATTTTGAATGAAGGTAGCAGCTATTTTTATGGGACAT<br>TTTCAGAACTCCAAAATCTACAGCCAGACTTTAGCTCAAAACTCATGGGATGTGATTCT<br>TTCGACCAATTTAGTGCAGAAAGAAGAAATTCAATCCTAACTGAGACCTTACACCGTTT<br>CTCATTAGAAGGAGATGCTCCTGTCTCCTGGACAGAAACAAAAAAACAATCTTTTAAAC<br>AGACTGGAGAGTTTGGGGAAAAAAGGAAGAATTCTATTCTCAATCCAATCAACTCTATA<br>CGAAAATTTTCCATTGTGCAAAAGACTCCCTTACAAATGAATGGCATCGAAGAGGATTC<br>TGATGAGCCTTTAGAGAGAAGGCTGTCCTTAGTACCAGATTCTGAGCAGGGAGAGGCGA<br>TACTGCCTCGCATCAGCGTGATCAGCACTGGCCCCACGCTTCAGGCACGAAGGAGGCAG<br>TCTGTCCTGAACCTGATGACACACTCAGTTAACCAAGGTCAGAACATTCACCGAAAGAC<br>AACAGCATCCACACGAAAAGTGTCACTGGCCCCTCAGGCAAACTTGACTGAACTGGATA<br>TATATTCAAGAAGGTTATCTCAAGAAACTGGCTTGGAAATAAGTGAAGAAATTAACGAA<br>GAAGACTTAAAGGAGTGCCTTTTTGATGATATGGAGAGCATACCAGCAGTGACTACATG<br>GAACACATACCTTCGATATATTACTGTCCACAAGAGCTTAATTTTTGTGCTAATTTGGT<br>GCTTAGTAATTTTTCTGGCAGAGGTGGCTGCTTCTTTGGTTGTGCTGTGGCTCCTTGGA<br>AACACTCCTCTTCAAGACAAAGGGAATAGTACTCATAGTAGAAATAACAGCTATGCAGT<br>GATTATCACCAGCACCAGTTCGTATTATGTGTTTTACATTTACGTGGGAGTAGCCGACA<br>CTTTGCTTGCTATGGGATTCTTCAGAGGTCTACCACTGGTGCATACTCTAATCACAGTG<br>TCGAAAATTTTACACCACAAAATGTTACATTCTGTTCTTCAAGCACCTATGTCAACCCT<br>CAACACGTTGAAAGCAGGTGGGATTCTTAATAGATTCTCCAAAGATATAGCAATTTTGG<br>ATGACCTTCTGCCTCTTACCATATTTGACTTCATCCAGTTGTTATTAATTGTGATTGGA<br>GCTATAGCAGTTGTCGCAGTTTTACAACCCTACATCTTTGTTGCAACAGTGCCAGTGAT<br>AGTGGCTTTTATTATGTTGAGAGCATATTTCCTCCAAACCTCACAGCAACTCAAACAAC<br>TGGAATCTGAAGGCAGGAGTCCAATTTTCACTCATCTTGTTACAAGCTTAAAAGGACTA<br>TGGACACTTCGTGCCTTCGGACGGCAGCCTTACTTTGAAACTCTGTTCCACAAAGCTCT<br>GAATTTACATACTGCCAACTGGTTCTTGTACCTGTCAACACTGCGCTGGTTCCAAATGA<br>GAATAGAAATGATTTTTGTCATCTTCTTCATTGCTGTTACCTTCATTTCCATTTTAACA<br>ACAGGAGAAGGAGAAGGAAGAGTTGGTATTATCCTGACTTTAGCCATGAATATCATGAG<br>TACATTGCAGTGGGCTGTAAACTCCAGCATAGATGTGGATAGCTTGATGCGATCTGTGA<br>GCCGAGTCTTTAAGTTCATTGACATGCCAACAGAAGGTAAACCTACCAAGTCAACCAAA<br>CCATACAAGAATGGCCAACTCTCGAAAGTTATGATTATTGAGAATTCACACGTGAAGAA<br>AGATGACATCTGGCCCTCAGGGGGCCAAATGACTGTCAAAGATCTCACAGCAAAATACA<br>CAGAAGGTGGAAATGCCATATTAGAGAACATTTCCTTCTCAATAAGTCCTGGCCAGAGG<br>GTGGGCCTCTTGGGAAGAACTGGATCAGGGAAGAGTACTTTGTTATCAGCTTTTTTGAG<br>ACTACTGAACACTGAAGGAGAAATCCAGATCGATGGTGTGTCTTGGGATTCAATAACTT<br>TGCAACAGTGGAGGAAAGCCTTTGGAGTGATACCACAGAAAGTATTTATTTTTTCTGGA<br>ACATTTAGAAAAAACTTGGATCCCTATGAACAGTGGAGTGATCAAGAAATATGGAAAGT<br>TGCAGATGAGGTTGGGCTCAGATCTGTGATAGAACAGTTTCCTGGGAAGCTTGACTTTG<br>TCCTTGTGGATGGGGGCTGTGTCCTAAGCCATGGCCACAAGCAGTTGATGTGCTTGGCT<br>AGATCTGTTCTCAGTAAGGCGAAGATCTTGCTGCTTGATGAACCCAGTGCTCATTTGGA<br>TCCAGTAACATACCAAATAATTAGAAGAACTCTAAAACAAGCATTTGCTGATTGCACAG<br>TAATTCTCTGTGAACACAGGATAGAAGCAATGCTGGAATGCCAACAATTTTTGGTCATA | 5 |

TABLE 1-continued

Example CFTR ORF sequences

| Construct | DNA sequence (from 5' to 3') | SEQ ID NO. |
|---|---|---|
| | GAAGAGAACAAAGTGCGGCAGTACGATTCCATCCAGAAACTGCTGAACGAGAGGAGCCT | |
| | CTTCCGGCAAGCCATCAGCCCCTCCGACAGGGTGAAGCTCTTTCCCCACCGGAACTCAA | |
| | GCAAGTGCAAGTCTAAGCCCCAGATTGCTGCTCTGAAAGAGGAGACAGAAGAAGAGGTG | |
| | CAAGATACAAGGCTTTAG | |
| CFTR0006 | ATGTACCCATACGATGTTCCTGACTATGCGGCGGCCGTTATGCAGAGAAGCCCCCTGGA | 23 |
| | AAAGGCCAGCGTGGTGAGCAAGCTGTTCTTCAGCTGGACCCGGCCCATCCTGCGGAAGG | |
| | GCTACAGACAGAGACTGGAACTGAGCGACATCTACCAGATCCCCAGCGTGGACAGCGCC | |
| | GACAACCTGAGCGAGAAGCTGGAAAGAGAGTGGGACAGAGAGCTGGCCAGCAAGAAGAA | |
| | CCCCAAGCTGATCAACGCCCTGCGGCGGTGCTTCTTCTGGCGGTTCATGTTCTACGGCA | |
| | TCTTCCTGTACCTGGGCGAAGTGACCAAAGCCGTGCAGCCCCTGCTGCTGGGCAGAATC | |
| | ATCGCCAGCTACGACCCCGACAACAAAGAGGAACGGAGCATCGCCATCTACCTCGGCAT | |
| | CGGCCTGTGCCTGCTGTTCATCGTCAGAACCCTGCTGCTGCACCCCGCCATCTTCGGAC | |
| | TGCACCACATCGGCATGCAGATGCGGATCGCCATGTTCAGCCTGATCTACAAGAAAACC | |
| | CTGAAGCTGAGCAGCAGAGTGCTGGACAAGATCAGCATCGGACAGCTGGTGAGCCTGCT | |
| | GAGCAACAACCTGAACAAGTTCGACGAAGGCCTGGCCCTGGCCCACTTCGTGTGGATCG | |
| | CCCCCCTGCAAGTGGCCCTGCTGATGGGCCTGATCTGGGAACTGCTGCAGGCCAGCGCC | |
| | TTCTGCGGACTGGGATTCCTGATCGTGCTGGCCCTGTTCCAGGCCGGACTGGGGAGAAT | |
| | GATGATGAAGTACCGGGACCAGAGAGCCGGCAAGATCAGCGAGAGACTGGTCATCACCA | |
| | GCGAGATGATCGAGAACATCCAGAGCGTGAAGGCCTACTGCTGGGAAGAGGCCATGGAA | |
| | AAGATGATCGAGAACCTGCGGCAGACCGAGCTGAAGCTGACAAGAAAGGCCGCCTACGT | |
| | GCGCTACTTCAACAGCAGCGCCTTCTTCTTCAGCGGCTTCTTCGTGGTGTTCCTGAGCG | |
| | TGCTGCCCTACGCCCTGATCAAGGGCATCATCCTGAGAAAGATCTTCACCACCATCAGC | |
| | TTCTGCATCGTGCTGCGGATGGCCGTGACCAGACAGTTCCCCTGGGCCGTGCAGACCTG | |
| | GTACGACAGCCTGGGCGCCATCAACAAGATCCAGGACTTCCTGCAGAAGCAAGAGTACA | |
| | AGACCCTCGAGTACAACCTGACCACCACCGAGGTGGTCATGGAAAACGTGACCGCCTTC | |
| | TGGGAGGAAGGCTTCGGCGAGCTGTTCGAGAAGGCCAAGCAGAACAACAACAACCGCAA | |
| | GACCAGCAACGGCGACGACAGCCTGTTCTTCAGCAACTTCAGCCTGCTGGGGACCCCCG | |
| | TGCTGAAGGACATCAACTTCAAGATCGAGCGGGGACAGCTGCTGGCCGTGGCCGGAAGC | |
| | ACAGGCGCCGGAAAAACCAGCCTGCTCATGGTCATCATGGGCGAGCTGGAACCCAGCGA | |
| | GGGCAAGATCAAGCACAGCGGCAGGATCAGCTTCTGCAGCCAGTTCAGCTGGATCATGC | |
| | CCGGCACCATCAAAGAGAACATCATCTTCGGCGTGAGCTACGACGAGTACAGATACCGC | |
| | AGCGTGATCAAGGCCTGCCAGCTGGAAGAGGACATCAGCAAGTTCGCCGAGAAGGACAA | |
| | CATCGTGCTCGGCGAAGGCGGCATCACACTGAGCGGCGGACAGAGGGCCAGAATCAGCC | |
| | TGGCCAGAGCCGTGTACAAGGACGCCGACCTGTACCTGCTGGACAGCCCCTTCGGCTAC | |
| | CTGGACGTGCTGACCGAGAAAGAGATCTTCGAGAGCTGCGTGTGCAAGCTGATGGCCAA | |
| | CAAGACCCGGATCCTGGTCACCAGCAAGATGGAACACCTGAAGAAGGCCGACAAGATCC | |
| | TGATCCTGCACGAGGGCAGCAGCTACTTCTACGGCACCTTCAGCGAGCTGCAGAACCTG | |
| | CAGCCCGACTTCAGCAGCAAACTGATGGGCTGCGACAGCTTCGACCAGTTCAGCGCCGA | |
| | GCGGAGAAACAGCATCCTGACAGAGACACTGCACCGGTTCAGCCTGGAAGGCGACGCCC | |
| | CCGTGAGCTGGACCGAGACAAAGAAGCAGAGCTTCAAGCAGACCGGCGAGTTCGGCGAG | |
| | AAGCGGAAGAACAGCATCCTGAACCCCATCAACAGCATCCGGAAGTTCAGCATCGTCCA | |
| | GAAAACCCCCCTGCAGATGAACGGCATCGAAGAGGACAGCGACGAGCCCCTGGAAAGAC | |
| | GGCTGAGCCTGGTGCCCGACAGCGAACAGGGCGAAGCCATCCTGCCCCGGATCAGCGTG | |
| | ATCAGCACAGGCCCCACACTGCAGGCCCGGAGAAGGCAGAGCGTGCTGAACCTGATGAC | |
| | CCACAGCGTGAACCAGGGACAGAACATCCACAGAAAGACCACCGCCAGCACACGGAAAG | |
| | TGAGCCTGGCCCCCCAGGCCAACCTGACTGAGCTGGACATCTACAGCAGACGGCTGAGC | |
| | CAAGAGACAGGCCTGGAAATCAGCGAGGAAATCAACGAAGAGGACCTGAAAGAGTGCTT | |
| | CTTCGACGACATGGAAAGCATCCCCGCCGTGACAACCTGGAACACCTACCTGCGGTACA | |
| | TCACCGTGCACAAGAGCCTGATCTTCGTGCTGATCTGGTGCCTCGTGATCTTCCTGGCC | |
| | GAAGTGGCCGCCAGCCTGGTGGTGCTGTGGCTGCTCGGAAACACCCCACTGCAGGACAA | |
| | GGGCAACAGCACCCACAGCCGGAACAACAGCTACGCCGTGATCATCACCAGCACCAGCA | |
| | GCTACTACGTGTTCTACATCTACGTGGGCGTCGCCGACACTCTGCTCGCCATGGGCTTC | |
| | TTCAGAGGACTGCCCCTGGTGCACACCCTGATCACCGTGAGCAAGATCCTGCACCACAA | |
| | GATGCTGCACAGCGTCCTGCAGGCCCCCATGAGCACACTGAACACCCTGAAAGCCGGCG | |
| | GAATCCTGAACAGATTCAGCAAGGACATCGCCATCCTGGACGACCTGCTGCCCCTGACC | |
| | ATCTTCGACTTCATCCAGCTGCTGCTGATCGTGATCGGCGCCATCGCCGTGGTGGCCGT | |
| | GCTGCAGCCCTACATCTTCGTGGCCACCGTGCCCGTGATCGTGGCCTTCATCATGCTGC | |
| | GGGCCTACTTCCTGCAGACCAGCCAGCAGCTGAAGCAGCTCGAGAGCGAGGGCAGAAGC | |
| | CCCATCTTCACCCACCTCGTGACCAGCCTGAAAGGCCTGTGGACCCTGAGAGCCTTCGG | |
| | CAGACAGCCCTACTTCGAGACACTGTTCCACAAGGCCCTGAACCTGCACACCGCCAACT | |
| | GGTTCCTGTACCTGAGCACCCTGCGGTGGTTCCAGATGAGGATCGAGATGATCTTCGTC | |
| | ATCTTCTTCATCGCCGTGACCTTCATCAGCATCCTCACCACTGGCGAAGGCGAGGGCAG | |
| | AGTGGGAATCATCCTGACCCTGGCCATGAACATCATGAGCACACTCCAGTGGGCCGTGA | |
| | ACAGCAGCATCGACGTGGACAGCCTGATGCGGAGCGTGAGCCGGGTGTTCAAGTTCATC | |
| | GACATGCCCACAGAGGGCAAGCCCACCAAGAGCACCAAGCCCTACAAGAACGGCCAGCT | |
| | GAGCAAAGTCATGATCATCGAGAACAGCCACGTCAAGAAGGACGACATCTGGCCCAGCG | |
| | GAGGCCAGATGACCGTGAAGGACCTGACCGCCAAGTACACCGAAGGCGGAAACGCCATC | |
| | CTGGAAAACATCAGCTTCAGCATCAGCCCCGGCCAGCGCGTGGGACTCCTGGGAAGAAC | |
| | CGGAAGCGGCAAGAGCACTCTGCTGAGCGCCTTCCTGAGACTGCTGAACACCGAGGGCG | |
| | AGATCCAGATCGACGGGGTGAGCTGGGACAGCATCACCCTGCAACAATGGCGGAAGGCC | |
| | TTCGGCGTGATCCCCCAGAAGGTGTTCATCTTCAGCGGCACGTTCCGGAAGAACCTGGA | |
| | CCCCTACGAGCAGTGGAGCGACCAAGAGATCTGGAAGGTGGCCGACGAAGTGGGACTGA | |
| | GAAGCGTGATCGAGCAGTTCCCCGGCAAGCTGGACTTCGTGCTGGTGGACGGCGGCTGC | |
| | GTGCTGAGCCACGGACACAAGCAGCTGATGTGCCTGGCCAGAAGCGTGCTGAGCAAGGC | |

TABLE 1-continued

| Example CFTR ORF sequences | | |
|---|---|---|
| Construct | DNA sequence (from 5' to 3') | SEQ ID NO. |
| | CAAGATCCTGCTGCTCGACGAGCCCAGCGCCCACCTGGACCCCGTGACCTACCAGATCA TCCGGCGGACACTGAAGCAGGCCTTCGCCGACTGCACCGTGATCCTGTGCGAGCACAGA ATCGAGGCCATGCTGGAATGCCAGCAGTTCCTGGTGATCGAAGAGAACAAAGTGCGGCA GTACGACAGCATCCAGAAGCTGCTGAACGAGCGGAGCCTGTTCAGACAGGCCATCAGCC CCAGCGACAGAGTGAAGCTGTTCCCCCACCGGAACAGCAGCAAGTGCAAGAGCAAGCCC CAGATCGCCGCCCTGAAAGAAGAAACCGAGGAAGAGGTGCAGGACACACGGCTGTGA | |

Untranslated Regions

In some embodiments, the polynucleotide of the present disclosure further comprises 3'- or 5'-untranslated regions or a 3'- or 5'-noncoding region. In some embodiments, said untranslated region or noncoding region improves a pharmacokinetic characteristic (e.g., a prolonged half-life) of said synthetic polynucleotide in a cell. In some embodiments, the polynucleotide of the present disclosure comprises a 5' untranslated region (UTR) or 3' UTR having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to one set forth in SEQ ID NOs 6-22. In some embodiments, the polynucleotide comprises a 5' cap structure. In some embodiments, the 5' cap structure comprises a sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID 6. In some embodiments, the polynucleotide comprises a 3' poly adenosine tail. In some embodiments, the 3' poly adenosine tail comprises a sequence having at least 75%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs 7 or 8.

TABLE 2

| Example untranslated region sequences | | |
|---|---|---|
| UTR | DNA sequence (from 5' to 3') | SEQ ID NO. |
| 5'UTR | GGGAGACCCAAGCTGGCTAGCGTTTAAACTTCAGCTTGGCAATCCGGTACTGTTGGTA AAGCCACC | 6 |
| 3' UTR-poly(A)-001 | GAATTCTGCAGAAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAAAAAAAAAAAAAA AAAAAAAAAAAAAAAAAAAAAAAAAAAATTCG | 7 |
| 3' UTR-poly(A)-002 | GAATTCTGCAGAAAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAAAAAAAAAAAAAA AAAAAAAAAAAAAAAAAAAAAAAAAAAAATT | 8 |
| α-globin 5' UTR (HBA1) | GGGAGACATAAACCCTGGCGCGCTCGCGGCCCGGCACTCTTCTGGTCCCCACAGACTC AGAGAGAAGCCACC | 9 |
| α-globin 5' UTR (HBA2) | GGGAGACATAAACCCTGGCGCGCTCGCGGGCCGGCACTCTTCTGGTCCCCACAGACTC AGAGAGAAGCCACC | 10 |
| α-globin 5' UTR | GGGAGACTCTTCTGGTCCCCACAGACTCAGAGAGAACGCCACC | 11 |
| IRES of EMCV 5'-UTR | GTTATTTTCCACCATATTGCCGTCTTTTGGCAATGTGAGGGCCCGGAAACCTGGCCCT GTCTTCTTGACGAGCATTCCTAGGGGTCTTTCCCCTCTCGCCAAAGGAATGCAAGGTC TGTTGAATGTCGTGAAGGAAGCAGTTCCTCTGGAAGCTTCTTGAAGACAAACAACGTC TGTAGCGACCCTTTGCAGGCAGCGGAACCCCCCACCTGGCGACAGGTGCCTCTGCGGC CAAAAGCCACGTGTATAAGATACACCTGCAAAGGCGGCACAACCCCAGTGCCACGTTG TGAGTTGGATAGTTGTGGAAAGAGTCAAATGGCTCTCCTCAAGCGTATTCAACAAGGG GCTGAAGGATGCCCAGAAGGTACCCCATTGTATGGGATCTGATCTGGGGCCTCGGTGC ACATGCTTTACGTGTGTTTAGTCGAGGTTAAAAAACGTCTAGGCCCCCCGAACCACGG GGACGTGGTTTTCCTTTGAAAAACACGATGATAATATGGCCACAACC | 12 |
| IRES of TEV 5'-UTR | AAATAACAAATCTCAACACAACATATACAAAACAAACGAATCTCAAGCAATCAAGCAT TCTACTTCTATTGCAGCAATTTAAATCATTTCTTTTAAAGCAAAAGCAATTTTCTGAA AATTTTCACCATTTACGAACGATAGCA | 13 |
| ssRNA1 5'UTR | GGGAGACAAGAGAGAAAAGAAGAGCAAGAAGAAATATAAGAGCCACC | 14 |
| ssRNA2 5'UTR | GGGAGACCCAAGCTGGCTAGCGTTTAAACTTAAGCTTGGCAATCCGGTACTGTTGGTA AAGCCACC | 15 |
| native 5' UTR | GTAGTAGGTCTTTGGCATTAGGAGCTTGAGCCCAGACGGCCCTAGCAGGGACCCCAGC GCCCGAGAGACC | 16 |

TABLE 2-continued

Example untranslated region sequences

| UTR | DNA sequence (from 5' to 3') | SEQ ID NO. |
|---|---|---|
| TMV 3'-UTR | GGATTGTGTCCGTAATCACACGTGGTGCGTACGATAACGCATAGTGTTTTTCCCTCCA CTTAAATCGAAGGGTTGTGTCTTGGATCGCGCGGGTCAAATGTATATGGTTCATATAC ATCCGCAGGCACGTAATAAAGCGAGGGGTTCGAATCCCCCCGTTACCCCCGGTAGGGG CCCATTGTCTTC | 17 |
| MALAT1 3'-UTR | TCAGTAGGGTCATGAAGGTTTTTCTTTTCCTGAGAAAACAACACGTATTGTTTTCTCA GGTTTTGCTTTTTGGCCTTTTTCTAGCTTAAAAAAAAAAAAAGCAAAATTGTCTTC | 18 |
| NEAT2 3'-UTR | TCAGTAGGGTTGTAAAGGTTTTTCTTTTCCTGAGAAAACAACCTTTTGTTTTCTCAGG TTTTGCTTTTTGGCCTTTCCCTAGCTTTAAAAAAAAAAAAGCAAAATTGTCTTC | 19 |
| histone cluster 2, H3c 3'-UTR | GAAGTGGCGGTTCGGCCGGAGGTTCCATCGTATCCAAAAGGCTCTTTTCAGAGCCACC CATTGTCTTC | 20 |
| Native 3' UTR | AGAGCAGCATAAATGTTGACATGGGACATTTGCTCATGGAATTGGAGCTCGTGGGACA GTCACCTCATGGAATTGGAGCTCGTGGAACAGTTACCTCTGCCTCAGAAAACAAGGAT GAATTAAGTTTTTTTTTAAAAAAGAAACATTTGGTAAGGGGAATTGAGGACACTGATA TGGGTCTTGATAAATGGCTTCCTGGCAATAGTCAAATTGTGTGAAAGGTACTTCAAAT CCTTGAAGATTTACCACTTGTGTTTTGCAAGCCAGATTTTCCTGAAAACCCTTGCCAT GTGCTAGTAATTGGAAAGGCAGCTCTAAATGTCAATCAGCCTAGTTGATCAGCTTATT GTCTAGTGAAACTCGTTAATTTGTAGTGTTGGAGAAGAACTGAAATCATACTTCTTAG GGTTATGATTAAGTAATGATAACTGGAAACTTCAGCGGTTTATATAAGCTTGTATTCC TTTTTCTCTCCTCTCCCCATGATGTTTAGAAACACAACTATATTGTTTGCTAAGCATT CCAACTATCTCATTTCCAAGCAAGTATTAGAATACCACAGGAACCACAAGACTGCACA TCAAAATATGCCCCATTCAACATCTAGTGAGCAGTCAGGAAAGAGAACTTCCAGATCC TGGAAATCAGGGTTAGTATTGTCCAGGTCTACCAAAAATCTCAATATTTCAGATAATC ACAATACATCCCTTACCTGGGAAAGGGCTGTTATAATCTTTCACAGGGGACAGGATGG TTCCCTTGATGAAGAAGTTGATATGCCTTTTCCCAACTCCAGAAAGTGACAAGCTCAC AGACCTTTGAACTAGAGTTTAGCTGGAAAAGTATGTTAGTGCAAATTGTCACAGGACA GCCCTTCTTTCCACAGAAGCTCCAGGTAGAGGGTGTGTAAGTAGATAGGCCATGGGCA CTGTGGGTAGACACACATGAAGTCCAAGCATTTAGATGTATAGGTTGATGGTGGTATG TTTTCAGGCTAGATGTATGTACTTCATGCTGTCTACACTAAGAGAGAATGAGAGACAC ACTGAAGAAGCACCAATCATGAATTAGTTTTATATGCTTCTGTTTTATAATTTTGTGA AGCAAAATTTTTTCTCTAGGAAATATTTATTTTAATAATGTTTCAAACATATATAACA ATGCTGTATTTTAAAAGAATGATTATGAATTACATTTGTATAAAATAATTTTTATATT TGAAATATTGACTTTTTATGGCACTAGTATTTCTATGAAATATTATGTTAAAACTGGG ACAGGGGAGAACCTAGGGTGATATTAACCAGGGGCCATGAATCACCTTTTGGTCTGGA GGGAAGCCTTGGGGCTGATGCAGTTGTTGCCCACAGCTGTATGATTCCCAGCCAGCAC AGCCTCTTAGATGCAGTTCTGAAGAAGATGGTACCACCAGTCTGACTGTTTCCATCAA GGGTACACTGCCTTCTCAACTCCAAACTGACTCTTAAGAAGACTGCATTATATTTATT ACTGTAAGAAAATATCACTTGTCAATAAAATCCATACATTTGTGTGAAA | 21 |
| ssRNA2 5'UTR (A32C) | GGGAGACCCAAGCTGGCTAGCGTTTAAACTTCAGCTTGGCAATCCGGTACTGTTGGTA AAGCCACC | 22 |

Nucleotide Analogues

In some embodiments of the synthetic polynucleotide, the polynucleotide may comprise one or more nucleotide analogues. In some embodiments, the nucleotide analogues replace uridines in a sequence. For example, a sequence using standard nucleotides (A, C, U, T, G) may comprises a uridine at a particular position in a sequence. A sequence may instead have a nucleotide analogue in place of the uridine. The nucleotide analogue may have structure that may still be recognized by the cellular translation machinery such that the polynucleotide comprising a nucleotide analogue may still be translated. The nucleotide analogue may be recognized as synonymous with a standard nucleotide. For example, the nucleotide analogue may be recognized as synonymous with uridine and the resulting translation product is generated as if the nucleotide analogue is a uridine. In some embodiments, at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% of nucleotides replacing uridine within said polynucleotide are nucleotide analogues. In some embodiments, fewer than about 15% of nucleotides within said polynucleotide are nucleotide analogues In some fewer than about 30% of the nucleotides are nucleotide analogues. In other cases, fewer than about 27.5%, fewer than about 25%, fewer than about 22.5%, fewer than about 20%, fewer than about 17.5%, fewer than about 15%, fewer than about 12.5%, fewer than about 10%, fewer than about 7.5%, fewer than about 5%, or fewer than about 2.5% of the nucleotides are nucleotide analogues.

A polyribonucleotide can have the same or a mixture of different nucleotide analogues or modified nucleotides. The nucleotide analogues or modified nucleotides can have structural changes that are naturally or not naturally occurring in messenger RNA. A mixture of various analogues or modified nucleotides can be used. For example, one or more analogues within a polynucleotide can have natural modifications, while another part has modifications that are not naturally found in mRNA. Additionally, some analogues or modified ribonucleotides can have a base modification, while other modified ribonucleotides have a sugar modification. In the same way, it is possible that all modifications are base modifications, or all modifications are sugar modifications or any suitable mixture thereof.

A nucleotide analogue or modified nucleotide can be selected from the group comprising pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments of the synthetic polynucleotide, the nucleotide analogue is a purine or pyrimidine analogue. In some cases, a polyribonucleotide of the disclosure comprises a modified pyrimidine, such as a modified uridine. A nucleotide analogue may be a pseudouridine (Ψ). A nucleotide analogue may be a methylpseudouridine. A nucleotide analogue may be a 1-methylpseudouridine ($m^1\Psi$). In some embodiments, the polynucleotide comprises a 1-methylpseudouridine. In some cases a uridine analogue is selected from pseudouridine 1-methylpseudouridine, 2-thiouridine ($s^2U$), 5-methyluridine ($m^5U$), 5-methoxyuridine ($mo^5U$), 4-thiouridine ($s^4U$), 5-bromouridine ($Br^5U$), 2'O-methyluridine (U2'm), 2'-amino-2'-deoxyuridine ($U2'NH_2$), 2'-azido-2'-deoxyuridine ($U2'N_3$), and 2'-fluoro-2'-deoxyuridine (U2'F).

In some embodiments, the synthetic polynucleotide comprises (e.g., one or more) 1-methylpseudouridine. In some embodiments, at least about 80% of nucleotides replacing uridine within said polynucleotide are 1-methylpseudouridine. In some embodiments, at least (about) 5%, 10%, 15%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of nucleotides replacing uridine within said polynucleotide are 1-methylpseudouridine. In some embodiments, 100% of nucleotides replacing uridine within said polynucleotide are 1-methylpseudouridine.

Nucleic Acid Constructs, Vectors, and Engineered Polyribonucleotides

In some embodiments, the present disclosure provides nucleic acid molecules, such as polynucleotides, which encode one or more polypeptides of interest. The term nucleic acid includes any compound and/or substance that comprise a polymer of nucleotides. Nucleotide polymers that contain greater than 50% of ribose bases or ribonucleotide analogues are referred to as polyribonucleotides. Nucleotide polymers may use altered nucleotide usage that encode a protein or functional fragment thereof, such as CFTR. The sequence of the engineered polynucleotides can be derived from, for example, DNA, RNA, mRNA transcripts, genomic DNA, mitochondrial DNA, mitochondrial RNA, or another suitable nucleic acid that comprises the genetic information of a gene of interest. The nucleic acid constructs, vectors, engineered polyribonucleotides, or compositions can be derived from nucleic acids carrying mutated genes and polymorphisms.

In addition to the four canonical ribonucleotides, namely, adenosine, guanosine, cytidine and uridine, several cellular RNAs also contain a number of structurally diverse ribonucleotides. About a hundred structurally different nucleotides or nucleotide analogues have been identified in transfer RNAs (tRNAs), ribosomal RNAs (rRNAs), messenger RNAs (mRNAs) and small nuclear RNAs (snRNAs). In tRNAs, some nucleotides can be important determinants of the specificity and efficiency of aminoacylation and codon recognition. Such structurally diverse ribonucleotides can be a modified ribonucleotide or a nucleotide analogue. In some cases, a polynucleotide of the disclosure is engineered to comprise a ribonucleotide analogue.

In some cases, a nucleic acid construct, a vector, or a polynucleotide is engineered to contain the four classical ribonucleotides and can be modified post-transcriptionally, after being administered to a subject. For instance, in some cases the disclosure provides a composition, vector, or a nucleic acid construct comprising a nucleic acid construct encoding CFTR, wherein fewer than 30% of the nucleic acids encoding CFTR are nucleotide analogues. In other cases, fewer than 27.5%, fewer than 25%, fewer than 22.5%, fewer than 20%, fewer than 17.5%, fewer than 15%, fewer than 12.5%, fewer than 10%, fewer than 7.5%, fewer than 5%, or fewer than 2.5% of the nucleotides encoding CFTR are nucleotide analogues.

Example nucleic acids that can form a polynucleotide of the disclosure include, but are not limited to, ribonucleic acids (RNAs), deoxyribonucleic acids (DNAs), or hybrids thereof. Example modified nucleotides that can form at least a fraction of a polynucleotide of the disclosure include, but are not limited to, pseudouridine (T) and 1-methylpseudouridine (m1Ψ).

A chemical modification can be located on one or more nucleoside(s) or the backbone of the nucleic acid molecule. They can be located on both a nucleoside and a backbone linkage. A modification can be engineered into a polynucleotide in vitro. Modified ribonucleotides and nucleic acid analogues can also be introduced post-transcriptionally by covalent modification of the classical ribonucleotides.

A nucleic acid construct, a vector, or an engineered polyribonucleotide of the disclosure can comprise purine and pyrimidine analogues. In some cases, a polyribonucleotide of the disclosure comprises a modified pyrimidine, such as a modified uridine. In some cases, a uridine analogue is selected from pseudouridine (Ψ), 1-methylpseudouridine (m1Ψ), 2-thiouridine (s2U), 5-methyluridine (m5U), 5-methoxyuridine (mo5U), 4-thiouridine (s4U), 5-bromouridine (Br5U), 2'O-methyluridine (U2'm), 2'-amino-2'-deoxyuridine (U2'NH2), 2'-azido-2'-deoxyuridine (U2'N3), and 2'-fluoro-2'-deoxyuridine (U2F).

In some instances, the nucleic acid construct(s), vector(s), engineered polyribonucleotide(s), or composition(s) encodes CFTR or a variant thereof at a level that is increased by a factor of at least about 1.5 as compared to levels within cells exposed to a composition comprising a nucleic acid construct that does not include the codons encoding CFTR or a variant thereof. In some cases, the factor is at least about 1.1, at least about 1.2, at least about 1.3, at least about 1.4, at least about 1.5, at least about 2, at least about 3, at least about 4, at least about 5, at least about 10, at least about 20, at least about 30, at least about 40, at least about 50, at least about 60, at least about 70, at least about 80, at least about 90, or at least about 100.

A polyribonucleotide can have the same or a mixture of different nucleotide analogues or modified nucleotides. The nucleotide analogues or modified nucleotides can have structural changes that are naturally or not naturally occurring in messenger RNA. A mixture of various analogues or modified nucleotides can be used. For example, one or more analogues within a polynucleotide can have natural modifications, while another part has modifications that are not naturally found in mRNA. Additionally, some analogues or modified ribonucleotides can have a base modification, while other modified ribonucleotides have a sugar modification. In the same way, it is possible that all modifications are base modifications or all modifications are sugar modifications or any suitable mixture thereof.

A nucleotide analogue or modified nucleotide can be selected from the group comprising pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some cases, at least about 5% of the nucleic acid construct(s), a vector(s), engineered polyribonucleotide(s), or compositions includes non-naturally occurring (e.g., modified, analogues, or engineered) uridine, adenosine, guanine, or cytosine, such as the nucleotides described herein. In some cases, 100% of the modified nucleotides in the composition are either 1-methylpseudouridine or pseudouridine. In some cases, at least about 10%, 15%, 20%, 25%, 30%, 35%, 40%, 45%, 50%, 55%, 60%, 65%, 70%, 75%, 80%, 85%, 90%, 95% of the nucleic acid construct(s), a vector(s), engineered polyribonucleotide(s), or compositions includes non-naturally occurring uracil, adenine, guanine, or cytosine. In some cases, at most about 99%, 95%, 90%, 85%, 80%, 75%, 70%, 65%, 60%, 55%, 50%, 45%, 40%, 35%, 30%, 25%, 20%, 15%, 10%, 5%, 1%, of the nucleic acid construct(s), a vector(s), engineered polyribonucleotide(s), or compositions includes non-naturally occurring uracil, adenine, guanine, or cytosine.

A nucleic acid construct(s), a vector(s), or an engineered polyribonucleotide(s) of the disclosure can comprise one or more promoter sequences and any associated regulatory sequences. A promoter sequence and/or an associated regulatory sequence can comprise any number of modified or unmodified nucleotides, and any number of nucleic acid analogues. Promoter sequences and/or any associated regulatory sequences can comprise, for example, at least 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 11 bases or base pairs, 12 bases or base pairs, 13 bases or base pairs, 14 bases or base pairs, 15 bases or base pairs, 16 bases or base pairs, 17 bases or base pairs, 18 bases or base pairs, 19 bases or base pairs, 20 bases or base pairs, 21 bases or base pairs, 22 bases or base pairs, 23 bases or base pairs, 24 bases or base pairs, 25 bases or base pairs, 26 bases or base pairs, 27 bases or base pairs, 28 bases or base pairs, 29 bases or base pairs, 30 bases or base pairs, 35 bases or base pairs, 40 bases or base pairs, 50 bases or base pairs, 75 bases or base pairs, 100 bases or base pairs, 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, at least 10000 bases or base pairs or more. A promoter sequence and/or an associated regulatory sequence can comprise any number of modified or unmodified nucleotides, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 75 bases or base pairs, 50 bases or base pairs, 40 bases or base pairs, 35 bases or base pairs, 30 bases or base pairs, 29 bases or base pairs, 28 bases or base pairs, 27 bases or base pairs, 26 bases or base pairs, 25 bases or base pairs, 24 bases or base pairs, 23 bases or base pairs, 22 bases or base pairs, 21 bases or base pairs, 20 bases or base pairs, 19 bases or base pairs, 18 bases or base pairs, 17 bases or base pairs, 16 bases or base pairs, 15 bases or base pairs, 14 bases or base pairs, 13 bases or base pairs, 12 bases or base pairs, 11 bases or base pairs, 10 bases or base pairs, 9 bases or base pairs, 8 bases or base pairs, 7 bases or base pairs, 6 bases or base pairs, 5 bases or base pairs, 4 bases or base pairs, 3 bases or base pairs or 2 bases or base pairs.

In some cases, less than all of the nucleotides in the promoter sequence or associated regulatory region are nucleotide analogues or modified nucleotides. For instance, in some cases, less than or equal to 99%, 95%, 90%, 85%, 80%, 75%, 70%, 65%, 60%, 55%, 50%, 45%, 40%, 35%, 30%, 25%, 20%, 15%, 10%, or 5% of the nucleotides in a promoter or associated regulatory region. In some cases, all of the nucleotides in a promoter or associated regulatory region are nucleic acid analogues or modified nucleotides.

A nucleic acid construct(s), a vector(s), an engineered polyribonucleotide(s), or compositions of the disclosure can comprise an engineered 5' cap structure, or a 5'-cap can be added to a polyribonucleotide intracellularly. The 5' cap structure of an mRNA can be involved in binding to the mRNA Cap Binding Protein (CBP), which is responsible for mRNA stability in the cell and translation competency through the association of CBP with poly(A) binding protein to form the mature pseudo-circular mRNA species. The 5' cap structure can also be involved in nuclear export, increases in mRNA stability, and in assisting the removal of 5' proximal introns during mRNA splicing.

A nucleic acid construct(s), a vector(s), or an engineered polyribonucleotide(s) can be 5'-end capped generating a 5'-GpppN-3'-triphosphate linkage between a terminal guanosine cap residue and the 5'-terminal transcribed sense nucleotide of the mRNA molecule. The cap-structure can comprise a modified or unmodified 7-methylguanosine linked to the first nucleotide via a 5'-5' triphosphate bridge. This 5'-guanylate cap can then be methylated to generate an N7-methyl-guanylate residue (Cap-0 structure). The ribose sugars of the terminal and/or anteterminal transcribed nucleotides of the 5' end of the mRNA may optionally also be 2'-O-methylated (Cap-1 structure). 5'-decapping through hydrolysis and cleavage of the guanylate cap structure may target a nucleic acid molecule, such as an mRNA molecule, for degradation.

In some cases, a cap can comprise further modifications, including the methylation of the 2' hydroxy-groups of the first 2 ribose sugars of the 5' end of the mRNA. For instance, an eukaryotic cap-1 has a methylated 2'-hydroxy group on the first ribose sugar, while a cap-2 has methylated 2'-hydroxy groups on the first two ribose sugars. The 5' cap can be chemically similar to the 3' end of an RNA molecule (the 5' carbon of the cap ribose is bonded, and the free 3'-hydroxyls on both 5'- and 3'-ends of the capped transcripts. Such double modification can provide significant resistance to 5' exonucleases. Non-limiting examples of 5' cap structures that can be used with an engineered polyribonucleotide include, but are not limited to, m7G(5')ppp(5')N(Cap-0), m7G(5')ppp(5')N1mpNp (Cap-1), and m7G(5')-ppp(5) N1mpN2mp (Cap-2).

Modifications to the modified mRNA of the present disclosure may generate a non-hydrolyzable cap structure preventing decapping and thus increasing mRNA half-life while facilitating efficient translation. Because cap structure hydrolysis requires cleavage of 5'-ppp-5' triphosphate linkages, modified nucleotides may be used during the capping reaction. For example, a Vaccinia Capping Enzyme from New England Biolabs (Ipswich, Mass.) may be used with guanosine α-thiophosphate nucleotides according to the manufacturer's instructions to create a phosphorothioate linkage in the 5'-ppp-5' cap. Additional modified guanosine nucleotides may be used such as α-methyl-phosphonate and seleno-phosphate nucleotides. Additional modifications include, but are not limited to, 2'-O-methylation of the ribose sugars of 5'-terminal and/or 5'-anteterminal nucleotides of the mRNA on the 2'-hydroxyl group of the sugar ring. Multiple distinct 5'-cap structures can be used to generate the 5'-cap of a polyribonucleotide.

The modified mRNA may be capped post-transcriptionally. According to the present disclosure, 5' terminal caps may include endogenous caps or cap analogues. According to the present disclosure, a 5' terminal cap may comprise a guanine analogue. Useful guanine analogues include, but are not limited to, inosine, N1-methyl-guanosine, 2' fluoro-guanosine, 7-deaza-guanosine, 8-oxo-guanosine, 2-amino-guanosine, LNA-guanosine, and 2-azido-guanosine.

Further, a nucleic acid construct(s), a vector(s), or an engineered polyribonucleotide(s) can contain one or more internal ribosome entry site(s) (IRES). IRES sequences can initiate protein synthesis in absence of the 5' cap structure. An IRES sequence can also be the sole ribosome binding site, or it can serve as one of multiple ribosome binding sites of an mRNA. Engineered polyribonucleotides containing more than one functional ribosome binding site can encode several peptides or polypeptides that are translated by the ribosomes ("polycistronic or multicistronic polynucleotides"). An engineered polynucleotide described here can comprise at least 1 IRES sequence, two IRES sequences, three IRES sequences, four IRES sequences, five IRES sequences, six IRES sequences, seven IRES sequences, eight IRES sequences, nine IRES sequences, ten IRES sequences, or another suitable number are present in an engineered polyribonucleotide. Examples of IRES sequences that can be used according to the present disclosure include without limitation, those from tobacco etch virus (TEV), picornaviruses (e.g., FMDV), pest viruses (CFFV), polio viruses (PV), encephalomyocarditis viruses (EMCV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV). An IRES sequence can be derived, for example, from commercially available vectors such as the IRES sequences available from Clontech™, GeneCopoeia™, or Sigma-Aldrich™. IRES sequences can be, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or 10000 bases or base pairs. IRES sequences can at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 50 bases or base pairs, or 10 bases or base pairs.

A nucleic acid construct(s), a vector(s), or an engineered polyribonucleotide(s) of the disclosure can comprise one or more untranslated regions. An untranslated region can comprise any number of modified or unmodified nucleotides. Untranslated regions (UTRs) of a gene are transcribed but not translated into a polypeptide. In some cases, an untranslated sequence can increase the stability of the nucleic acid molecule and the efficiency of translation. The regulatory features of a UTR can be incorporated into the modified mRNA molecules of the present disclosure, for instance, to increase the stability of the molecule. The specific features can also be incorporated to ensure controlled down-regulation of the transcript in case they are misdirected to undesired organs sites. Some 5' UTRs play roles in translation initiation. A 5' UTR can comprise a Kozak sequence which is involved in the process by which the ribosome initiates translation of many genes. Kozak sequences can have the consensus GCC(R)CCAUGG, where R is a purine (adenine or guanine) that is located three bases upstream of the start codon (AUG). A Kozak sequence may comprise GCCACC. 5' UTRs may form secondary structures which are involved in binding of translation elongation factor. In some cases, one can increase the stability and protein production of the engineered polynucleotide molecules of the disclosure, by engineering the features typically found in abundantly expressed genes of specific target organs. For example, introduction of 5'UTR of liver-expressed mRNA, such as albumin, serum amyloid A, Apolipoprotein AB/E, transferrin, alpha fetoprotein, erythropoietin, or Factor VIII, can be used to increase expression of an engineered polynucleotide in a liver. Likewise, use of 5' UTR from muscle proteins (MyoD, Myosin, Myoglobin, Myogenin, Herculin), for endothelial cells (Tie-1, CD36), for myeloid cells (C/EBP, AML1, G-CSF, GM-CSF, CD1 lb, MSR, Fr-1, i-NOS), for leukocytes (CD45, CD18), for adipose tissue (CD36, GLUT4, ACRP30, adiponectin) and for lung epithelial cells (SP-A/B/C/D) can be used to increase expression of an engineered polynucleotide in a desired cell or tissue.

Other non-UTR sequences can be incorporated into the 5' (or 3' UTR) UTRs of the polyribonucleotides of the present disclosure. The 5' and/or 3' UTRs can provide stability and/or translation efficiency of polyribonucleotides. For example, introns or portions of intron sequences can be incorporated into the flanking regions of an engineered polyribonucleotide. Incorporation of intronic sequences can also increase the rate of translation of the polyribonucleotide.

3' UTRs may have stretches of Adenosines and Uridines embedded therein. These AU rich signatures are particularly prevalent in genes with high rates of turnover. Based on their sequence features and functional properties, the AU rich elements (AREs) can be separated into classes: Class I AREs contain several dispersed copies of an AUUUA motif within U-rich regions. C-Myc and MyoD contain class I AREs. Class II AREs possess two or more overlapping UUAUUUA (U/A)(U/A) nonamers. Molecules containing this type of AREs include GM-CSF and TNF-α. Class III ARES are less well defined. These U rich regions do not contain an AUUUA motif c-Jun and Myogenin are two well-studied examples of this class. Proteins binding to the AREs may destabilize the messenger, whereas members of the ELAV family, such as HuR, may increase the stability of mRNA. HuR may bind to AREs of all the three classes. Engineering the HuR specific binding sites into the 3' UTR of nucleic acid molecules can lead to HuR binding and thus, stabilization of the message in vivo.

Engineering of 3' UTR AU rich elements (AREs) can be used to modulate the stability of an engineered polyribonucleotide. One or more copies of an ARE can be engineered into a polyribonucleotide to modulate the stability of a polyribonucleotide. AREs can be identified, removed or mutated to increase the intracellular stability and thus increase translation and production of the resultant protein. Transfection experiments can be conducted in relevant cell lines, using engineered polyribonucleotides and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

An untranslated region can comprise any number of nucleotides. An untranslated region can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. An untranslated region can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length.

An engineered polyribonucleotide of the disclosure can comprise one or more introns. An intron can comprise any number of modified or unmodified nucleotides. An intron can comprise, for example, at least 1 base or base pair, 50 bases or base pairs, 100 bases or base pairs, 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, or 5000 bases or base pairs. In some cases, an intron can comprise, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs.

In some cases, a percentage of the nucleotides in an intron are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in an intron are modified. In some cases, all of the nucleotides in an intron are modified.

An engineered polyribonucleotide of the disclosure can comprise a polyA sequence. A polyA sequence (e.g., polyA tail) can comprise any number of nucleotides. A polyA sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. In some examples, a polyA sequence is at least about 100, 110, 120, 130, 140, 150, 160, 170, 180, 190, or 200 nucleotides in length. A polyA sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length. A polyA sequence can comprise a length of at most 100 bases or base pairs, 90 bases or base pairs, 80 bases or base pairs, 70 bases or base pairs, 60 bases or base pairs, 50 bases or base pairs, 40 bases or base pairs, 30 bases or base pairs, 20 bases or base pairs, 10 bases or base pairs, or 5 bases or base pairs.

In some cases, a percentage of the nucleotides in a poly-A sequence are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a poly-A sequence are modified. In some cases, all of the nucleotides in a poly-A are modified.

A linker sequence can comprise any number of nucleotides. A linker can be attached to the modified nucleobase at an N-3 or C-5 position. The linker attached to the nucleobase can be diethylene glycol, dipropylene glycol, triethylene glycol, tripropylene glycol, tetraethylene glycol, tetraethylene glycol, divalent alkyl, alkenyl, alkynyl moiety, ester, amide, or an ether moiety. A linker sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. A linker sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or at least 10000 bases or base pairs in length. A linker at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs in length.

In some cases, a percentage of the nucleotides in a linker sequence are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a linker sequence are modified. In some cases, all of the nucleotides in a linker sequence are modified.

In some cases, a nucleic acid construct(s), a vector(s), or an engineered polyribonucleotide(s) can include at least one stop codon before the 3' untranslated region (UTR). In some cases, a nucleic acid construct(s), a vector(s), or an engineered polyribonucleotide(s) includes multiple stop codons. The stop codon can be selected from TGA, TAA and TAG. The stop codon may be modified or unmodified. In some cases, the nucleic acid construct(s), vector(s), or engineered polyribonucleotide(s) includes the stop codon TGA and one additional stop codon. In some cases, the nucleic acid construct(s), vector(s), or engineered polyribonucleotide(s) includes the addition of the TAA stop codon.

Lipid Compositions

In some embodiments of the (e.g., pharmaceutical) composition, the lipid composition comprises: (1) an ionizable cationic lipid; and (2) a selective organ targeting (SORT) lipid separate from said ionizable cationic lipid. In some embodiments, the (e.g., pharmaceutical) composition further comprises a zwitterionic lipid (e.g. a phospholipid).

Ionizable Cationic Lipids

In some embodiments of the lipid composition of the present application, the lipid composition comprises an ionizable cationic lipid. In some embodiments, the cationic ionizable lipids contain one or more groups which is protonated at physiological pH but may deprotonated and has no charge at a pH above 8, 9, 10, 11, or 12. The ionizable cationic group may contain one or more protonatable amines which are able to form a cationic group at physiological pH. The cationic ionizable lipid compound may also further comprise one or more lipid components such as two or more fatty acids with $C_6$-$C_{24}$ alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

In some embodiments of the lipid composition of the present application, the ionizable cationic lipids refer to lipid and lipid-like molecules with nitrogen atoms that can acquire charge (pKa). These lipids may be known in the literature as cationic lipids. These molecules with amino groups typically have between 2 and 6 hydrophobic chains, often alkyl or alkenyl such as $C_6$-$C_{24}$ alkyl or alkenyl groups, but may have at least 1 or more that 6 tails. In some embodiments, these cationic ionizable lipids are dendrimers, which are a polymer exhibiting regular dendritic branching, formed by the sequential or generational addition of branched layers to or from a core and are characterized by a core, at least one interior branched layer, and a surface branched layer. (See *Petar R. Dvornic and Donald A. Tomalia in Chem. in Britain,* 641-645, August 1994.) In other embodiments, the term "dendrimer" as used herein is intended to include, but is not limited to, a molecular architecture with an interior core, interior layers (or "generations") of repeating units regularly attached to this initiator core, and an exterior surface of terminal groups attached to the outermost generation. A "dendron" is a species of dendrimer having branches emanating from a focal point which is or can be joined to a core, either directly or through a linking moiety to form a larger dendrimer. In some embodiments, the dendrimer structures have radiating repeating groups from a central core which doubles with each repeating unit for each branch. In some embodiments, the dendrimers described herein may be described as a small molecule, medium-sized molecules, lipids, or lipid-like material. These terms may be used to described compounds described herein which have a dendron like appearance (e.g. molecules which radiate from a single focal point).

While dendrimers are polymers, dendrimers may be preferable to traditional polymers because they have a controllable structure, a single molecular weight, numerous and controllable surface functionalities, and traditionally adopt a globular conformation after reaching a specific generation. Dendrimers can be prepared by sequentially reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bioattachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible resulting from only the first condensation reaction with the amine and not the second condensation reaction with the thiol.

Preparation of dendrimers requires a level of synthetic control achieved through series of stepwise reactions comprising building the dendrimer by each consecutive group. Dendrimer synthesis can be of the convergent or divergent type. During divergent dendrimer synthesis, the molecule is assembled from the core to the periphery in a stepwise process involving attaching one generation to the previous and then changing functional groups for the next stage of reaction. Functional group transformation is necessary to prevent uncontrolled polymerization. Such polymerization would lead to a highly branched molecule that is not monodisperse and is otherwise known as a hyperbranched polymer. Due to steric effects, continuing to react dendrimer repeat units leads to a sphere shaped or globular molecule, until steric overcrowding prevents complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some embodiments of the lipid composition of the present application, the dendrimers are assembled using the differential reactivity of the acrylate and methacrylate groups with amines and thiols. The dendrimers may include secondary or tertiary amines and thioethers formed by the reaction of an acrylate group with a primary or secondary amine and a methacrylate with a mercapto group. Additionally, the repeating units of the dendrimers may contain groups which are degradable under physiological conditions. In some embodiments, these repeating units may contain one or more germinal diethers, esters, amides, or disulfides groups. In some embodiments, the core molecule is a monoamine which allows dendritic polymerization in only one direction. In other embodiments, the core molecule is a polyamine with multiple different dendritic branches which each may comprise one or more repeating units. The dendrimer may be formed by removing one or more hydrogen atoms from this core. In some embodiments, these hydrogen atoms are on a heteroatom such as a nitrogen atom. In some embodiments, the terminating group is a lipophilic groups such as a long chain alkyl or alkenyl group. In other embodiments, the terminating group is a long chain haloalkyl or haloalkenyl group. In other embodiments, the terminating group is an aliphatic or aromatic group containing an ionizable group such as an amine ($—NH_2$) or a carboxylic acid ($—CO_2H$). In still other embodiments, the terminating group is an aliphatic or aromatic group containing one or more hydrogen bond donors such as a hydroxide group, an amide group, or an ester.

The cationic ionizable lipids of the present application may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Cationic ionizable lipids may occur as racemates and racemic mixtures, single enantiomers, diastereomeric mixtures and individual diastereomers. In some embodiments, a single diastereomer is obtained. The chiral centers of the cationic ionizable lipids of the present application can have the S or the R configuration. Furthermore, it is contemplated that one or more of the cationic ionizable lipids may be present as constitutional isomers. In some embodiments, the compounds have the same formula but different connectivity to the nitrogen atoms of the core. Without wishing to be bound by any theory, it is believed that such cationic ionizable lipids exist because the starting monomers react first with the primary amines and then statistically with any secondary amines present. Thus, the constitutional isomers may present the fully reacted primary amines and then a mixture of reacted secondary amines.

Chemical formulas used to represent cationic ionizable lipids of the present application will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given formula, and regardless of which one is most prevalent, all tautomers of a given chemical formula are intended.

The cationic ionizable lipids of the present application may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the cationic ionizable lipids of the present application are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a cationic ionizable lipids provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

In some embodiments of the lipid composition of the present application, the ionizable cationic lipid is a dendrimer or dendron. In some embodiments, the ionizable cationic lipid comprises an ammonium group which is positively charged at physiological pH and contains at least two hydrophobic groups. In some embodiments, the ammonium group is positively charged at a pH from about 6 to about 8. In some embodiments, the ionizable cationic lipid is a dendrimer or dendron. In some embodiments, the ionizable cationic lipid comprises at least two $C_6$-$C_{24}$ alkyl or alkenyl groups.

Dendrimers of Formula (I)

In some embodiments of the lipid composition, the ionizable cationic lipid comprises at least two $C_8$-$C_{24}$ alkyl groups. In some embodiments, the ionizable cationic lipid is a dendrimer further defined by the formula:

Core-Repeating Unit-Terminating Group(D-I)

wherein the core is linked to the repeating unit by removing one or more hydrogen atoms from the core and replacing the atom with the repeating unit and wherein:

the core has the formula:

(D-II)

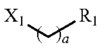

wherein:

$X_1$ is amino or alkylamino$_{(C\leq12)}$, dialkylamino$_{(C\leq12)}$, heterocycloalkyl$_{(C\leq12)}$, heteroaryl$_{(C\leq12)}$, or a substituted version thereof;

$R_1$ is amino, hydroxy, or mercapto, or alkylamino$_{(C\leq12)}$, dialkylamino$_{(C\leq12)}$, or a substituted version of either of these groups; and a is 1, 2, 3, 4, 5, or 6; or the core has the formula:

(D-III)

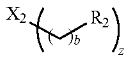

wherein:

$X_2$ is $N(R_5)_y$;

$R_5$ is hydrogen, alkyl$_{(C\leq18)}$, or substituted alkyl$_{(C\leq18)}$; and y is 0, 1, or 2, provided that the sum of y and z is 3;

$R_2$ is amino, hydroxy, or mercapto, or alkylamino$_{(C\leq12)}$, dialkylamino$_{(C\leq12)}$, or a substituted version of either of these groups;

b is 1, 2, 3, 4, 5, or 6; and z is 1, 2, 3; provided that the sum of z and y is 3; or the core has the formula:

(D-IV)

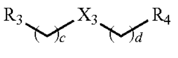

wherein:

$X_3$ is —$NR_6$—, wherein $R_6$ is hydrogen, alkyl$_{(C\leq8)}$, or substituted alkyl$_{(C\leq8)}$, —O—, or alkylaminodiyl$_{(C\leq8)}$, alkoxydiyl$_{(C\leq8)}$, arenediyl$_{(C\leq8)}$, heteroarenediyl$_{(C\leq8)}$, heterocycloalkanediyl$_{(C\leq8)}$, or a substituted version of any of these groups;

$R_3$ and $R_4$ are each independently amino, hydroxy, or mercapto, or alkylamino$_{(C\leq12)}$, dialkylamino$_{(C\leq12)}$, or a substituted version of either of these groups; or a group of the formula: $—N(R_f)_f(CH_2CH_2N(R_c))_eR_d$,

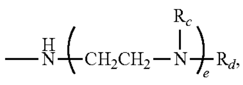 , 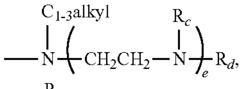 , or

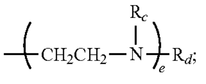 ;

wherein:

e and f are each independently 1, 2, or 3; provided that the sum of e and f is 3;

$R_c$, $R_d$, and $R_f$ are each independently hydrogen, alkyl$_{(C\leq6)}$, or substituted alkyl$_{(C\leq6)}$;

c and d are each independently 1, 2, 3, 4, 5, or 6; or the core is alkylamine$_{(C\leq18)}$, dialkylamine$_{(C\leq36)}$, heterocycloalkane$_{(C\leq12)}$, or a substituted version of any of these groups;

wherein the repeating unit comprises a degradable diacyl and a linker;

the degradable diacyl group has the formula:

(D-VII)

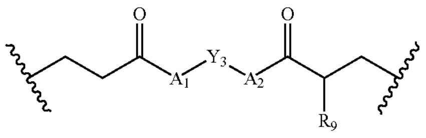

wherein:

$A_1$ and $A_2$ are each independently —O—, —S—, or —$NR_a$—, wherein:

$R_a$ is hydrogen, $alkyl_{(C\leq6)}$, or substituted $alkyl_{(C\leq6)}$;

$Y_3$ is $alkanediyl_{(C\leq12)}$, $alkenediyl_{(C\leq12)}$, $arenediyl_{(C\leq12)}$, or a substituted version of any of these groups; or a group of the formula:

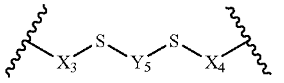 or

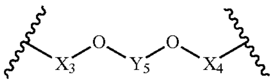

wherein:

$X_3$ and $X_4$ are $alkanediyl_{(C\leq12)}$, $alkenediyl_{(C\leq12)}$, $arenediyl_{(C\leq12)}$, or a substituted version of any of these groups;

$Y_5$ is a covalent bond, $alkanediyl_{(C\leq12)}$, $alkenediyl_{(C\leq12)}$, $arenediyl_{(C\leq12)}$, or a substituted version of any of these groups; and $R_9$ is $alkyl_{(C\leq8)}$ or substituted $alkyl_{(C\leq8)}$;

the linker group has the formula:

(D-VI)

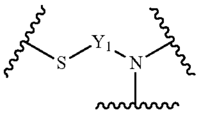

wherein:

$Y_1$ is $alkanediyl_{(C\leq12)}$, $alkenediyl_{(C\leq12)}$, $arenediyl_{(C\leq12)}$, or a substituted version of any of these groups; and wherein when the repeating unit comprises a linker group, then the linker group comprises an independent degradable diacyl group attached to both the nitrogen and the sulfur atoms of the linker group if n is greater than 1, wherein the first group in the repeating unit is a degradable diacyl group, wherein for each linker group, the next repeating unit comprises two degradable diacyl groups attached to the nitrogen atom of the linker group; and wherein n is the number of linker groups present in the repeating unit; and the terminating group has the formula:

(D-VIII)

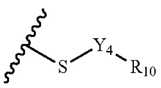

wherein:

$Y_4$ is $alkanediyl_{(C\leq18)}$ or an $alkanediyl_{(C\leq18)}$ wherein one or more of the hydrogen atoms on the $alkanediyl_{(C\leq18)}$ has been replaced with —OH, —F, —Cl, —Br, —I, —SH, —$OCH_3$, —$OCH_2CH_3$, —$SCH_3$, or —OC(O)$CH_3$;

$R_{10}$ is hydrogen, carboxy, hydroxy, or $aryl_{(C\leq12)}$, $alkylamino_{(C\leq12)}$, $dialkylamino_{(C\leq12)}$, N-$heterocycloalkyl_{(C\leq12)}$, —C(O)N($R_{11}$)-$alkanediyl_{(C\leq6)}$-$heterocycloalkyl_{(C\leq12)}$, —C(O)-alkyl-$amino_{(C\leq12)}$, —C(O)-$dialkylamino_{(C\leq12)}$, —C(O)—N-$heterocycloalkyl_{(C\leq12)}$, wherein:

$R_{11}$ is hydrogen, $alkyl_{(C\leq6)}$, or substituted $alkyl_{(C\leq6)}$;

wherein the final degradable diacyl in the chain is attached to a terminating group;

n is 0, 1, 2, 3, 4, 5, or 6;

or a pharmaceutically acceptable salt thereof. In some embodiments, the terminating group is further defined by the formula:

(D-VIII)

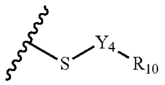

wherein:

$Y_4$ is $alkanediyl_{(C\leq18)}$; and $R_{10}$ is hydrogen. In some embodiments, $A_1$ and $A_2$ are each independently —O— or —$NR_a$—.

In some embodiments of the dendrimer of formula (D-I), the core is further defined by the formula:

(D-III)

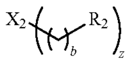

wherein:

$X_2$ is $N(R_5)_y$;

$R_5$ is hydrogen or $alkyl_{(C\leq8)}$, or substituted $alkyl_{(C\leq18)}$; and y is 0, 1, or 2, provided that the sum of y and z is 3;

$R_2$ is amino, hydroxy, or mercapto, or $alkylamino_{(C\leq12)}$, $dialkylamino_{(C\leq12)}$, or a substituted version of either of these groups;

b is 1, 2, 3, 4, 5, or 6; and z is 1, 2, 3; provided that the sum of z and y is 3.

In some embodiments of the dendrimer of formula (D-I), the core is further defined by the formula:

(D-IV)

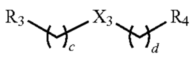

wherein:

$X_3$ is —$NR_6$—, wherein $R_6$ is hydrogen, $alkyl_{(C\leq8)}$, or substituted $alkyl_{(C\leq8)}$, —O—, or $alkylaminodiyl_{(C\leq8)}$, $alkoxydiyl_{(C\leq8)}$, $arenediyl_{(C\leq8)}$, $heteroarenediyl_{(C\leq8)}$, $heterocycloalkanediyl_{(C\leq8)}$, or a substituted version of any of these groups;

$R_3$ and $R_4$ are each independently amino, hydroxy, or mercapto, or $alkylamino_{(C\leq12)}$, $dialkylamino_{(C\leq12)}$, or a substituted version of either of these groups; or a group of the formula: —$N(R_f)_f(CH_2CH_2N(R_c))_eR_d$,

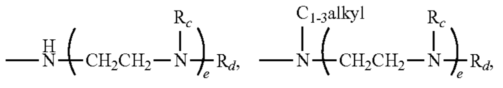

or

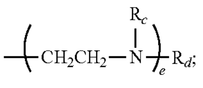

wherein:

e and f are each independently 1, 2, or 3; provided that the sum of e and f is 3;

$R_c$, $R_d$, and $R_f$ are each independently hydrogen, $alkyl_{(C\leq 6)}$, or substituted $alkyl_{(C\leq 6)}$;

c and d are each independently 1, 2, 3, 4, 5, or 6.

In some embodiments of the dendrimer of formula (I), the terminating group is represented by the formula:

(D-VIII)

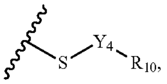

wherein:

$Y_4$ is $alkanediyl_{(C\leq 18)}$; and $R_{10}$ is hydrogen.

In some embodiments of the dendrimer of formula (D-I), the core is further defined as:

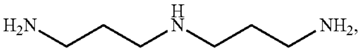

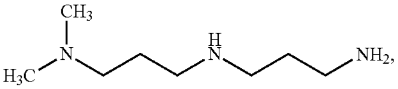

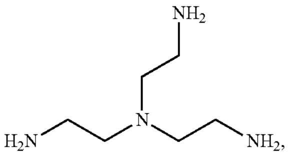

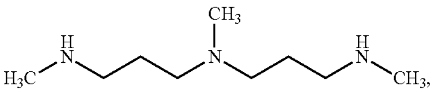

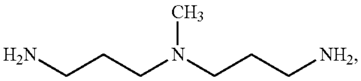

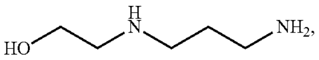

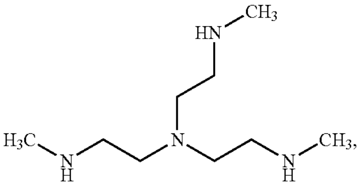

-continued

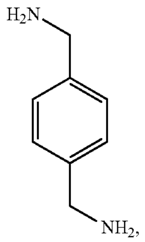

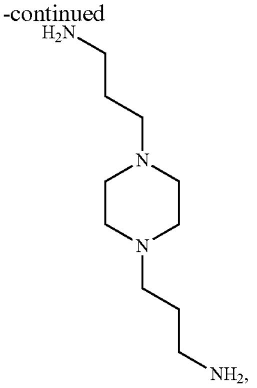

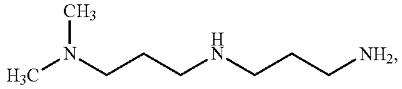

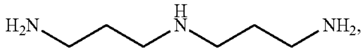

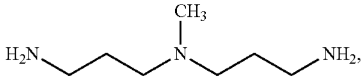

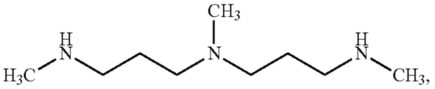

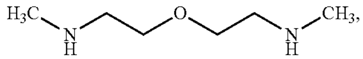

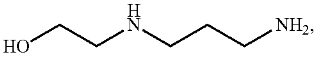

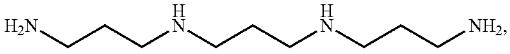

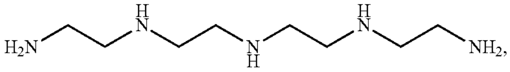

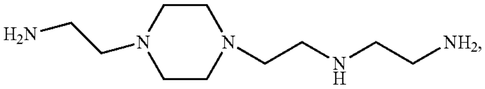

or

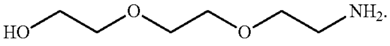

In some embodiments of the dendrimer of formula (D-I), the degradable diacyl is further defined as:

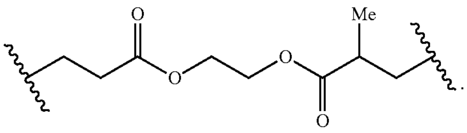 [SMILES: *CCC(=O)OCCOC(=O)C(C)C*]

In some embodiments of the dendrimer of formula (D-I), the linker is further defined as (D-VI)

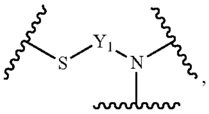

wherein $Y_1$ is $alkanediyl_{(C\leq 8)}$ or substituted $alkanediyl_{(C\leq 8)}$.

In some embodiments of the dendrimer of formula (D-I), the dendrimer is selected from the group consisting of:

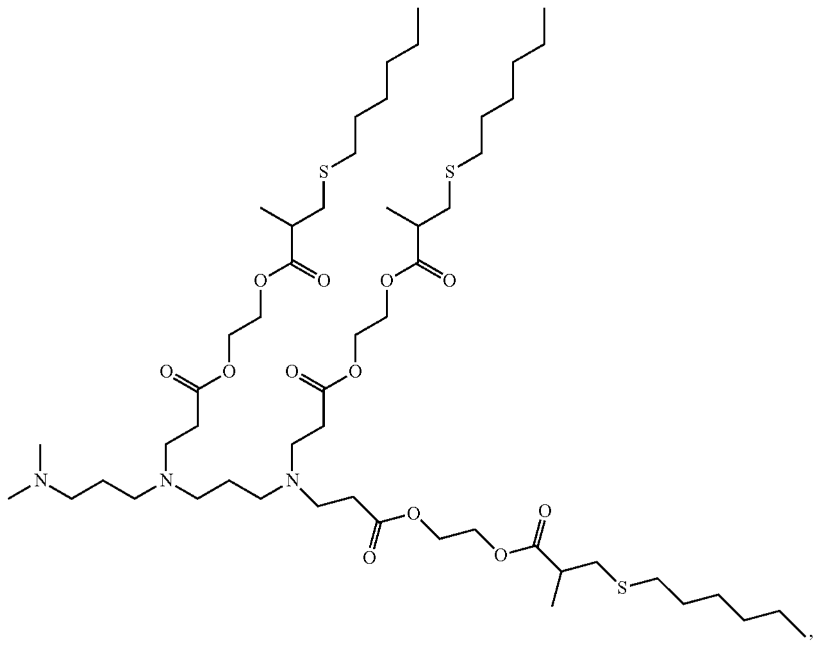
,
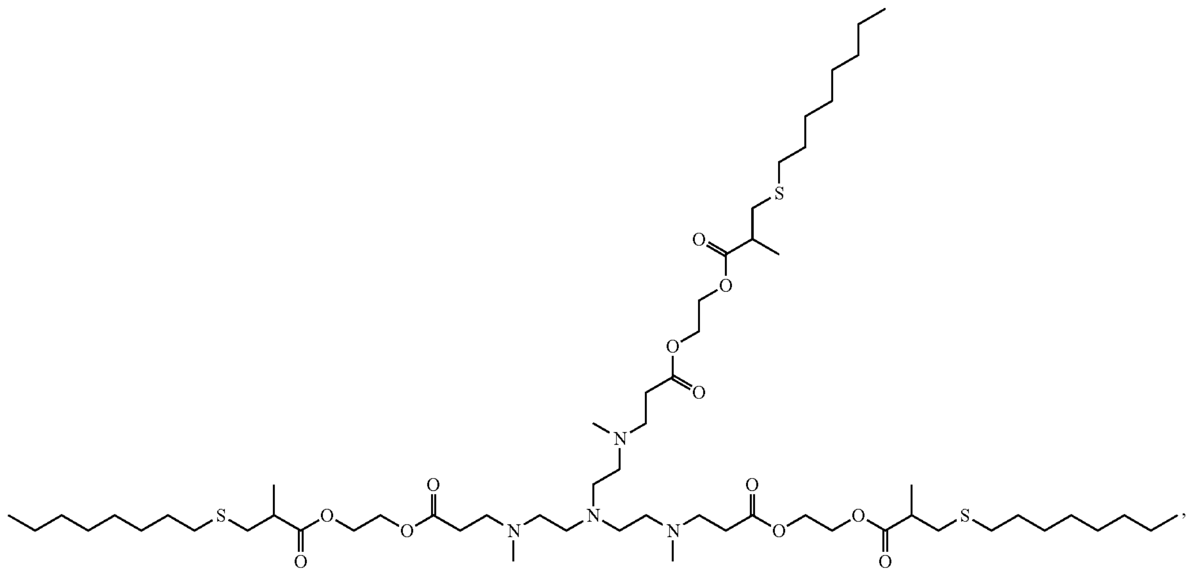
,
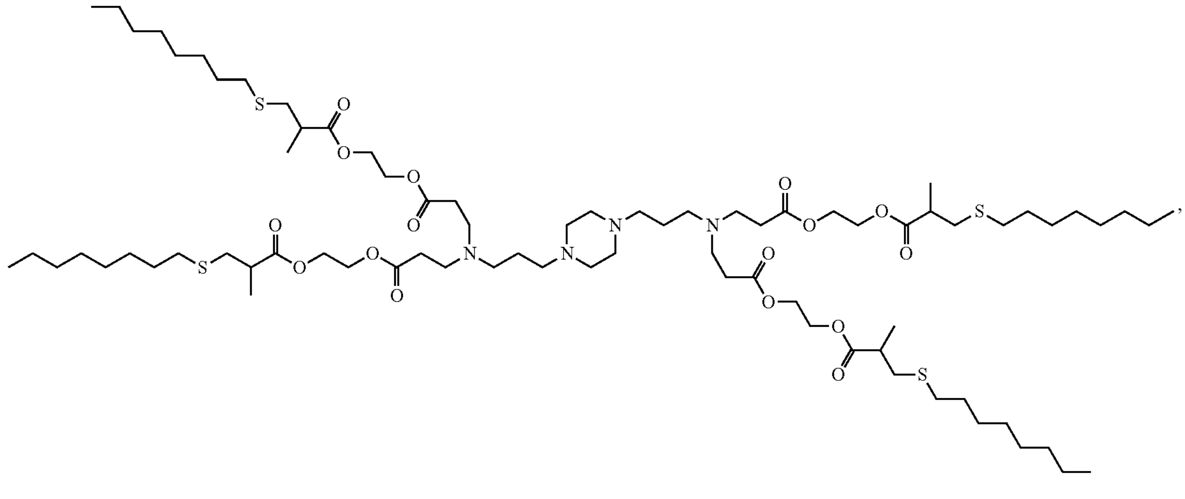
,

-continued
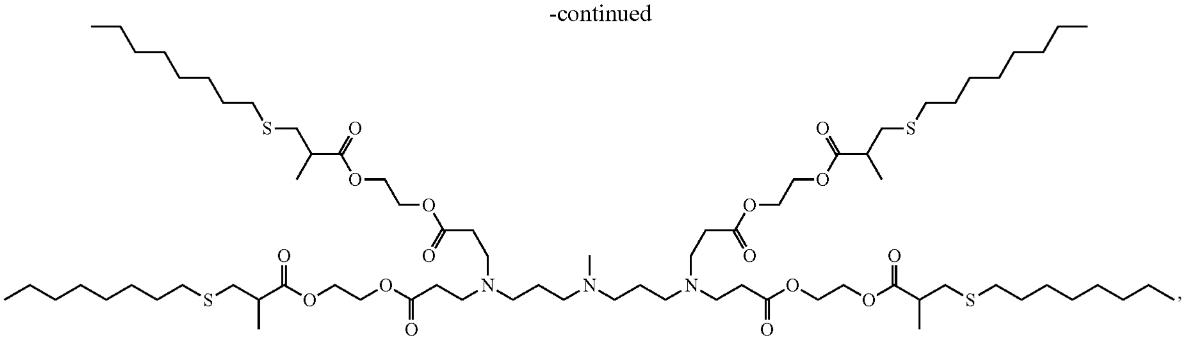
,
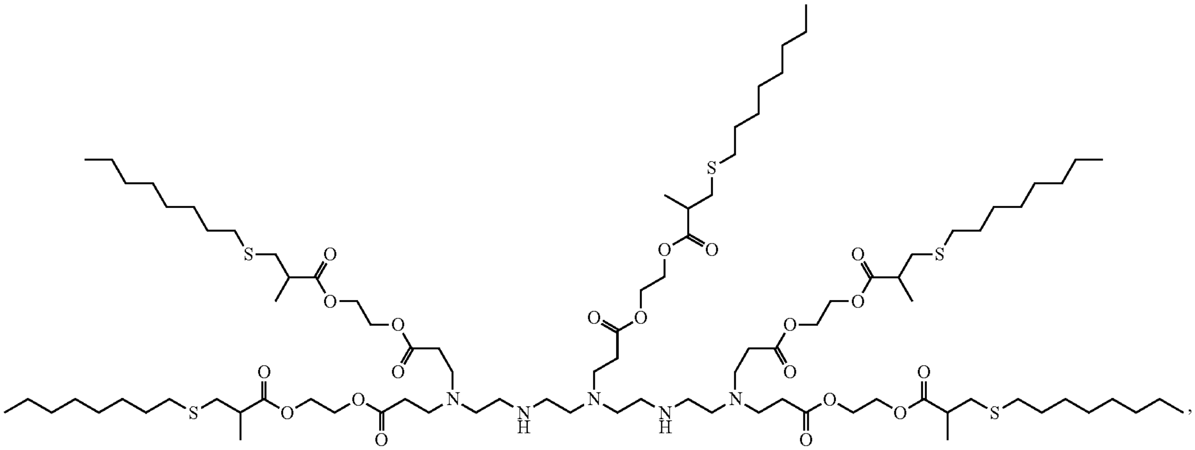
,
or
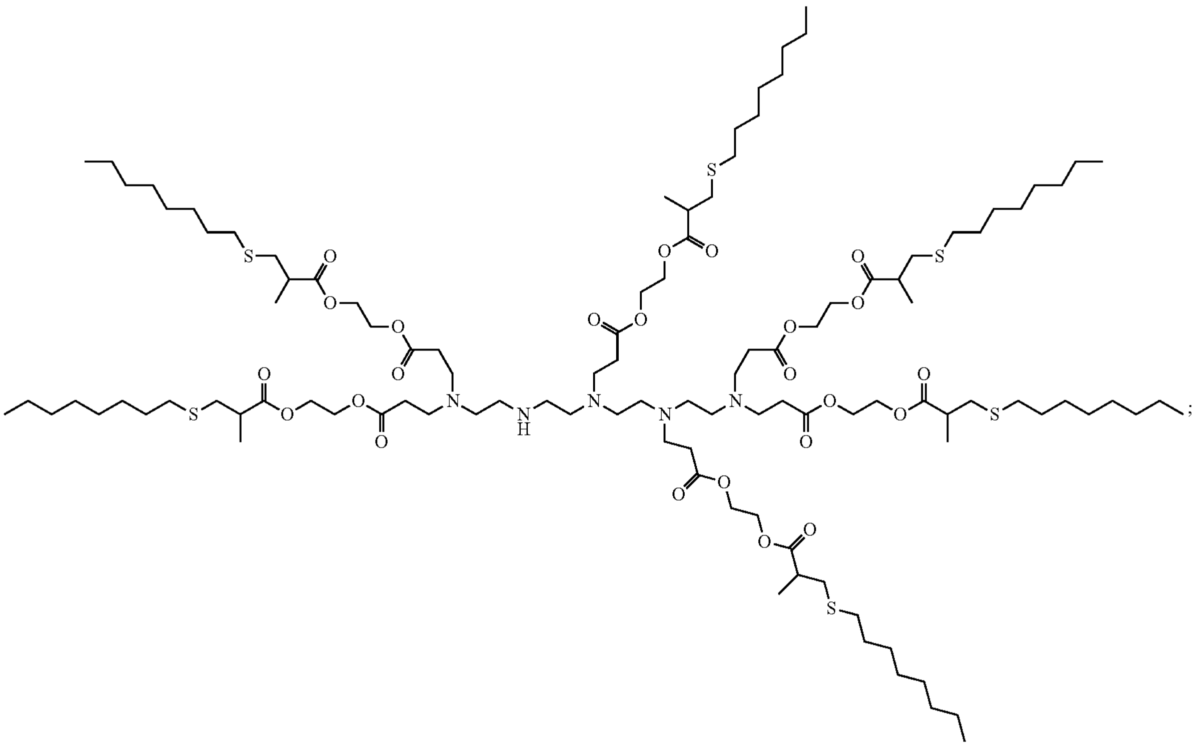 [SMILES: CCCCCCCCSCC(C)C(=O)OCCOC(=O)CCN(CCNCCN(CCC(=O)OCCOC(=O)C(C)CSCCCCCCCC)CCN(CCC(=O)OCCOC(=O)C(C)CSCCCCCCCC)CCN(CCC(=O)OCCOC(=O)C(C)CSCCCCCCCC)CCC(=O)OCCOC(=O)C(C)CSCCCCCCCC)CCC(=O)OCCOC(=O)C(C)CSCCCCCCCC]
;
and pharmaceutically acceptable salts thereof.
Dendrimers of Formula (X)
In some embodiments of the lipid composition, the ionizable cationic lipid is a dendrimer of the formula
$$Core-(Branch)_N.$$

In some embodiments, the ionizable cationic lipid is a dendrimer of the formula (X)

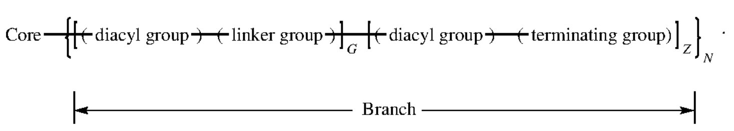

In some embodiments of the lipid composition, the ionizable cationic lipid is a dendrimer of a generation (g) having a structural formula:

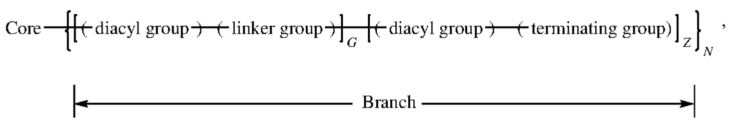

or a pharmaceutically acceptable salt thereof, wherein:

(a) the core comprises a structural formula ($X_{Core}$):

($X_{Core}$)

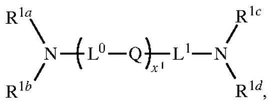

wherein:

Q is independently at each occurrence a covalent bond, —O—, —S—, —$NR^2$—, or —$CR^{3a}R^{3b}$—;

$R^2$ is independently at each occurrence $R^{1g}$ or —$L^2$—$NR^{1e}R^{1f}$;

$R^{3a}$ and $R^{3b}$ are each independently at each occurrence hydrogen or an optionally substituted (e.g., $C_1$-$C_6$, such as $C_1$-$C_3$) alkyl;

$R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen, or an optionally substituted (e.g., $C_1$-$C_{12}$) alkyl;

$L^0$, $L^1$, and $L^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of $L^1$ form a (e.g., $C_4$-$C_6$) heterocycloalkyl (e.g., containing one or two nitrogen atoms and, optionally, an additional heteroatom selected from oxygen and sulfur) with one of $R^{1c}$ and $R^{1d}$; and $x^1$ is 0, 1, 2, 3, 4, 5, or 6; and (b) each branch of the plurality (N) of branches independently comprises a structural formula ($X_{Branch}$):

($X_{Branch}$)

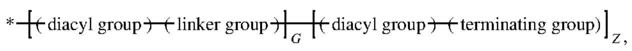

wherein:

indicates a point of attachment of the branch to the core;

g is 1, 2, 3, or 4;

$$Z = 2^{(g-1)};$$

G=0, when g=1; or $G=\Sigma_{i=0}^{i=g-2} 2^i$, when g≠1;

(c) each diacyl group independently comprises a structural formula

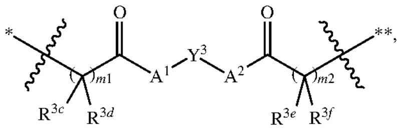

wherein:

indicates a point of attachment of the diacyl group at the proximal end thereof;

indicates a point of attachment of the diacyl group at the distal end thereof;

$Y^3$ is independently at each occurrence an optionally substituted (e.g., $C_1$-$C_{12}$); alkylene, an optionally substituted (e.g., $C_1$-$C_{12}$) alkenylene, or an optionally substituted (e.g., $C_1$-$C_{12}$) arenylene;

$A^1$ and $A^2$ are each independently at each occurrence —O—, —S—, or —$NR^4$—, wherein:

$R^4$ is hydrogen or optionally substituted (e.g., $C_1$-$C_6$) alkyl;

$m^1$ and $m^2$ are each independently at each occurrence 1, 2, or 3; and $R^{3c}$, $R^{3d}$, $R^{3e}$, and $R^{3f}$ are each independently at each occurrence hydrogen or an optionally substituted (e.g., $C_1$-$C_8$) alkyl; and (d) each linker group independently comprises a structural formula

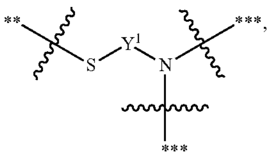

wherein:

indicates a point of attachment of the linker to a proximal diacyl group;

* indicates a point of attachment of the linker to a distal diacyl group; and $Y_1$ is independently at each occurrence an optionally substituted (e.g., $C_1$-$C_{12}$) alkylene, an optionally substituted (e.g., $C_1$-$C_{12}$) alkenylene, or an optionally substituted (e.g., $C_1$-$C_{12}$) arenylene; and (e) each terminating group is independently selected from optionally substituted (e.g., $C_1$-$C_{18}$, such as $C_4$-$C_{18}$) alkylthiol, and optionally substituted (e.g., $C_1$-$C_{18}$, such as $C_4$-$C_{18}$) alkenylthiol.

In some embodiments of $X_{Core}$, Q is independently at each occurrence a covalent bond, —O—, —S—, —$NR^2$—, or —$CR^{3a}R^{3b}$. In some embodiments of $X_{Core}$, Q is independently at each occurrence a covalent bond. In some embodiments of $X_{Core}$, Q is independently at each occurrence an —O—. In some embodiments of $X_{Core}$, Q is independently at each occurrence a —S—. In some embodiments of $X_{Core}$, Q is independently at each occurrence a —$NR^2$ and $R^2$ is independently at each occurrence $R^{1g}$ or —$L^2$—$NR^{1e}R^{1f}$. In some embodiments of $X_{Core}$, Q is independently at each occurrence a —$CR^{3a}R^{3b}R^{3a}$, and $R^{3a}$ and $R^{3b}$ are each independently at each occurrence hydrogen or an optionally substituted alkyl (e.g., $C_1$-$C_6$, such as $C_1$-$C_3$).

In some embodiments of $X_{Core}$, $R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen, or an optionally substituted alkyl. In some embodiments of $X_{Core}$, $R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen. In some embodiments of $X_{Core}$, $R^{1a}$, $R^{1b}$, $R^{1c}$, $R^{1d}$, $R^{1e}$, $R^{1f}$, and $R^{1g}$ (if present) are each independently at each occurrence a point of connection to a branch an optionally substituted alkyl (e.g., $C_1$-$C_{12}$).

In some embodiments of $X_{Core}$, $L^0$, $L^1$, and $L^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of $L^1$ form a heterocycloalkyl (e.g., $C_4$-$C_6$ and containing one or two nitrogen atoms and, optionally, an additional heteroatom selected from oxygen and sulfur) with one of $R^{1c}$ and $R^{1d}$. In some embodiments of $X_{Core}$, $L^0$, $L^1$, and $L^2$ are each independently at each occurrence can be a covalent bond. In some embodiments of $X_{Core}$, $L^0$, $L^1$, and $L^2$ are each independently at each occurrence can be a hydrogen. In some embodiments of $X_{Core}$, $L^0$, $L^1$, and $L^2$ are each independently at each occurrence can be an alkylene (e.g., $C_1$-$C_{12}$, such as $C_1$-$C_6$ or $C_1$-$C_3$). In some embodiments of $X_{Core}$, $L^0$, $L^1$, and $L^2$ are each independently at each occurrence can be a heteroalkylene (e.g., $C_1$-$C_{12}$, such as $C_1$-$C_8$ or $C_1$-$C_6$). In some embodiments of $X_{Core}$, $L^0$, $L^1$, and $L^2$ are each independently at each occurrence can be a heteroalkylene (e.g., $C_2$-$C_8$ alkyleneoxide, such as oligo(ethyleneoxide)). In some embodiments of $X_{Core}$, $L^0$, $L^1$, and $L^2$ are each independently at each occurrence can be a [alkylene]-[heterocycloalkyl]-[alkylene][(e.g., $C_1$-$C_6$) alkylene]-[(e.g., $C_4$-$C_6$) heterocycloalkyl]-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene][(e.g., $C_1$-$C_6$) alkylene]-(arylene)-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene] (e.g., [(e.g., $C_1$-$C_6$) alkylene]-phenylene-[(e.g., $C_1$-$C_6$) alkylene]). In some embodiments of $X_{Core}$, $L^0$, $L^1$, and $L^2$ are each independently at each occurrence can be a heterocycloalkyl (e.g., $C_4$-$C_6$ heterocycloalkyl). In some embodiments of $X_{Core}$, $L^0$, $L^1$, and $L^2$ are each independently at each occurrence can be an arylene (e.g., phenylene). In some embodiments of $X_{Core}$, part of $L^1$ form a heterocycloalkyl with one of $R^{1c}$ and $R^{1d}$. In some embodiments of $X_{Core}$, part of $L^1$ form a heterocycloalkyl (e.g., $C_4$-$C_6$ heterocycloalkyl) with one of $R^{1c}$ and $R^{1d}$ and the heterocycloalkyl can contain one or two nitrogen atoms and, optionally, an additional heteroatom selected from oxygen and sulfur.

In some embodiments of $X_{Core}$, $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$) alkyleneoxide (e.g., oligo(ethyleneoxide), such as —$(CH_2CH_2O)_{1-4}$—$(CH_2CH_2)$—), [($C_1$-$C_4$) alkylene]-[($C_4$-$C_6$) heterocycloalkyl]-[($C_1$-$C_4$) alkylene] (e.g.,

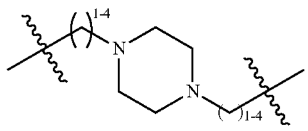

), and [($C_1$-$C_4$) alkylene]-phenylene-[($C_1$-$C_4$) alkylene] (e.g.,

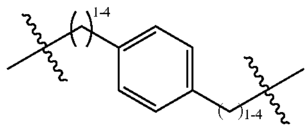

).

In some embodiments of $X_{Core}$, $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$—($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-. In some embodiments of $X_{Core}$, $L^0$, $L^1$, and $L^2$ are each independently at each occurrence $C_1$-$C_6$ alkylene (e.g., $C_1$-$C_3$ alkylene). In some embodiments, $L^0$, $L^1$, and $L^2$ are each independently at each occurrence $C_2$-$C_{12}$ (e.g., $C_2$-$C_8$) alkyleneoxide (e.g., —($C_1$-$C_3$ alkylene-O)$_{1-4}$—($C_1$-$C_3$ alkylene)). In some embodiments of $X_{Core}$, $L^0$, $L^1$, and $L^2$ are each independently at each occurrence selected from [($C_1$-$C_4$) alkylene]-[($C_4$-$C_6$) heterocycloalkyl]-[($C_1$-$C_4$) alkylene] (e.g., —($C_1$-$C_3$ alkylene)-phenylene-($C_1$-$C_3$ alkylene)-) and [($C_1$-$C_4$) alkylene]-[($C_4$-$C_6$) heterocycloalkyl]-[($C_1$-$C_4$) alkylene] (e.g., —($C_1$-$C_3$ alkylene)-piperazinyl-($C_1$-$C_3$ alkylene)-).

In some embodiments of $X_{Core}$, $x^1$ is 0, 1, 2, 3, 4, 5, or 6. In some embodiments of $X_{Core}$, $x^1$ is 0. In some embodiments of $X_{Core}$, $x^1$ is 1. In some embodiments of $X_{Core}$, $x^1$ is 2. In some embodiments of $X_{Core}$, $x^1$ is 0, 3. In some embodiments of $X_{Core}$, $x^1$ is 4. In some embodiments of $X_{Core}$, $x^1$ is 5. In some embodiments of $X_{Core}$, $x^1$ is 6.

In some embodiments of $X_{Core}$, the core comprises a structural formula:

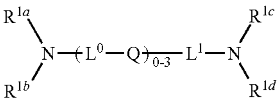
(e.g.,
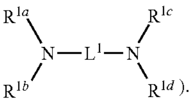
).

In some embodiments of $X_{Core}$, the core comprises a structural formula:

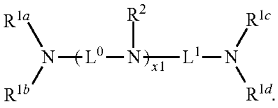

In some embodiments of $X_{Core}$, the core comprises a structural formula:

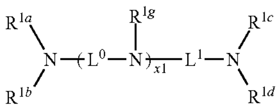
(e.g.,
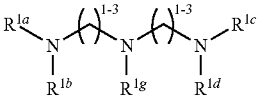
,
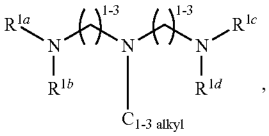
,
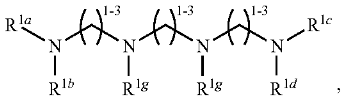
, or
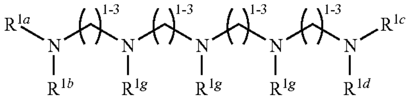
).

In some embodiments of $X_{Core}$, the core comprises a structural formula:

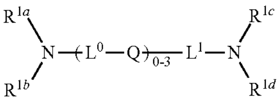
(e.g.,
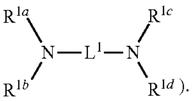
).

In some embodiments of $X_{Core}$, the core comprises a structural formula:

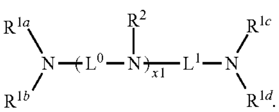

In some embodiments of $X_{Core}$, the core comprises a structural formula:

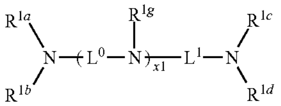
(e.g.,
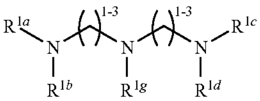
,
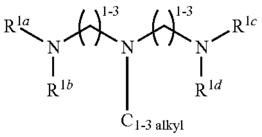
,
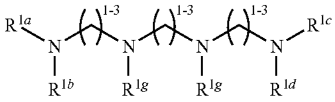
, or
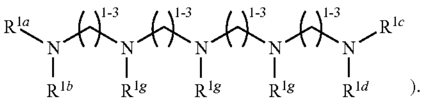
).

In some embodiments of $X_{Core}$, the core comprises a structural formula:

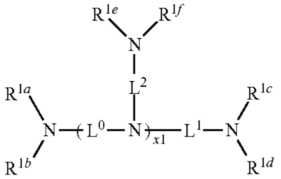

e.g.,

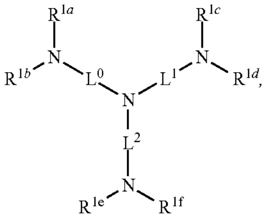

such as

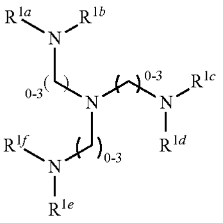
or
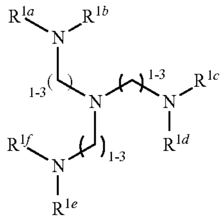
).

In some embodiments of $X_{Core}$, the core comprises a structural formula:

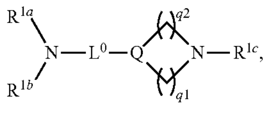

wherein Q' is —$NR^2$— or —$CR^{3a}R^{3b}$—; $q^1$ and $q^2$ are each independently 1 or 2. In some embodiments of $X_{Core}$, the core comprises a structural formula:

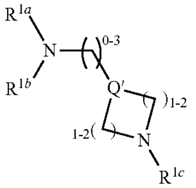

or

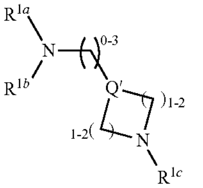

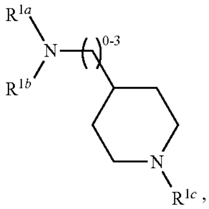

(e.g.,

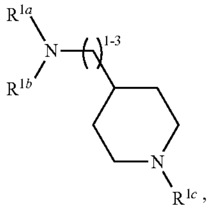

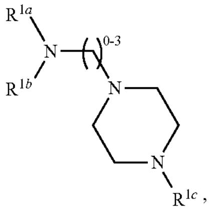

or

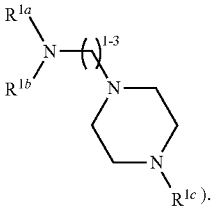

In some embodiments of $X_{Core}$, the core comprises a structural formula

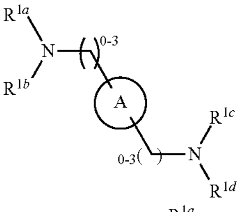

or

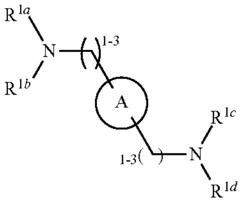

(e.g.,

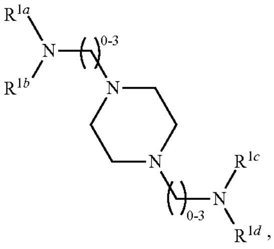

-continued

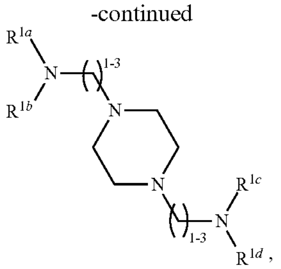

(e.g.,

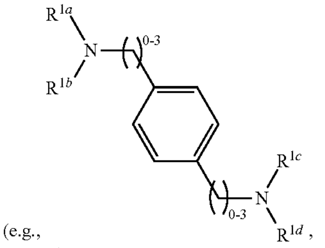

or

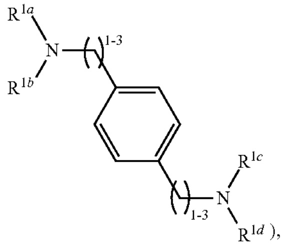

wherein ring A is an optionally substituted aryl or an optionally substituted (e.g., $C_3$-$C_{12}$, such as $C_3$-$C_5$) heteroaryl. In some embodiments of $X_{Core}$, the core comprises has a structural formula

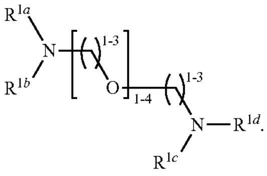

In some embodiments of $X_{Core}$, the core comprises a structural formula set forth in Table. 3 and pharmaceutically acceptable salts thereof, wherein * indicates a point of attachment of the core to a branch of the plurality of branches. In some embodiments, the example cores of Table. 3 are not limiting of the stereoisomers (i.e. enantiomers, diastereomers) listed.

TABLE 3

| Example core structures | |
|---|---|
| ID # | Structure |
| 1A1 | 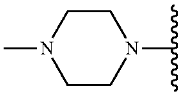 [SMILES: *N1CCN(C)CC1] |

TABLE 3-continued
| Example core structures | |
|---|---|
| ID # | Structure |
| 1A2-1 | 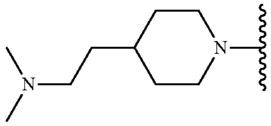 [SMILES: *N1CCC(CCN(C)C)CC1] |
| 1A2-2 | 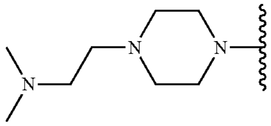 [SMILES: *N1CCN(CCN(C)C)CC1] |
| 1A3-1 | 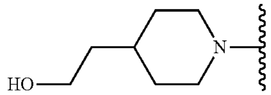 [SMILES: *N1CCC(CCO)CC1] |
| 1A3-2 | 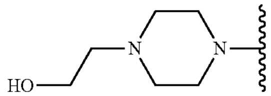 [SMILES: *N1CCN(CCO)CC1] |
| 1A4 | 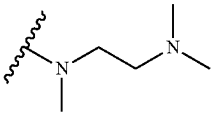 [SMILES: *N(C)CCN(C)C] |
| 1A5-1 | 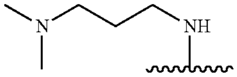 [SMILES: *NCCCN(C)C] |
| 1A5-2 | 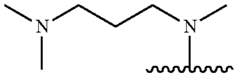 |
| 2A1-1 | 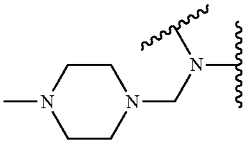 |
| 2A1-2 | 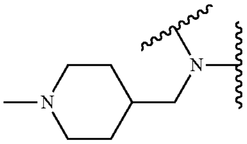 [SMILES: *N(*)CC1CCN(C)CC1] |
| 2A2-1 | 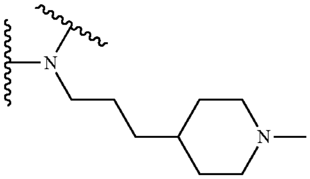 [SMILES: *N(*)CCCC1CCN(C)CC1] |
| 2A2-2 | 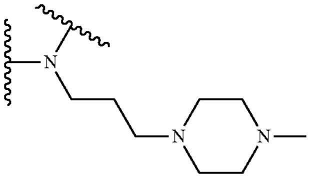 [SMILES: *N(*)CCCN1CCN(C)CC1] |

TABLE 3-continued
| Example core structures | |
|---|---|
| ID # | Structure |
| 2A3 | 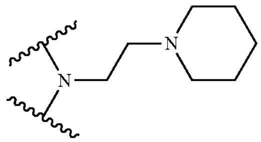 [SMILES: *N(*)CCN1CCCCC1] |
| 2A4 | 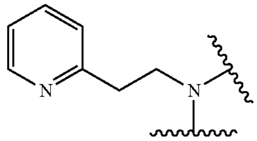 [SMILES: *N(*)CCc1ccccn1] |
| 2A5 | 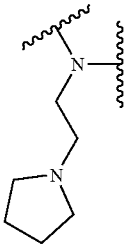 [SMILES: *N(*)CCN1CCCC1] |
| 2A6 | 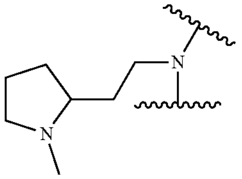 [SMILES: *N(*)CCC1CCCN1C] |
| 2A7-1 | 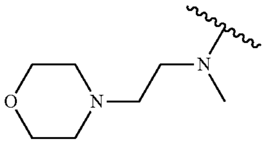 [SMILES: *N(C)CCN1CCOCC1] |
| 2A7-2 | 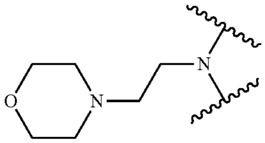 [SMILES: *N(*)CCN1CCOCC1] |
| 2A8 | 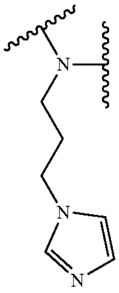 [SMILES: *N(*)CCCn1ccnc1] |
| 2A9 | 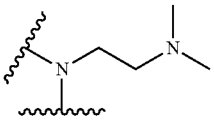 [SMILES: *N(*)CCN(C)C] |

TABLE 3-continued
| Example core structures | |
|---|---|
| ID # | Structure |
| 2A9V | 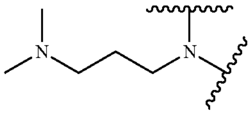 [SMILES: *N(*)CCCN(C)C] |
| 2A10 | 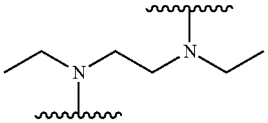 [SMILES: *N(CC)CCN(*)CC] |
| 2A11 | 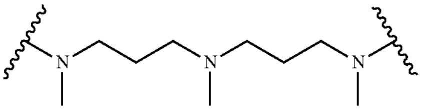 [SMILES: *N(C)CCCN(C)CCCN(*)C] |
| 2A12 | 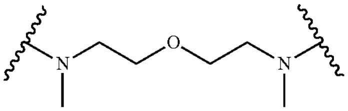 [SMILES: *N(C)CCOCCN(*)C] |
| 3A1 | 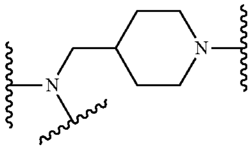 [SMILES: *N(*)CC1CCN(*)CC1] |
| 3A2 | 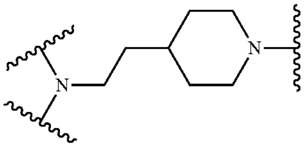 [SMILES: *N(*)CCC1CCN(*)CC1] |
| 3A3 | 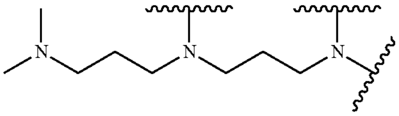 [SMILES: *N(*)CCCN(*)CCCN(C)C] |
| 3A4 | 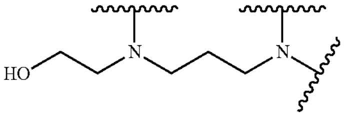 [SMILES: *N(*)CCCN(*)CCO] |
| 3A5 | 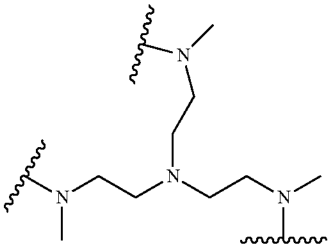 [SMILES: *N(C)CCN(CCN(*)C)CCN(*)C] |
| 3A6 | 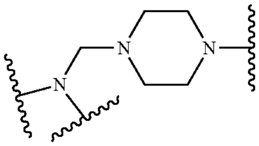 [SMILES: *N(*)CN1CCN(*)CC1] |

TABLE 3-continued
| Example core structures | |
|---|---|
| ID # | Structure |
| 3A7 | 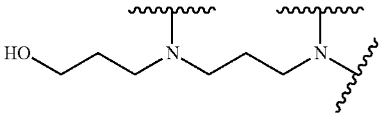 [SMILES: *N(*)CCCN(*)CCCO] |
| 4A1 | 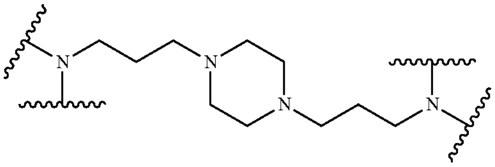 [SMILES: *N(*)CCCN1CCN(CCCN(*)*)CC1] |
| 4A2 | 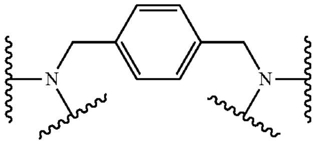 [SMILES: *N(*)Cc1ccc(CN(*)*)cc1] |
| 4A3 | 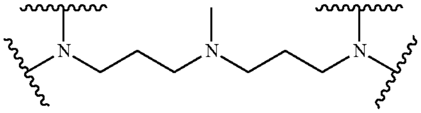 [SMILES: *N(*)CCCN(C)CCCN(*)*] |
| 4A4 | 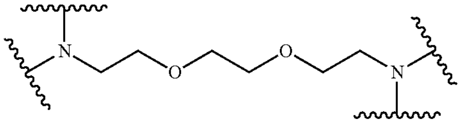 [SMILES: *N(*)CCOCCOCCN(*)*] |
| 5A1 | 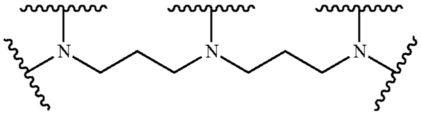 [SMILES: *N(*)CCCN(*)CCCN(*)*] |
| 5A2-1 (5-arm) | 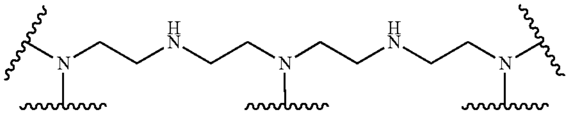 [SMILES: *N(*)CCNCCN(*)CCNCCN(*)*] |
| 5A2-2 (5-arm) | 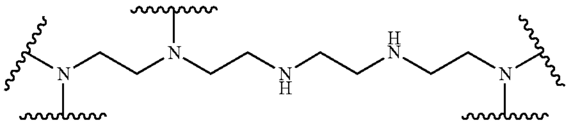 [SMILES: *N(*)CCNCCNCCN(*)CCN(*)*] |
| 5A2-3 (5-arm) | 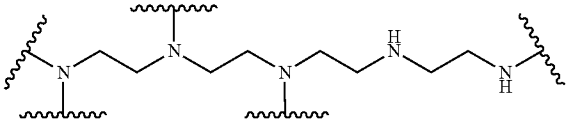 [SMILES: *NCCNCCN(*)CCN(*)CCN(*)*] |
| 5A2-4 (5-arm) | 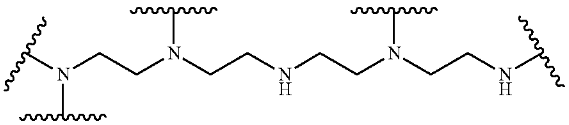 [SMILES: *NCCN(*)CCNCCN(*)CCN(*)*] |
| 5A3-1 (5-arm) | 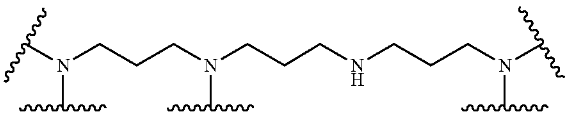 [SMILES: *N(*)CCCNCCCN(*)CCCN(*)*] |

TABLE 3-continued
| Example core structures | |
|---|---|
| ID # | Structure |
| 5A4-1 (5-arm) | 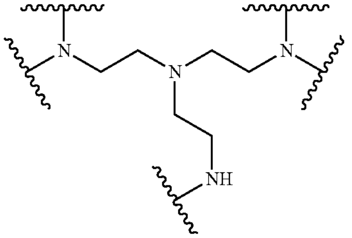 [SMILES: *NCCN(CCN(*)*)CCN(*)*] |
| 5A5 | 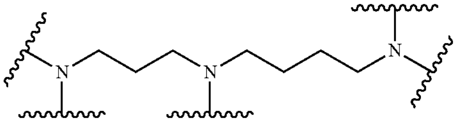 [SMILES: *N(*)CCCCN(*)CCCN(*)*] |
| 5A6 | 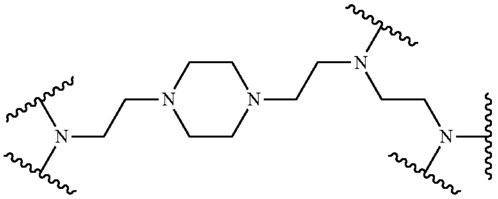 [SMILES: *N(*)CCN(*)CCN1CCN(CCN(*)*)CC1] |
| 5A2-4 (6 arm) | 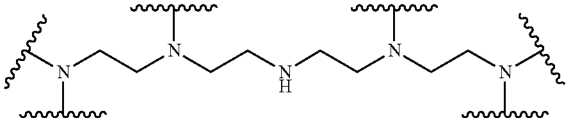 [SMILES: *N(*)CCN(*)CCNCCN(*)CCN(*)*] |
| 5A2-5 (6 arm) | 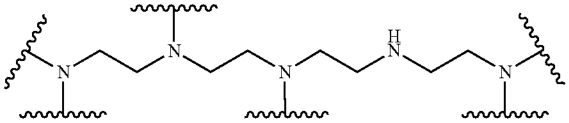 [SMILES: *N(*)CCNCCN(*)CCN(*)CCN(*)*] |
| 5A2-6 (6 arm) | 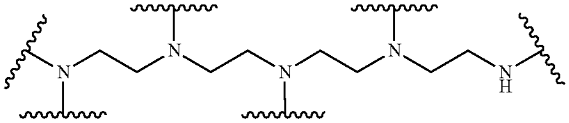 [SMILES: *NCCN(*)CCN(*)CCN(*)CCN(*)*] |
| 5A3-2 (6 arm) | 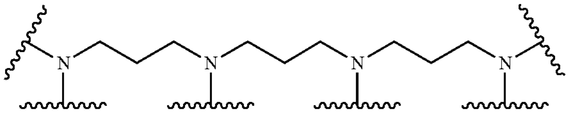 [SMILES: *N(*)CCCN(*)CCCN(*)CCCN(*)*] |
| 5A4-2 (6 arm) | 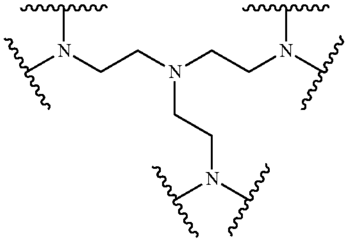 [SMILES: *N(*)CCN(CCN(*)*)CCN(*)*] |
| 6A4 | 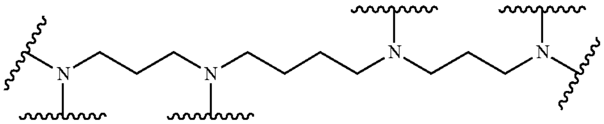 [SMILES: *N(*)CCCN(*)CCCCN(*)CCCN(*)*] |

TABLE 3-continued
| Example core structures | |
|---|---|
| ID # | Structure |
| 1H1 | 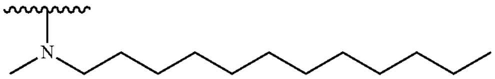 [SMILES: *N(C)CCCCCCCCCCCC] |
| 1H2 | 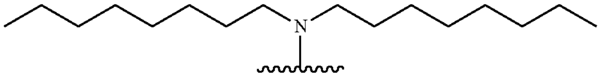 [SMILES: *N(CCCCCCCC)CCCCCCCC] |
| 1H3 | 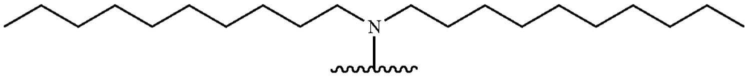 [SMILES: *N(CCCCCCCCCC)CCCCCCCCCC] |
| 2H1 | 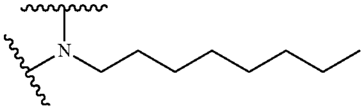 [SMILES: *N(*)CCCCCCCC] |
| 2H2 | 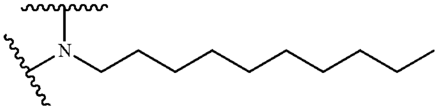 [SMILES: *N(*)CCCCCCCCCC] |
| 2H3 | 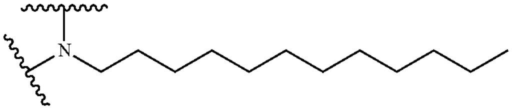 [SMILES: *N(*)CCCCCCCCCCCC] |
| 2H4 | 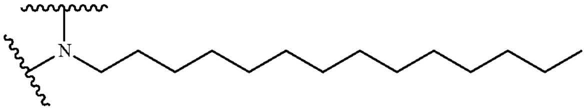 [SMILES: *N(*)CCCCCCCCCCCCCC] |
| 2H5 | 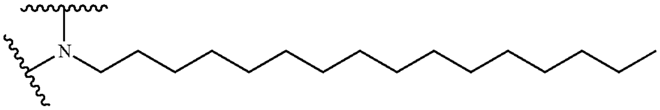 [SMILES: *N(*)CCCCCCCCCCCCCCCC] |
| 2H6 | 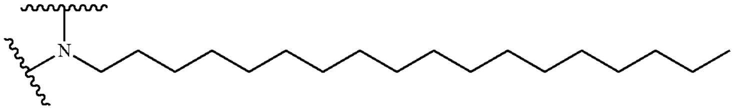 [SMILES: *N(*)CCCCCCCCCCCCCCCCCC] |
In some embodiments of $X_{Core}$, the core comprises a structural formula selected from the group consisting of:
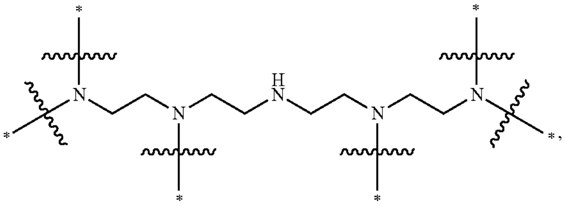
,
-continued
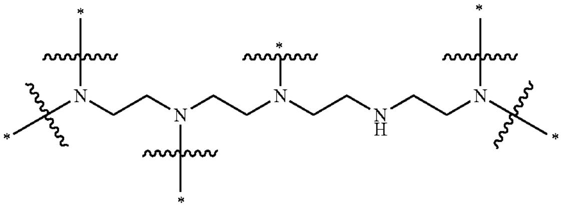
,
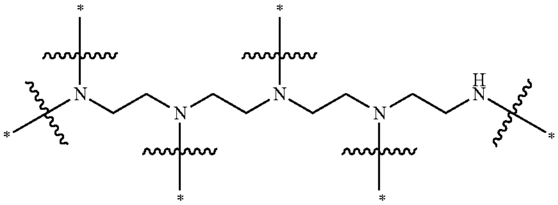
, -continued
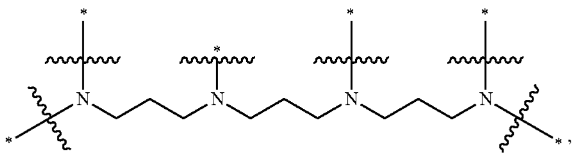
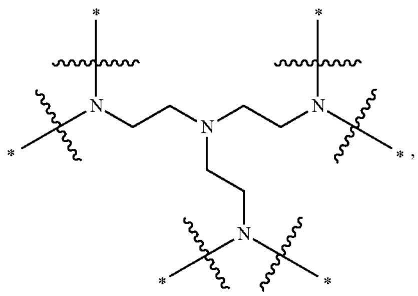
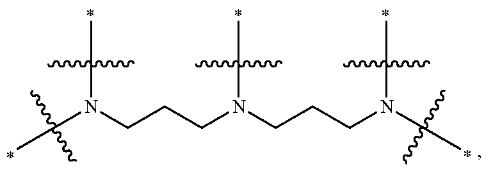
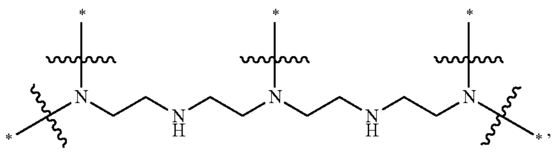
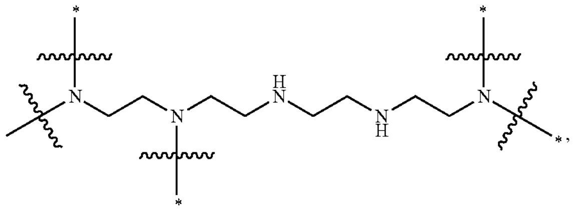
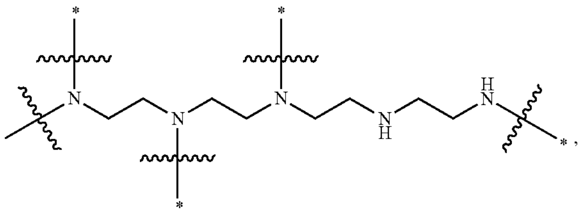
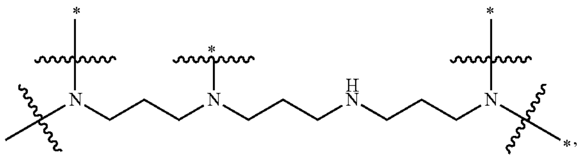
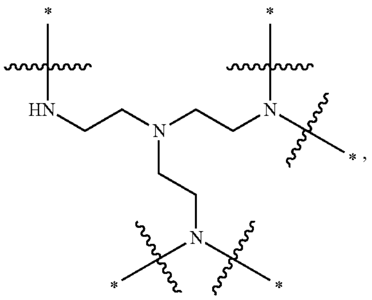
-continued
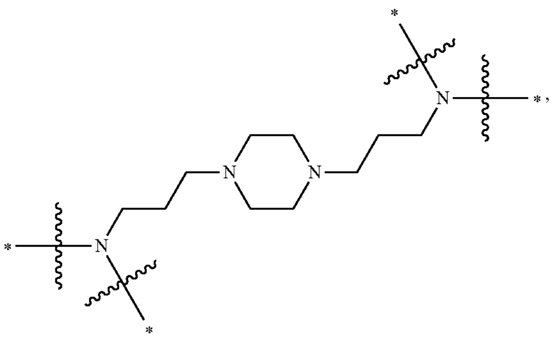
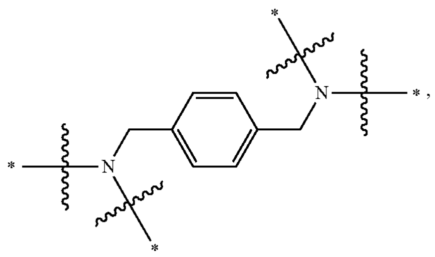
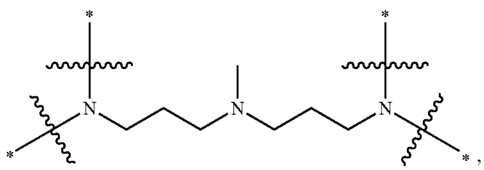
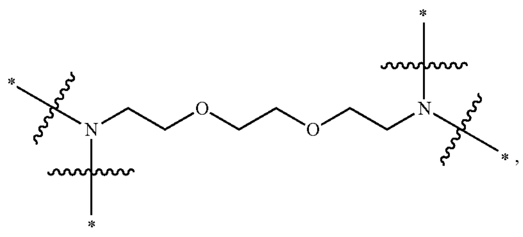
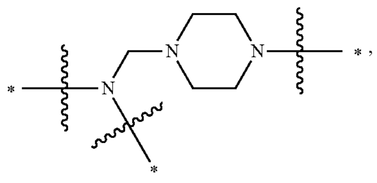
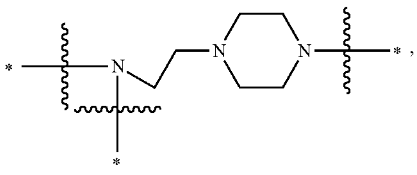
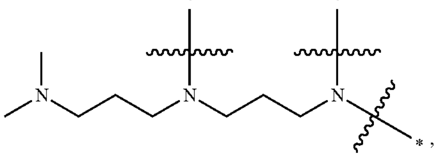

-continued

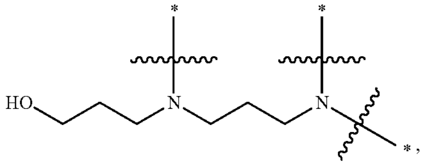,

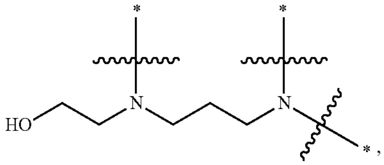,

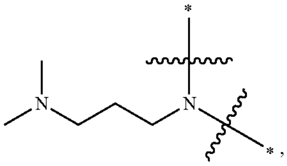, 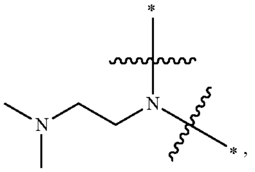,

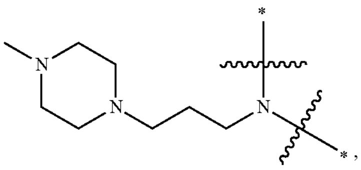,

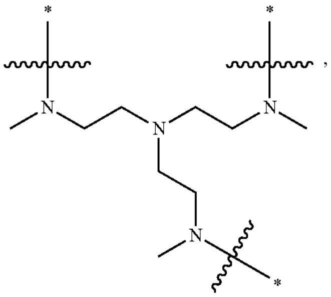

and pharmaceutically acceptable salts thereof, wherein * indicates a point of attachment of the core to a branch of the plurality of branches or H. In some embodiments, wherein * indicates a point of attachment of the core to a branch of the plurality of branches.

In some embodiments of $X_{Core}$, the core comprises a structural formula selected from the group consisting of:

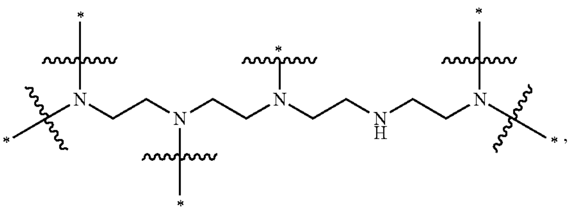,

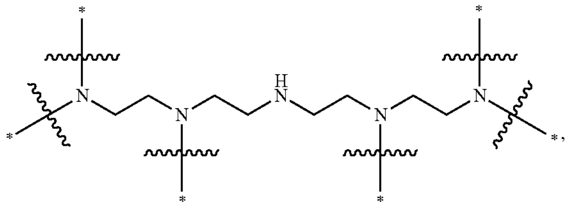,

-continued

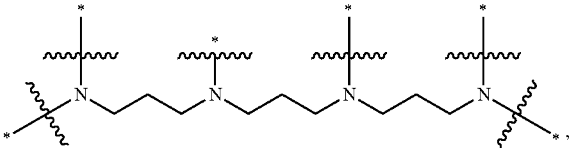,

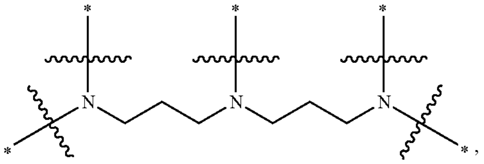,

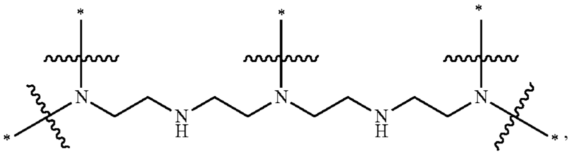,

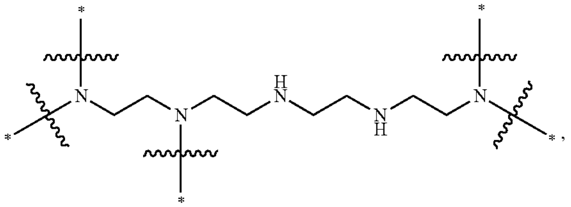,

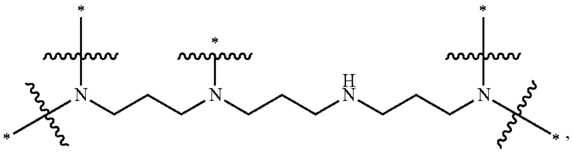,

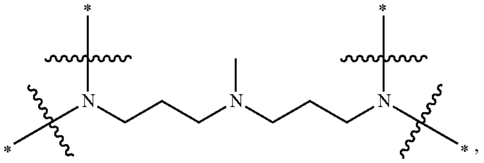,

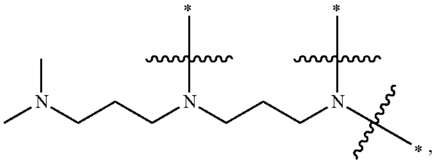, and pharmaceutically acceptable salts thereof, wherein * indicates a point of attachment of the core to a branch of the plurality of branches.

In some embodiments of $X_{Core}$, the core has the structure

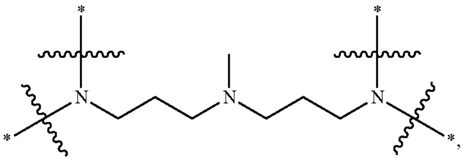, wherein * indicates a point of attachment of the core to a branch of the plurality of branches or H. In some embodiments, at least 2 branches are attached to the core. In some embodiments, at least 3 branches are attached to the core. In some embodiments, at least 4 branches are attached to the core.

In some embodiments of $X_{Core}$, the core has the structure

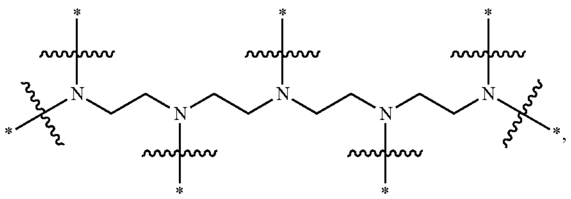

wherein * indicates a point of attachment of the core to a branch of the plurality of branches or H. In some embodiments, at least 4 branches are attached to the core. In some embodiments, at least 5 branches are attached to the core. In some embodiments, at least 6 branches are attached to the core.

In some embodiments, the plurality (N) of branches comprises at least 3 branches, at least 4 branches, at least 5 branches. In some embodiments, the plurality (N) of branches comprises at least 3 branches. In some embodiments, the plurality (N) of branches comprises at least 4 branches. In some embodiments, the plurality (N) of branches comprises at least 5 branches.

In some embodiments of $X_{Branch}$, g is 1, 2, 3, or 4. In some embodiments of $X_{Branch}$, g is 1. In some embodiments of $X_{Branch}$, g is 2. In some embodiments of $X_{Branch}$, g is 3. In some embodiments of $X_{Branch}$, g is 4.

In some embodiments of $X_{Branch}$, $Z=2^{(g-1)}$ and when g=1, G=0. In some embodiments of $X_{Branch}$, $Z=2^{(g-1)}$ and $G=\Sigma_{i=0}^{i=g-2} 2^i$, when $g \neq 1$.

In some embodiments of $X_{Branch}$, g=1, G=0, Z=1, and each branch of the plurality of branches comprises a structural formula each branch of the plurality of branches comprises a structural formula

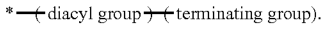

In some embodiments of $X_{Branch}$, g=2, G=1, Z=2, and each branch of the plurality of branches comprises a structural formula

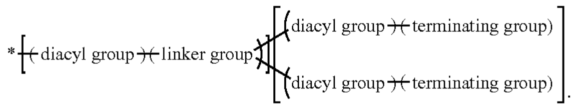

In some embodiments of $X_{Branch}$, g=3, G=3, Z=4, and each branch of the plurality of branches comprises a structural formula

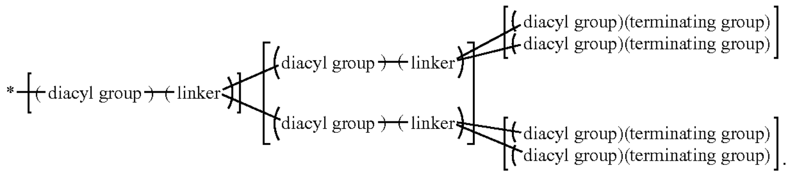

In some embodiments of $X_{Branch}$, g=4, G=7, Z=8, and each branch of the plurality of branches comprises a structural formula

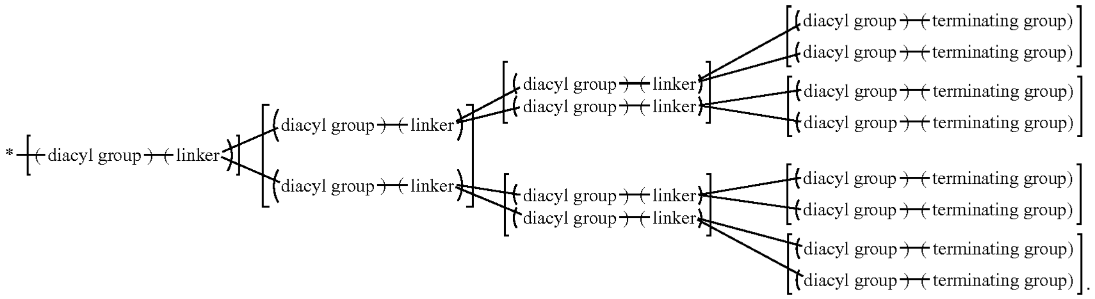

In some embodiments, the dendrimers described herein with a generation (g)=1 has the structure:

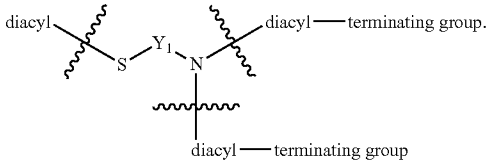

GEN "g-1" GEN "g"

In some embodiments, the dendrimers described herein with a generation (g)=1 has the structure:

occurrence an optionally substituted alkylene (e.g., $C_1$-$C_{12}$). In some embodiments of the diacyl group of $X_{Branch}$, $Y^3$ is independently at each occurrence an optionally substituted alkenylene (e.g., $C_1$-$C_{12}$). In some embodiments of the diacyl group of $X_{Branch}$, $Y^3$ is independently at each occurrence an optionally substituted arenylene (e.g., $C_1$-$C_{12}$).

In some embodiments of the diacyl group of $X_{Branch}$, $A^1$ and $A^2$ are each independently at each occurrence —O—, —S—, or —$NR^4$—. In some embodiments of the diacyl group of $X_{Branch}$, $A^1$ and $A^2$ are each independently at each occurrence —O—. In some embodiments of the diacyl group of $X_{Branch}$, $A^l$ and $A^2$ are each independently at each occurrence —S—. In some embodiments of the diacyl group of $X_{Branch}$, $A^1$ and $A^2$ are each independently at each occurrence —$NR^4$— and $R^4$ is hydrogen or optionally substituted alkyl (e.g., $C_1$-$C_6$). In some embodiments of the diacyl group of $X_{Branch}$, $m^1$ and $m^2$ are each independently at each occurrence 1, 2, or 3. In some embodiments of the diacyl group of $X_{Branch}$, $m^1$ and $m^2$ are each independently at each occurrence 1. In some embodiments of the diacyl group of $X_{Branch}$, $m^1$ and $m^2$ are each independently at each occurrence 2. In some embodiments of the diacyl group of $X_{Branch}$, $m^1$ and $m^2$ are each independently at each occurrence 3. In some embodiments of the diacyl group of $X_{Branch}$, $R^{3c}$, $R^{3d}$, $R^{3e}$, and $R^{3f}$ are each independently at each occurrence hydrogen or an optionally substituted alkyl. In some embodiments of the diacyl group of $X_{Branch}$, $R^{3c}$, $R^{3d}$, $R^{3e}$, and $R^{3f}$ are each independently at each occurrence hydrogen. In some embodiments of the diacyl group of $X_{Branch}$, $R^{3c}$, $R^{3d}$, $R^{3e}$, and $R^{3f}$ are each independently at each occurrence an optionally substituted (e.g., $C_1$-$C_8$) alkyl.

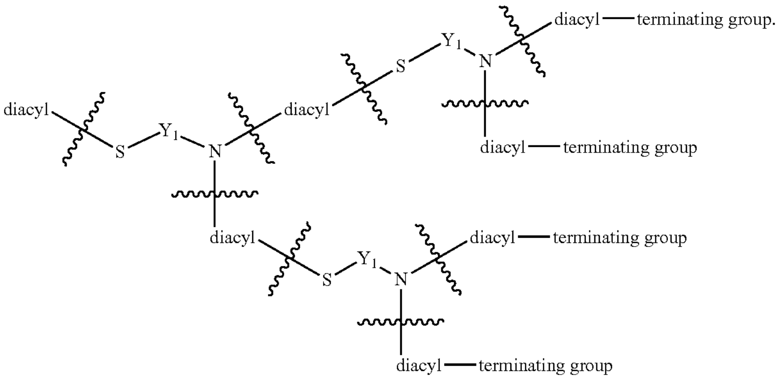

GEN "g-2" GEN "g-1" GEN "g"

The example formulation of the dendrimers described herein for generations 1-4 is shown in Table 4. The number of diacyl groups, linker groups, and terminating groups can be calculated based on g.

TABLE 4

Formulation of Dendrimer Groups Based on Generation (g)

| | g = 1 | g = 2 | g = 3 | g = 4 | |
|---|---|---|---|---|---|
| # of diacyl grp | 1 | 1 + 2 = 3 | 1 + 2 + $2^2$ = 7 | 1 + 2 + $2^2$ + $2^3$ = 15 | 1 + 2 + . . . + $2^{g-1}$ |
| # of linker grp | 0 | 1 | 1 + 2 | 1 + 2 + $2^2$ | 1 + 2 + . . . + $2^{g-2}$ |
| # of terminating grp | 1 | 2 | $2^2$ | $2^3$ | $2^{(g-1)}$ |

In some embodiments, the diacyl group independently comprises a structural formula

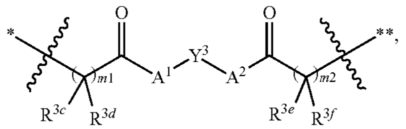

* indicates a point of attachment of the diacyl group at the proximal end thereof, and ** indicates a point of attachment of the diacyl group at the distal end thereof.

In some embodiments of the diacyl group of $X_{Branch}$, $Y^3$ is independently at each occurrence an optionally substituted; alkylene, an optionally substituted alkenylene, or an optionally substituted arenylene. In some embodiments of the diacyl group of $X_{Branch}$, $Y^3$ is independently at each In some embodiments of the diacyl group, $A^1$ is —O— or —NH—. In some embodiments of the diacyl group, $A^1$ is —O—. In some embodiments of the diacyl group, $A^2$ is —O— or —NH—. In some embodiments of the diacyl group, $A^2$ is —O—. In some embodiments of the diacyl group, $Y^3$ is $C_1$-$C_{12}$ (e.g., $C_1$-$C_6$, such as $C_1$-$C_3$) alkylene.

In some embodiments of the diacyl group, the diacyl group independently at each occurrence comprises a structural formula

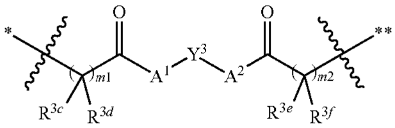

(e.g.,

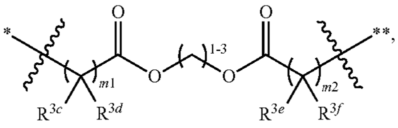

such as

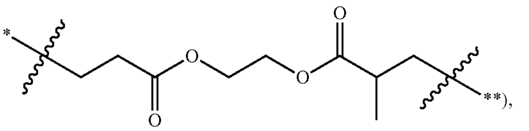

and optionally $R^{3c}$, $R^{3d}$, $R^{3e}$, and $R^{3f}$ are each independently at each occurrence hydrogen or $C_1$-$C_3$ alkyl.

In some embodiments, linker group independently comprises a structural formula

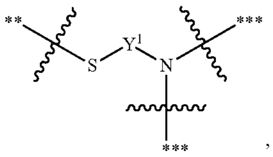

, indicates a point of attachment of the linker to a proximal diacyl group, and * indicates a point of attachment of the linker to a distal diacyl group.

In some embodiments of the linker group of $X_{Branch}$ if present, $Y_1$ is independently at each occurrence an optionally substituted alkylene, an optionally substituted alkenylene, or an optionally substituted arenylene. In some embodiments of the linker group of $X_{Branch}$ if present, $Y_1$ is independently at each occurrence an optionally substituted alkylene (e.g., $C_1$-$C_{12}$). In some embodiments of the linker group of $X_{Branch}$ if present, $Y_1$ is independently at each occurrence an optionally substituted alkenylene (e.g., $C_1$-$C_{12}$). In some embodiments of the linker group of $X_{Branch}$ if present, $Y_1$ is independently at each occurrence an optionally substituted arenylene (e.g., $C_1$-$C_{12}$).

In some embodiments of the terminating group of $X_{Branch}$, each terminating group is independently selected from optionally substituted alkylthiol and optionally substituted alkenylthiol. In some embodiments of the terminating group of $X_{Branch}$, each terminating group is an optionally substituted alkylthiol (e.g., $C_1$-$C_{18}$, such as $C_4$-$C_{18}$). In some embodiments of the terminating group of $X_{Branch}$, each terminating group is optionally substituted alkenylthiol (e.g., $C_1$-$C_{18}$, such as $C_4$-$C_{18}$).

In some embodiments of the terminating group of $X_{Branch}$, each terminating group is independently $C_1$-$C_{18}$ alkenylthiol or $C_1$-$C_{18}$ alkylthiol, and the alkyl or alkenyl moiety is optionally substituted with one or more substituents each independently selected from halogen, $C_6$-$C_{12}$ aryl, $C_1$-$C_{12}$ alkylamino, $C_4$-$C_6$ N-heterocycloalkyl, —OH, —C(O)OH, —C(O)N($C_1$-$C_3$ alkyl)-($C_1$-$C_6$ alkylene)-($C_1$-$C_{12}$ alkylamino), —C(O)N($C_1$-$C_3$ alkyl)-($C_1$-$C_6$ alkylene)-($C_4$-$C_6$ N-heterocycloalkyl), —C(O)—($C_1$-$C_{12}$ alkylamino), and —C(O)—($C_4$-$C_6$ N-heterocycloalkyl), and the $C_4$-$C_6$ N-heterocycloalkyl moiety of any of the preceding substituents is optionally substituted with $C_1$-$C_3$ alkyl or $C_1$-$C_3$ hydroxyalkyl.

In some embodiments of the terminating group of $X_{Branch}$, each terminating group is independently $C_1$-$C_{18}$ (e.g., $C_4$-$C_{18}$) alkenylthiol or $C_1$-$C_{18}$ (e.g., $C_4$-$C_{18}$) alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as

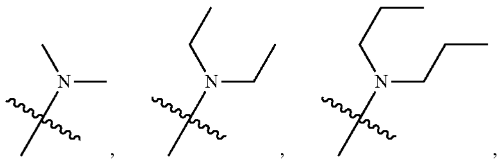

,

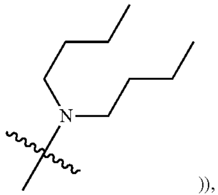

)), $C_4$-$C_6$ N-heterocycloalkyl (e.g., N-pyrrolidinyl (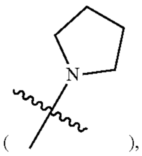),

N-piperidinyl (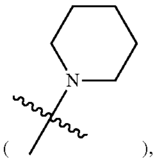),

N-azepanyl (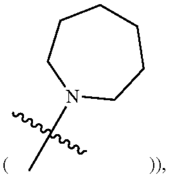)),

—OH, —C(O)OH, —C(O)N($C_1$-$C_3$ alkyl)-($C_1$-$C_6$ alkylene)-($C_1$-$C_{12}$ alkylamino (e.g., mono- or di-alkylamino)) (e.g.,

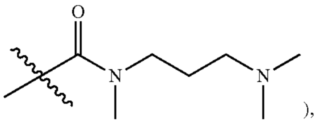 [SMILES: *C(=O)N(C)CCCN(C)C]

),

—C(O)N($C_1$-$C_3$ alkyl)-($C_1$-$C_6$ alkylene)-($C_4$-$C_6$ N-heterocycloalkyl) (e.g.,

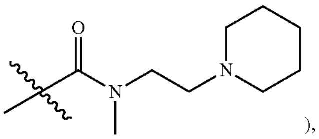 [SMILES: *C(=O)N(C)CCN1CCCCC1]

),

—C(O)—($C_1$-$C_{12}$ alkylamino (e.g., mono- or di-alkylamino)), and —C(O)—($C_4$-$C_6$ N-heterocycloalkyl) (e.g.,

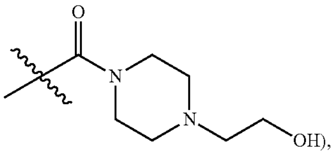

), wherein the $C_4$-$C_6$ N-heterocycloalkyl moiety of any of the preceding substituents is optionally substituted with $C_1$-$C_3$ alkyl or $C_1$-$C_3$ hydroxyalkyl. In some embodiments of the terminating group of $X_{Branch}$, each terminating group is independently $C_1$-$C_{18}$ (e.g., $C_4$-$C_{18}$) alkylthiol, wherein the alkyl moiety is optionally substituted with one substituent —OH. In some embodiments of the terminating group of $X_{Branch}$, each terminating group is independently $C_1$-$C_{18}$ (e.g., $C_4$-$C_{18}$) alkylthiol, wherein the alkyl moiety is optionally substituted with one substituent selected from $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as,

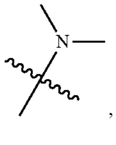

,

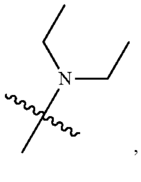

,

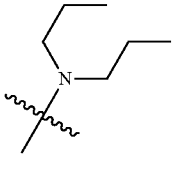

,

-continued

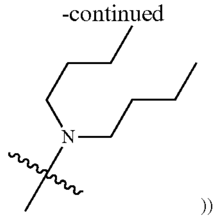

))

and $C_4$-$C_6$ N-heterocycloalkyl (e.g., N-pyrrolidinyl ( 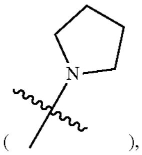 ),

N-piperidinyl ( 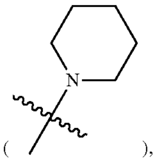 ),

N-azepanyl ( 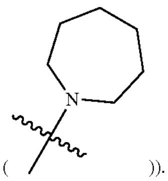 [SMILES: *N1CCCCCC1] )).

In some embodiments of the terminating group of $X_{Branch}$, each terminating group is independently $C_1$-$C_{18}$ (e.g., $C_4$-$C_{18}$) alkenylthiol or $C_1$-$C_{18}$ (e.g., $C_4$-$C_{18}$) alkylthiol. In some embodiments of the terminating group of $X_{Branch}$, each terminating group is independently $C_1$-$C_{18}$ (e.g., $C_4$-$C_{18}$) alkylthiol.

In some embodiments of the terminating group of $X_{Branch}$, each terminating group is independently a structural set forth in Table 5. In some embodiments, the dendrimers described herein can comprise a terminating group or pharmaceutically acceptable salt, or thereof selected in Table 5. In some embodiments, the example terminating group of Table 5 are not limiting of the stereoisomers (i.e. enantiomers, diastereomers) listed.

TABLE 5

Example terminating group/peripheries structures

| ID # | Structure |
|---|---|
| SC1 | 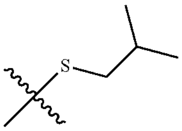 [SMILES: *SCC(C)C] |

TABLE 5-continued
| Example terminating group/peripheries structures | |
|---|---|
| ID # | Structure |
| SC2 | 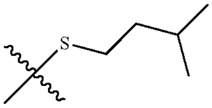 [SMILES: *SCCC(C)C] |
| SC3 | 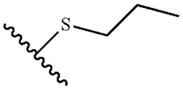 [SMILES: *SCCC] |
| SC4 | 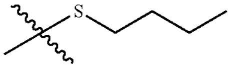 [SMILES: *SCCCC] |
| SC5 | 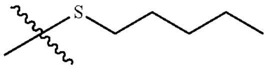 [SMILES: *SCCCCC] |
| SC6 | 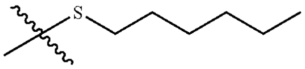 [SMILES: *SCCCCCC] |
| SC7 | 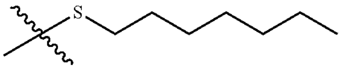 [SMILES: *SCCCCCCC] |
| SC8 | 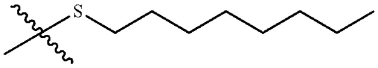 [SMILES: *SCCCCCCCC] |
| SC9 | 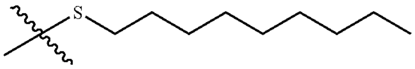 [SMILES: *SCCCCCCCCC] |
| SC10 | 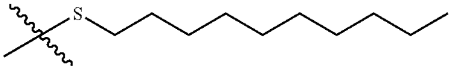 [SMILES: *SCCCCCCCCCC] |
| SC11 | 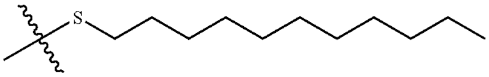 [SMILES: *SCCCCCCCCCCC] |
| SC12 | 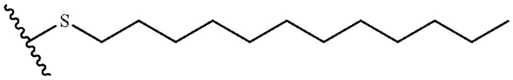 [SMILES: *SCCCCCCCCCCCC] |
| SC14 | 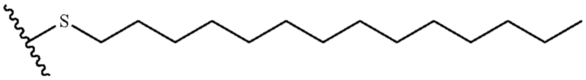 [SMILES: *SCCCCCCCCCCCCCC] |
| SC16 | 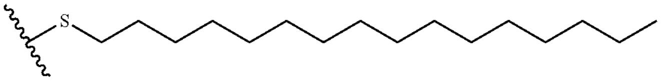 [SMILES: *SCCCCCCCCCCCCCCCC] |
| SC18 | 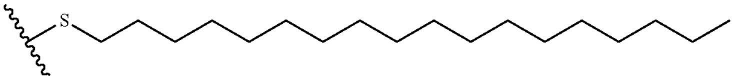 [SMILES: *SCCCCCCCCCCCCCCCCCC] |
| SC19 | 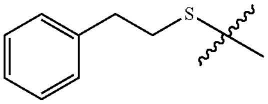 [SMILES: *SCCc1ccccc1] |
| SO1 | 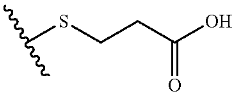 [SMILES: *SCCC(=O)O] |

TABLE 5-continued
| Example terminating group/peripheries structures | |
|---|---|
| ID # | Structure |
| SO2 | 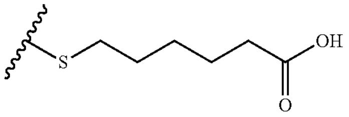 [SMILES: *SCCCCCC(=O)O] |
| SO3 | 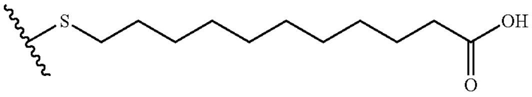 [SMILES: *SCCCCCCCCCCC(=O)O] |
| SO4 | 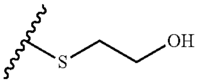 [SMILES: *SCCO] |
| SO5 | 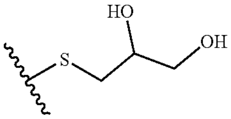 [SMILES: *SCC(O)CO] |
| SO6 | 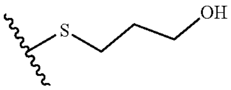 [SMILES: *SCCCO] |
| SO7 | 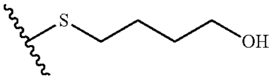 [SMILES: *SCCCCO] |
| SO8 | 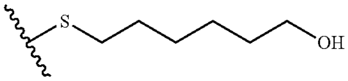 [SMILES: *SCCCCCCO] |
| SO9 | 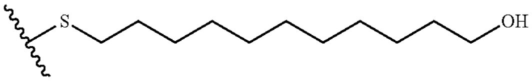 [SMILES: *SCCCCCCCCCCCO] |
| SN1 | 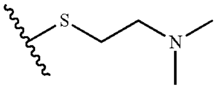 [SMILES: *SCCN(C)C] |
| SN2 | 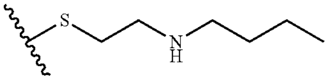 [SMILES: *SCCNCCCC] |
| SN3 | 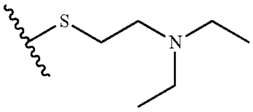 [SMILES: *SCCN(CC)CC] |
| SN4 | 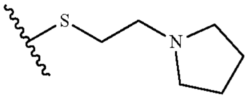 [SMILES: *SCCN1CCCC1] |
| SN5 | 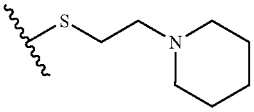 [SMILES: *SCCN1CCCCC1] |

TABLE 5-continued
| Example terminating group/peripheries structures | |
|---|---|
| ID # | Structure |
| SN6 | 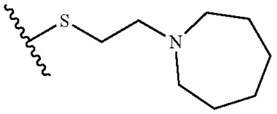 [SMILES: *SCCN1CCCCCC1] |
| SN7 | 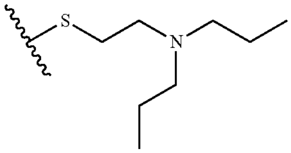 [SMILES: *SCCN(CCC)CCC] |
| SN8 | 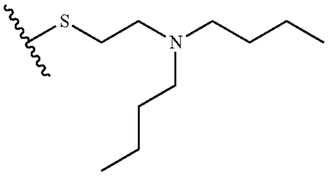 [SMILES: *SCCN(CCCC)CCCC] |
| SN9 | 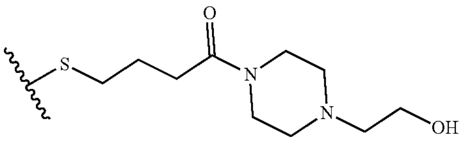 [SMILES: *SCCCC(=O)N1CCN(CCO)CC1] |
| SN10 | 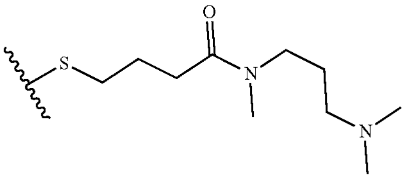 [SMILES: *SCCCC(=O)N(C)CCCN(C)C] |
| SN11 | 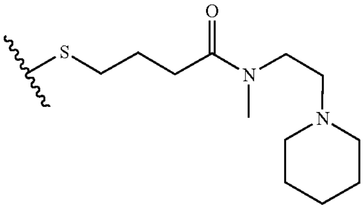 [SMILES: *SCCCC(=O)N(C)CCN1CCCCC1] |
In some embodiments, the dendrimer of Formula (X) is selected from those set forth in Table 6 and pharmaceutically acceptable salts thereof.

TABLE 6
| Example ionizable cationic lipo-dendrimers | |
|---|---|
| ID # | Structure |
| 2A2-SC14 | 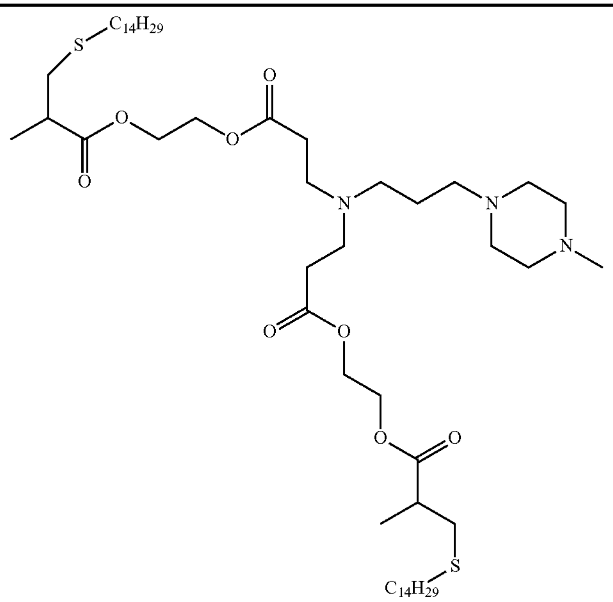 |
| 2A6-SC14 | 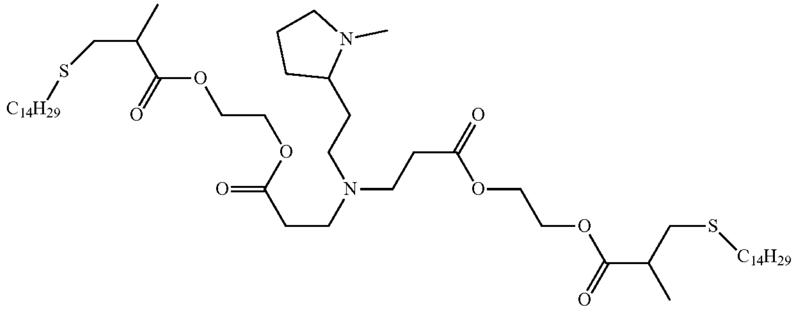 |

TABLE 6-continued
| Example ionizable cationic lipo-dendrimers | |
|---|---|
| ID # | Structure |
| 2A9-SC14 | 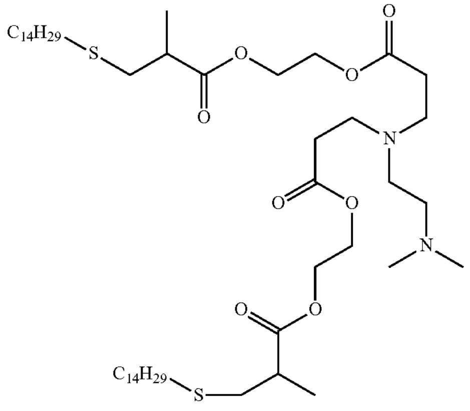 |

TABLE 6-continued
Example ionizable cationic lipo-dendrimers
| ID # | Structure |
|---|---|
| 3A3-SC10 | 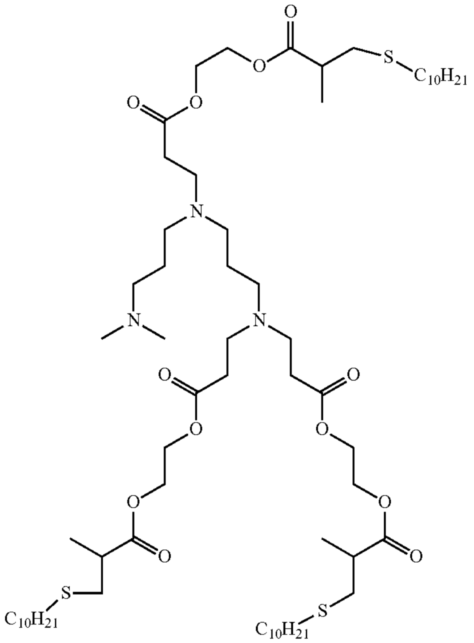 |

TABLE 6-continued
| Example ionizable cationic lipo-dendrimers | |
|---|---|
| ID # | Structure |
| 3A3-SC14 | 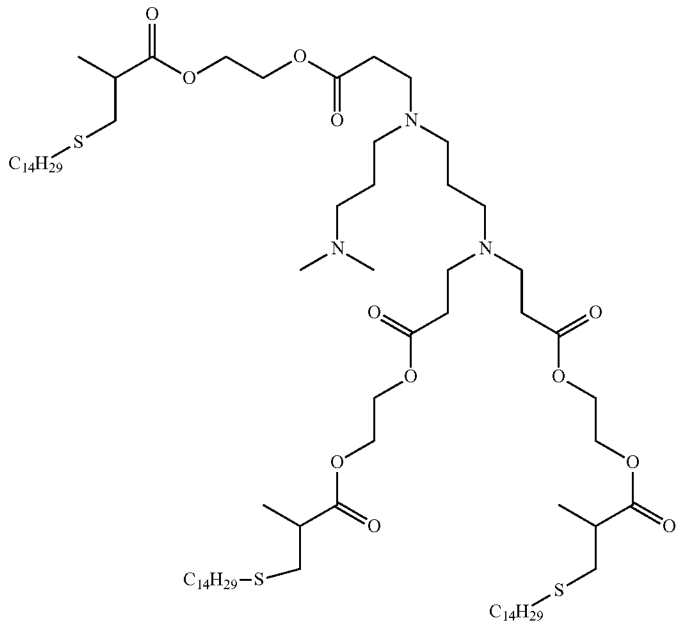 |

TABLE 6-continued
| Example ionizable cationic lipo-dendrimers | |
|---|---|
| ID # | Structure |
| 3A5-SC10 | 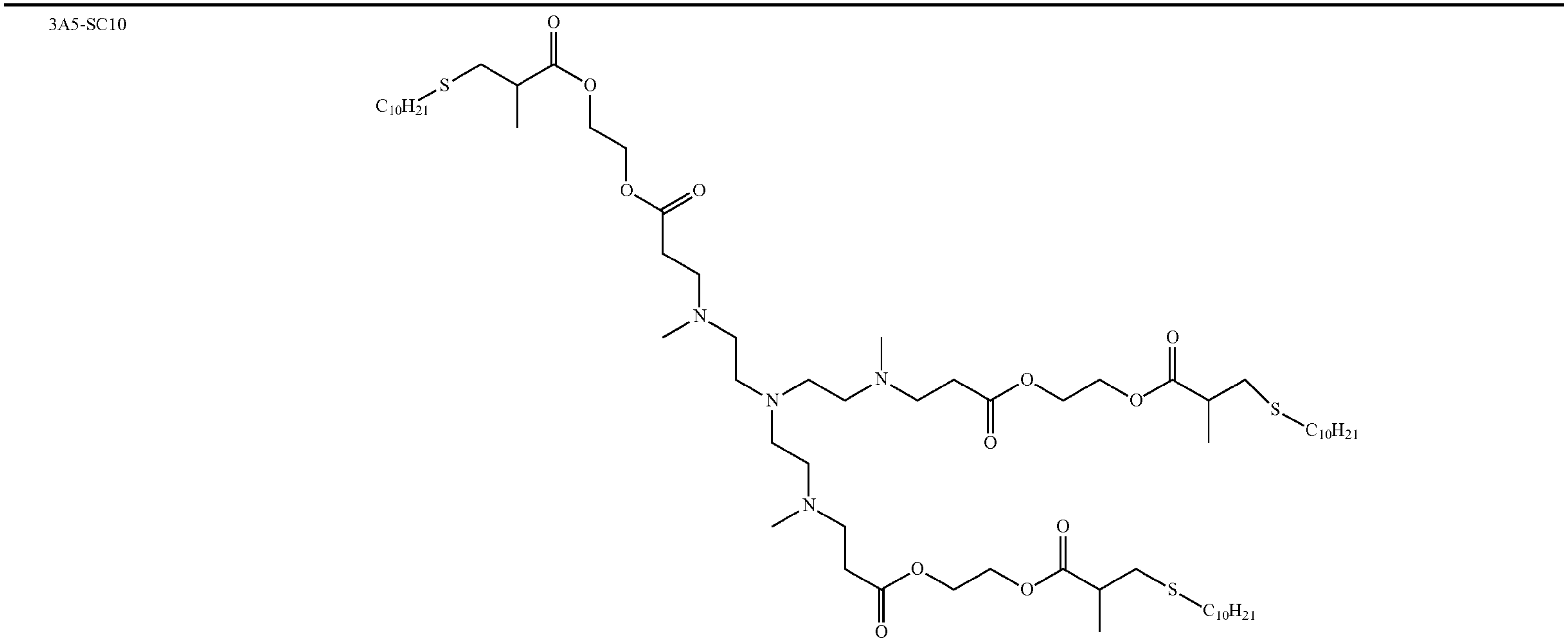 |

TABLE 6-continued
| Example ionizable cationic lipo-dendrimers | |
|---|---|
| ID # | Structure |
| 3A5-SC14 | 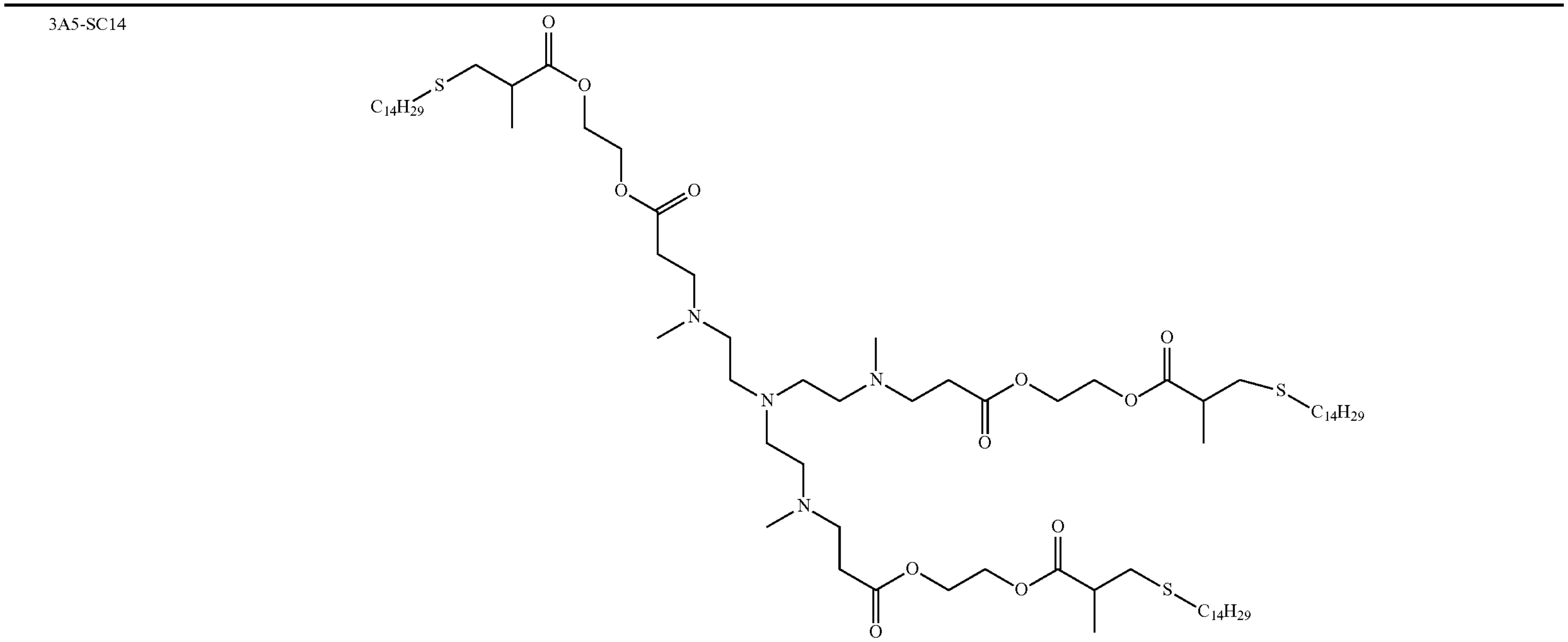 |

TABLE 6-continued
| Example ionizable cationic lipo-dendrimers | |
|---|---|
| ID # | Structure |
| 4A1-SC12 | 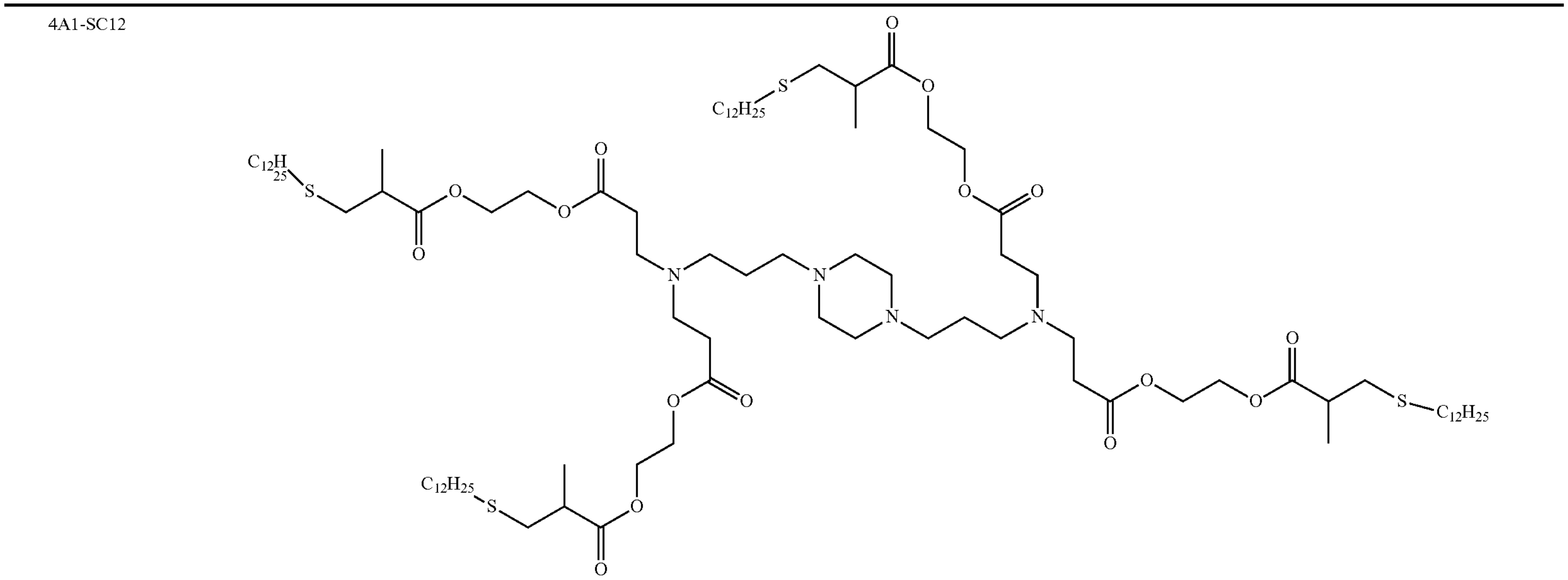 |

TABLE 6-continued
| Example ionizable cationic lipo-dendrimers | |
|---|---|
| ID # | Structure |
| 4A3-SC12 | 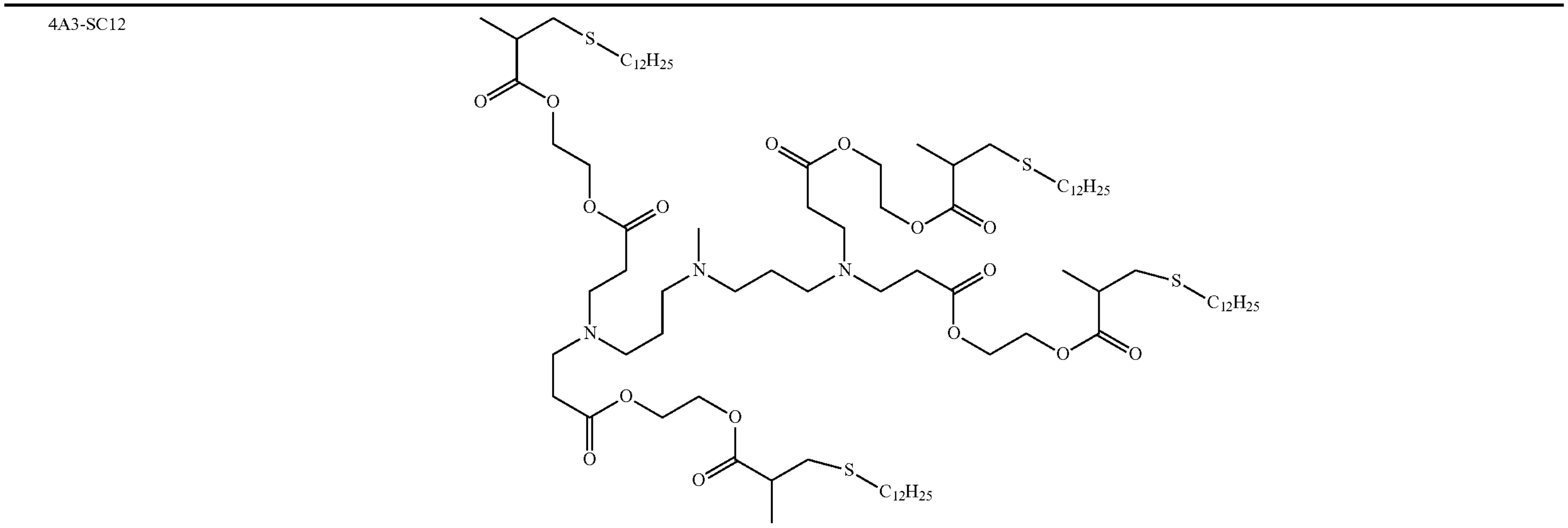 |
| 5A1-SC12 | 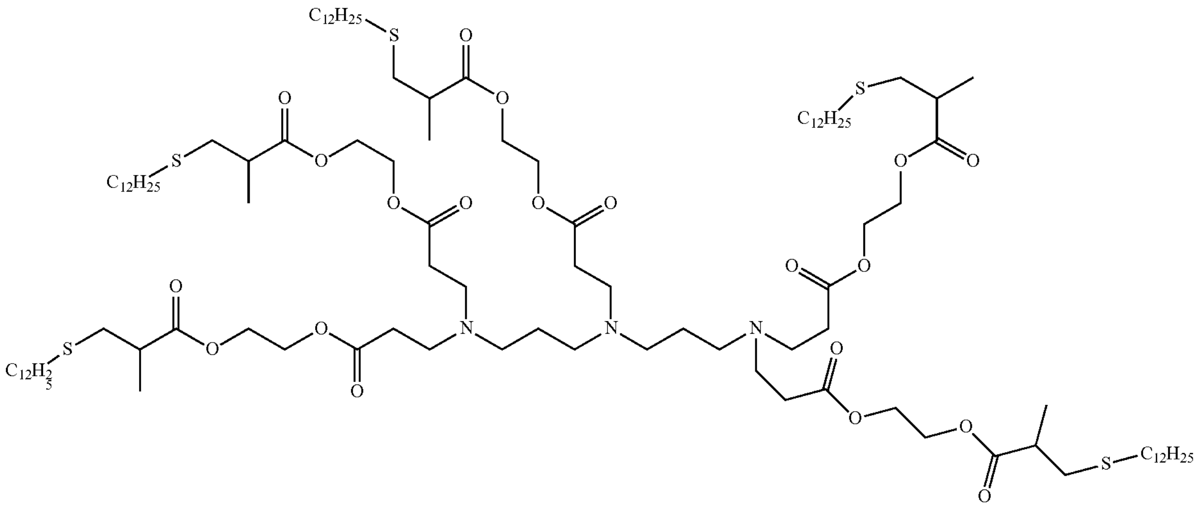 |

TABLE 6-continued
| Example ionizable cationic lipo-dendrimers | |
|---|---|
| ID # | Structure |
| 5A1-SC8 | 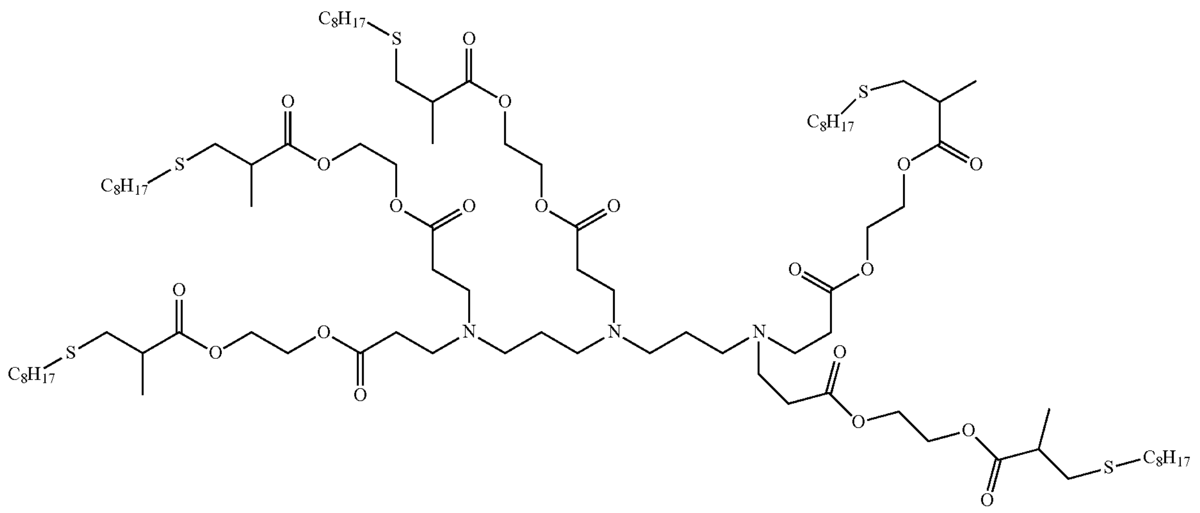 |

TABLE 6-continued
| Example ionizable cationic lipo-dendrimers | |
|---|---|
| ID # | Structure |
| 5A2-2-SC12 (5-arm) | 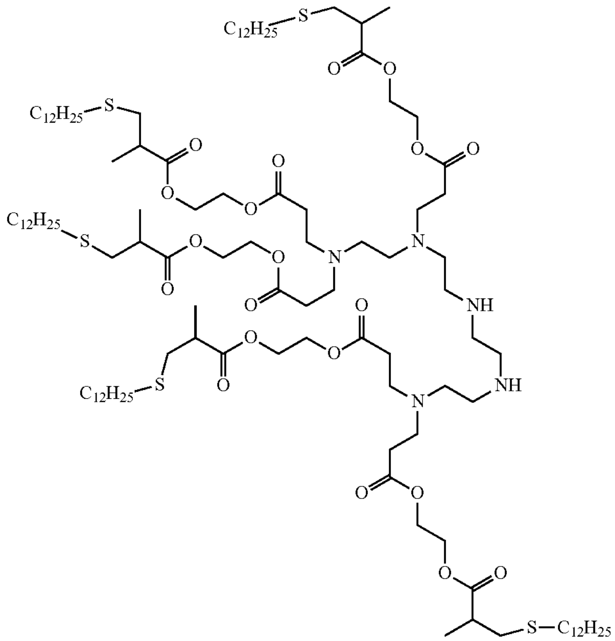 |

TABLE 6-continued
| Example ionizable cationic lipo-dendrimers | |
|---|---|
| ID # | Structure |
| 5A3-1-SC12 (5 arm) | 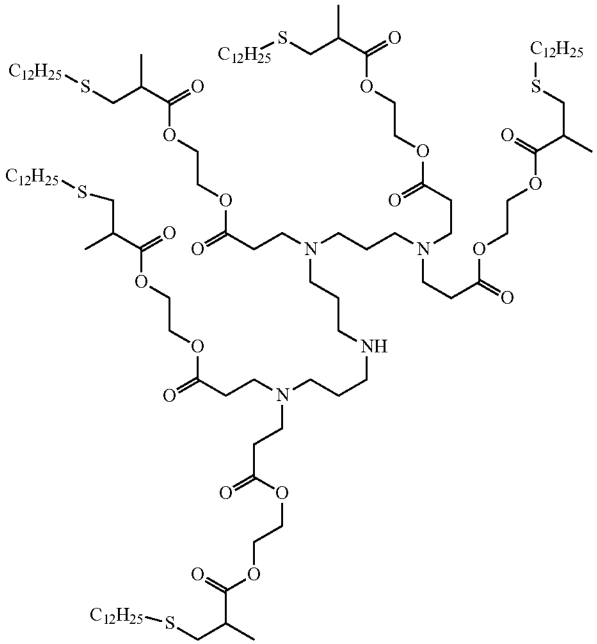 |

TABLE 6-continued
| Example ionizable cationic lipo-dendrimers | |
|---|---|
| ID # | Structure |
| 5A3-1-SC8 (5-arm) | 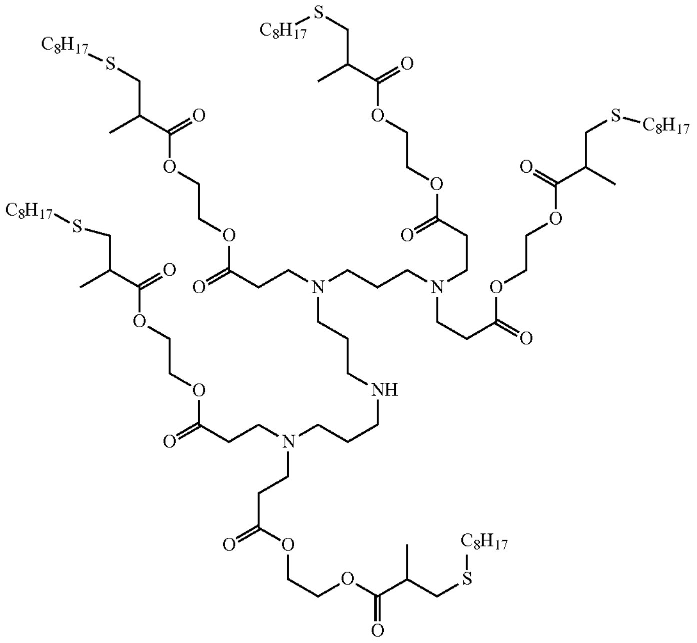 |

TABLE 6-continued
| Example ionizable cationic lipo-dendrimers | |
|---|---|
| ID # | Structure |
| 5A4-1-SC12 (5-arm) | 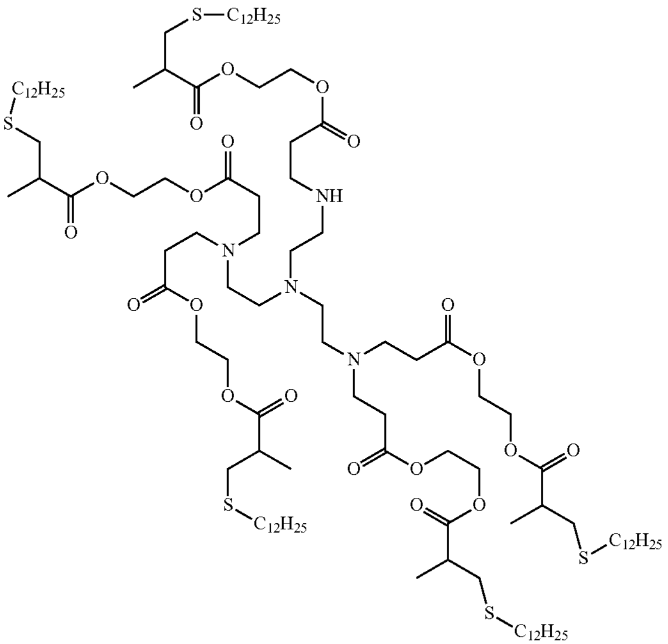 |

TABLE 6-continued
| Example ionizable cationic lipo-dendrimers | |
|---|---|
| ID # | Structure |
| 5A4-1-SC8 (5-arm) | 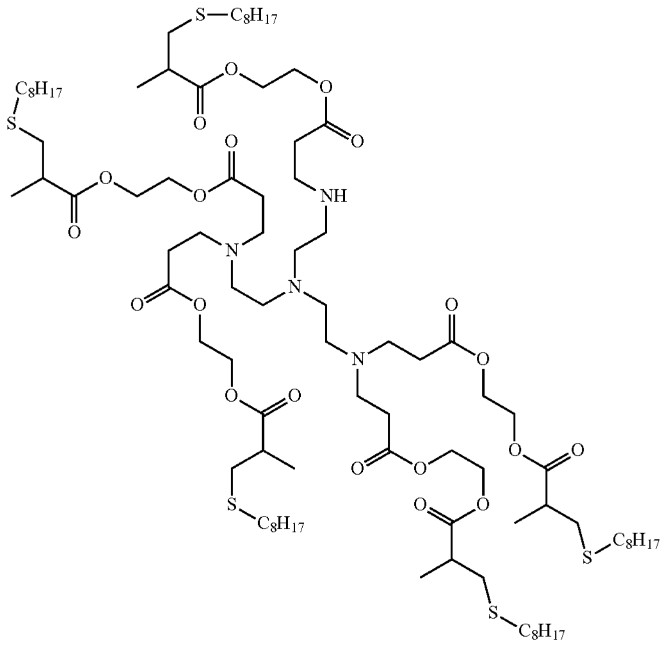 |

TABLE 6-continued
| Example ionizable cationic lipo-dendrimers | |
|---|---|
| ID # | Structure |
| 5A5-SC8 | 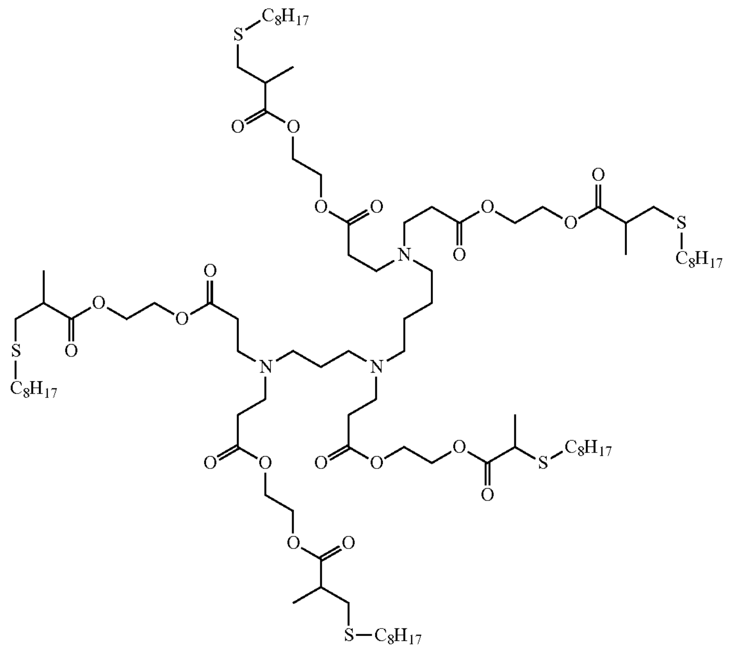 |

TABLE 6-continued
| Example ionizable cationic lipo-dendrimers | |
| --- | --- |
| ID # | Structure |
| 5A5-SC12 | 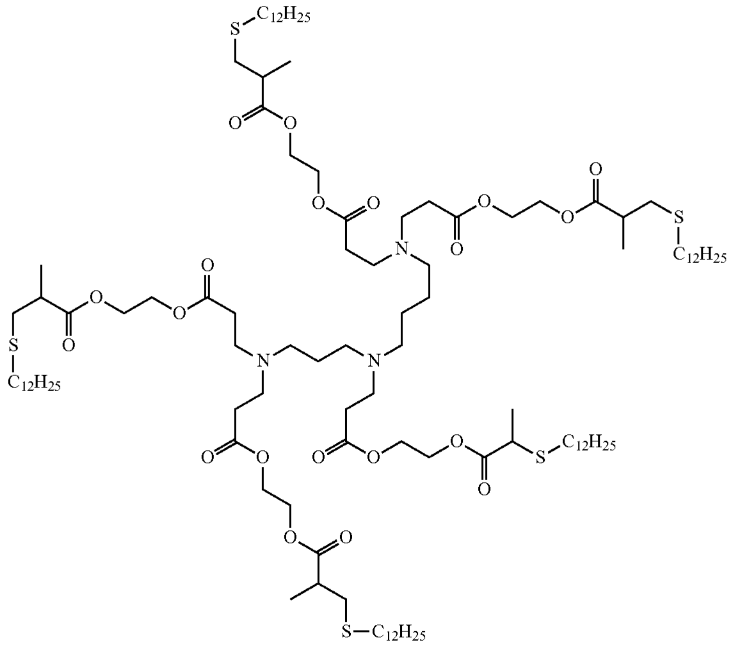 |

TABLE 6-continued
| Example ionizable cationic lipo-dendrimers | |
|---|---|
| ID # | Structure |
| 5A2-4-SC12 (6-arm) | 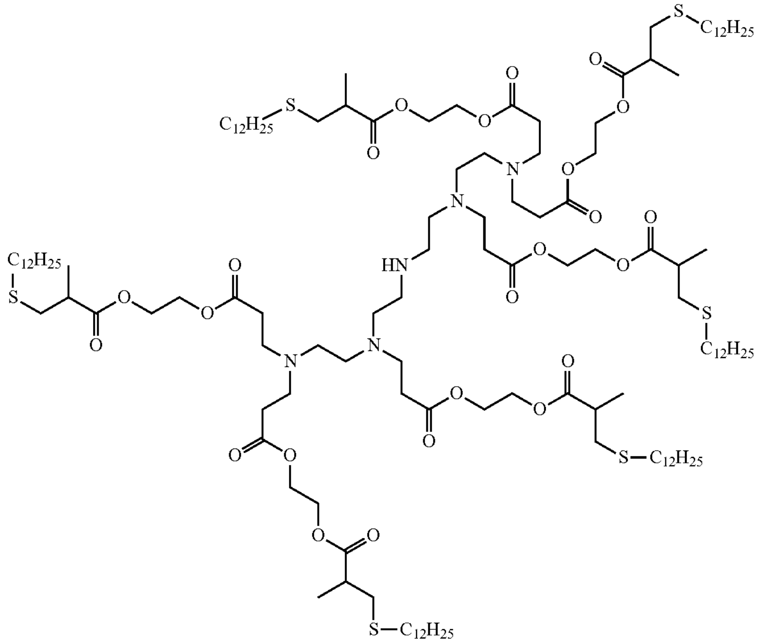 |

TABLE 6-continued
| Example ionizable cationic lipo-dendrimers | |
|---|---|
| ID # | Structure |
| 5A2-4-SC10 (6-arm) | 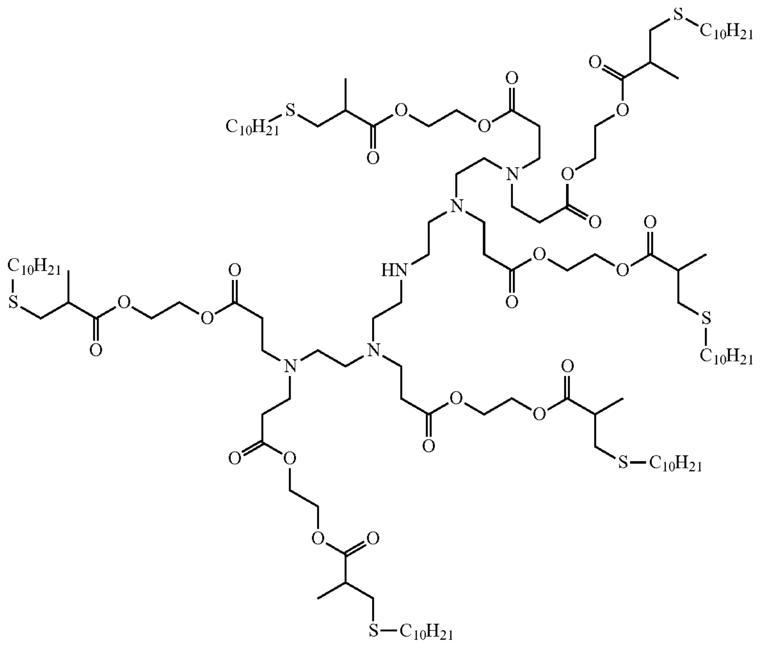 |

TABLE 6-continued
| Example ionizable cationic lipo-dendrimers | |
|---|---|
| ID # | Structure |
| 5A3-2--SC8 (6-arm) | 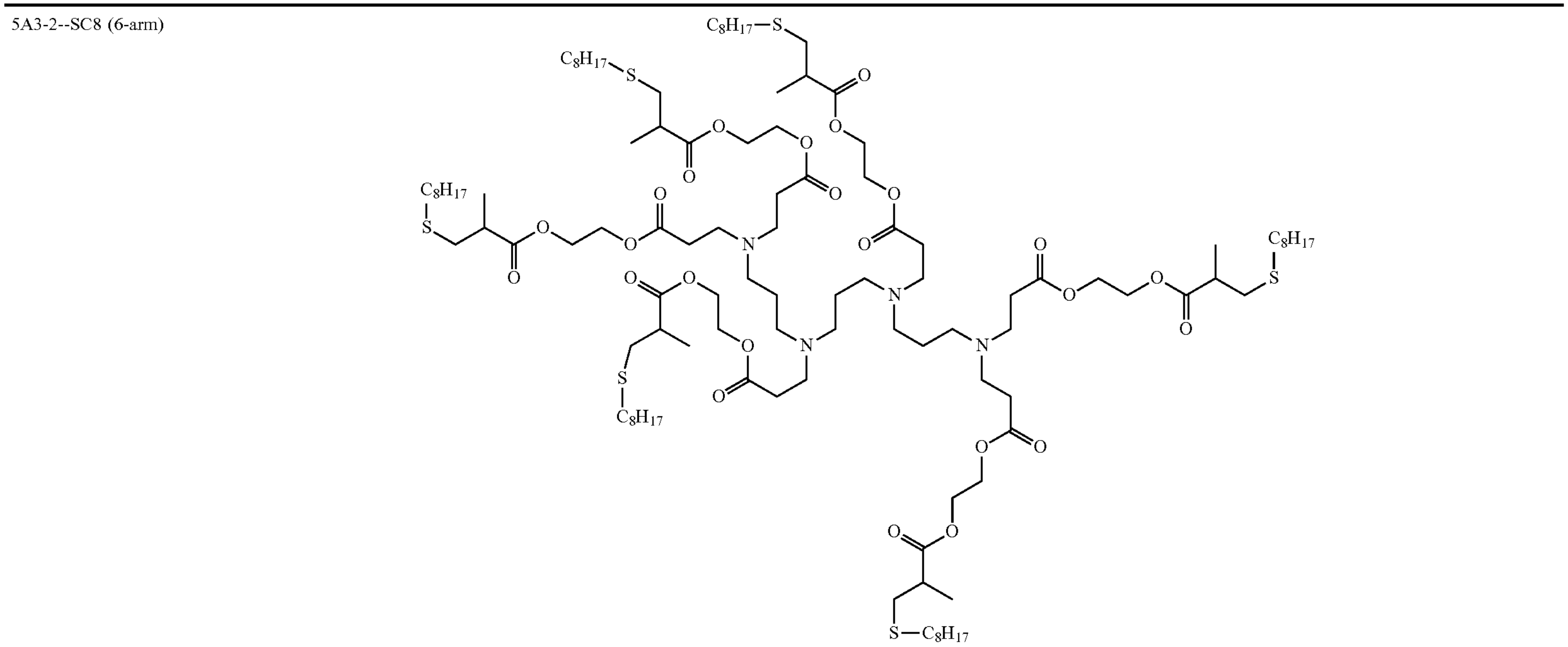 |

TABLE 6-continued
| Example ionizable cationic lipo-dendrimers | |
|---|---|
| ID # | Structure |
| 5A3-2-SC12 (6-arm) | 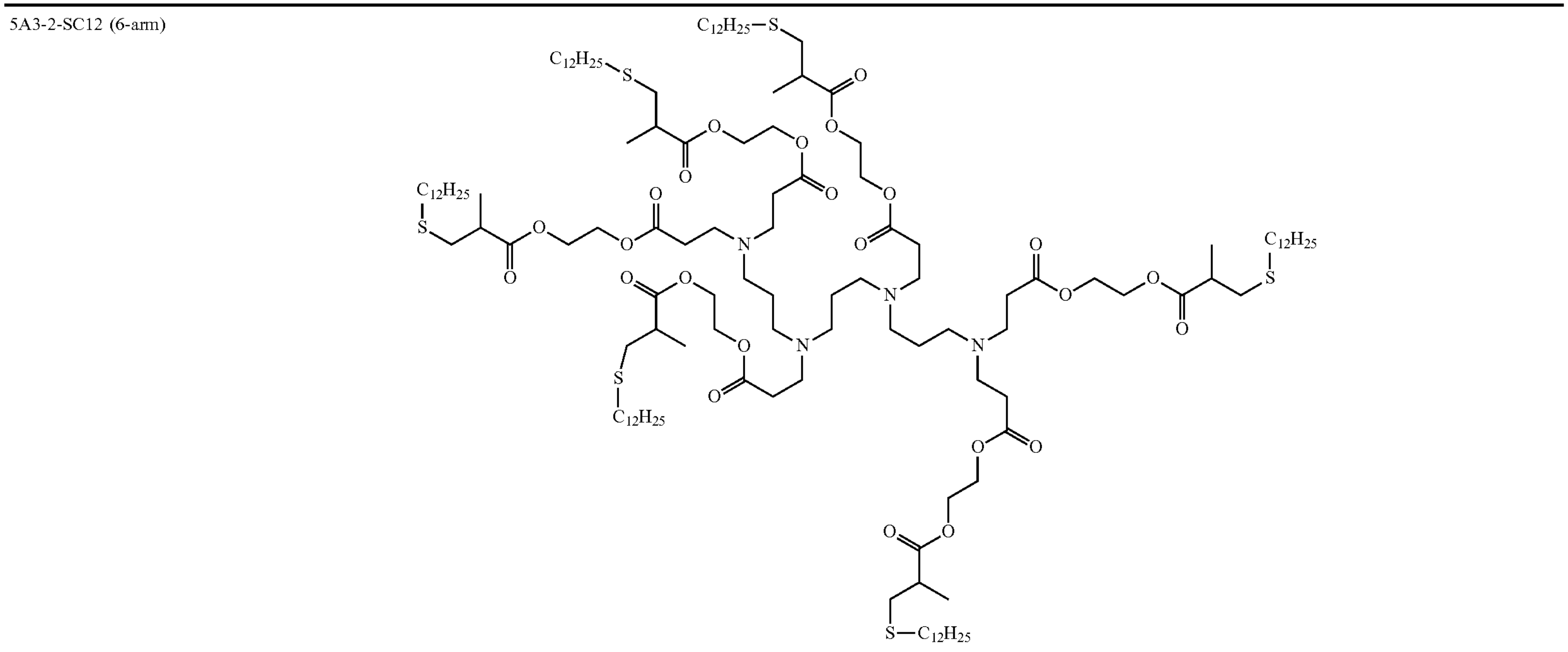 |

TABLE 6-continued
| Example ionizable cationic lipo-dendrimers | |
|---|---|
| ID # | Structure |
| 5A4-2-SC8 (6-arm) | 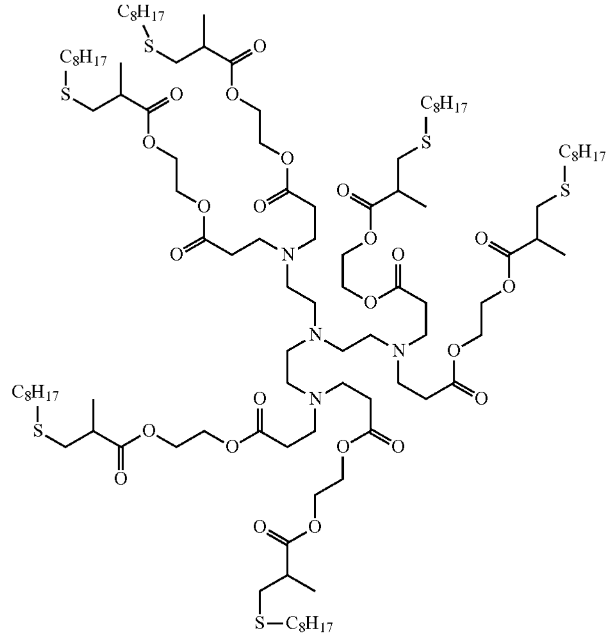 |

TABLE 6-continued
| Example ionizable cationic lipo-dendrimers | |
|---|---|
| ID # | Structure |
| 5A4-2-SC12 (6-arm) | 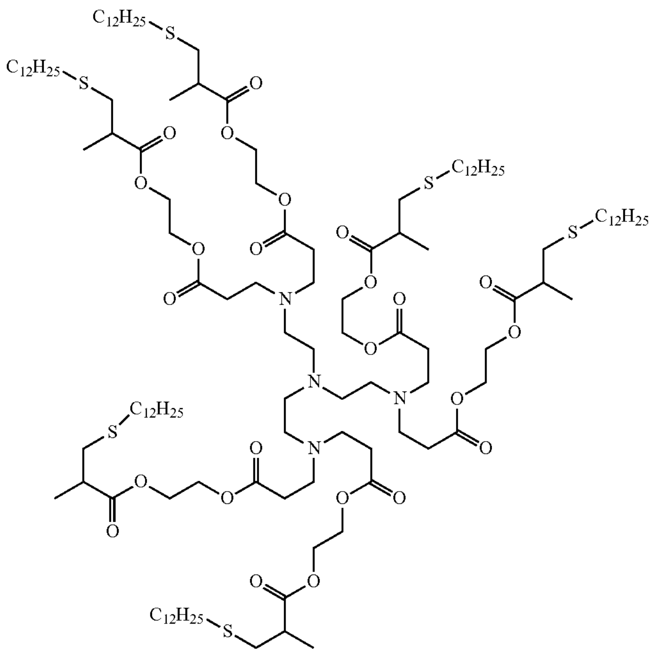 |

TABLE 6-continued
| Example ionizable cationic lipo-dendrimers | |
|---|---|
| ID # | Structure |
| 6A4-SC8 | 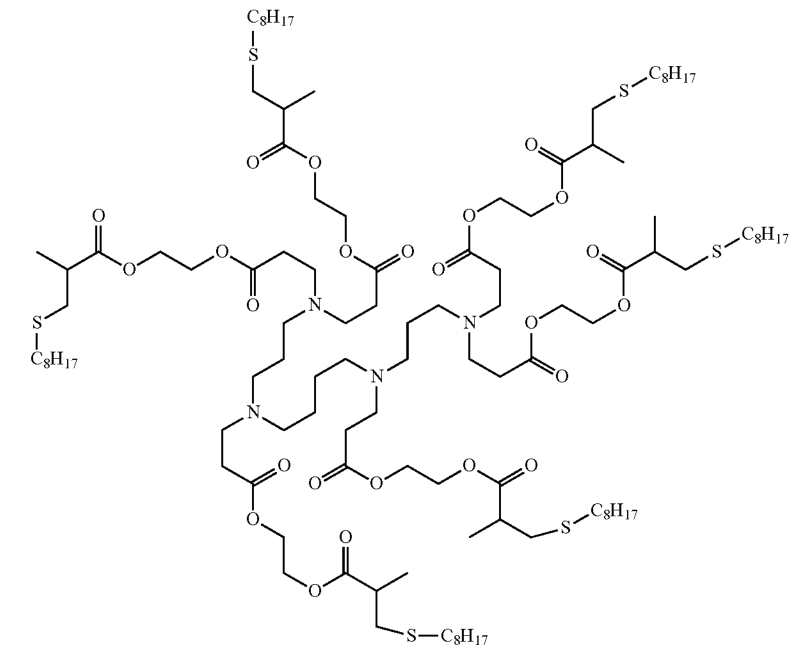 |

TABLE 6-continued
| Example ionizable cationic lipo-dendrimers | |
|---|---|
| ID # | Structure |
| 6A4-SC12 | 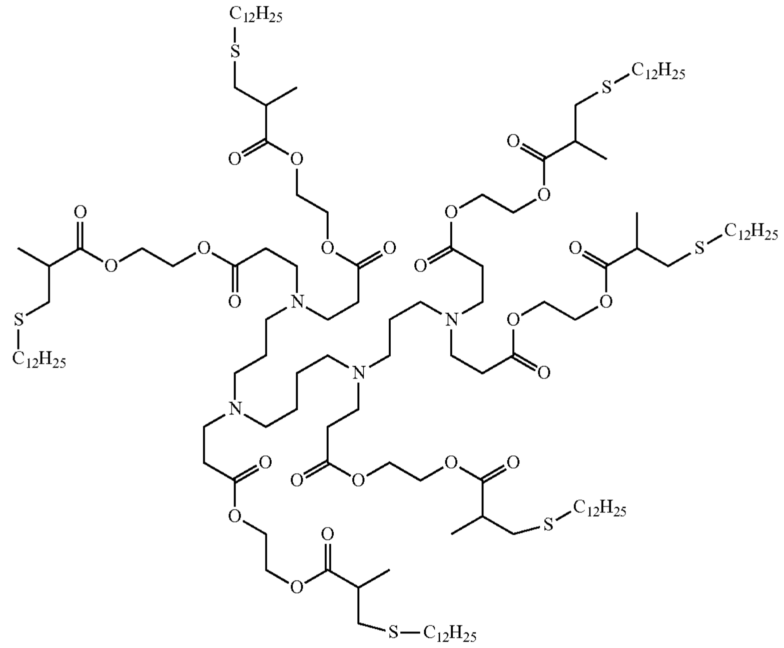 |

TABLE 6-continued
| Example ionizable cationic lipo-dendrimers | |
|---|---|
| ID # | Structure |
| 2A2-g2-SC12 | 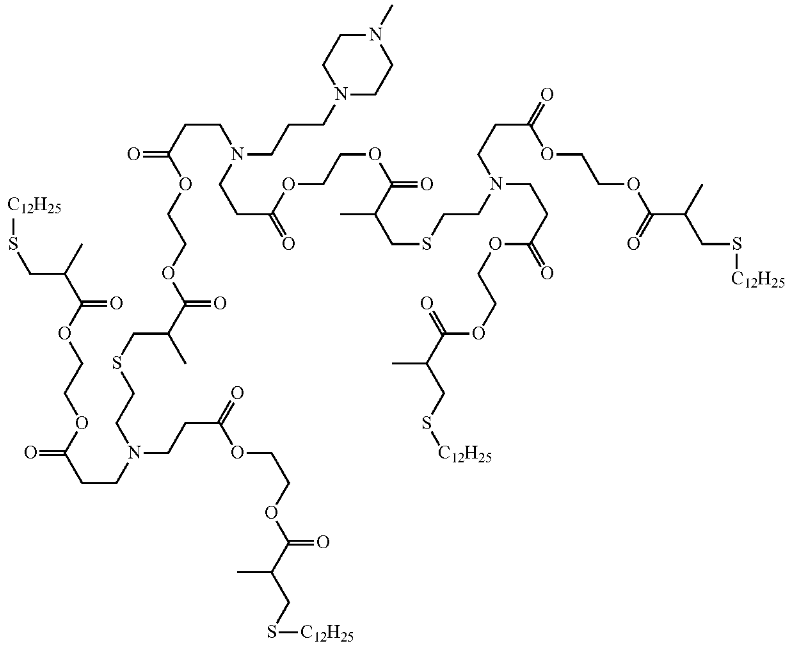 |

TABLE 6-continued
| Example ionizable cationic lipo-dendrimers | |
|---|---|
| ID # | Structure |
| 2A2-g2-SC8 | 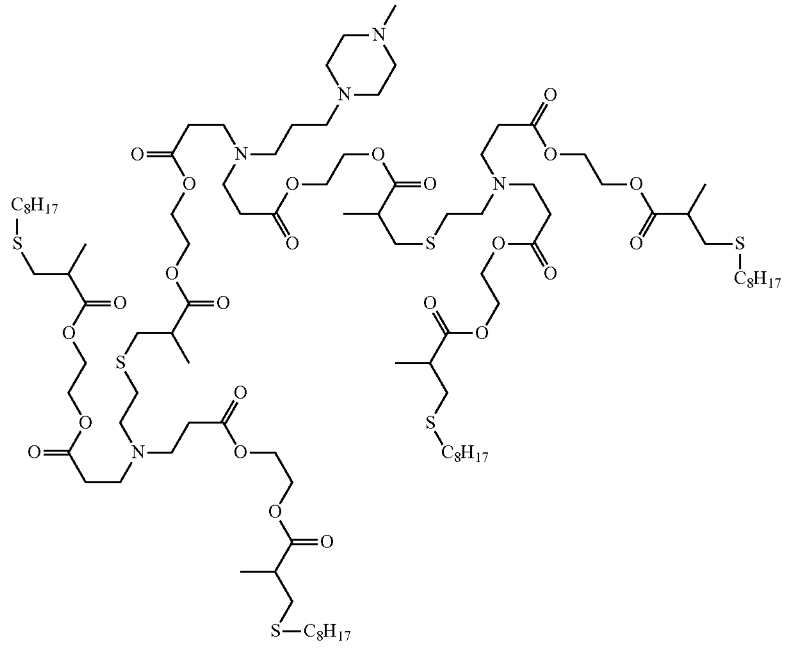 |

TABLE 6-continued
| Example ionizable cationic lipo-dendrimers | |
|---|---|
| ID # | Structure |
| 2A11-g2-SC12 | 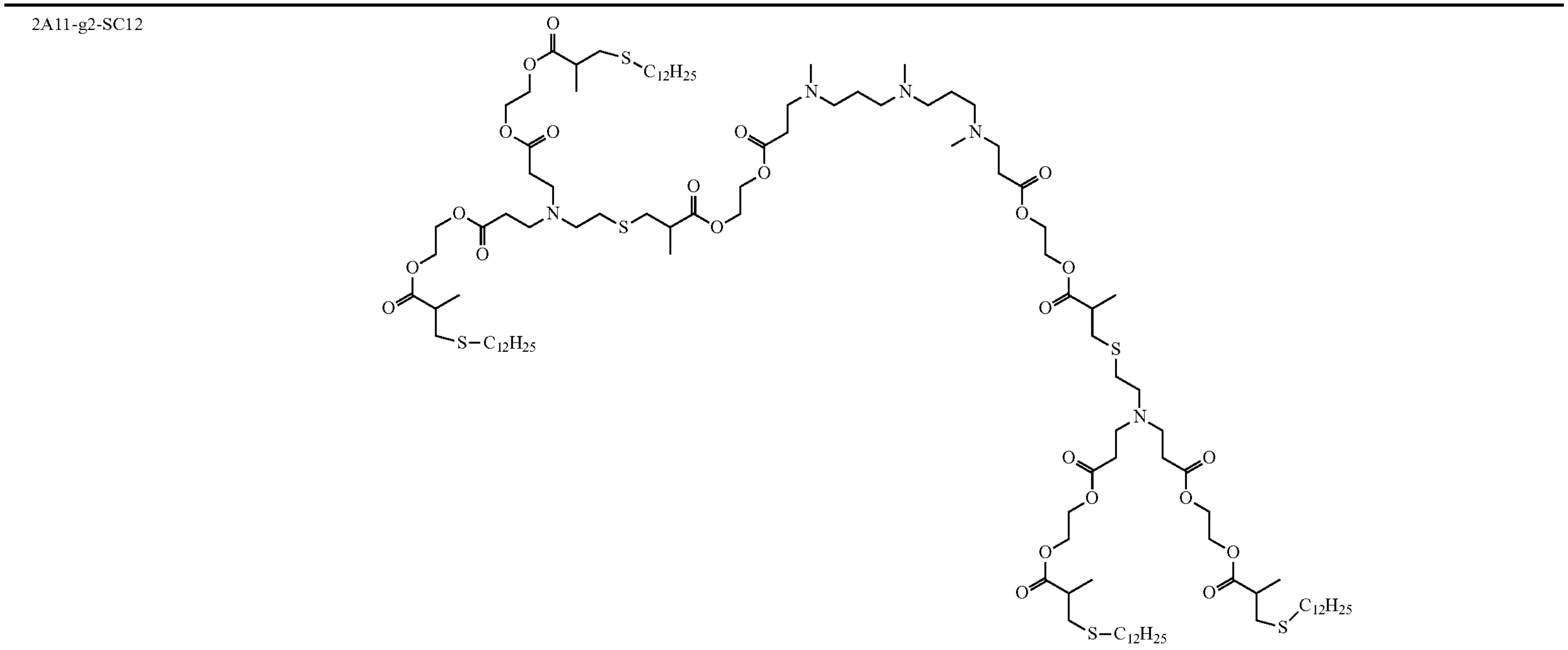 |

TABLE 6-continued
| Example ionizable cationic lipo-dendrimers | |
|---|---|
| ID # | Structure |
| 2A11-g2-SC8 | 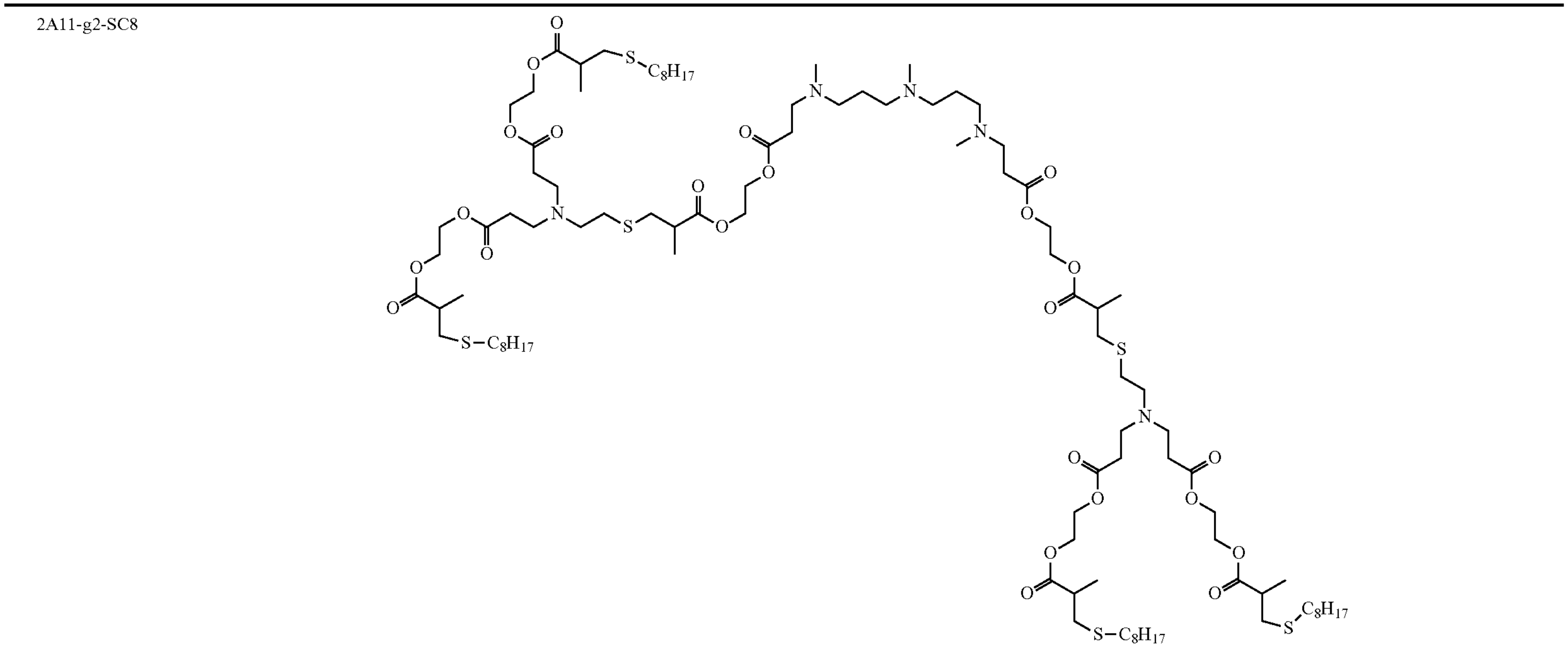 |

TABLE 6-continued
| Example ionizable cationic lipo-dendrimers | |
|---|---|
| ID # | Structure |
| 3A3-g2-SC12 | 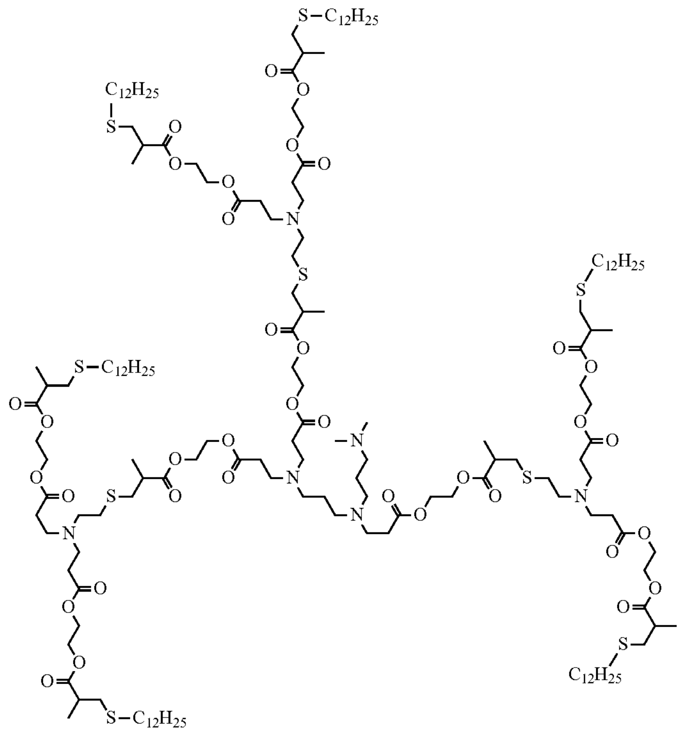 |

TABLE 6-continued
| Example ionizable cationic lipo-dendrimers | |
|---|---|
| ID # | Structure |
| 3A3-g2-SC8 | 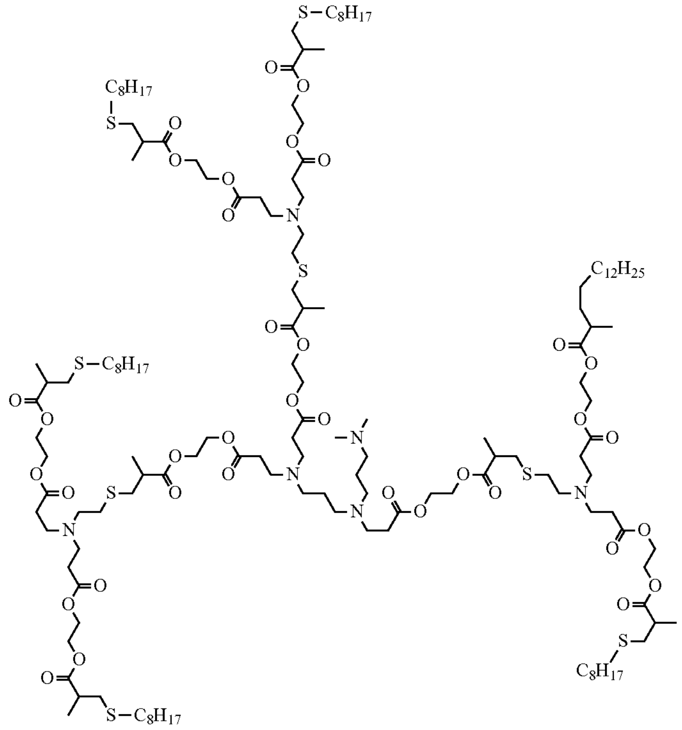 |

TABLE 6-continued
| Example ionizable cationic lipo-dendrimers | |
|---|---|
| ID # | Structure |
| 3A5-g2-SC12 | 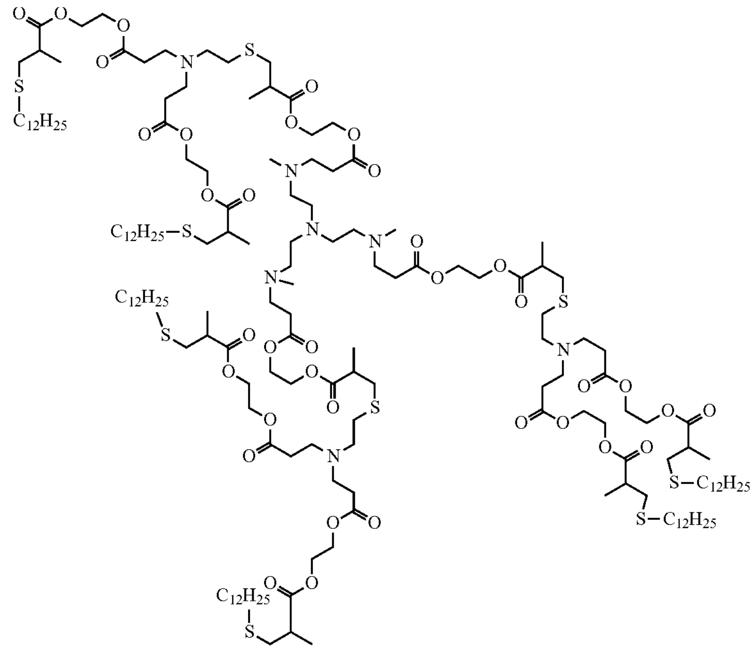 |

TABLE 6-continued
| Example ionizable cationic lipo-dendrimers | |
|---|---|
| ID # | Structure |
| 2A11-g3-SC12 | 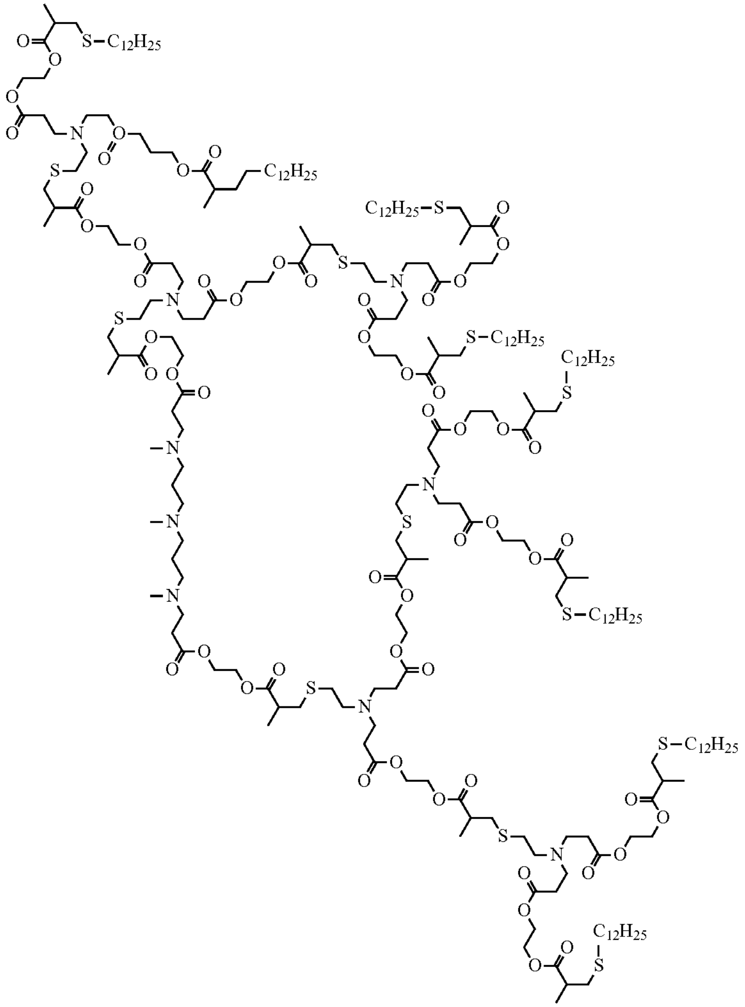 |

TABLE 6-continued
| Example ionizable cationic lipo-dendrimers | |
|---|---|
| ID # | Structure |
| 2A11-g3-SC8 | 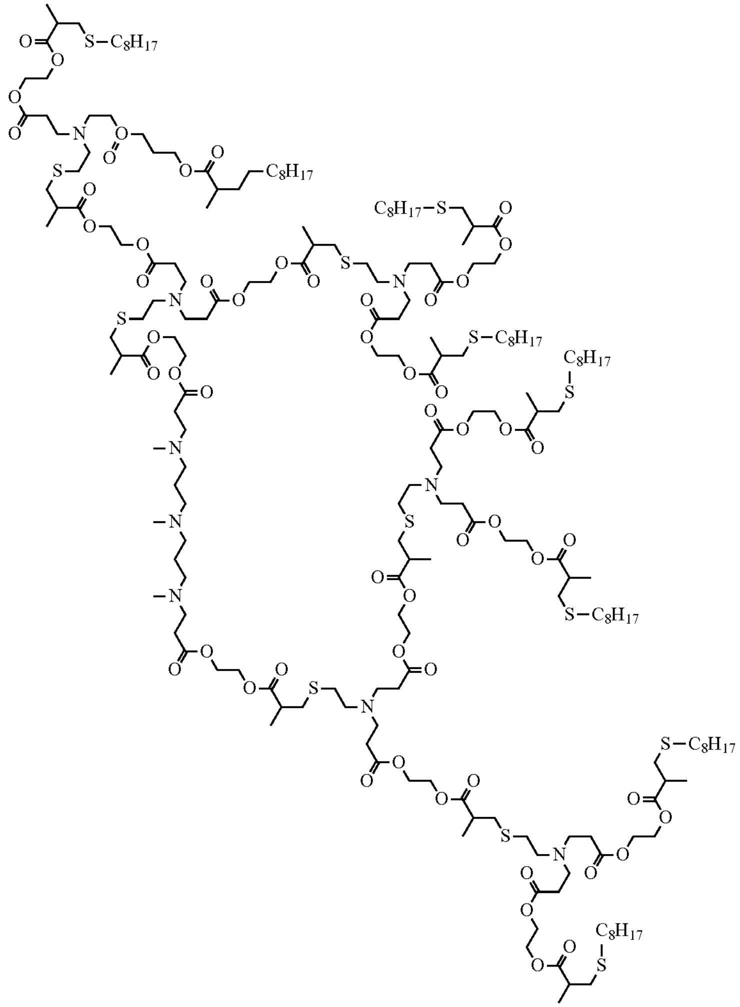 |

TABLE 6-continued
| Example ionizable cationic lipo-dendrimers | |
|---|---|
| ID # | Structure |
| 1A2-g4-SC12 | 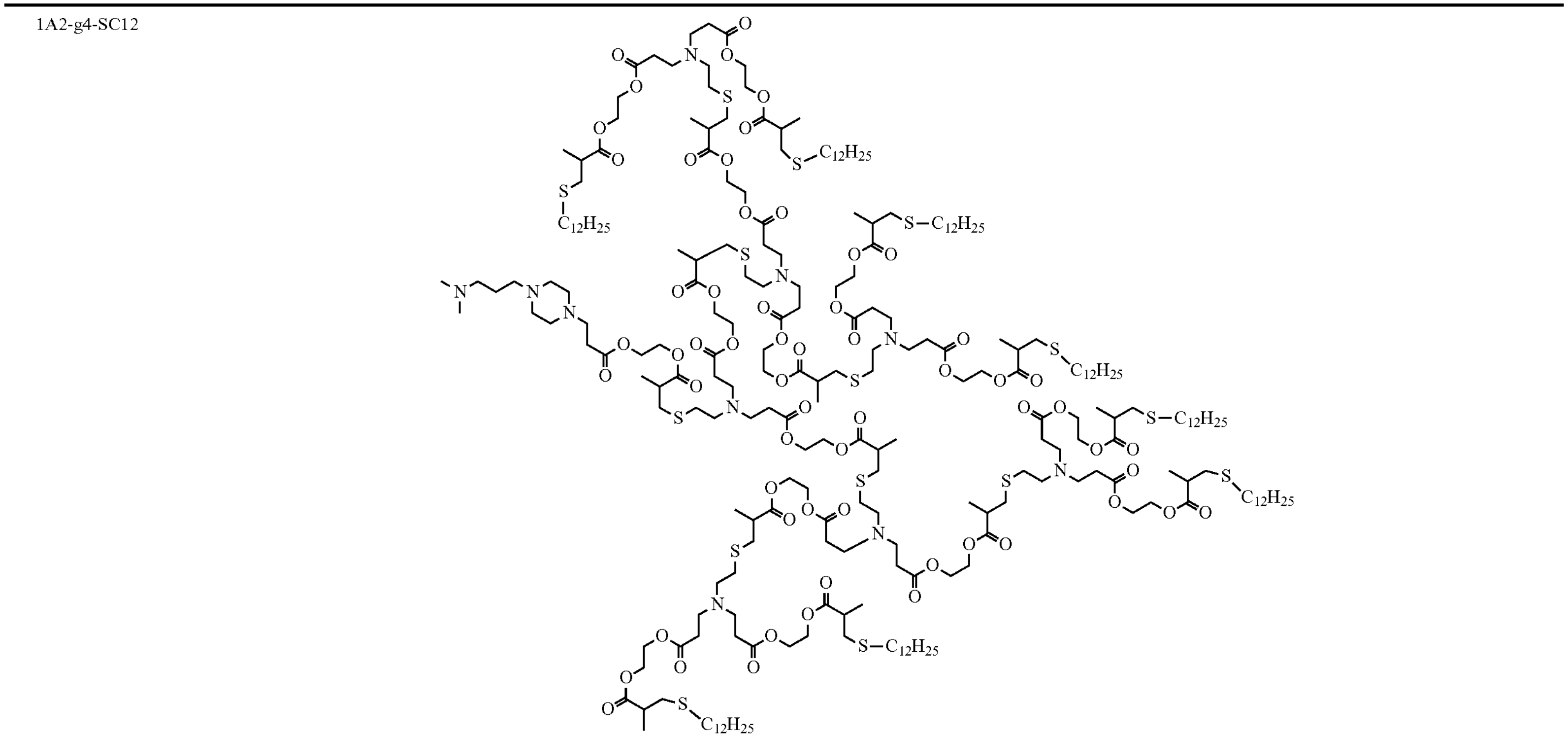 |

TABLE 6-continued
| Example ionizable cationic lipo-dendrimers | |
|---|---|
| ID # | Structure |
| 4A1-g2-SC12 | 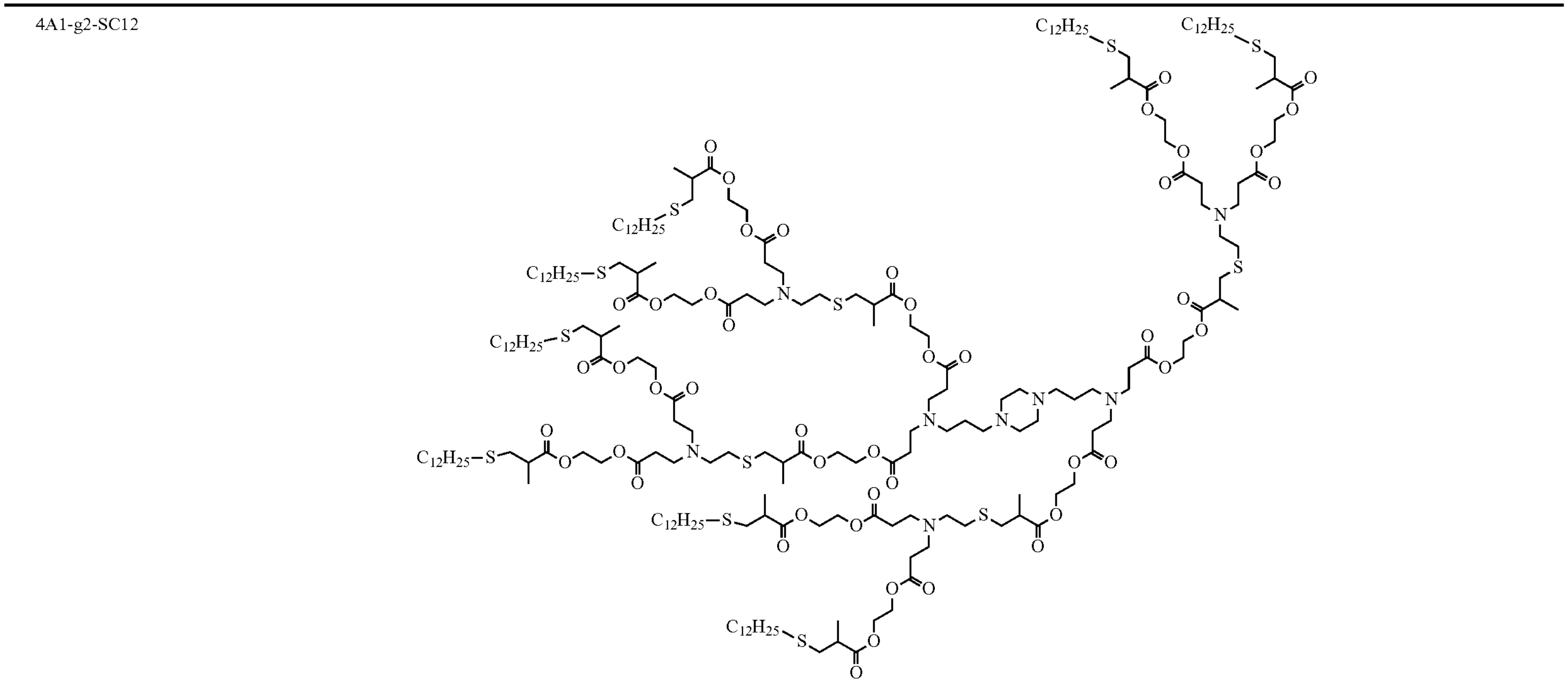 |

TABLE 6-continued
Example ionizable cationic lipo-dendrimers
| ID # | Structure |
| --- | --- |
| 1A2-g4-SC8 | 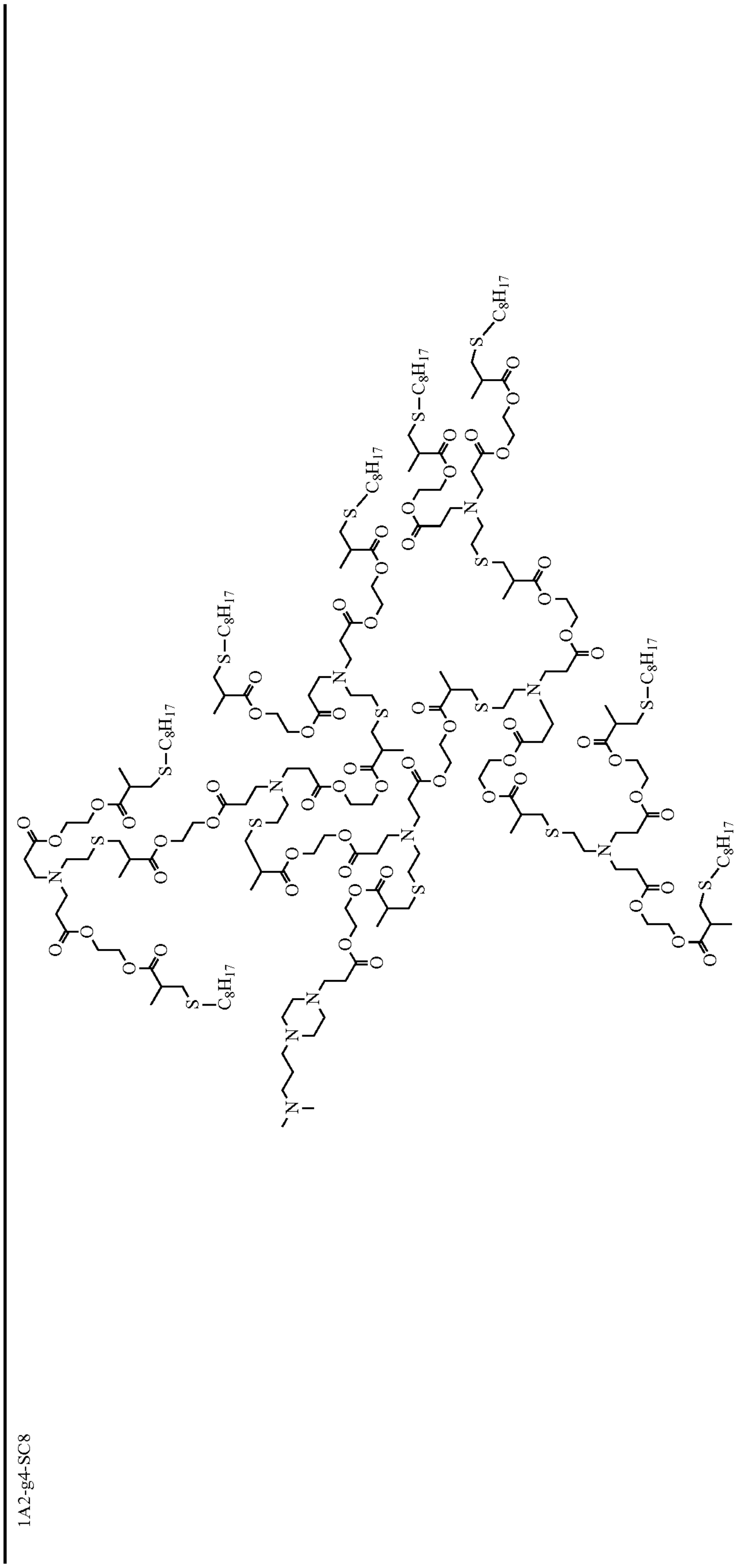 |

TABLE 6-continued
| Example ionizable cationic lipo-dendrimers | |
|---|---|
| ID # | Structure |
| 4A1-g2-SC8 | 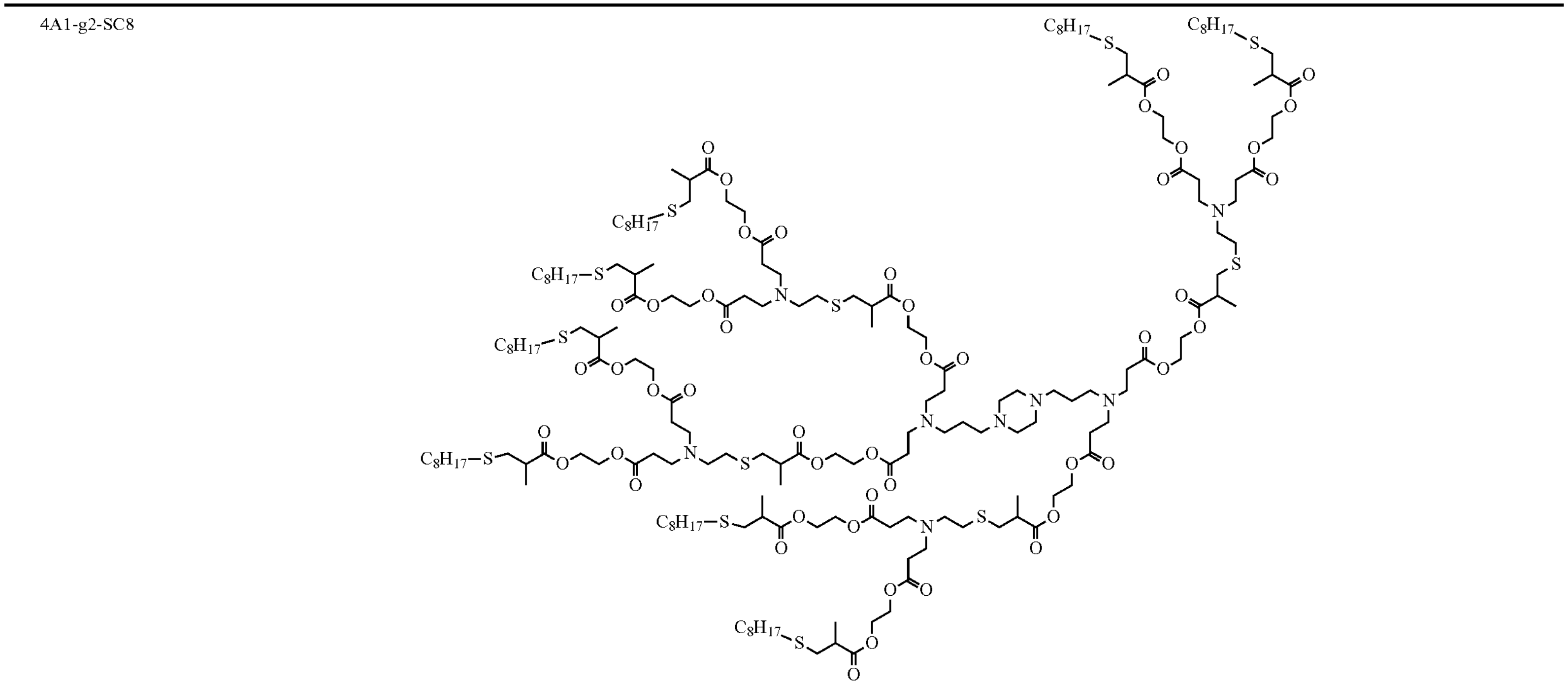 |

TABLE 6-continued
| Example ionizable cationic lipo-dendrimers | |
| --- | --- |
| ID # | Structure |
| 4A3-g2-SC12 | 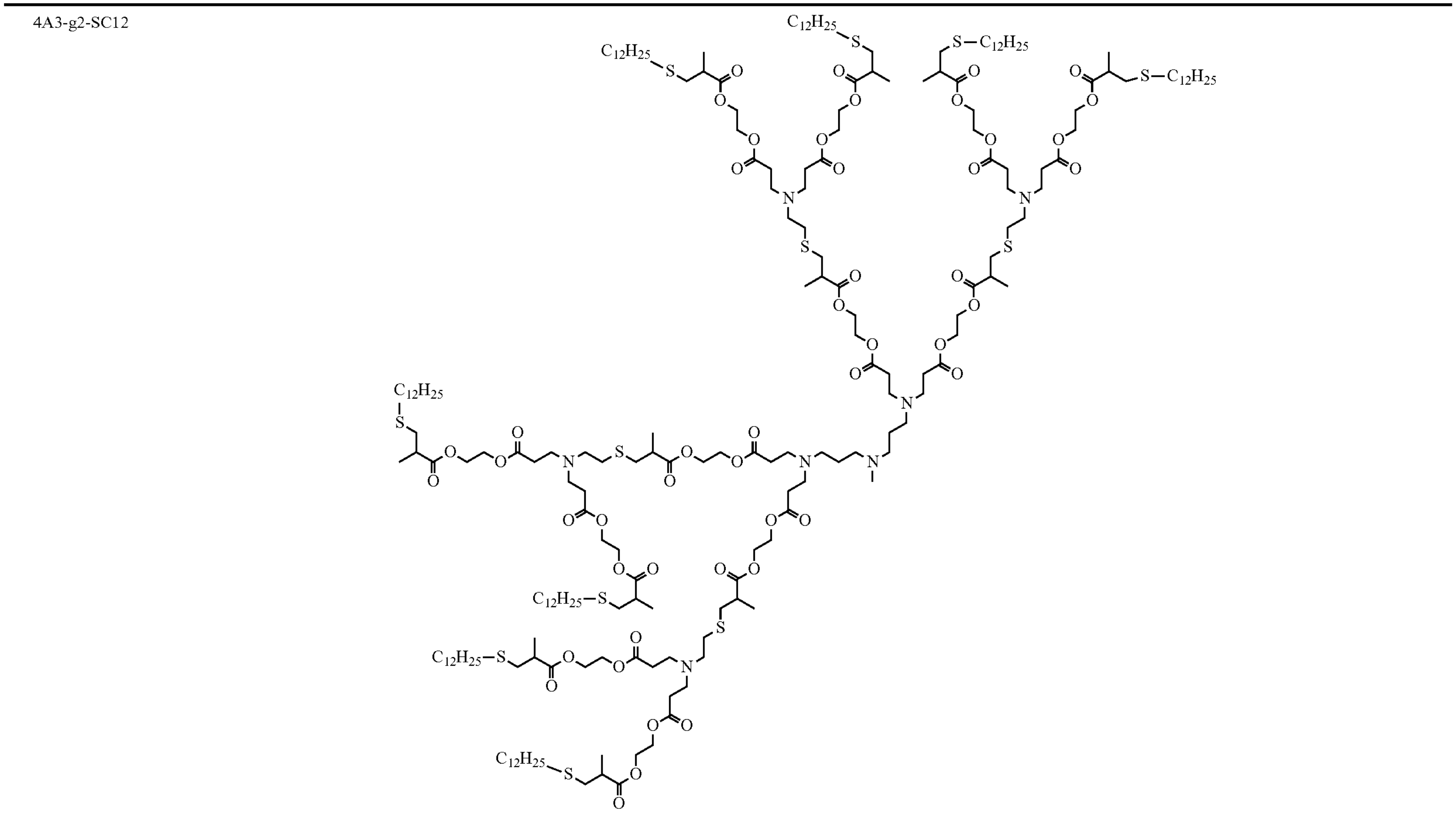 |

TABLE 6-continued
| Example ionizable cationic lipo-dendrimers | |
| --- | --- |
| ID # | Structure |
| 4A3-g2-SC8 | 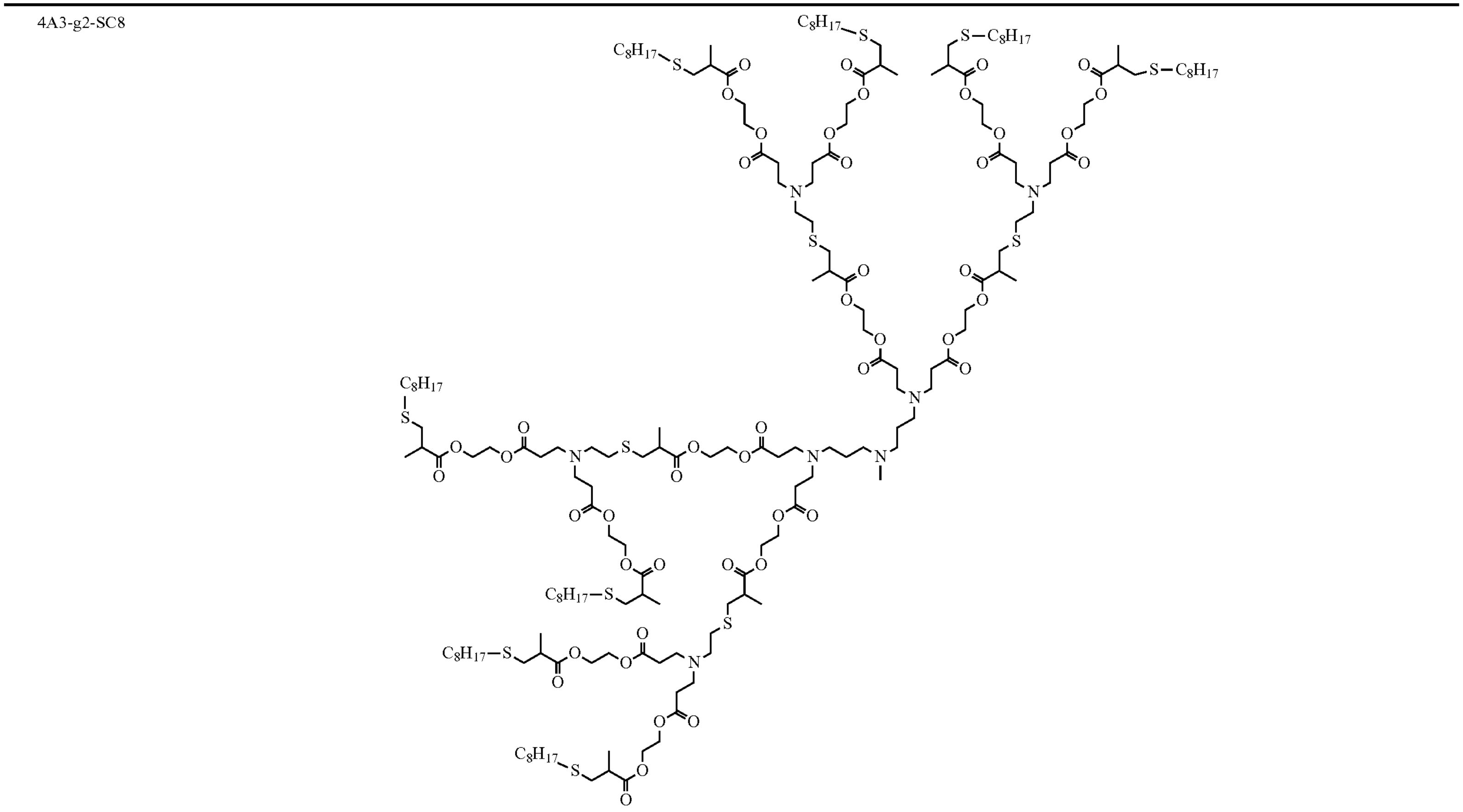 |

TABLE 6-continued
| Example ionizable cationic lipo-dendrimers | |
|---|---|
| ID # | Structure |
| 1A2-g3-SC12 | 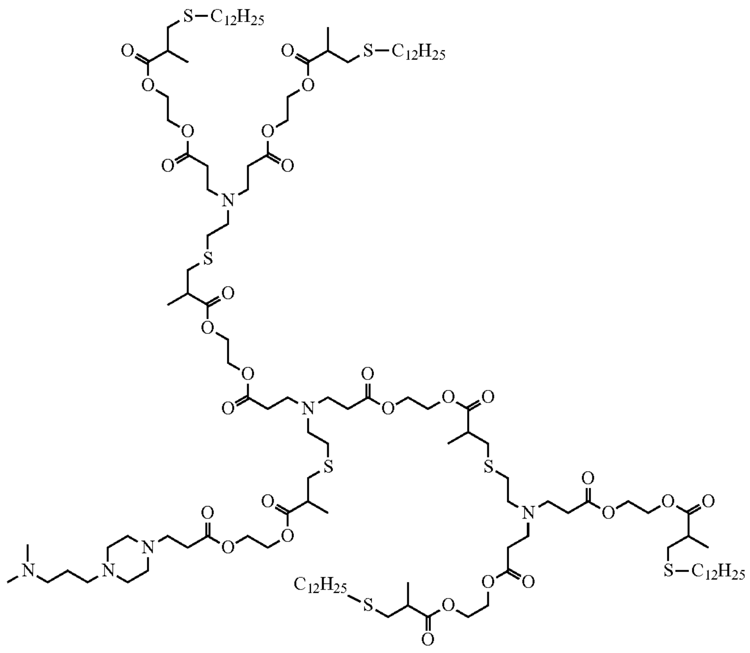 |

TABLE 6-continued
| Example ionizable cationic lipo-dendrimers | |
|---|---|
| ID # | Structure |
| 1A2-g3-SC8 | 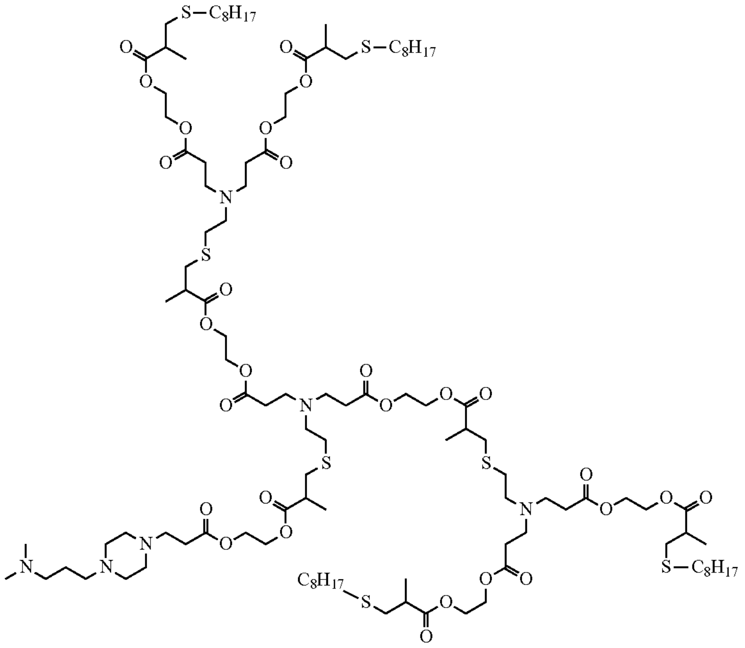 |

TABLE 6-continued
| Example ionizable cationic lipo-dendrimers | |
| --- | --- |
| ID # | Structure |
| 2A2-g3-SC12 | 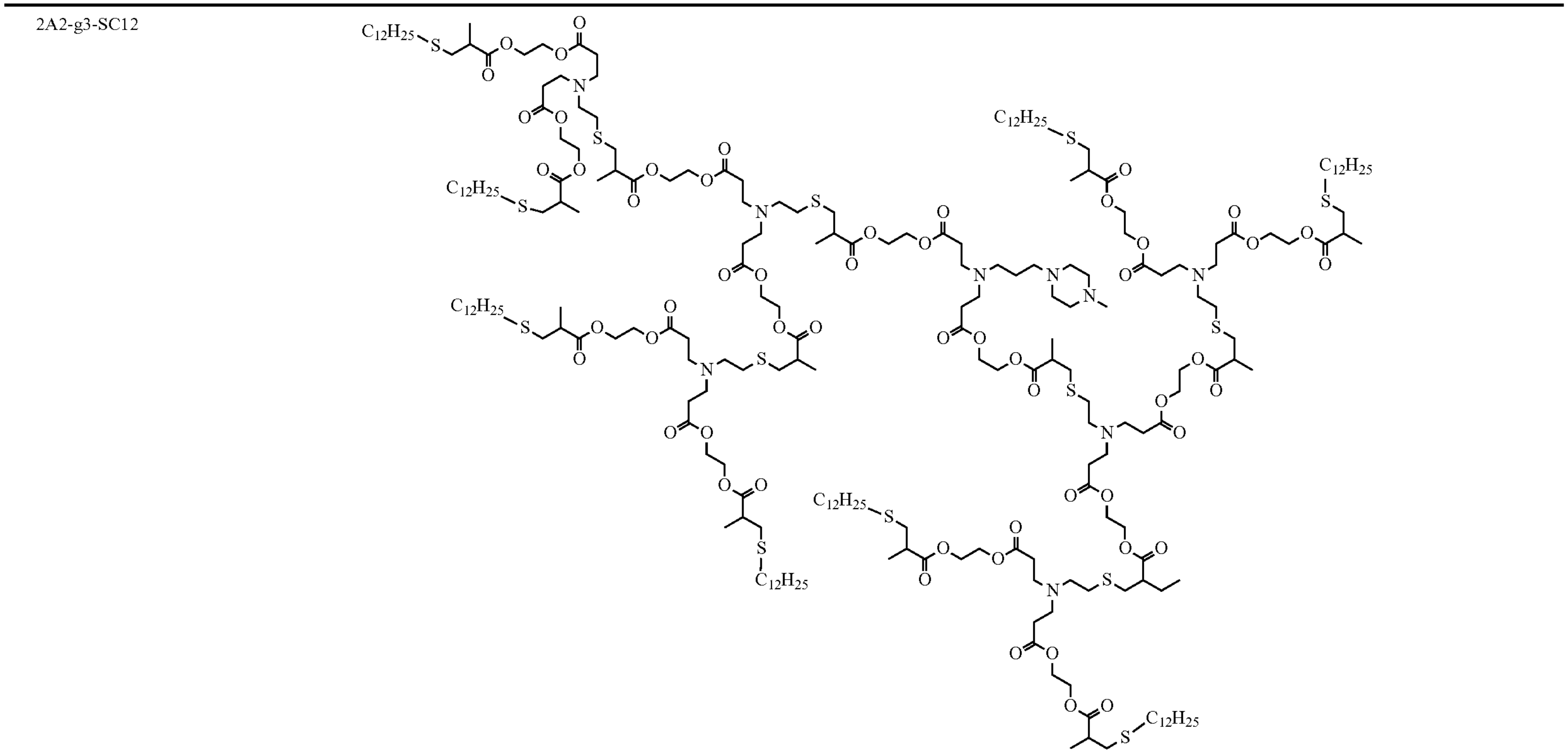 |

TABLE 6-continued
Example ionizable cationic lipo-dendrimers
| ID # | Structure |
|---|---|
| 2A2-g3-SC8 | 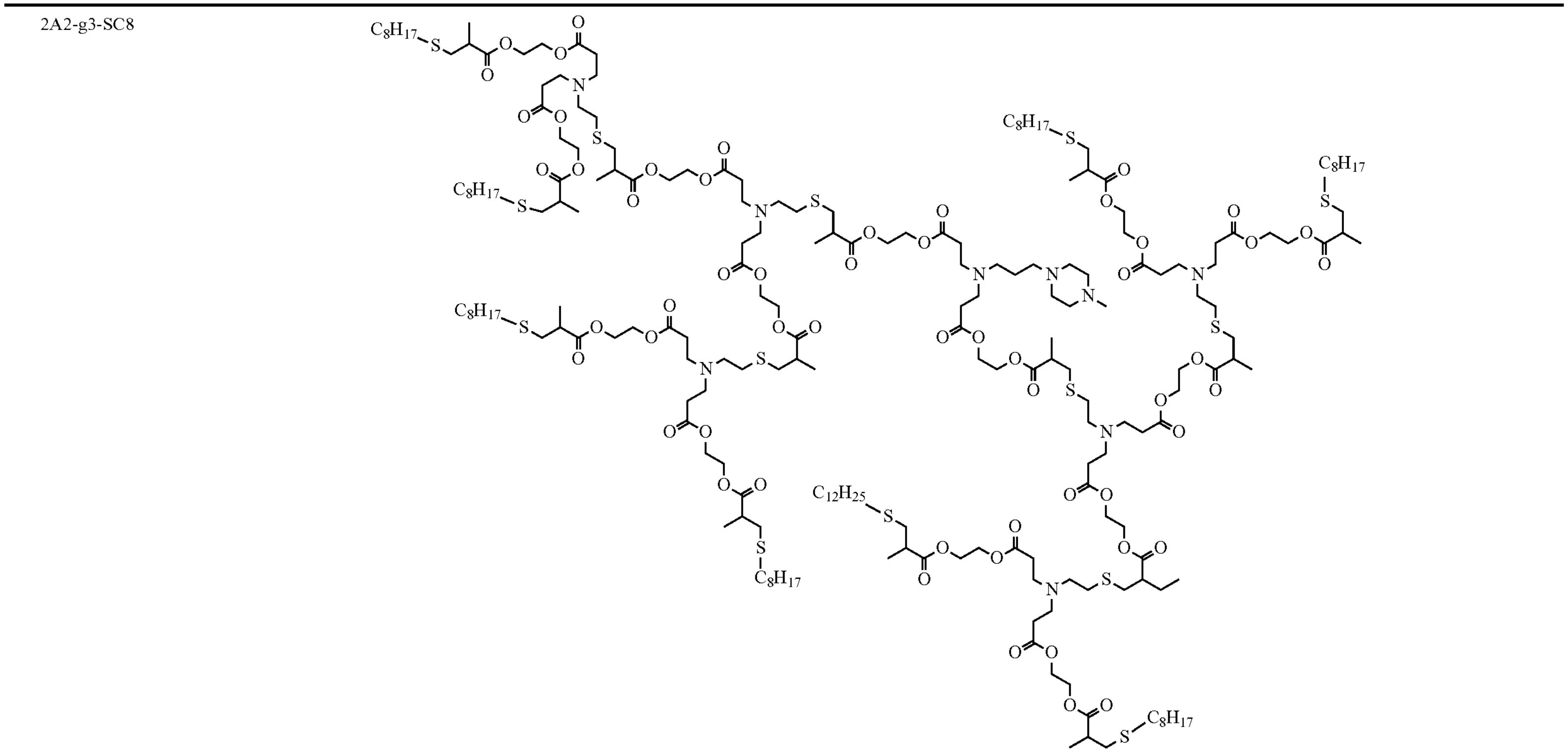 |

TABLE 6-continued
| Example ionizable cationic lipo-dendrimers | |
|---|---|
| ID # | Structure |
| 5A2-4-SC8 (6-arm) | 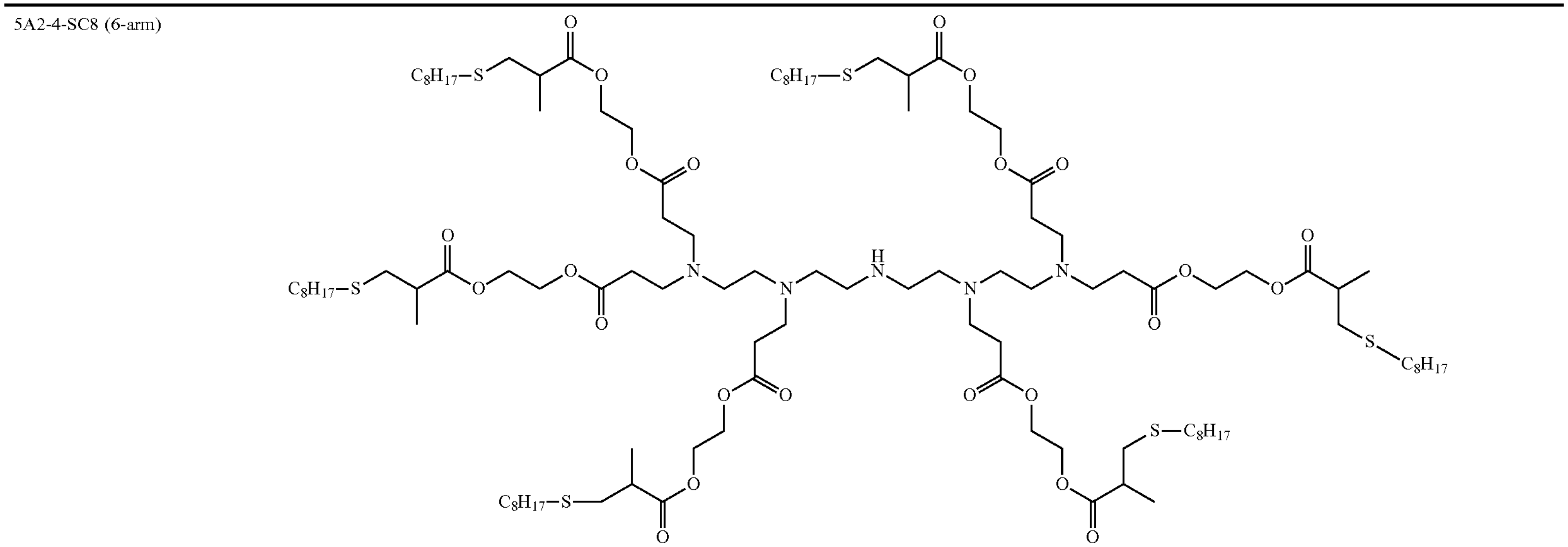 |
| 5A-5-SC8 (6 arm) | 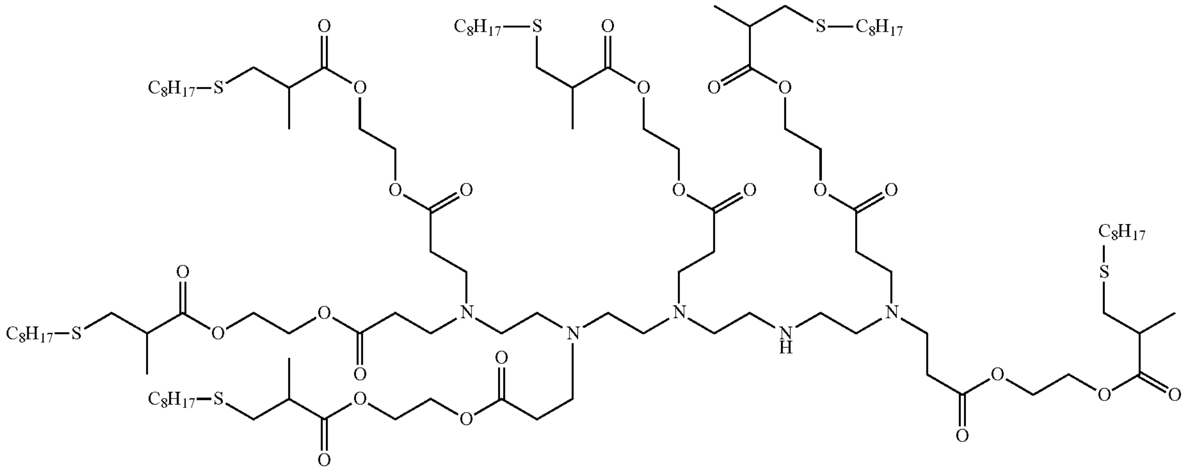 |

TABLE 6-continued
| Example ionizable cationic lipo-dendrimers | |
| --- | --- |
| ID # | Structure |
| 5A2-6-SC8 (6 arm) | 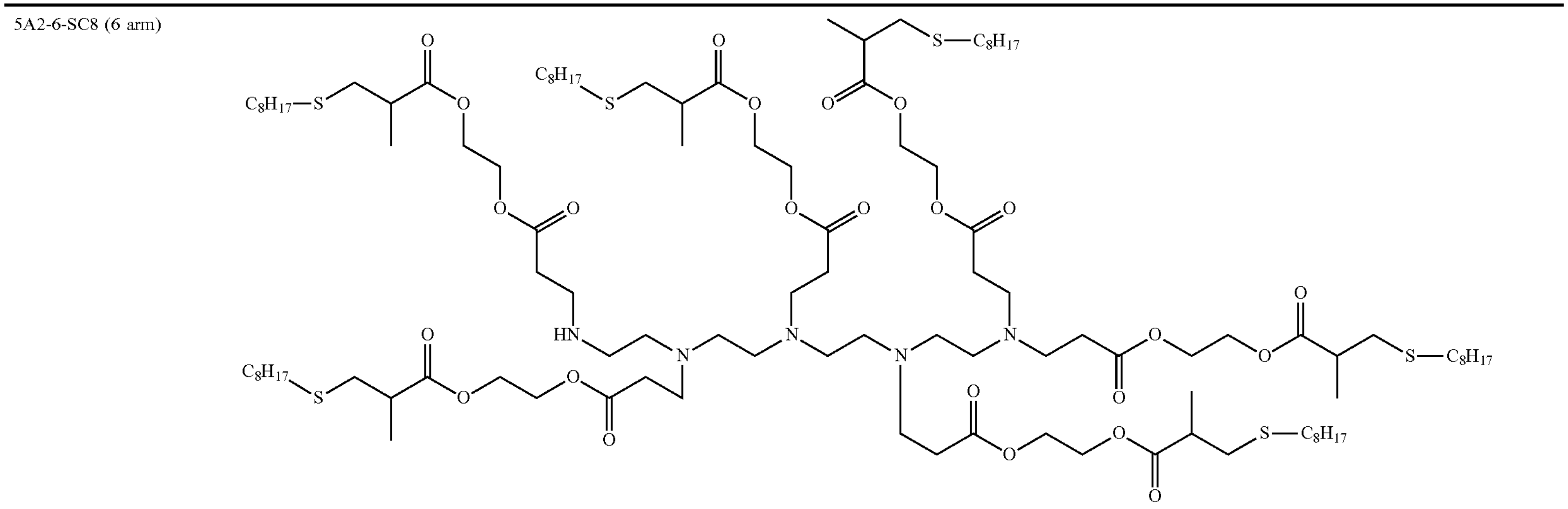 |
| 5A2-1-SC8 (5-arm) | 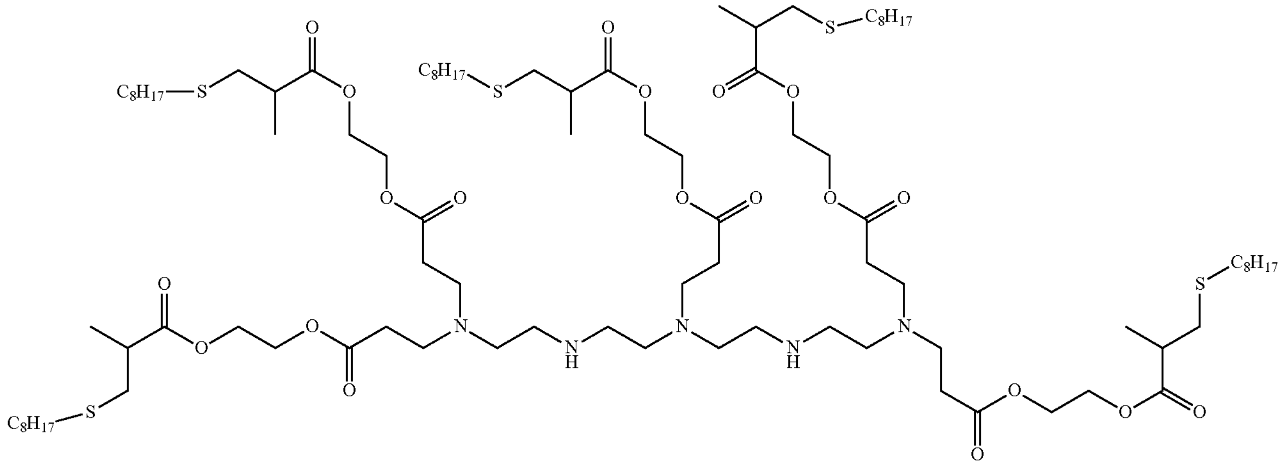 |

TABLE 6-continued
| Example ionizable cationic lipo-dendrimers | |
| --- | --- |
| ID # | Structure |
| 5A2-2-SC8 | 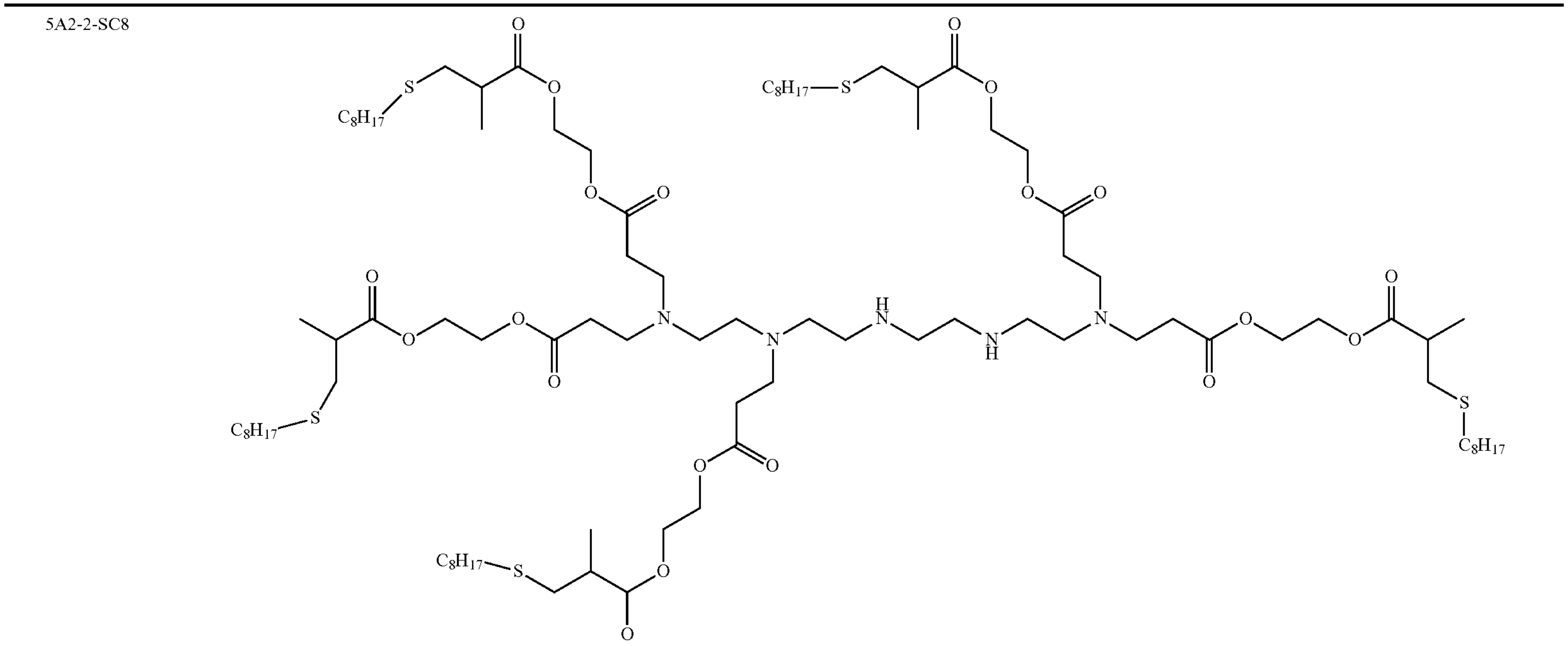 |

TABLE 6-continued
| Example ionizable cationic lipo-dendrimers | |
|---|---|
| ID # | Structure |
| 4A1-SC5 | 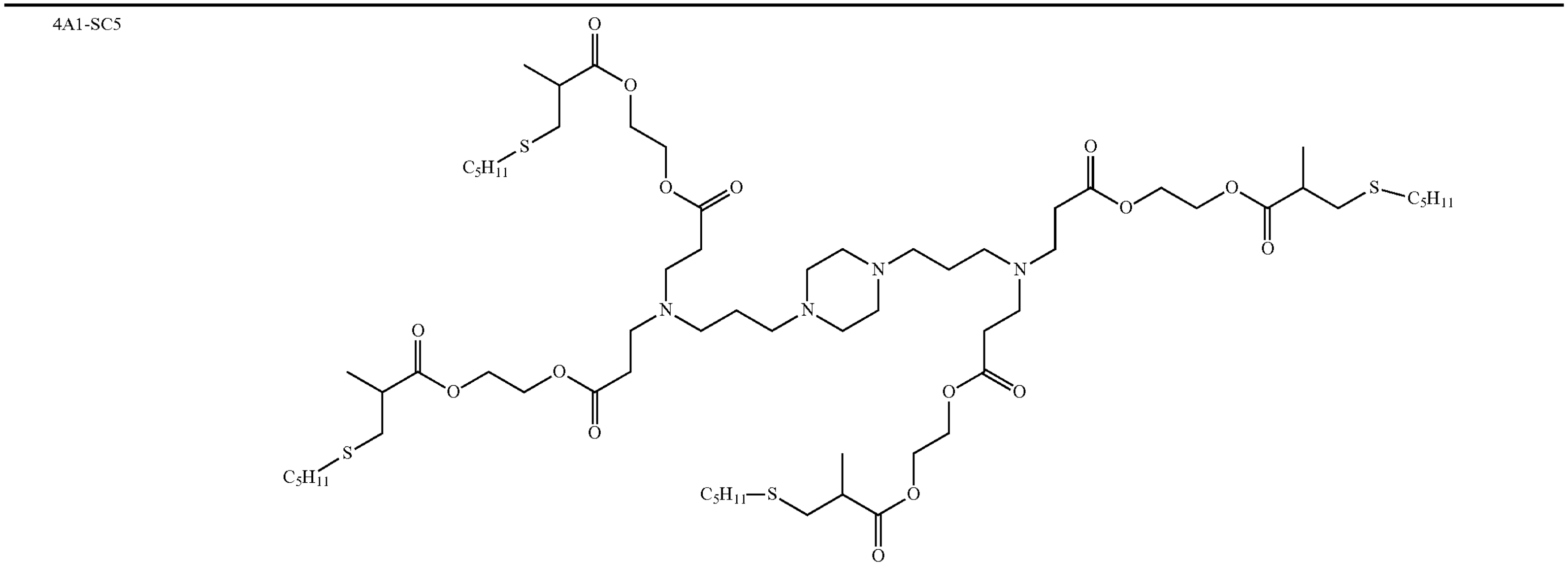 |

TABLE 6-continued
| Example ionizable cationic lipo-dendrimers | |
|---|---|
| ID # | Structure |
| 4A1-SC8 | 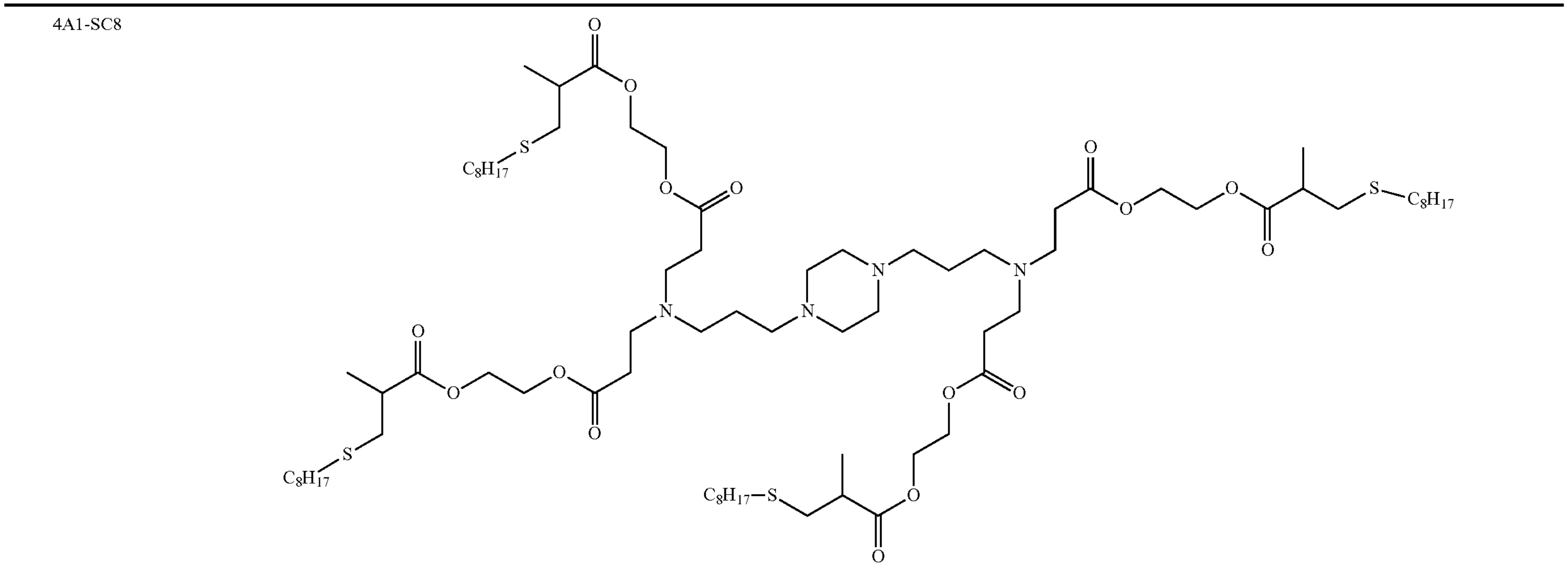 |
| 4A3-SC6 | 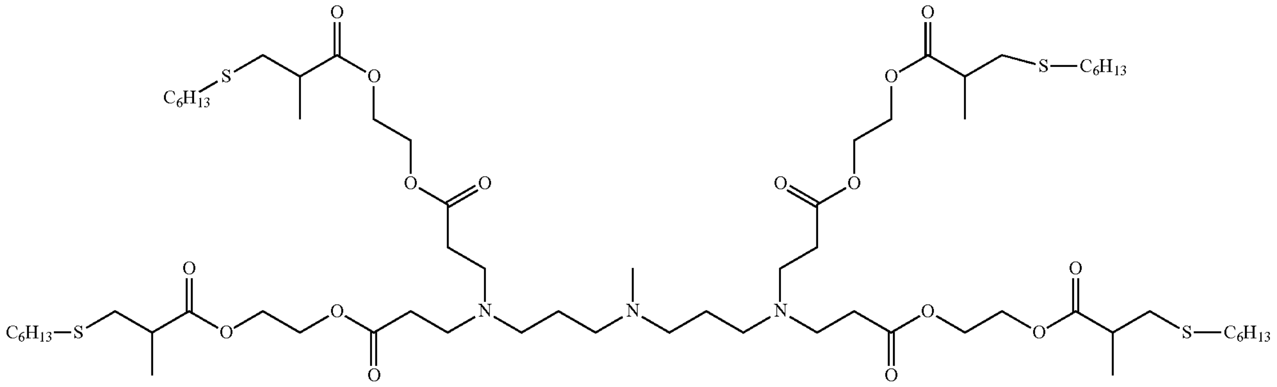 |

TABLE 6-continued
| Example ionizable cationic lipo-dendrimers | |
|---|---|
| ID # | Structure |
| 4A3-SC7 | 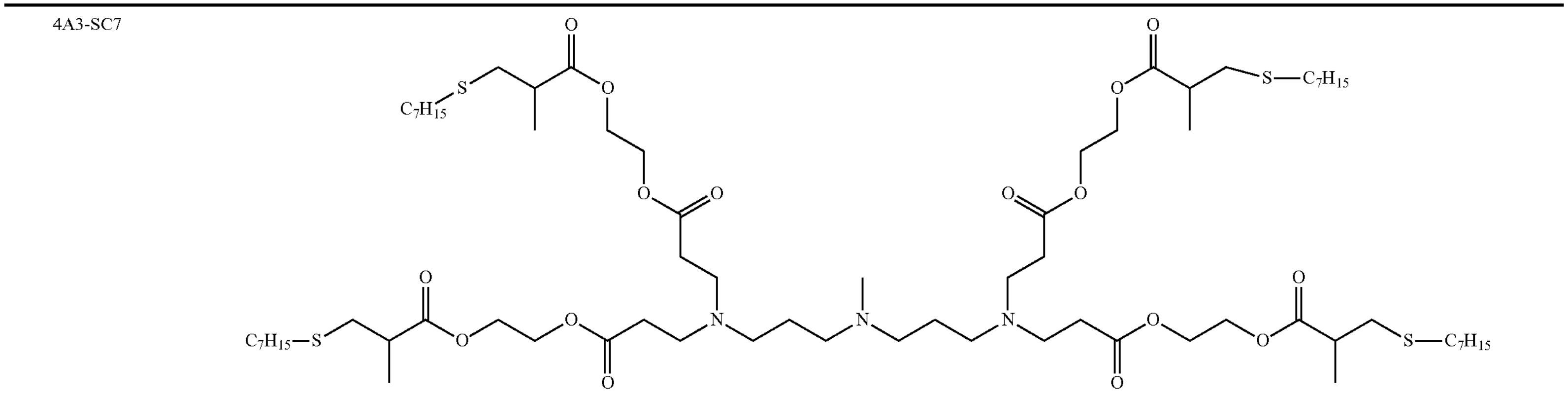 |
| 4A3-SC8 | 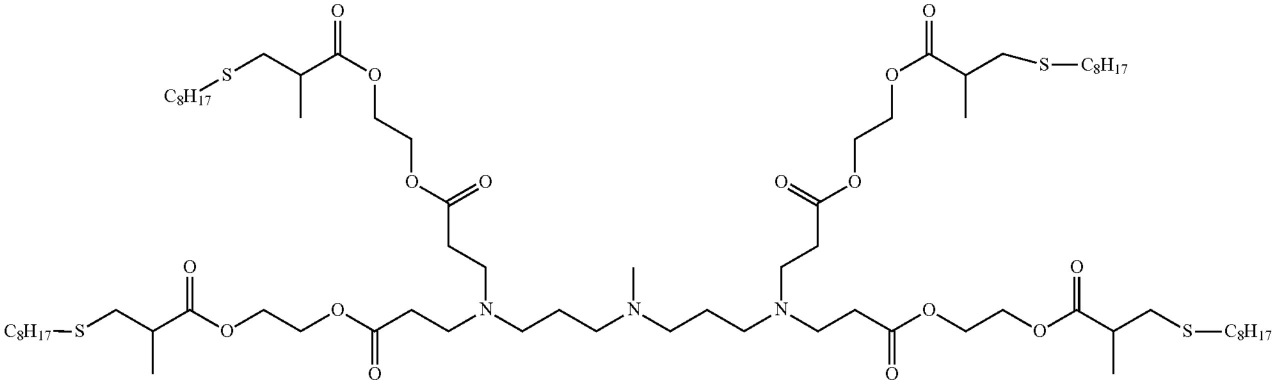 |

TABLE 6-continued
| Example ionizable cationic lipo-dendrimers | |
|---|---|
| ID # | Structure |
| 5A4-2-SC5 (6 arm) | 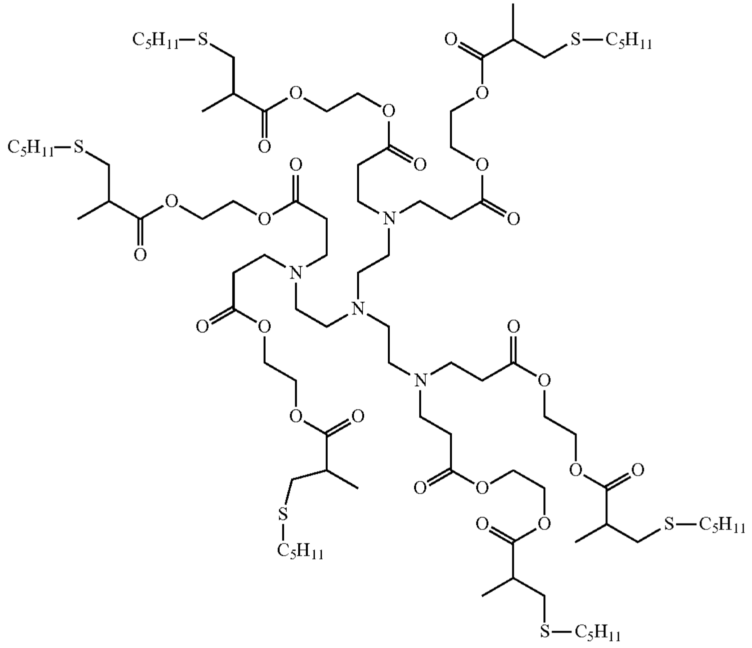 |

TABLE 6-continued
| Example ionizable cationic lipo-dendrimers | |
|---|---|
| ID # | Structure |
| 5A4-2-SC6 (6 arm) | 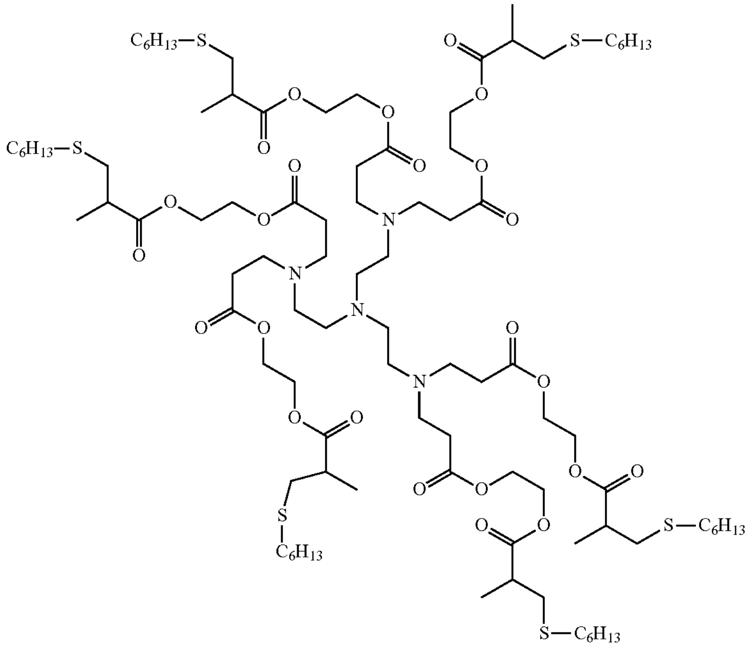 |

TABLE 6-continued
| Example ionizable cationic lipo-dendrimers | |
|---|---|
| ID # | Structure |
| 5A2-4-SC8 (5-arm) | 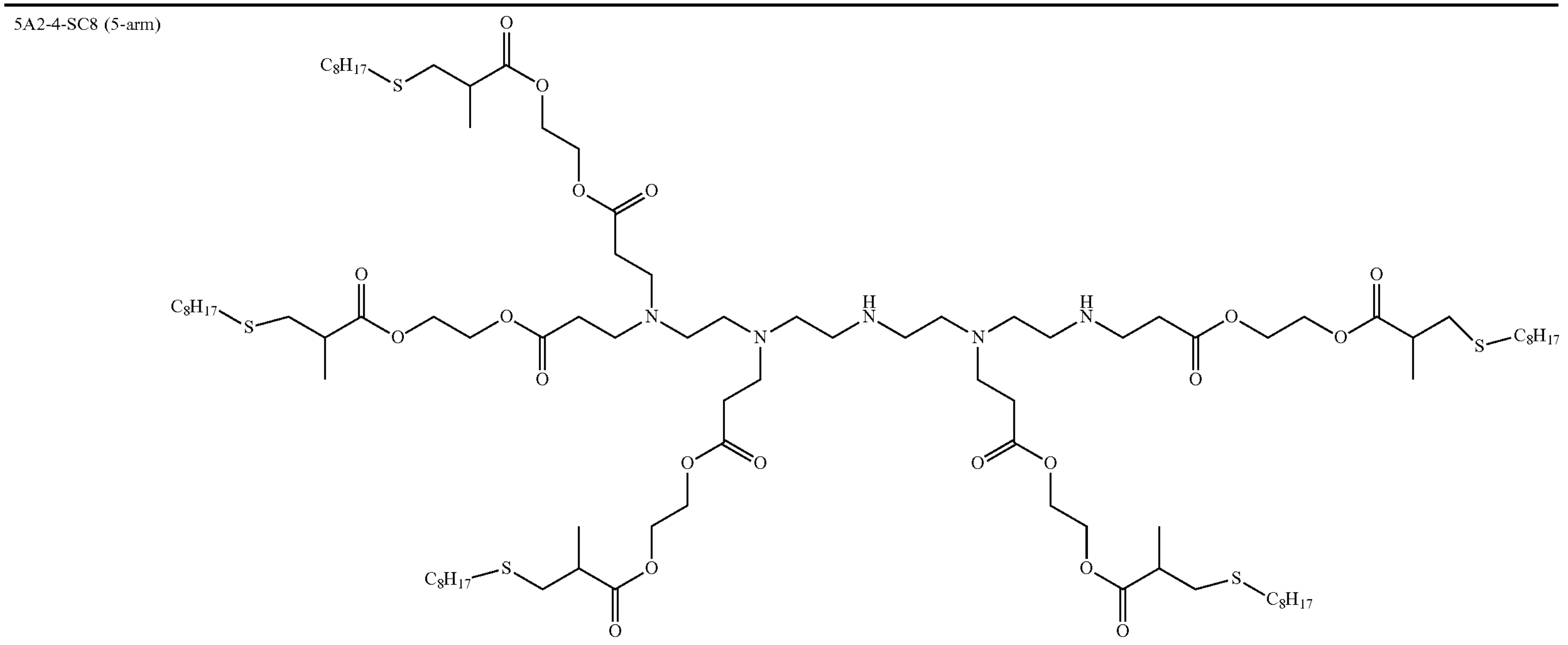 |

TABLE 6-continued
| Example ionizable cationic lipo-dendrimers | |
|---|---|
| ID # | Structure |
| 3A5-g2-SC8 | 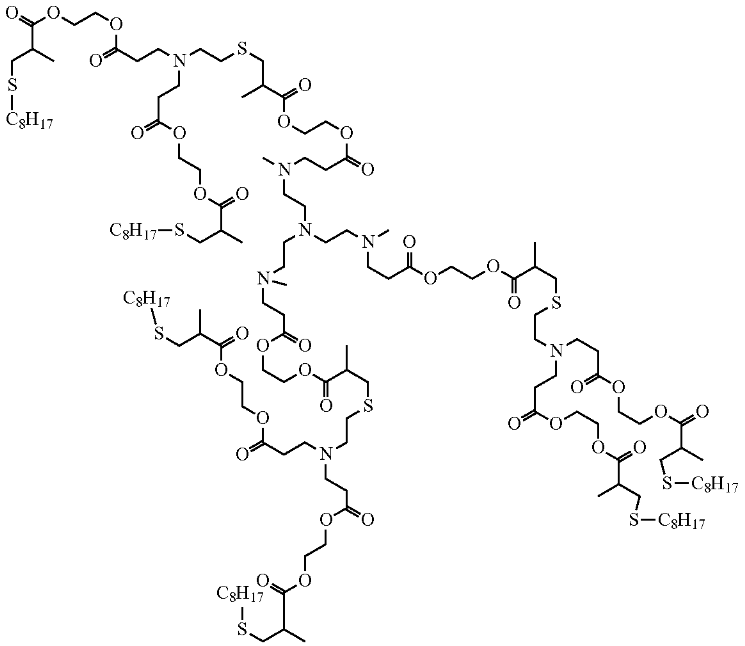 |

Other Ionizable Cationic Lipids

In some embodiments of the lipid composition, the cationic lipid comprises a structural formula (D-I'):

(D-I')

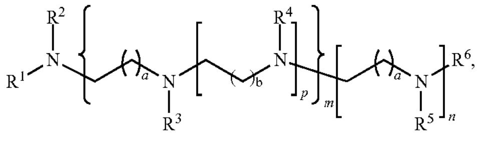

wherein:

a is 1 and b is 2, 3, or 4; or, alternatively, b is 1 and a is 2, 3, or 4;

m is 1 and n is 1; or, alternatively, m is 2 and n is 0; or, alternatively, m is 2 and n is 1; and $R^1$, $R^2$, $R^3$, $R^4$, $R^5$, and $R^6$ are each independently selected from the group consisting of H, $—CH_2CH(OH)R^7$, $—CH(R^7)CH_2OH$, $—CH_2CH_2C(═O)OR^7$, $—CH_2CH_2C(═O)NHR^7$, and $—CH_2R^7$, wherein $R^7$ is independently selected from $C_3$-$C_{18}$ alkyl, $C_3$-$C_{18}$ alkenyl having one C═C double bond, a protecting group for an amino group, $—C(═NH)NH_2$, a poly(ethylene glycol) chain, and a receptor ligand;

provided that at least two moieties among $R^1$ to $R^6$ are independently selected from $—CH_2CH(OH)R^7$, $—CH(R^7)CH_2OH$, $—CH_2CH_2C(═O)OR^7$, $—CH_2CH_2C(═O)NHR^7$, or $—CH_2R^7$, wherein $R^7$ is independently selected from $C_3$-$C_{18}$ alkyl or $C_3$-$C_{18}$ alkenyl having one C═C double bond; and wherein one or more of the nitrogen atoms indicated in formula (D-I') may be protonated to provide a cationic lipid.

In some embodiments of the cationic lipid of formula (D-I'), a is 1. In some embodiments of the cationic lipid of formula (D-I'), b is 2. In some embodiments of the cationic lipid of formula (D-I'), m is 1. In some embodiments of the cationic lipid of formula (D-I'), n is 1. In some embodiments of the cationic lipid of formula (D-I'), $R^1$, $R^2$, $R^3$, $R^4$, $R^5$, and $R^6$ are each independently H or $—CH_2CH(OH)R^7$. In some embodiments of the cationic lipid of formula (D-I'), $R^1$, $R^2$, $R^3$, $R^4$, $R^5$, and $R^6$ are each independently H or

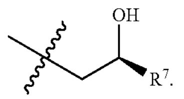

In some embodiments of the cationic lipid of formula (D-I'), $R^1$, $R^2$, $R^3$, $R^4$, $R^5$, and $R^6$ are each independently H or

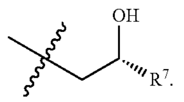

In some embodiments of the cationic lipid of formula (D-I'), $R^7$ is $C_3$-$C_{18}$ alkyl (e.g., $C_6$-$C_{12}$ alkyl).

In some embodiments, the cationic lipid of formula (D-I') is 13,16,20-tris(2-hydroxydodecyl)-13,16,20,23-tetraazapentatricontane-11,25-diol:

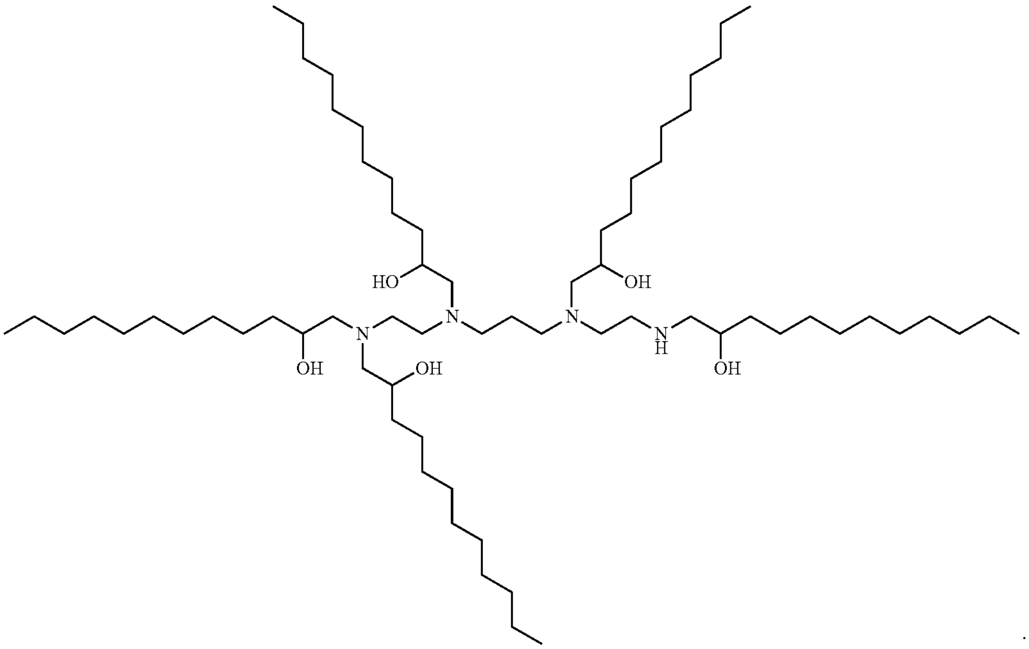 [SMILES: CCCCCCCCCCC(O)CNCCN(CCCN(CCN(CC(O)CCCCCCCCCC)CC(O)CCCCCCCCCC)CC(O)CCCCCCCCCC)CC(O)CCCCCCCCCC]

.

In some embodiments, the cationic lipid of formula (D-I') is (11R,25R)-13,16,20-tris((R)-2-hydroxydodecyl)-13,16,20,23-tetraazapentatricontane-11,25-diol:

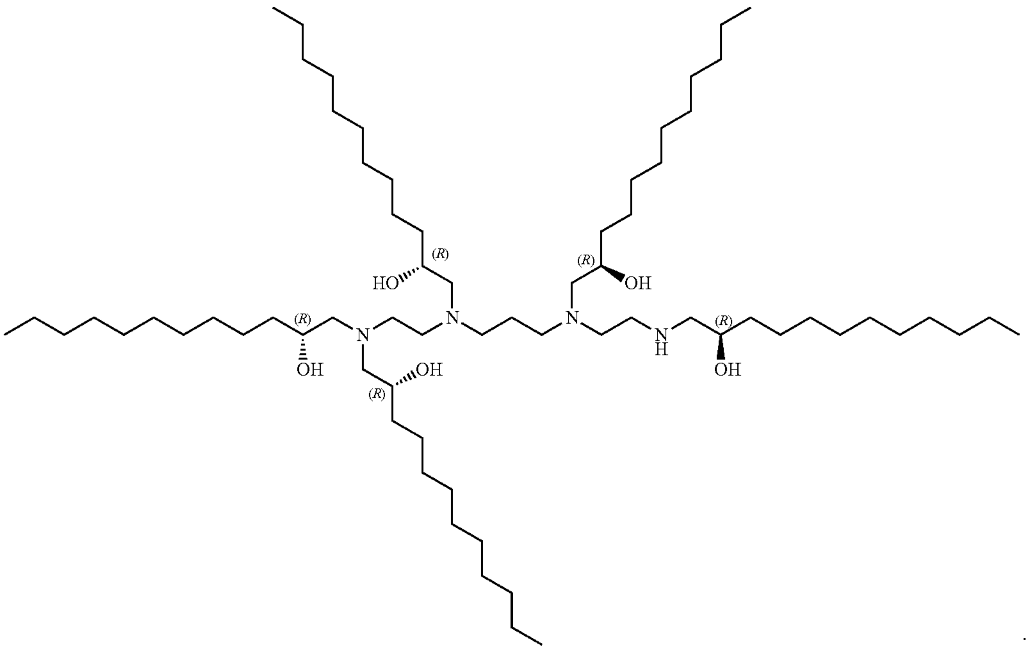

Additional cationic lipids that can be used in the compositions and methods of the present application include those cationic lipids as described in J. McClellan, M. C. King, Cell 2010, 141, 210-217, and International Patent Publication WO 2010/144740, WO 2013/149140, WO 2016/118725, WO 2016/118724, WO 2013/063468, WO 2016/205691, WO 2015/184256, WO 2016/004202, WO 2015/199952, WO 2017/004143, WO 2017/075531, WO 2017/117528, WO 2017/049245, WO 2017/173054 and WO 2015/095340, which are incorporated herein by reference for all purposes. Examples of those ionizable cationic lipids include but are not limited to those as shown in Table 7.

TABLE 7

| Example ionizable cationic lipids | |
|---|---|
| # | Structure of example ionizable cationic lipid |
| 1 | 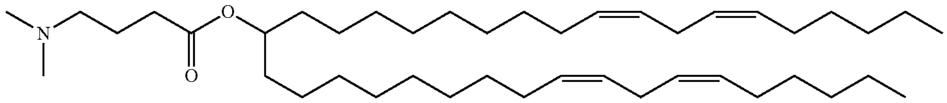 ; |
| 2 | 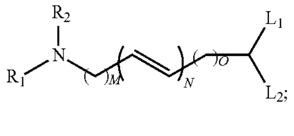 |
| 3 | 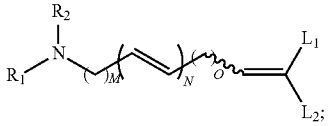 |
| 4 | 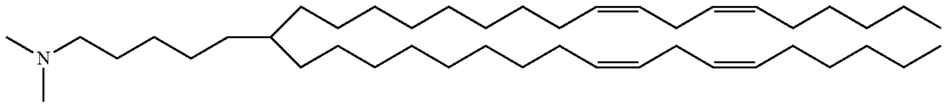 ; (HGT-5000) |

TABLE 7-continued
| Example ionizable cationic lipids | |
|---|---|
| # | Structure of example ionizable cationic lipid |
| 5 | 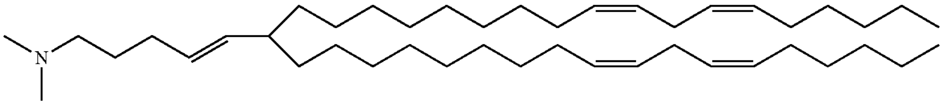 ; (HGT-5001) |
| 6 | 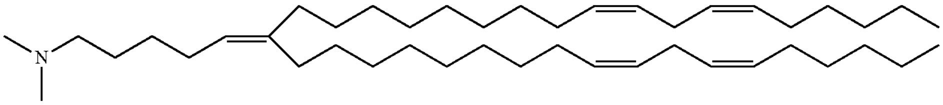 ; (HGT-5002) |
| 7 | 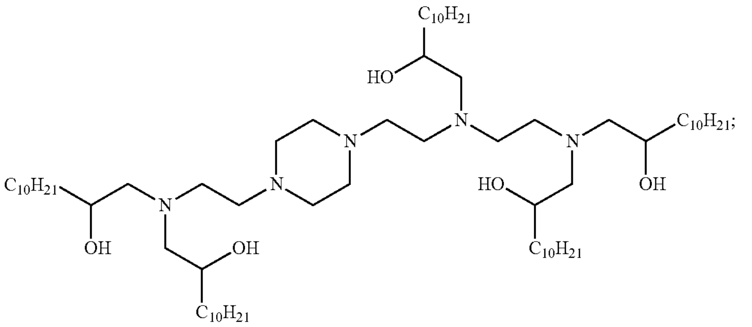 |
| 8 | 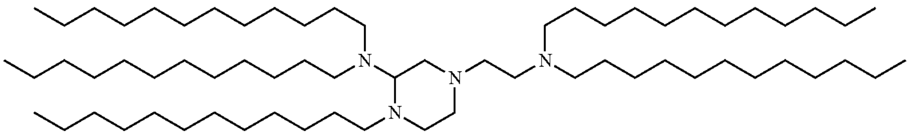 ; |
| 9 | 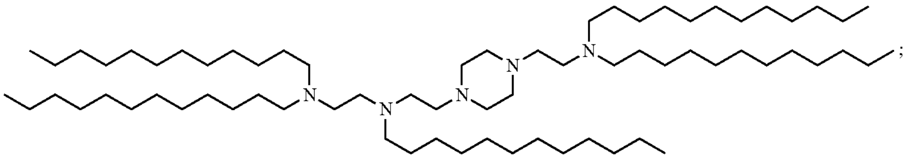 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1 ; ";"] ; |
| 10 | 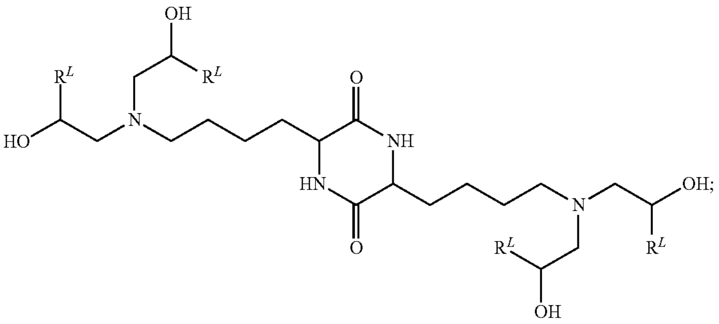 |

TABLE 7-continued
| Example ionizable cationic lipids | |
|---|---|
| # | Structure of example ionizable cationic lipid |
| 11 | 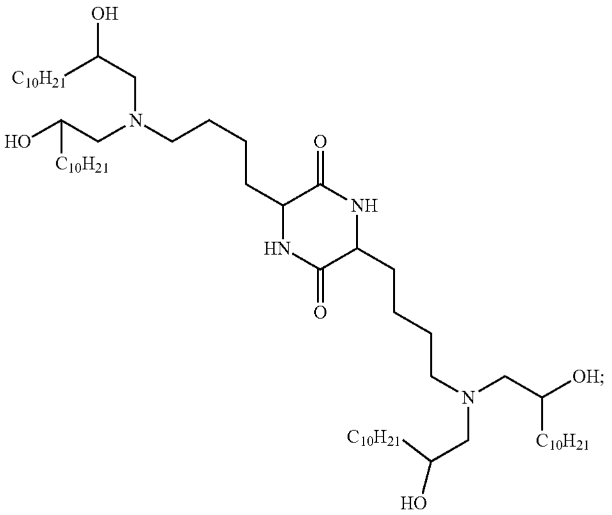 |
| 12 | 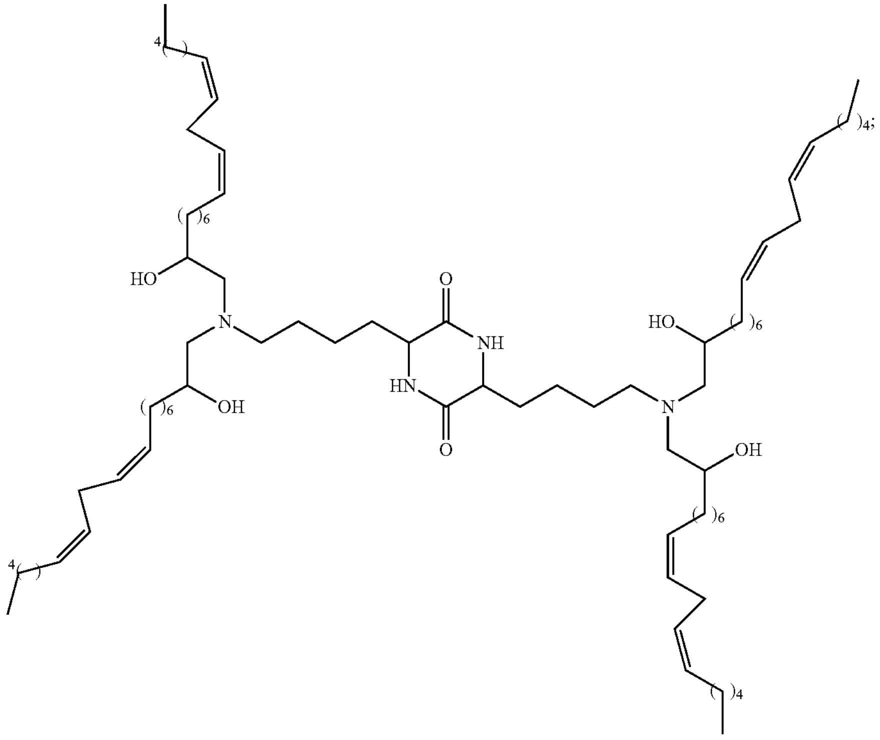 |

TABLE 7-continued
| Example ionizable cationic lipids | |
|---|---|
| # | Structure of example ionizable cationic lipid |
| 13 | 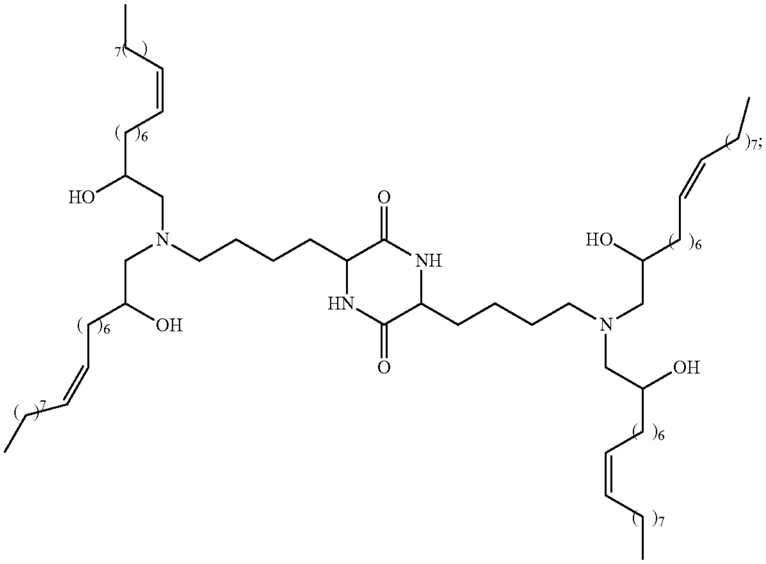 |
| 14 | 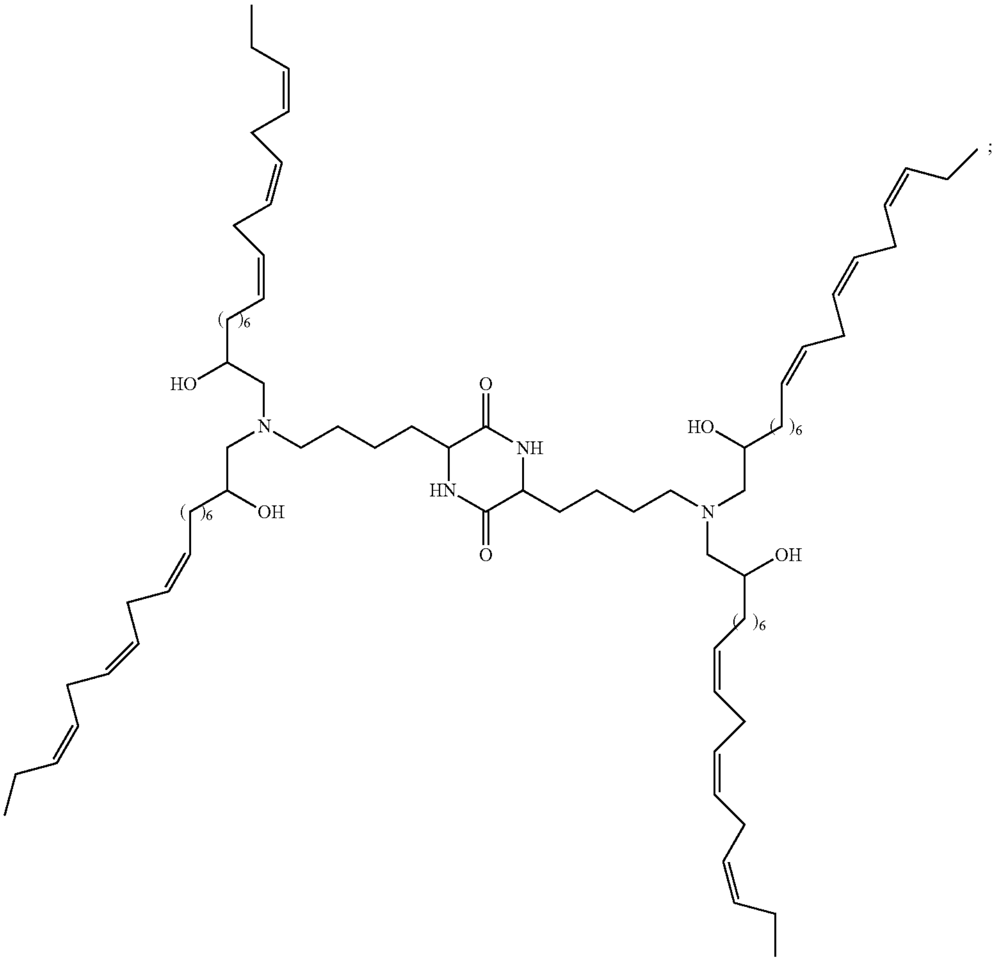 |

TABLE 7-continued
Example ionizable cationic lipids
| # | Structure of example ionizable cationic lipid |
|---|---|
| 15 | 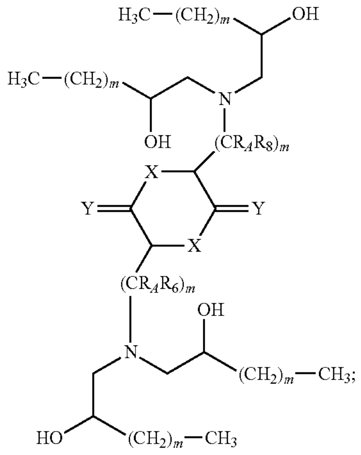 |
| 16 | 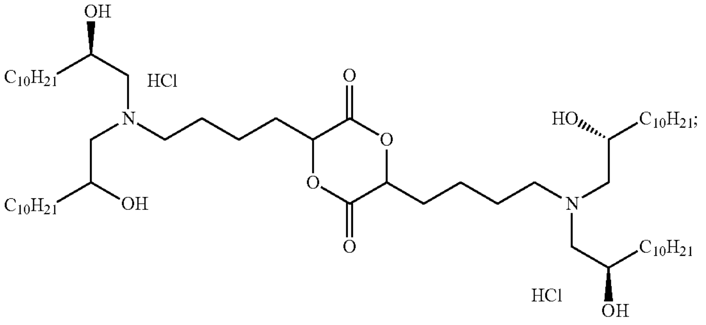<br>(Target 23) |
| 17 | 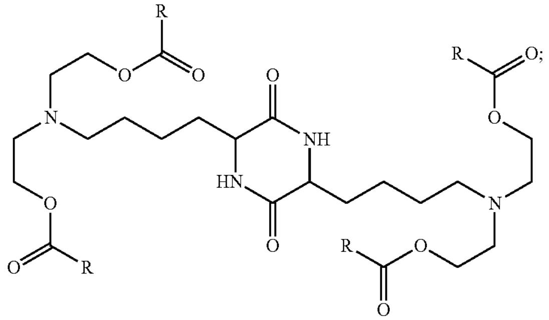 |
| 18 | R- 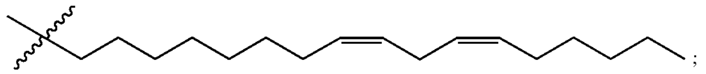 |
| 19 | 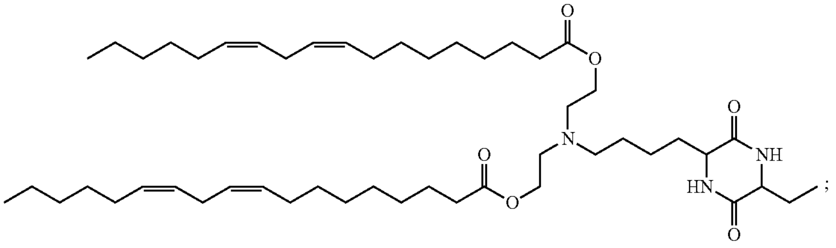 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC] |

TABLE 7-continued
| Example ionizable cationic lipids | |
|---|---|
| # | Structure of example ionizable cationic lipid |
| 20 | 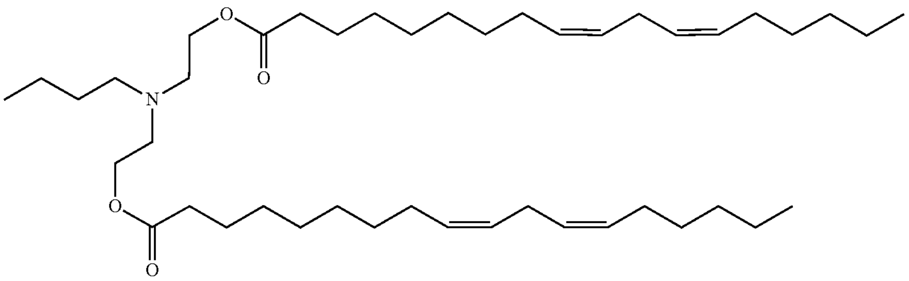 ; |
| 21 | 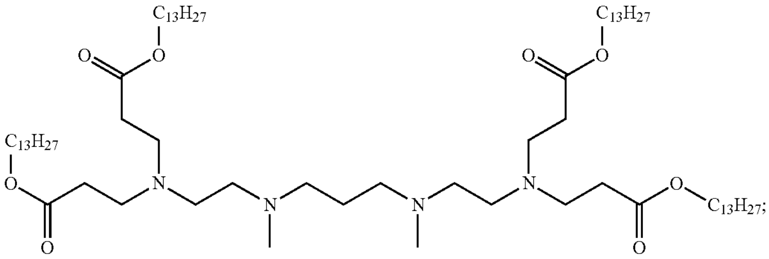 ; |
| 22 | 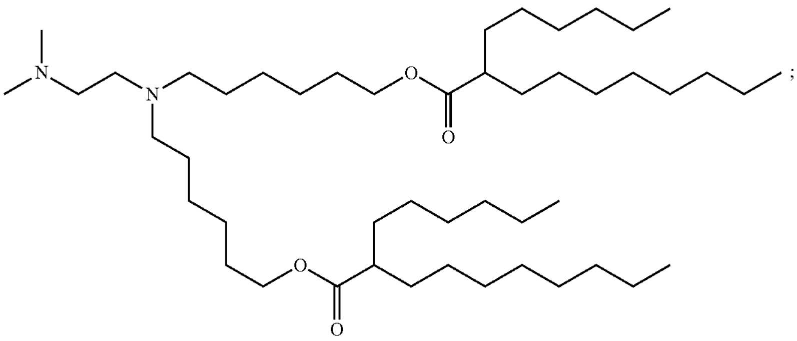 [SMILES: CCCCCCCCC(CCCCCC)C(=O)OCCCCCCN(CCCCCCOC(=O)C(CCCCCC)CCCCCCCC)CCN(C)C] ; |
| 23 | 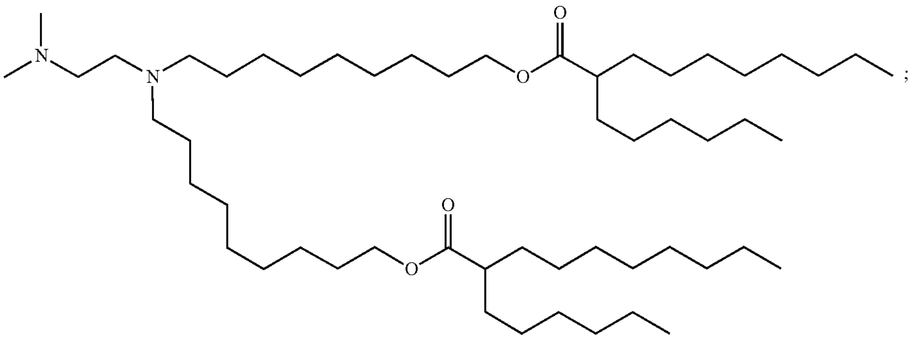 [SMILES: CCCCCCCCC(CCCCCC)C(=O)OCCCCCCCCCN(CCCCCCCCCOC(=O)C(CCCCCC)CCCCCCCC)CCN(C)C] ; |
| 24 | 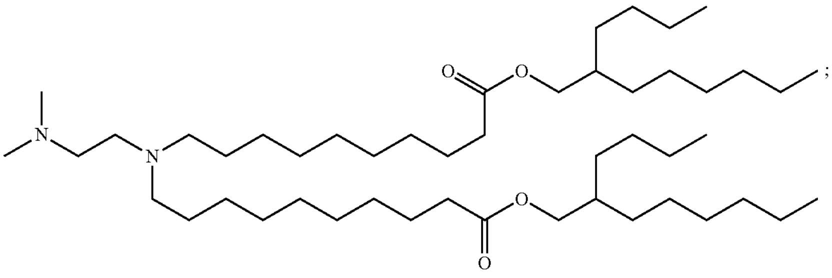 [SMILES: CCCCCCC(CCCC)COC(=O)CCCCCCCCCN(CCCCCCCCCC(=O)OCC(CCCC)CCCCCC)CCN(C)C] ; |

TABLE 7-continued
| Example ionizable cationic lipids | |
|---|---|
| # | Structure of example ionizable cationic lipid |
| 25 | 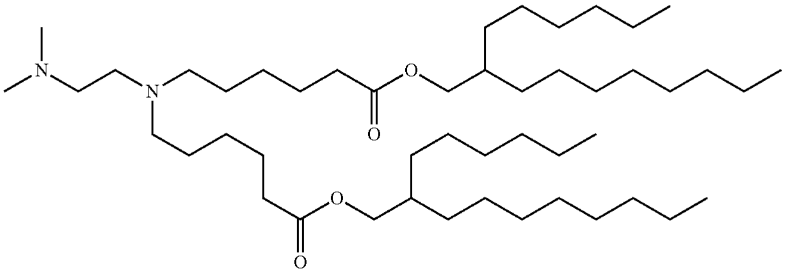 ; |
| 26 | 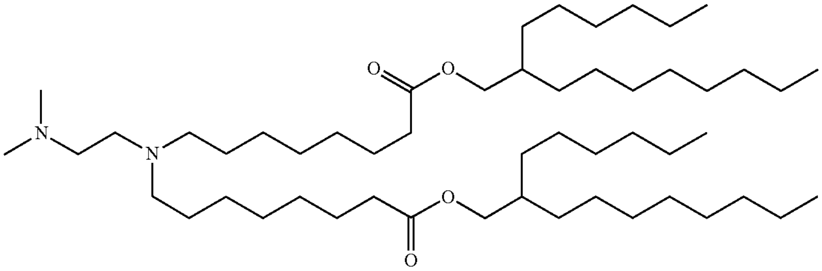 ; |
| 27 | 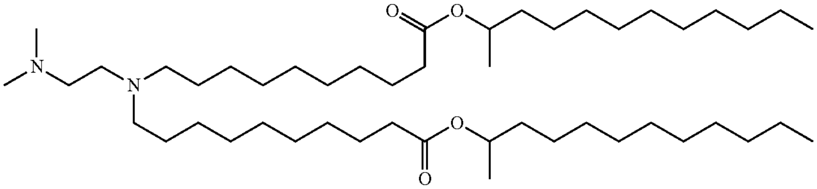 ; |
| 28 | 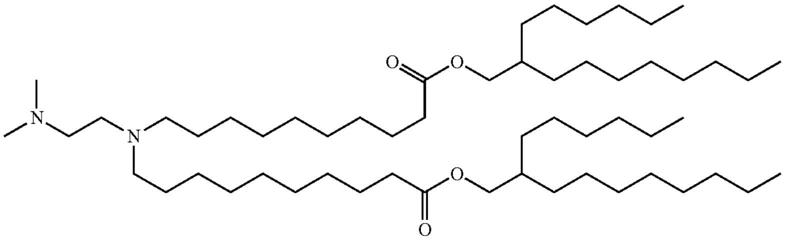 ; |
| 29 | 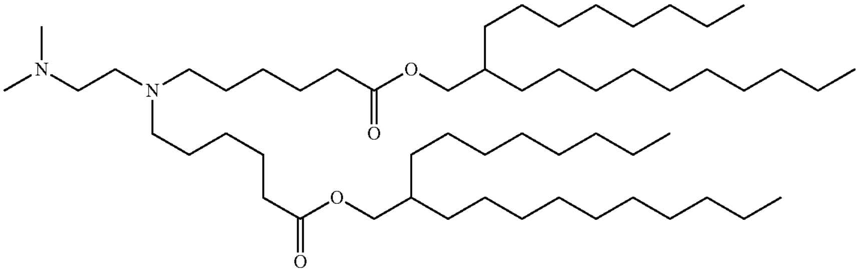 ; |
| 30 | 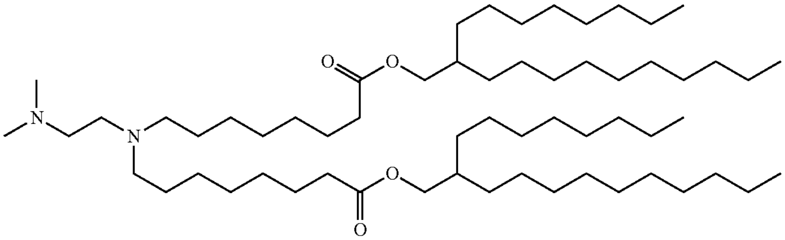 ; |

TABLE 7-continued
| Example ionizable cationic lipids | |
|---|---|
| # | Structure of example ionizable cationic lipid |
| 31 | 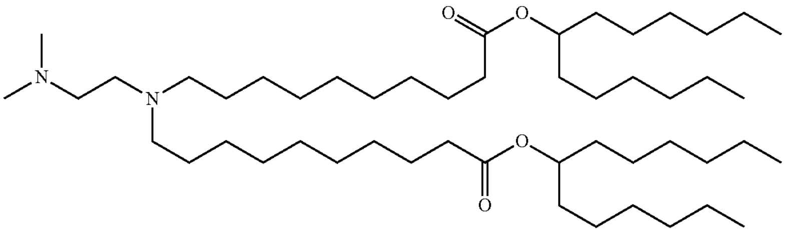 ; |
| 32 | 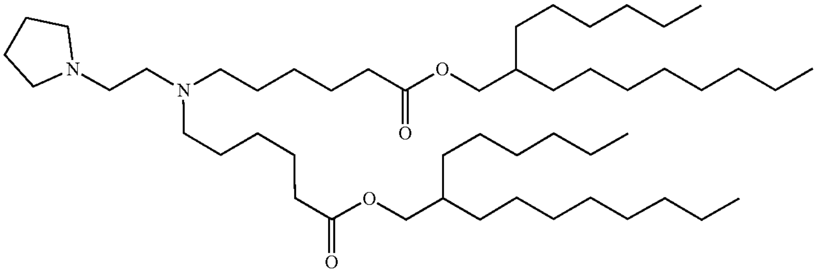 ; |
| 33 | 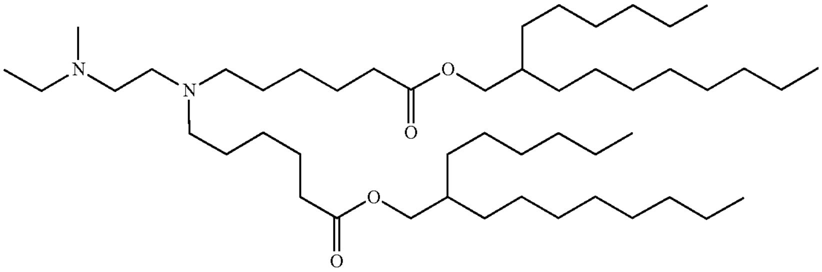 ; |
| 34 | 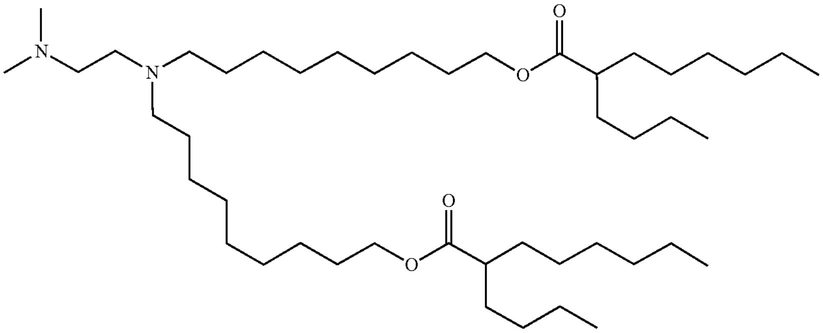 ; |
| 35 | 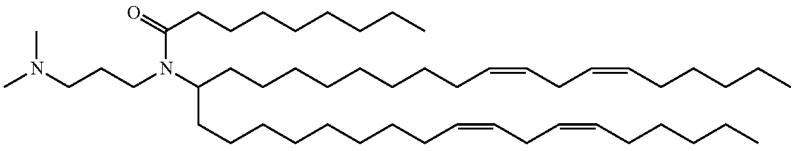 ; |
| 36 | 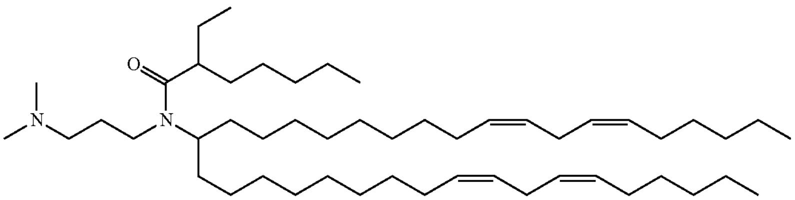 ; |

TABLE 7-continued
| Example ionizable cationic lipids | |
|---|---|
| # | Structure of example ionizable cationic lipid |
| 37 | 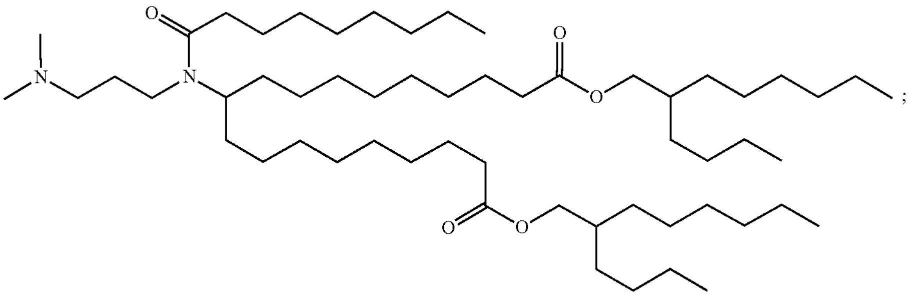 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] ; |
| 38 | 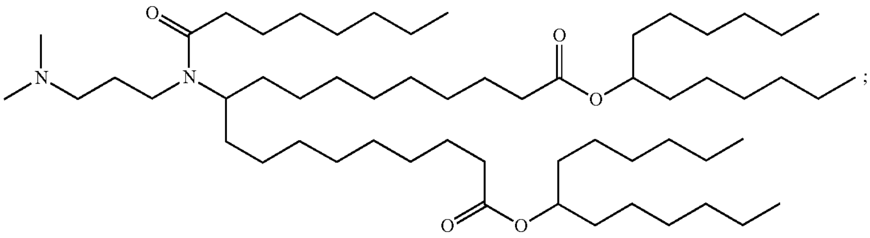 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] ; |
| 39 | 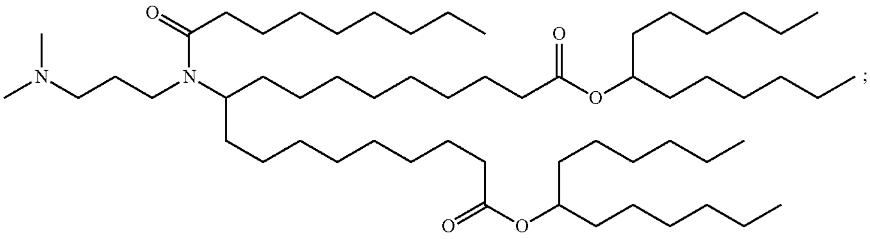 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] ; |
| 40 | 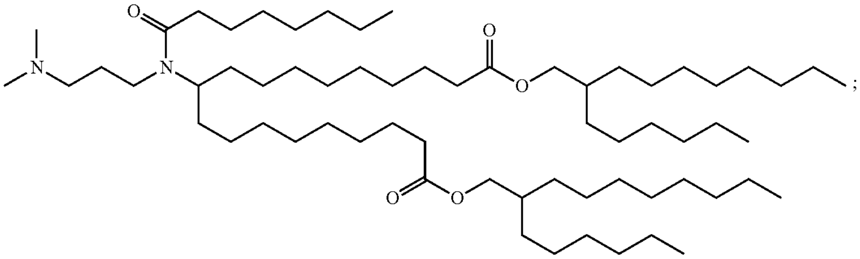 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] ; |
| 41 | 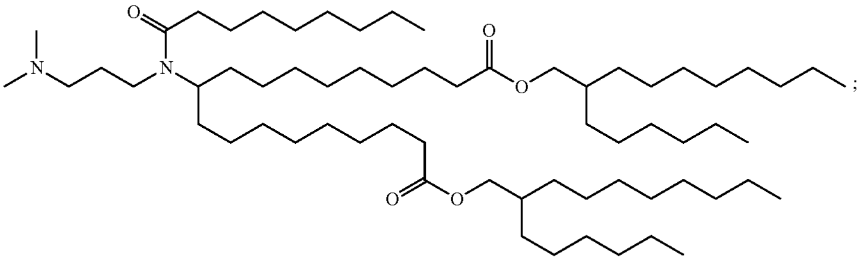 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] ; |

TABLE 7-continued
Example ionizable cationic lipids
| # | Structure of example ionizable cationic lipid |
|---|---|
| 42 | 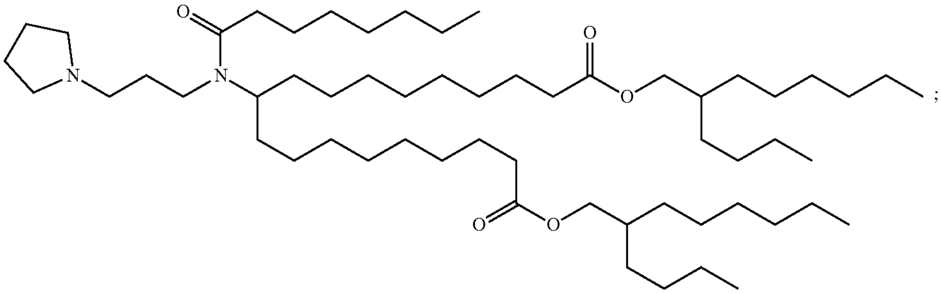 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] ; |
| 43 | 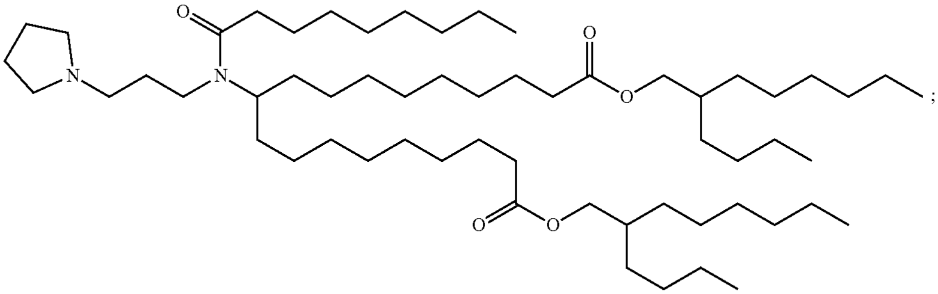 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] ; |
| 44 | 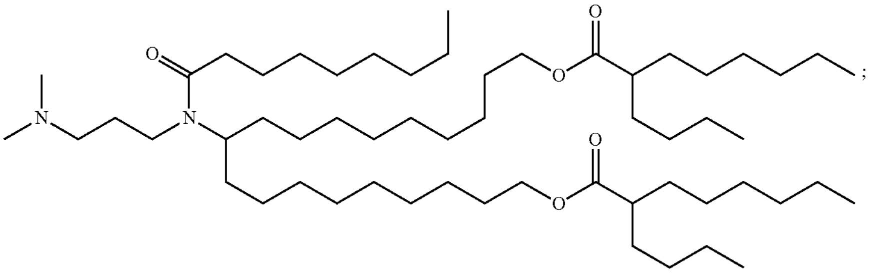 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] ; |
| 45 | 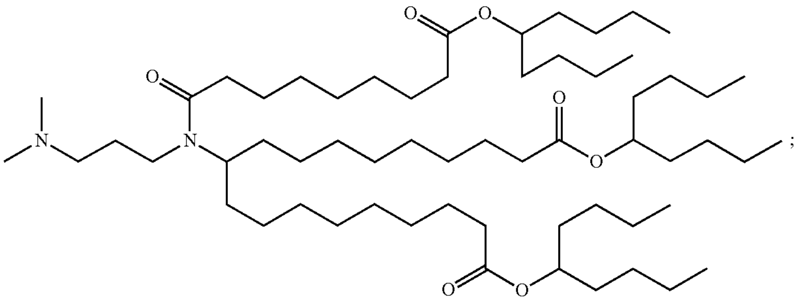 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] ; |
| 46 | 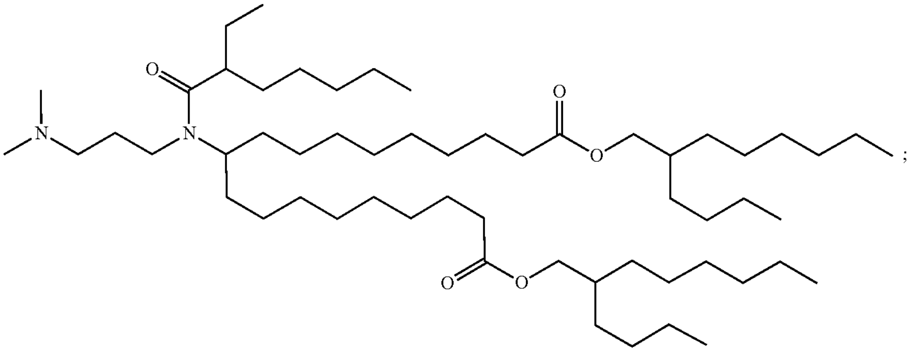 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC] ; |

TABLE 7-continued
| Example ionizable cationic lipids |
|---|
| # Structure of example ionizable cationic lipid |
| 47 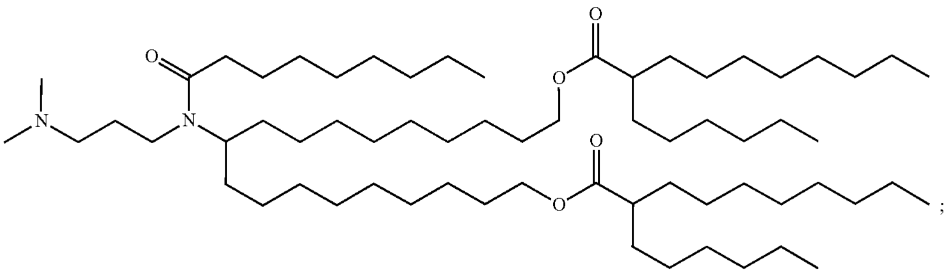 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC] ; |
| 48 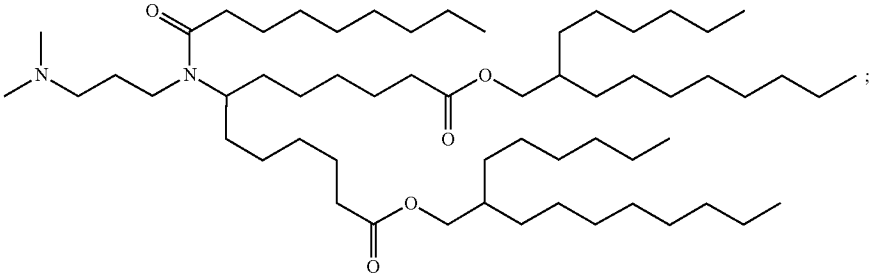 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC] ; |
| 49 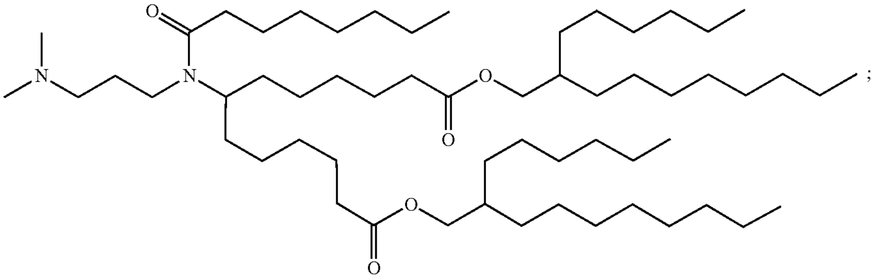 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC] ; |
| 50 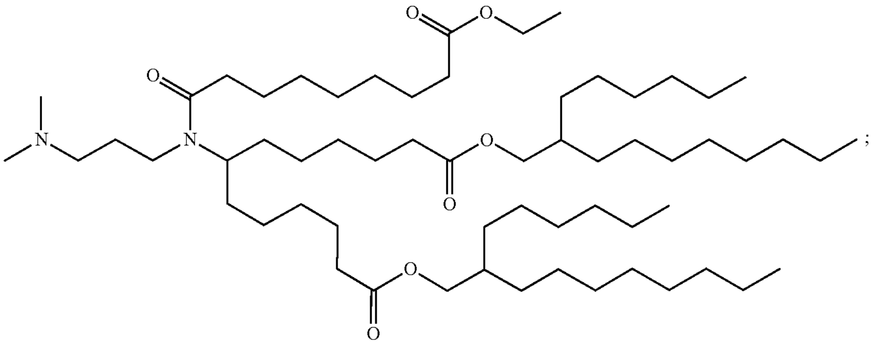 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] ; |
| 51 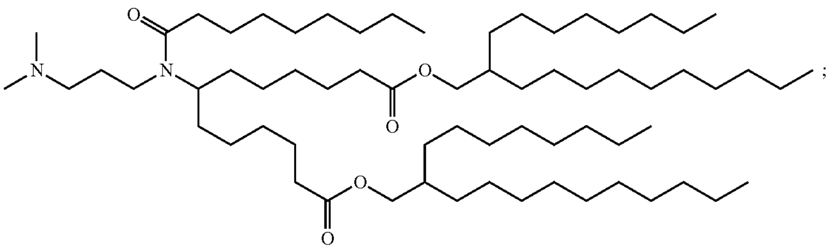 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] ; |

TABLE 7-continued
| Example ionizable cationic lipids | |
|---|---|
| # | Structure of example ionizable cationic lipid |
| 52 | 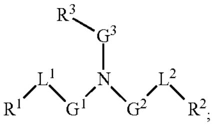 |
| 53 | 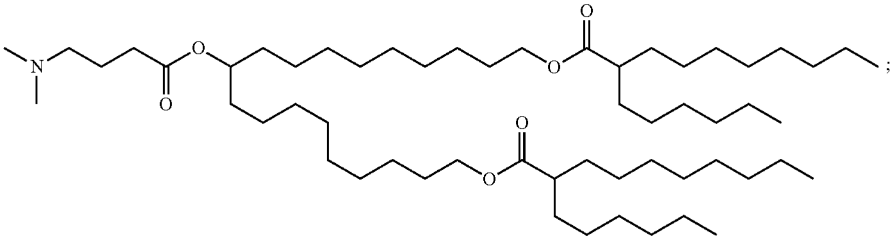 [SMILES: CCCCCCCCC(CCCCCC)C(=O)OCCCCCCCCCC(CCCCCCCCCOC(=O)C(CCCCCC)CCCCCCCC)OC(=O)CCCN(C)C] |
| 54 | 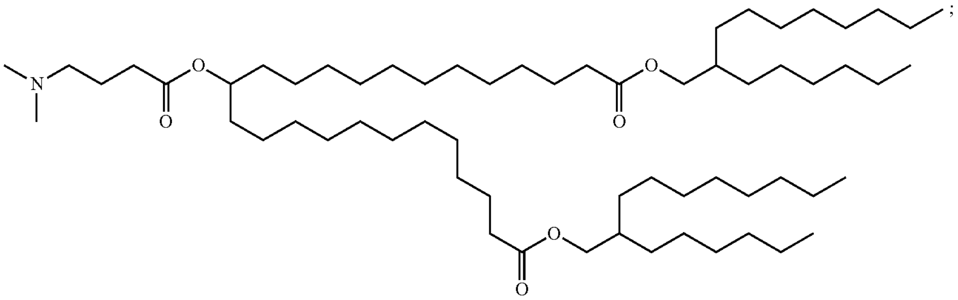 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C] |
| 55 | 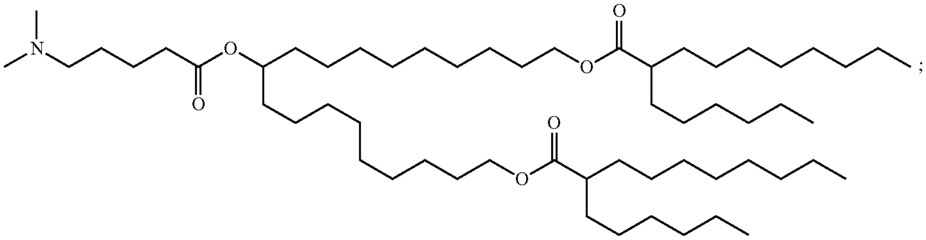 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] |
| 56 | 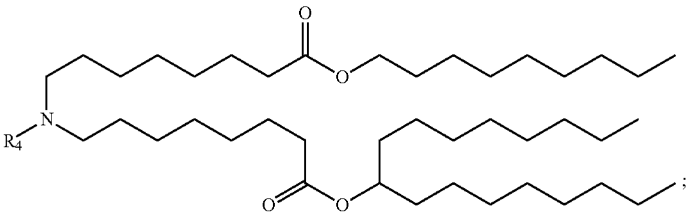 |
| 57 | 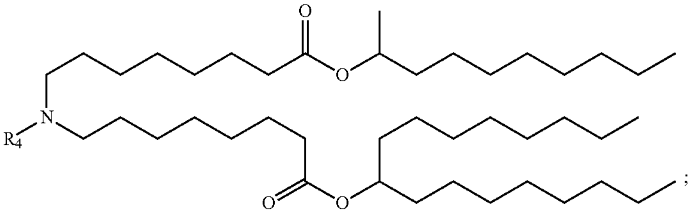 |

TABLE 7-continued
| Example ionizable cationic lipids | |
|---|---|
| # | Structure of example ionizable cationic lipid |
| 58 | 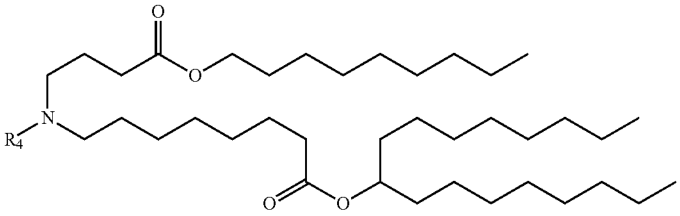 ; |
| 59 | 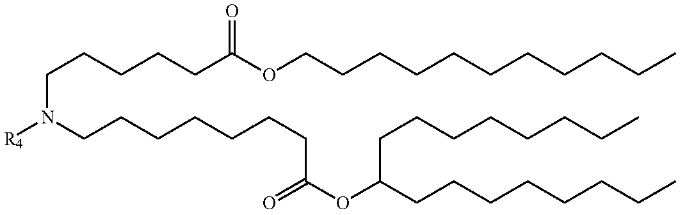 ; |
| 60 | 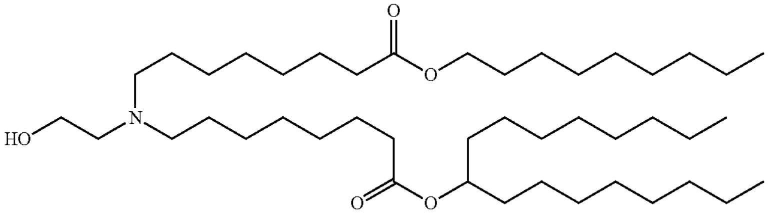 ; |
| 61 | 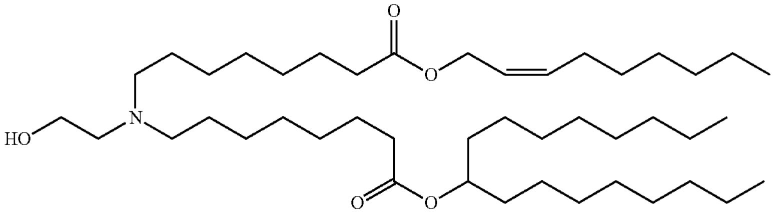 ; |
| 62 | 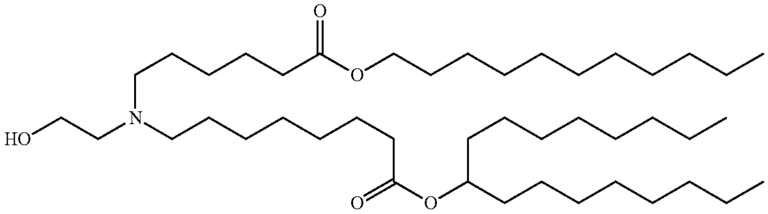 ; |
| 63 | 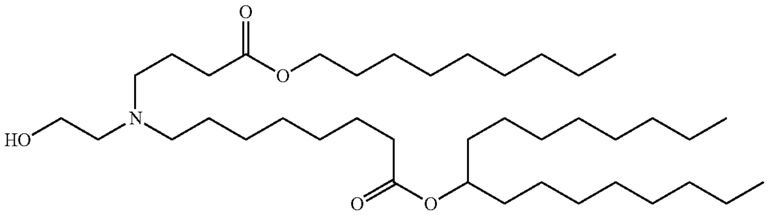 ; |

TABLE 7-continued
| Example ionizable cationic lipids |
|---|
| # Structure of example ionizable cationic lipid |
| 64 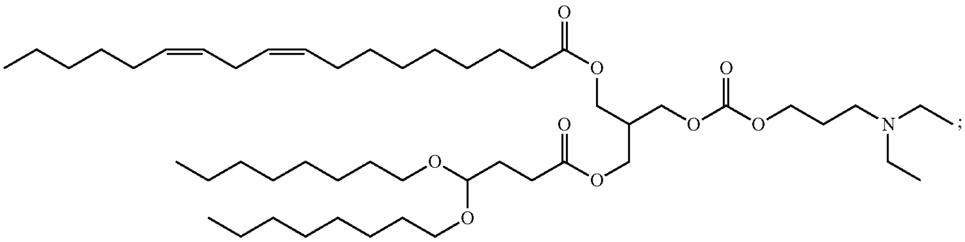 [SMILES: CCCCC/C=C\C/C=C\CCCCCCCC(=O)OCC(COC(=O)CCC(OCCCCCCCC)OCCCCCCCC)COC(=O)OCCCN(CC)CC] ; |
| 65 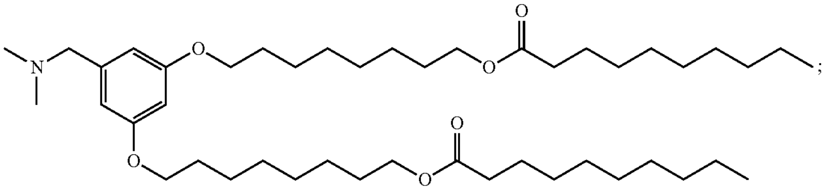 [SMILES: CCCCCCCCCC(=O)OCCCCCCCCOc1cc(CN(C)C)cc(OCCCCCCCCOC(=O)CCCCCCCCC)c1] ; |
| 66 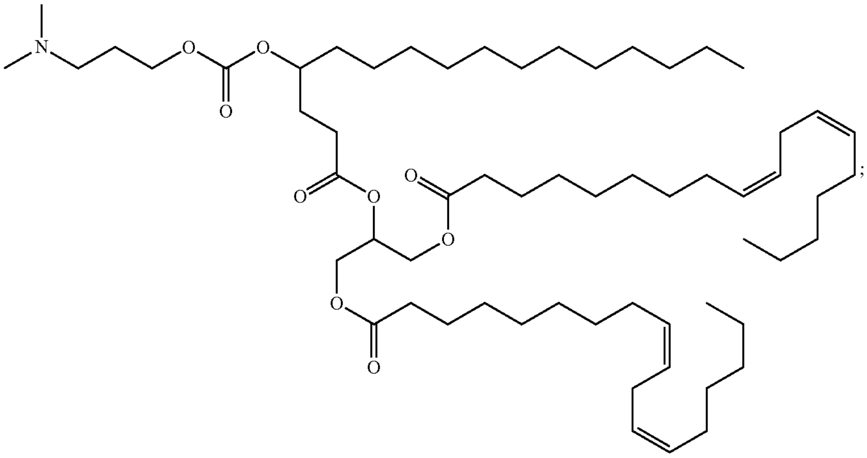 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C] ; |
| 67 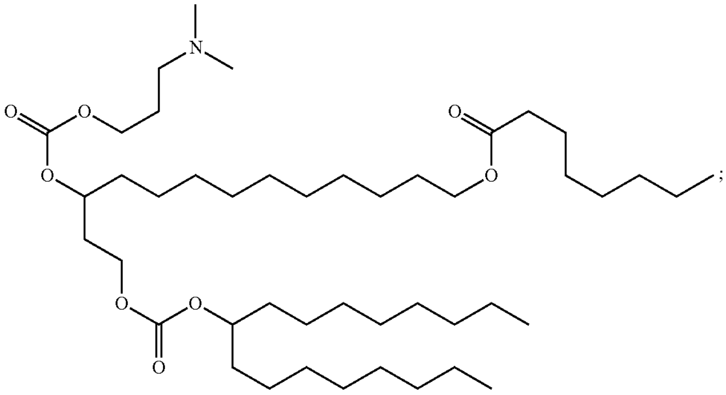 [SMILES: CCCCCCCCC(CCCCCCCC)OC(=O)OCCC(CCCCCCCCCCOC(=O)CCCCCCC)OC(=O)OCCCN(C)C] ; |

TABLE 7-continued
| Example ionizable cationic lipids | |
|---|---|
| # | Structure of example ionizable cationic lipid |
| 68 | 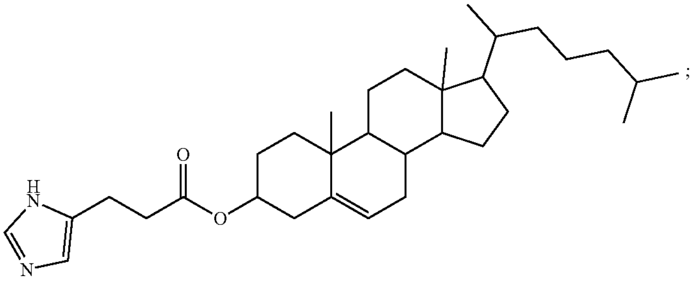 [SMILES: CC(C)CCCC(C)C1CCC2C3CC=C4CC(OC(=O)CCc5cnc[nH]5)CCC4(C)C3CCC12C] |
| 69 | 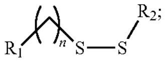 |
| 70 | 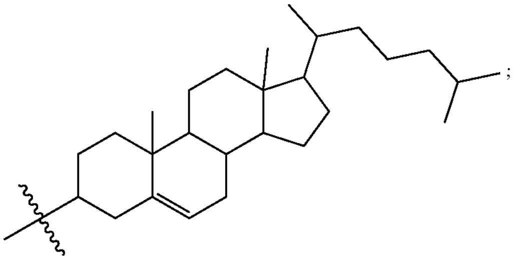 [SMILES: *C1CCC2(C)C(=CCC3C2CCC2(C)C(C(C)CCCC(C)C)CCC32)C1] |
| 71 | 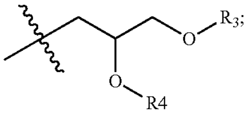 |
| 72 | 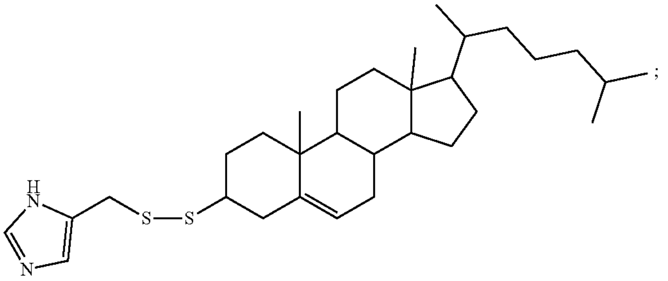 [SMILES: CC(C)CCCC(C)C1CCC2C3CC=C4CC(SSCc5cnc[nH]5)CCC4(C)C3CCC12C] (HGT4001) |
| 73 | 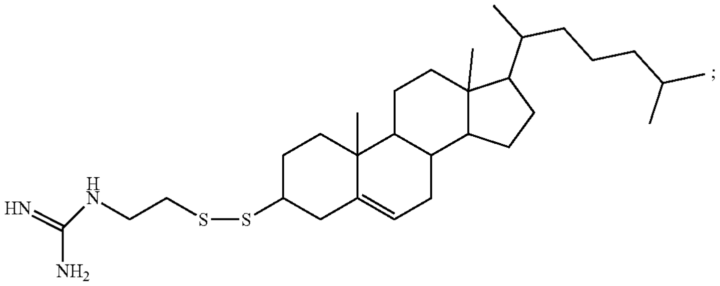 [SMILES: CC(C)CCCC(C)C1CCC2C3CC=C4CC(SSCCNC(=N)N)CCC4(C)C3CCC12C] (HGT4002) |
| 74 | 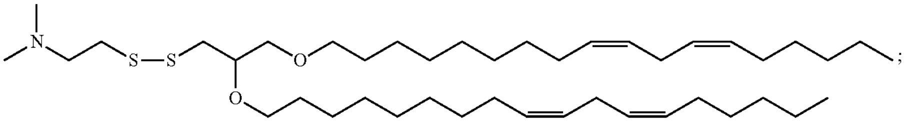 [SMILES: CCCCC/C=C\C/C=C\CCCCCCCCOCC(CSSCCN(C)C)OCCCCCCCC/C=C\C/C=C\CCCCC] (HGT4003) |

TABLE 7-continued

Example ionizable cationic lipids

| # | Structure of example ionizable cationic lipid |
|---|---|
| 75 | 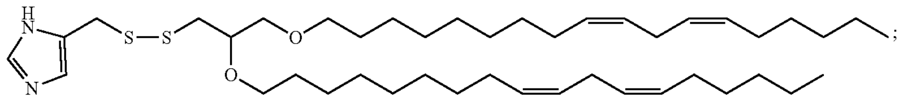 (HGT4004) |
| 76 | 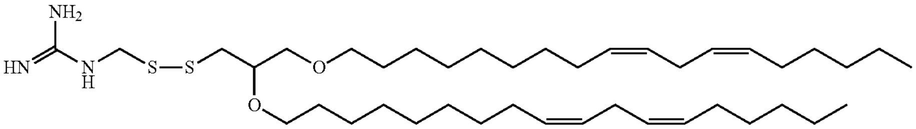 (HGT4005) |

In some embodiments of the lipid composition of the present application, the ionizable cationic lipid is present in an amount from about from about 20 to about 23. In some embodiments, the molar percentage is from about 20, 20.5, 21, 21.5, 22, 22.5, to about 23 or any range derivable therein. In other embodiments, the molar percentage is from about 7.5 to about 20. In some embodiments, the molar percentage is from about 7.5, 8, 9, 10, 11, 12, 13, 14, 15, 16, 17, 18, 19, to about 20 or any range derivable therein.

In some embodiments of the lipid composition of the present application, said lipid composition comprises said ionizable cationic lipid at a molar percentage from about 5% to about 30%. In some embodiments of the lipid composition of the present application, said lipid composition comprises said ionizable cationic lipid at a molar percentage from about 10% to about 25%. In some embodiments of the lipid composition of the present application, said lipid composition comprises said ionizable cationic lipid at a molar percentage from about 15% to about 20%. In some embodiments of the lipid composition of the present application, said lipid composition comprises said ionizable cationic lipid at a molar percentage from about 10% to about 20%. In some embodiments of the lipid composition of the present application, said lipid composition comprises said ionizable cationic lipid at a molar percentage from about 20% to about 30%. In some embodiments of the lipid composition of the present application, said lipid composition comprises said ionizable cationic lipid at a molar percentage of at least (about) 5%, at least (about) 10%, at least (about) 15%, at least (about) 20%, at least (about) 25%, or at least (about) 30%. In some embodiments of the lipid composition of the present application, said lipid composition comprises said ionizable cationic lipid at a molar percentage of at most (about) 5%, at most (about) 10%, at most (about) 15%, at most (about) 20%, at most (about) 25%, or at most (about) 30%.

In some embodiments, a (e.g., mass or weight) ratio of said ionizable cationic lipid to said synthetic polynucleotide is of no more than about 100:1, 90:1, 80:1, 70:1, 60:1, 50:1, 40:1, or 30:1. In some embodiments, a (e.g., mass or weight) ratio of said ionizable cationic lipid to said synthetic polynucleotide is of at least about 1:1, 2:1, 3:1, 4:1, or 5:1. In some embodiments, a (e.g., mass or weight) ratio of said ionizable cationic lipid to said synthetic polynucleotide is of about 1:1 to about 80:1, about 2:1 to about 80:1, about 3:1 to about 80:1, about 4:1 to about 80:1, or about 5:1 to about 80:1. In some embodiments, a (e.g., mass or weight) ratio of said ionizable cationic lipid to said synthetic polynucleotide is of about 1:1 to about 70:1, about 2:1 to about 70:1, about 3:1 to about 70:1, about 4:1 to about 70:1, or about 5:1 to about 70:1. In some embodiments, a (e.g., mass or weight) ratio of said ionizable cationic lipid to said synthetic polynucleotide is of about 1:1 to about 60:1, about 2:1 to about 60:1, about 3:1 to about 60:1, about 4:1 to about 60:1, or about 5:1 to about 60:1. In some embodiments, a (e.g., mass or weight) ratio of said ionizable cationic lipid to said synthetic polynucleotide is of about 1:1 to about 50:1, about 2:1 to about 50:1, about 3:1 to about 50:1, about 4:1 to about 50:1, or about 5:1 to about 50:1.

Selective Organ Targeting (SORT) Lipids

In some embodiments of the lipid composition of the present application, the lipid (e.g., nanoparticle) composition is preferentially delivered to a target organ. In some embodiments, the target organ is a lung, a lung tissue or a lung cell. As used herein, the term "preferentially delivered" is used to refer to a composition, upon being delivered, which is delivered to the target organ (e.g., lung), tissue, or cell in at least 25% (e.g., at least 30%, 35%, 40%, 45%, 50%, 55%, 60%, 65%, 70%, or 75%) of the amount administered.

In some embodiments of the lipid composition, the lipid composition comprises one or more selective organ targeting (SORT) lipid which leads to the selective delivery of the composition to a particular organ. In some embodiments, the SORT lipid may have two or more alkyl or alkenyl chains of $C_6$-$C_{24}$.

In some embodiments of the lipid compositions, the SORT lipid comprises permanently positively charged moiety. The permanently positively charged moiety may be positively charged at a physiological pH such that the SORT lipid comprises a positive charge upon delivery of a polynucleotide to a cell. In some embodiments the positively charged moiety is quaternary amine or quaternary ammonium ion. In some embodiments, the SORT lipid comprises, or is otherwise complexed to or interacting with, a counterion.

In some embodiments, of the lipid compositions, the SORT lipid is a second ionizable cationic lipid. The SORT lipid may be an ionizable cationic lipid as described elsewhere in this disclosure.

In some embodiments of the lipid compositions, the SORT lipid is a permanently cationic lipid (i.e., comprising one or more hydrophobic components and a permanently cationic group). The permanently cationic lipid may contain a group which has a positive charge regardless of the pH. One permanently cationic group that may be used in the permanently cationic lipid is a quaternary ammonium group. The permanently cationic lipid may comprise a structural formula:

(S-I)

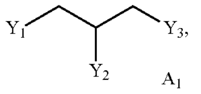

wherein:

$Y_1$, $Y_2$, or $Y_3$ are each independently $X_1C(O)R_1$ or $X_2N^+R_3R_4R_5$;

provided at least one of $Y_1$, $Y_2$, and $Y_3$ is $X_2N^+R_3R_4R_5$;

$R_1$ is $C_1$-$C_{24}$ alkyl, $C_1$-$C_{24}$ substituted alkyl, $C_1$-$C_{24}$ alkenyl, $C_1$-$C_{24}$ substituted alkenyl;

$X_1$ is O or $NR_a$, wherein $R_a$ is hydrogen, $C_1$-$C_4$ alkyl, or $C_1$-$C_4$ substituted alkyl;

$X_2$ is $C_1$-$C_6$ alkanediyl or $C_1$-$C_6$ substituted alkanediyl;

$R_3$, $R_4$, and $R_5$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; and $A_1$ is an anion with a charge equal to the number of $X_2N^+R_3R_4R_5$ groups in the compound.

In some embodiments of the SORT lipids, the permanently cationic SORT lipid has a structural formula:

(S-II)

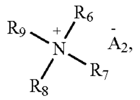

wherein:

$R_6$-$R_9$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; provided at least one of $R_6$-$R_9$ is a group of $C_8$-$C_{24}$; and $A_2$ is a monovalent anion.

In some embodiments of the lipid compositions, the SORT lipid is a second ionizable cationic lipid (i.e., comprising one or more hydrophobic components and an ionizable cationic group). The ionizable positively charged moiety may be positively charged at a physiological pH. One ionizable cationic group that may be used in the second ionizable cationic lipid is a tertiary ammine group. In some embodiments of the lipid compositions, the SORT lipid has a structural formula:

(S-I'a)

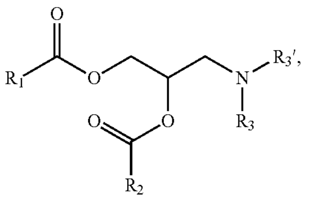

wherein:

$R_1$ and $R_2$ are each independently alkyl$_{(C8-C24)}$, alkenyl$_{(C8-C24)}$, or a substituted version of either group; and $R_3$ and $R_{3'}$ are each independently alkyl$_{(C\leq 6)}$ or substituted alkyl$_{(C\leq 6)}$.

In some embodiments of the lipid compositions, the SORT lipid comprises a head group of a particular structure. In some embodiments, the SORT lipid comprises a headgroup having a structural formula:

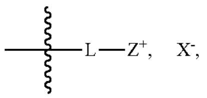

wherein L is a linker; $Z^+$ is positively charged moiety and $X^-$ is a counterion. In some embodiment, the linker is a biodegradable linker. The biodegradable linker may be degradable under physiological pH and temperature. The biodegradable linker may be degraded by proteins or enzymes from a subject. In some embodiments, the positively charged moiety is a quaternary ammonium ion or quaternary amine.

In some embodiments of the lipid compositions, the SORT lipid has a structural formula:

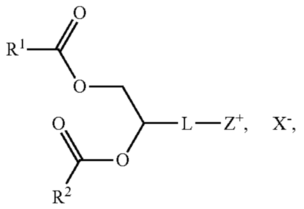

wherein $R^1$ and $R^2$ are each independently an optionally substituted $C_6$-$C_{24}$ alkyl, or an optionally substituted $C_6$-$C_{24}$ alkenyl.

In some embodiments of the lipid compositions, the SORT lipid has a structural formula:

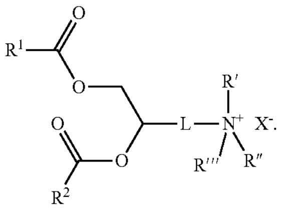

In some embodiments of the lipid compositions, the SORT lipid comprises a Linker (L). In some embodiments, L is

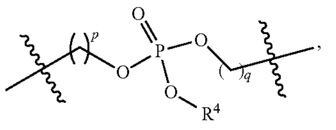

wherein:

p and q are each independently 1, 2, or 3; and $R^4$ is an optionally substituted $C_1$-$C_6$ alkyl In some embodiments of the lipid compositions, the SORT lipid has a structural formula:

(IA)

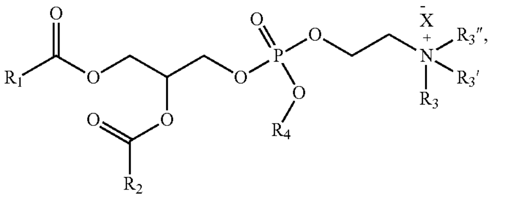

wherein:

$R_1$ and $R_2$ are each independently alkyl$_{(C8-C24)}$, alkenyl$_{(C8-C24)}$, or a substituted version of either group;

$R_3$, $R_{3'}$, and $R_3''$ are each independently alkyl$_{(C\leq6)}$ or substituted alkyl$_{(C\leq6)}$;

$R_4$ is alkyl$_{(C\leq6)}$ or substituted alkyl$_{(C\leq6)}$; and $X^-$ is a monovalent anion.

In some embodiments of the lipid compositions, the SORT lipid is a phosphotidylcholine (e.g., 14:0 EPC). In some embodiments, the phophotidylcholine compound is further defined as:

(IA)

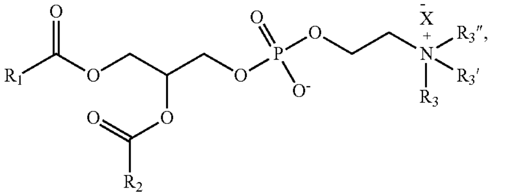

wherein:

$R_1$ and $R_2$ are each independently alkyl$_{(C8-C24)}$, alkenyl$_{(C8-C24)}$, or a substituted version of either group;

$R_3$, $R_{3'}$, and $R_3''$ are each independently alkyl$_{(C\leq6)}$ or substituted alkyl$_{(C\leq6)}$; and $X^-$ is a monovalent anion.

In some embodiments of the lipid compositions, the SORT lipid is a phosphocholine lipid. In some embodiments, the SORT lipid is an ethylphosphocholine. The ethylphosphocholine may be, by way of example, without being limited to, 1,2-dimyristoleoyl-sn-glycero-3-ethylphosphocholine, 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, 1,2-dimyristoyl-sn-glycero-3-ethylphosphocholine, 1,2-dilauroyl-sn-glycero-3-ethylphosphocholine, 1-palmitoyl-2-oleoyl-sn-glycero-3-ethylphosphocholine.

In some embodiments of the lipid compositions, the SORT lipid has a structural formula (S-I')

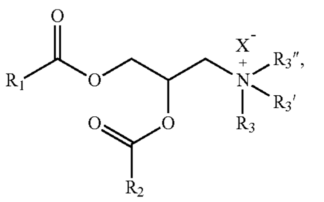

wherein:

$R_1$ and $R_2$ are each independently alkyl$_{(C8-C24)}$, alkenyl$_{(C8-C24)}$, or a substituted version of either group;

$R_3$, $R_{3'}$, and $R_3''$ are each independently alkyl$_{(C\leq6)}$ or substituted alkyl$_{(C\leq6)}$;

$X^+$ is a monovalent anion.

By way of example, and without being limited thereto, a SORT lipid of the structural formula of the immediately preceding paragraph is 1,2-dioleoyl-3-trimethylammonium-propane (18:1 DOTAP) (e.g., chloride salt).

In some embodiments of the lipid compositions, the SORT lipid has a structural formula:

(S-II')

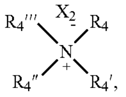

wherein:

$R_4$ and $R_{4'}$ are each independently alkyl$_{(C6-C24)}$, alkenyl$_{(C6-C24)}$, or a substituted version of either group;

$R_4''$ is alkyl$_{(C\leq24)}$, alkenyl$_{(C\leq24)}$, or a substituted version of either group;

$R_{4'}''$ is alkyl$_{(C1-C8)}$, alkenyl$_{(C2-C8)}$, or a substituted version of either group; and $X_2$ is a monovalent anion.

By way of example, and without being limited thereto, a SORT lipid of the structural formula of the immediately preceding paragraph is dimethyldioctadecylammonium (DDAB) (e.g., bromide salt).

In some embodiments of the lipid compositions, the SORT lipid has a structural formula:

(S-III)

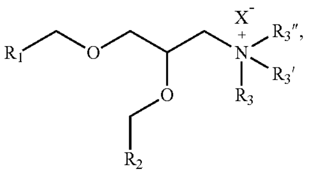

wherein:

$R_1$ and $R_2$ are each independently alkyl$_{(C8-C24)}$, alkenyl$_{(C8-C24)}$, or a substituted version of either group;

$R_3$, $R_{3'}$, and $R_3''$ are each independently alkyl$_{(C\leq6)}$ or substituted alkyl$_{(C\leq6)}$; and $X^-$ is a monovalent anion.

By way of example, and without being limited thereto, a SORT lipid of the structural formula of the immediately preceding paragraph is N-[1-(2,3-dioleyloxy)propyl]-N,N,N-trimethylammonium chloride (DOTMA).

In some embodiments of the lipid compositions, the SORT lipid is an anionic lipid. In some embodiments of the lipid compositions, the SORT lipid has a structural formula:

(S-IV)

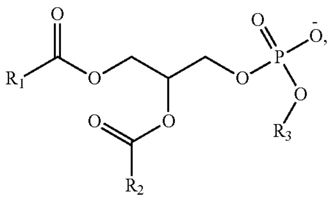

wherein:

$R_1$ and $R_2$ are each independently alkyl$_{(C8-C24)}$, alkenyl$_{(C8-C24)}$, or a substituted version of either group;

$R_3$ is hydrogen, alkyl$_{(C\leq6)}$, or substituted alkyl$_{(C\leq6)}$, or —$Y_1$—$R_4$, wherein:

$Y_1$ is alkanediyl$_{(C\leq6)}$ or substituted alkanediyl$_{(C\leq6)}$; and $R_4$ is acyloxy$_{(C\leq8-24)}$ or substituted acyloxy$_{(C\leq8-24)}$.

In some embodiments of the lipid compositions, the SORT lipid comprises one or more selected from the lipids set forth in Table 8.

TABLE 8

Example SORT lipids

| Lipid Name | Structure |
|---|---|
| 1,2-Dioleoyl-3-dimethylammonium-propane (18:1 DODAP) | 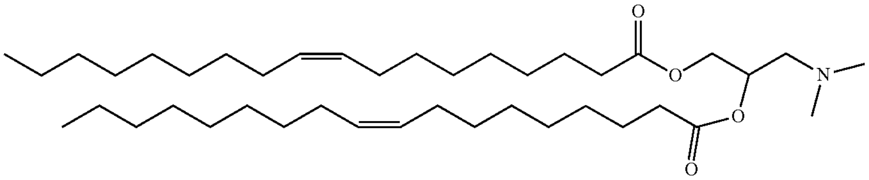 [SMILES: CCCCCCCC/C=C\CCCCCCCC(=O)OCC(CN(C)C)OC(=O)CCCCCCC/C=C\CCCCCCCC] |
| 1,2-dimyristoyl-3-trimethylammonium-propane (14:0 TAP) (e.g., chloride salt) | 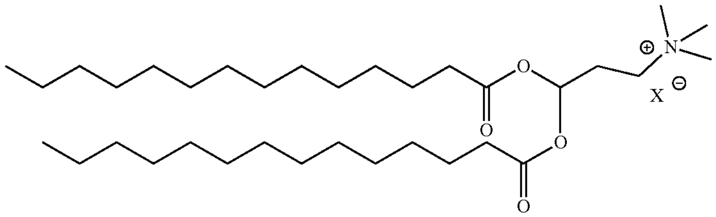 |
| 1,2-dipalmitoyl-3-trimethylammonium-propane (16:0 TAP) (e.g., chloride salt) | 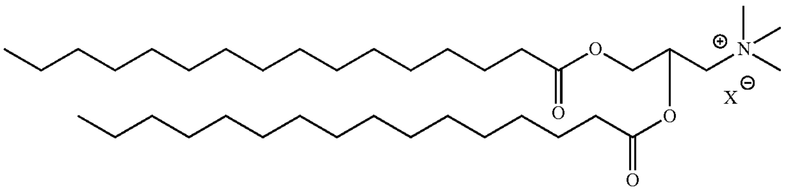 |
| 1,2-stearoyl-3-trimethylammonium-propane (18:0 TAP) (e.g., chloride salt) | 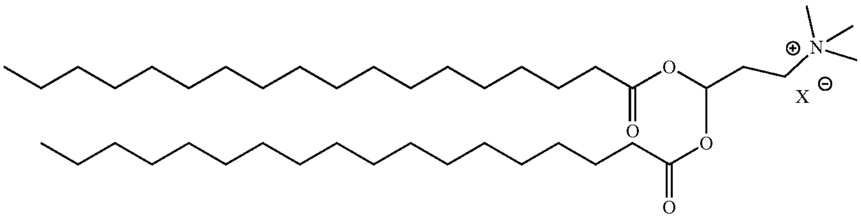 |
| 1,2-Dioleoyl-3-trimethylammonium-propane (18:1 DOTAP) (e.g., chloride salt) | 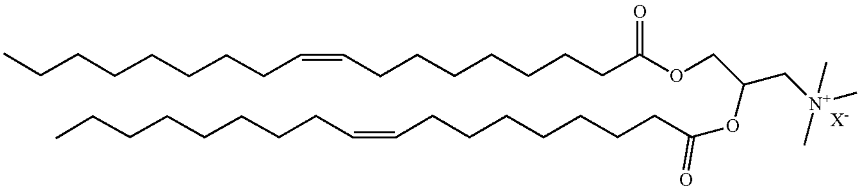 |
| 1,2-Di-O-octadecenyl-3-trimethylammonium propane (DOTMA) (e.g., chloride salt) | 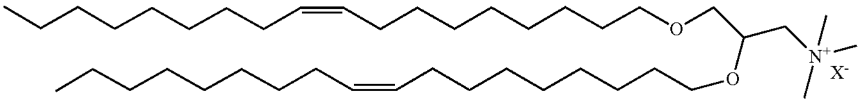 |
| Dimethyldioctadecylammonium (DDAB) (e.g., bromide salt) | 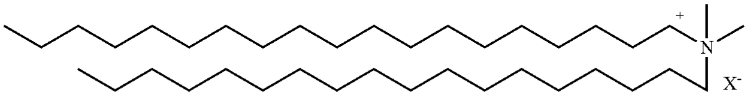 |

TABLE 8-continued

Example SORT lipids

| Lipid Name | Structure |
|---|---|
| 1,2-dilauroyl-sn-glycero-3-ethylphosphocholine (12:0 EPC) (e.g., chloride salt) | 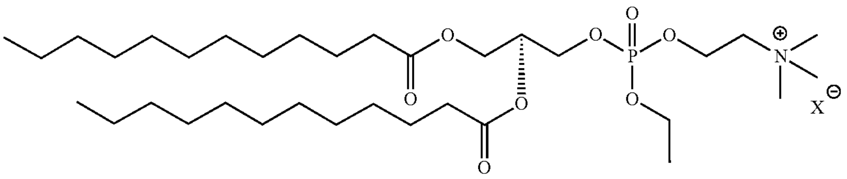 |
| 1,2-Dioleoyl-sn-glycero-3-ethylphosphocholine (14:0 EPC) (e.g., chloride salt) | 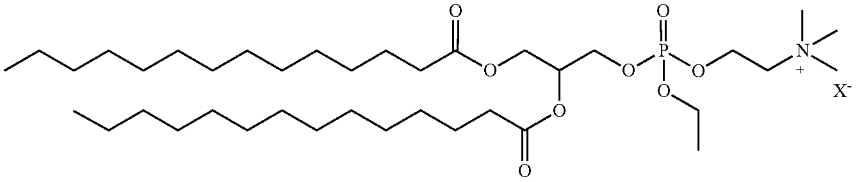 |
| 1,2-dimyristoleoyl-sn-glycero-3-ethylphosphocholine (14:1 EPC) (e.g., triflate salt) | 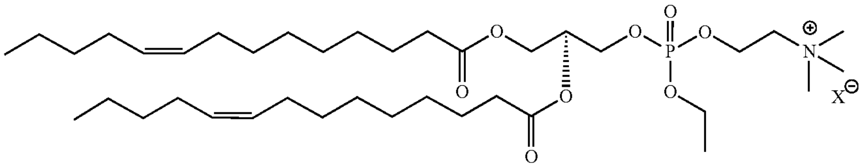 |
| 1,2-dipalmitoyl-sn-glycero-3-ethylphosphocholine (16:0 EPC) (e.g., chloride salt) | 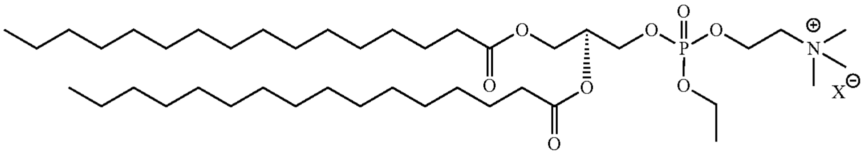 |
| 1,2-distearoyl-sn-glycero-3-ethylphosphocholine (18:0 EPC) (e.g., chloride salt) | 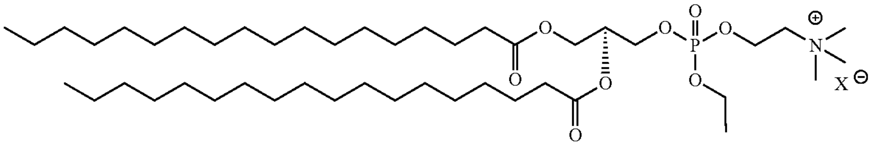 |
| 1,2-dioleoyl-sn-glycero-3-ethylphosphocholine (18:1 EPC) (e.g., chloride salt) | 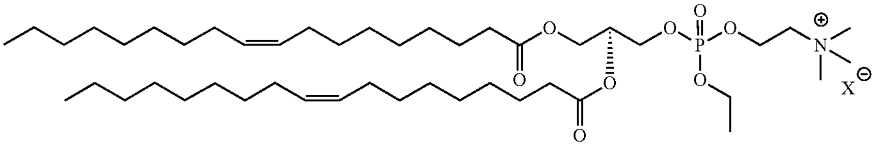 |
| 1-palmitoyl-2-oleoyl-sn-glycero-3-ethylphosphocholine (16:0-18:1 EPC) (e.g., chloride salt) | 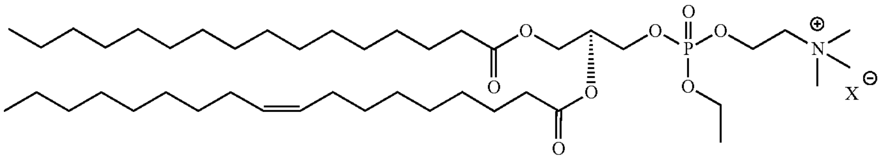 |
| 1,2-di-O-octadeceny1-3-trimethylammonium propane (18:1 DOTMA) (e.g., chloride salt) | 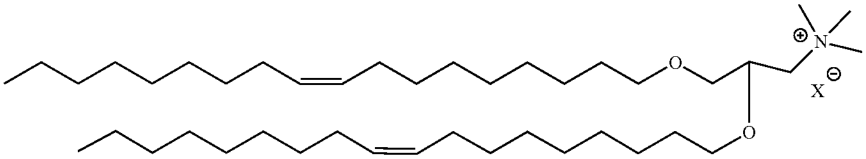 |

TABLE 8-continued

| Example SORT lipids | |
|---|---|
| Lipid Name | Structure |
| 1,2-dioleoyl-sn-glycero-3-phosphate (18.1 PA) | 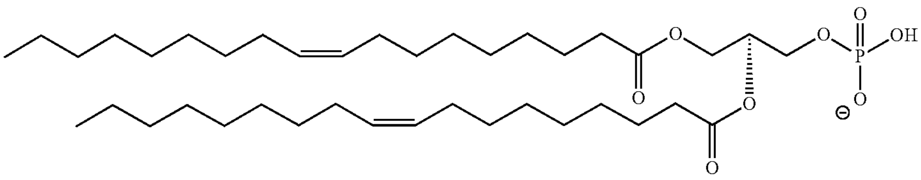 [SMILES: CCCCCCCC/C=C\CCCCCCCC(=O)OC[C@@H](COP(=O)([O-])O)OC(=O)CCCCCCC/C=C\CCCCCCCC] |

$X^-$ is a counterion (e.g., $Cl^-$, $Br^-$, etc.)

In some embodiments of the lipid composition of the present application, said lipid composition comprises said SORT lipid at a molar percentage from about 5% to about 65%. In some embodiments of the lipid composition of the present application, said lipid composition comprises said SORT lipid at a molar percentage from about 5% to about 30%. In some embodiments of the lipid composition of the present application, said lipid composition comprises said SORT lipid at a molar percentage from about 30% to about 55%. In some embodiments of the lipid composition of the present application, said lipid composition comprises said SORT lipid at a molar percentage from about 20% to about 50%. In some embodiments of the lipid composition of the present application, said lipid composition comprises said SORT lipid at a molar percentage from about 30% to about 60%. In some embodiments of the lipid composition of the present application, said lipid composition comprises said SORT lipid at a molar percentage from about 25% to about 60%. In some embodiments of the lipid composition of the present application, said lipid composition comprises said SORT lipid at a molar percentage from about 10% to about 20%. In some embodiments of the lipid composition of the present application, said lipid composition comprises said SORT lipid at a molar percentage from about 20% to about 30%. In some embodiments of the lipid composition of the present application, said lipid composition comprises said SORT lipid at a molar percentage from about 10% to about 30%. In some embodiments of the lipid composition of the present application, said lipid composition comprises said SORT lipid at a molar percentage from about 10% to about 15%. In some embodiments of the lipid composition of the present application, said lipid composition comprises said SORT lipid at a molar percentage from about 15% to about 20%. In some embodiments of the lipid composition of the present application, said lipid composition comprises said SORT lipid at a molar percentage of at least (about) 25%, at least (about) 30%, at least (about) 35%, at least (about) 40%, at least (about) 45%, at least (about) 50%, at least (about) 55%, at least (about) 60%, or at least (about) 65%. In some embodiments of the lipid composition of the present application, said lipid composition comprises said SORT lipid at a molar percentage of at most (about) 25%, at most (about) 30%, at most (about) 35%, at most (about) 40%, at least (about) 45%, at most (about) 50%, at most (about) 55%, at most (about) 60%, or at most (about) 65%.

Additional Lipids

In some embodiments of the lipid composition of the present application, the lipid composition further comprises an additional lipid including but not limited to a zwitterionic lipid (e.g., a phospholipid), a steroid or a steroid derivative, a polymer-conjugated lipid (e.g., polyethylene glycol (PEG)-conjugated lipid), or a combination thereof.

In some embodiments, a molar ratio of nitrogen in the lipid composition to phosphate in the synthetic polynucleotide (N/P ratio) is of no more than about 50:1, no more than about 40:1, no more than about 30:1, or no more than about 20:1. In some embodiments, a molar ratio of nitrogen in the lipid composition to phosphate in the synthetic polynucleotide (N/P ratio) is of at least about 1:1, at least about 2:1, at least about 3:1, at least about 4:1, or at least about 5:1. In some embodiments, a molar ratio of nitrogen in the lipid composition to phosphate in the synthetic polynucleotide (N/P ratio) is of about 1:1 to about 50:1, at least about 2:1 to about 50:1, at least about 3:1 to about 50:1, at least about 4:1 to about 50:1, or at least about 5:1 to about 50:1. In some embodiments, a molar ratio of nitrogen in the lipid composition to phosphate in the synthetic polynucleotide (N/P ratio) is of about 1:1 to about 40:1, at least about 2:1 to about 40:1, at least about 3:1 to about 40:1, at least about 4:1 to about 40:1, or at least about 5:1 to about 40:1. In some embodiments, a molar ratio of nitrogen in the lipid composition to phosphate in the synthetic polynucleotide (N/P ratio) is of about 1:1 to about 30:1, at least about 2:1 to about 30:1, at least about 3:1 to about 30:1, at least about 4:1 to about 30:1, or at least about 5:1 to about 30:1.

Zwitterionic Lipids

In some embodiments of the lipid composition of the present application, the lipid composition further comprises a zwitterion lipid or a phospholipid. In some embodiments, the zwitterion lipid or phospholipid may contain one or two long chain (e.g., $C_6$-$C_{24}$) alkyl or alkenyl groups, a glycerol or a sphingosine, one or two phosphate groups, and, optionally, a small organic molecule. The small organic molecule may be an amino acid, a sugar, or an amino substituted alkoxy group, such as choline or ethanolamine. In some embodiments, the zwitterion lipid or phospholipid is a phosphatidylcholine. In some embodiments, the zwitterion lipid or phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some embodiments of the lipid compositions, the zwitterion lipid or phospholipid is not an ethylphosphocholine.

In some embodiments of the lipid composition of the present application, the compositions may further comprise a molar percentage of the zwitterion lipid or phospholipid to the total lipid composition from about 20 to about 23. In some embodiments, the molar percentage is from about 20, 20.5, 21, 21.5, 22, 22.5, to about 23 or any range derivable therein. In other embodiments, the molar percentage is from about 7.5 to about 60. In some embodiments, the molar percentage is from about 7.5, 8, 9, 10, 11, 12, 13, 14, 15, 16, 17, 18, 19, to about 20 or any range derivable therein.

In some embodiments of the lipid composition of the present application, said lipid composition comprises the zwitterionic lipid (e.g., phospholipid or zwitterionic phospholipid) at a molar percentage from about 5% to about 25%. In some embodiments of the lipid composition of the present application, said lipid composition comprises the zwitterionic lipid (e.g., phospholipid or zwitterionic phospholipid) at a molar percentage from about 10% to about 20%. In some embodiments of the lipid composition of the present application, said lipid composition comprises the zwitterionic lipid (e.g., phospholipid or zwitterionic phospholipid) at a molar percentage from about 15% to about 20%. In some embodiments of the lipid composition of the present application, said lipid composition comprises the zwitterionic lipid (e.g., phospholipid or zwitterionic phospholipid) at a molar percentage from about 8% to about 15%. In some embodiments of the lipid composition of the present application, said lipid composition comprises the zwitterionic lipid (e.g., phospholipid or zwitterionic phospholipid) at a molar percentage from about 10% to about 15%. In some embodiments of the lipid composition of the present application, said lipid composition comprises the zwitterionic lipid (e.g., phospholipid or zwitterionic phospholipid) at a molar percentage from about 12% to about 18%. In some embodiments of the lipid composition of the present application, said lipid composition comprises the zwitterionic lipid (e.g., phospholipid or zwitterionic phospholipid) at a molar percentage of at least (about) 8%, at least (about) 10%, at least (about) 12%, at least (about) 15%, at least (about) 18%, at least (about) 20%, or at least (about) 25%. In some embodiments of the lipid composition of the present application, said lipid composition comprises the zwitterionic lipid (e.g., phospholipid or zwitterionic phospholipid) at a molar percentage of at most (about) 8%, at most (about) 10%, at most (about) 12%, at most (about) 15%, at most (about) 18%, at most (about) 20%, or at most (about) 25%.

In some embodiments, a (e.g., mass or weight) ratio of the zwitterionic lipid to the synthetic polynucleotide is of no more than about 50:1, 40:1, 30:1, 20:1, 10:1, or 7:1. In some embodiments, a (e.g., mass or weight) ratio of the zwitterionic lipid to the synthetic polynucleotide is of at least about 1:1, 2:1, 3:1, 4:1, or 5:1. In some embodiments, a (e.g., mass or weight) ratio of the zwitterionic lipid to the synthetic polynucleotide is of about 1:1 to about 10:1, about 1:1 to about 20:1, about 1:1 to about 30:1, about 1:1 to about 40:1, or about 1:1 to about 50:1.

Steroids or Steroid Derivatives

In some embodiments of the lipid composition of the present application, the lipid composition further comprises a steroid or steroid derivative. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In some embodiments, the ring structure of a steroid comprises three fused cyclohexyl rings and a fused cyclopentyl ring as shown in the formula:

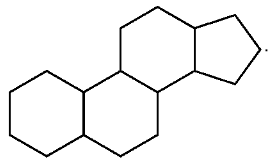 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

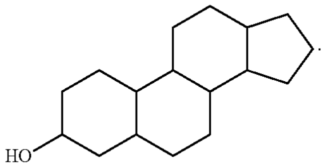 [SMILES: OC1CCC2C(CCC3C4CCCC4CCC23)C1]

In some embodiments of the present application, the steroid or steroid derivative is a cholestane or cholestane derivative. In a cholestane, the ring structure is further defined by the formula:

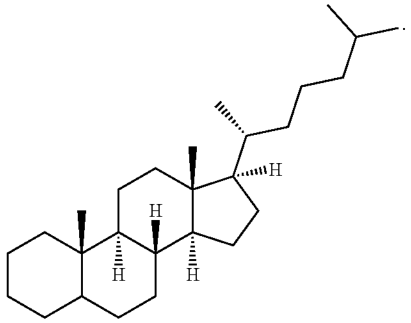

As described above, a cholestane derivative includes one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholestene and a sterol or a derivative thereof.

In some embodiments of the lipid composition, the compositions may further comprise a molar percentage of the steroid to the total lipid composition from about 40 to about 46. In some embodiments, the molar percentage is from about 40, 41, 42, 43, 44, 45, to about 46 or any range derivable therein. In other embodiments, the molar percentage of the steroid relative to the total lipid composition is from about 15 to about 40. In some embodiments, the molar percentage is 15, 16, 18, 20, 22, 24, 26, 28, 30, 32, 34, 36, 38, or 40, or any range derivable therein.

In some embodiments of the lipid composition of the present application, said lipid composition comprises said steroid or steroid derivative at a molar percentage from about 15% to about 46%. In some embodiments of the lipid composition of the present application, said lipid composition comprises said steroid or steroid derivative at a molar percentage from about 20% to about 40%. In some embodiments of the lipid composition of the present application, said lipid composition comprises said steroid or steroid derivative at a molar percentage from about 25% to about 35%. In some embodiments of the lipid composition of the present application, said lipid composition comprises said steroid or steroid derivative at a molar percentage from about 30% to about 40%. In some embodiments of the lipid composition of the present application, said lipid composition comprises said steroid or steroid derivative at a molar percentage from about 20% to about 30%. In some embodiments of the lipid composition of the present application, said lipid composition comprises said steroid or steroid derivative at a molar percentage of at least (about) 15%, of at least (about) 20%, of at least (about) 25%, of at least (about) 30%, of at least (about) 35%, of at least (about) 40%, of at least (about) 45%, or of at least (about) 46%. In some embodiments of the lipid composition of the present application, said lipid composition comprises said steroid or steroid derivative at a molar percentage of at most (about) 15%, of at most (about) 20%, of at most (about) 25%, of at most (about) 30%, of at most (about) 35%, of at most (about) 40%, of at most (about) 45%, or of at most (about) 46%.

Polymer-Conjugated Lipids

In some embodiments of the lipid composition of the present application, the lipid composition further comprises a polymer conjugated lipid. In some embodiments, the polymer conjugated lipid is a PEG lipid. In some embodiments, the PEG lipid is a diglyceride which also comprises a PEG chain attached to the glycerol group. In other embodiments, the PEG lipid is a compound which contains one or more $C_6$-$C_{24}$ long chain alkyl or alkenyl group or a $C_6$-$C_{24}$ fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified Phosphatidylethanolamine (PE). In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present application are taught by U.S. Pat. No. 5,820,873, WO 2010/141069, or U.S. Pat. No. 8,450,298, which is incorporated herein by reference.

In some embodiments of the lipid composition of the present application, the PEG lipid has a structural formula:

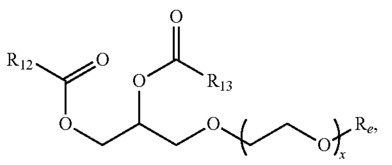

wherein: $R_{12}$ and $R_{13}$ are each independently alkyl$_{(C\leq24)}$, alkenyl$_{(C\leq24)}$, or a substituted version of either of these groups; $R_e$ is hydrogen, alkyl$_{(C\leq8)}$, or substituted alkyl$_{(C\leq8)}$; and x is 1-250. In some embodiments, $R_e$ is alkyl$_{(C\leq8)}$ such as methyl. $R_{12}$ and $R_{13}$ are each independently alkyl$_{(C\leq4\text{-}20)}$. In some embodiments, x is 5-250. In one embodiment, x is 5-125 or x is 100-250. In some embodiments, the PEG lipid is 1,2-dimyristoyl-sn-glycerol, methoxypolyethylene glycol.

In some embodiments of the lipid composition of the present application, the PEG lipid has a structural formula:

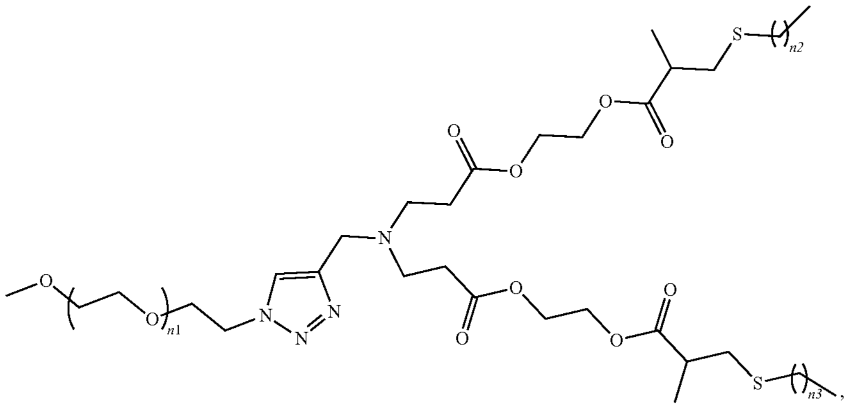

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments of the lipid composition of the present application, the compositions may further comprise a molar percentage of the PEG lipid to the total lipid composition from about 4.0 to about 4.6. In some embodiments, the molar percentage is from about 4.0, 4.1, 4.2, 4.3, 4.4, 4.5, to about 4.6 or any range derivable therein. In other embodiments, the molar percentage is from about 1.5 to about 4.0. In some embodiments, the molar percentage is from about 1.5, 1.75, 2, 2.25, 2.5, 2.75, 3, 3.25, 3.5, 3.75, to about 4.0 or any range derivable therein.

In some embodiments of the lipid composition of the present application, said lipid composition comprises said polymer-conjugated lipid at a molar percentage from about 0.5% to about 12%, or from about 0.5% to about 10%. In some embodiments of the lipid composition of the present application, the lipid composition comprises the polymer-conjugated lipid at a molar percentage from about 1% to about 10%. In some embodiments of the lipid composition of the present application, the lipid composition comprises the polymer-conjugated lipid at a molar percentage from about 2% to about 10%. In some embodiments of the lipid composition of the present application, said lipid composition comprises said polymer-conjugated lipid at a molar percentage from about 1% to about 8%. In some embodiments of the lipid composition of the present application, said lipid composition comprises said polymer-conjugated lipid at a molar percentage from about 2% to about 7%. In some embodiments of the lipid composition of the present application, said lipid composition comprises said polymer-conjugated lipid at a molar percentage from about 3% to about 5%. In some embodiments of the lipid composition of the present application, said lipid composition comprises said polymer-conjugated lipid at a molar percentage from about 5% to about 10%. In some embodiments of the lipid composition of the present application, said lipid composition comprises said polymer-conjugated lipid at a molar percentage of at least (about) 0.5%, at least (about) 1%, at least (about) 1.5%, at least (about) 2%, at least (about) 2.5%, at least (about) 3%, at least (about) 3.5%, at least (about) 4%, at least (about) 4.5%, at least (about) 5%, at least (about) 5.5%, at least (about) 6%, at least (about) 6.5%, at least (about) 7%, at least (about) 7.5%, at least (about) 8%, at least (about) 8.5%, at least (about) 9%, at least (about) 9.5%, or at least (about) 10%. In some embodiments of the lipid composition of the present application, said lipid composition comprises said polymer-conjugated lipid at a molar percentage of at most (about) 0.5%, at most (about) 1%, at most (about) 1.5%, at most (about) 2%, at most (about) 2.5%, at most (about) 3%, at most (about) 3.5%, at most (about) 4%, at most (about) 4.5%, at most (about) 5%, at most (about) 5.5%, at most (about) 6%, at most (about) 6.5%, at most (about) 7%, at most (about) 7.5%, at most (about) 8%, at most (about) 8.5%, at most (about) 9%, at most (about) 9.5%, or at most (about) 10%.

Some embodiments of the (e.g., pharmaceutical) composition disclosed herein comprise a particular molar ratio of the components or atoms. In some embodiments, the (e.g., pharmaceutical) composition comprises a particular molar ratio of nitrogen in the lipid composition to the phosphate in the polynucleotide (N/P ratio). In some embodiments, the molar ratio of nitrogen in the lipid composition to phosphate in the polynucleotide (N/P ratio) is no more than about 30:1. In some embodiments, the N/P ratio is from about 5:1 to about 30:1. In some embodiments, the N/P ratio is no more than 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, or less. In some embodiments, the N/P ratio is at least 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, or more. In some embodiments, the N/P ratio is of any one of the following values or within a range of any two of the following values: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, and 50:1.

In some embodiments, composition comprises a particular (e.g., mass or weight) ratio of the polynucleotide to total lipids of the lipid composition. In some embodiments, the (e.g., mass or weight) ratio of the polynucleotide to total lipids of the lipid composition is no more than about 1:1, 1:10, 1:50, or 1:100. In some embodiments, the (e.g., mass or weight) ratio of the polynucleotide to total lipids of the lipid composition is no more than about 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:75, or 1:100 or less. In some embodiments, the (e.g., mass or weight) ratio of the polynucleotide to total lipids of the lipid composition is at least about 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:75, or 1:100 or more. In some embodiments, the (e.g., mass or weight) ratio of the polynucleotide to total lipids of the lipid composition is of any one of the following values or within a range of any two of the following values: 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:75, and 1:100.

In some embodiments of the composition, the composition can be formulated as any suitable dosage form known in the art. In some embodiments, the composition is formulated in a nanoparticle or a nanocapsule. In some embodiments, the composition is formulated for administration by any suitable route known in the art including, for example, oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections.

In some embodiments, the composition of the present application is formulated for administration by a local rather than systemic manner, for example, via injection of the pharmaceutical composition directly into a targeted tissue, such as in a sustained release formulation. Local delivery can be affected in various ways, depending on the tissue to be targeted. The composition may be formulated for aerosol administration. The aerosol administration may be delivered to the respiratory epithelium. In some embodiments, the aerosol composition has a droplet size from 0.5 micron (μm) to 10 μm. In some embodiments, the aerosol composition has a median droplet size from 0.5 μm to 10 μm. In some embodiments, the aerosol composition has an average droplet size from 0.5 μm to 10 μm. The droplet size may be measured using cascade impactor analysis or laser diffraction, or other suitable techniques for measuring aerosol droplets.

In some embodiments, the composition of the present application can be injected into the site of injury, disease manifestation, or pain, for example. In some embodiments, the composition of the present application can be provided in lozenges for oral, tracheal, or esophageal application. In some embodiments, the composition of the present application can be supplied in liquid, tablet or capsule form for administration to the stomach or intestines. In some embodiments, the composition of the present application can be supplied in suppository form for rectal or vaginal application. In some embodiments, the composition of the present application can even be delivered to the eye by use of creams, drops, or even injection.

Methods

Methods for Enhancing CFTR Expression or Activity in Cell(s)

In some embodiments, provided herein is a method for enhancing an expression or activity of cystic fibrosis transmembrane conductance regulator (CFTR) protein in a cell, comprising: contacting said cell with a synthetic polynucleotide as described herein assembled with a lipid composition, wherein said synthetic polynucleotide encodes a CFTR protein; and wherein said lipid composition comprises: (1) an ionizable cationic lipid; (2) a selective organ targeting (SORT) lipid separate from said ionizable cationic lipid and said phospholipid, thereby resulting in an expression or activity of said CFTR protein in said cell. The lipid composition may further comprise a zwitterionic lipid or phospholipid.

In some embodiments, provided herein in a method for enhancing an expression or activity of cystic fibrosis transmembrane conductance regulator (CFTR) protein in a cell, the method comprising: contacting said cell with a composition comprising a synthetic polynucleotide assembled with a lipid composition, wherein said synthetic polynucleotide encodes a CFTR protein; and wherein said lipid composition comprises: an ionizable cationic lipid; and a selective organ targeting (SORT) lipid separate from said ionizable cationic lipid, thereby yielding a therapeutically effective amount or activity of a functional variant of CFTR protein in said cell at least 24 hours after contacting, optionally wherein said therapeutically effective activity of said functional variant of CFTR protein is determined by measuring a change in a transepithelial ion transport characteristic of a plurality of cells comprising said cell as compared to that of a reference plurality of cells in absence of said contacting. The lipid composition may further comprise a zwitterionic lipid or phospholipid.

In some embodiments of the method, the composition of the present application is formulated for administration by a local rather than systemic manner, for example, via injection of the pharmaceutical composition directly into a targeted tissue, such as in a sustained release formulation. Local delivery can be affected in various ways, depending on the tissue to be targeted. In some embodiments of the method, aerosols containing the composition of the present application can be inhaled (for nasal, tracheal, or bronchial delivery). The composition may be formulated for aerosol administration.

In some embodiments, the contacting is repeated. The contacting may be repeated 1, 2, 3, or more times. In some embodiments, the contacting is at least once a week. In some embodiments, the contacting is at least twice a week. In some embodiments, the method yields a therapeutically effective amount or activity of a functional variant of CFTR protein in said cell at least 24 hours after each contacting. In some embodiments, a second contacting is performed, optionally at least about 1, 2, or 3 day(s) after the first contacting. In some embodiments, the method further comprises a third contacting wherein said third contacting is performed optionally at least about 1, 2, or 3 day(s) after the second contacting. In embodiments, the method yields a therapeutically effective amount or activity of a functional variant of CFTR protein in said cell at least 24 hours after a second contacting. In some embodiments, the method yields a therapeutically effective amount or activity of a functional variant of CFTR protein in said cell at least 24 hours after a third contacting. The composition in each contacting may be the same or identical. The therapeutically effective amount or activity of a functional variant of CFTR protein may increase after repeated contacting.

The contacting(s) may be performed in vivo. The contacting(s) may be performed in vitro. The contacting(s) may be performed ex vivo.

In some embodiments, the methods achieve a therapeutically effective activity of said functional variant of CFTR protein. In some embodiments, therapeutically effective activity may be measured by a transepithelial assay. The transepithelial assay may measure a voltage or a current which may correspond to the function of a functional protein. In some embodiments, the therapeutically effective activity of said functional variant of CFTR protein corresponds to a transepithelial current of at least 5 micro-Amperes (μA). In some embodiments, the therapeutically effective activity of said functional variant of CFTR protein corresponds to a transepithelial current from at least 5 micro-Amperes (μA) to about 30 μA. In some embodiments, therapeutically effective activity of said functional variant of CFTR protein corresponds to a transepithelial current of at least about 2 micro-Ampere (μA) per squared centimeter per minute ($\mu A \cdot cm^{-2} \cdot min^{-1}$). In some embodiments, said therapeutically effective activity of said functional variant of CFTR protein corresponds to a transepithelial current from about 2 micro-Ampere (μA) per squared centimeter per minute ($\mu A \cdot cm^{-2} \cdot min^{-1}$) to about 20 $\mu A \cdot cm^{-2} \cdot min^{-1}$. The transepithelial current may be determined via an in vitro assay, such as those described elsewhere herein.

In some embodiments, the methods achieve a therapeutically effective activity of said functional variant of CFTR protein can be the measurement of the forced expiratory volume (FEV) of a subject. The FEV measures how much air a subject can exhale during a forced breath. The amount of air exhaled may be measured during the first (FEV1), second (FEV2), or third (FEV3) second(s) of the forced breath. In some embodiments, the method results in the subject having a FEV1, FEV2, or FEV3 of about 40% to about 90%, about 50% to about 90%, about 60% to about 90%, about 70% to about 90%, about 80% to about 90%, about 40% to about 80%, about 40% to about 70%, about 40% to about 60%, or about 40% to about 50%. In some embodiments, the method results in the subject having a FEV1, FEV2, or FEV3 of about 40%, about 45%, about 50%, about 55%, about 60%, about 65%, about 70%, about 75%, about 80%, about 85%, about 90%. In some embodiments, the method results in the subject having a FEV1, FEV2, or FEV3 of about 40% to about 90%.

In some embodiments of the methods, the method increases an amount of a functional variant of CFTR protein in the cell relative to a corresponding control. In some embodiments, the method increases an amount of WT CFTR protein in said cell relative to a corresponding control. In some embodiments, said control comprises a corresponding cell absent said contacting. In some embodiments, the method increases an amount of said functional variant of CFTR protein by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3.0-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4.0-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, or at least about 5.0-fold, in said cell relative to a corresponding control. In some embodiments, the method increases an amount of WT CFTR protein by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3.0-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4.0-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, or at least about 5.0-fold, in said cell relative to a cell absent said contacting.

In some embodiments, the method results in a therapeutically effective amount of said functional variant of CFTR protein in said cell. In some embodiments, the method results in a therapeutically effective amount of WT CFTR protein in said cell.

In some embodiment, the method enhances ion transport in said cell relative to a corresponding control. In some embodiment, the method enhances chloride transport in said cell relative to a corresponding control. In some embodiments, said control comprises a corresponding cell absent said contacting. In some embodiment, the method enhances ion transport by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3.0-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4.0-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, or at least about 5.0-fold, in said cell relative to a corresponding control.

Methods for Treating Cystic Fibrosis

In some embodiments, provided herein is a method for treating a subject having or suspected of having a cystic fibrosis transmembrane conductance regulator (CFTR)-associated condition. The method may comprise administering to the subject a composition as described herein. In some embodiments, the CFTR-associated condition is cystic fibrosis, hereditary emphysema, or chronic obstructive pulmonary disease (COPD), or a combination thereof. In some embodiments, said subject is a mammal, such as a human, monkey, cow, sheep, goat, dog, cat, mouse, rat, guinea pig, or transgenic species thereof. The subject may be a mammal. The subject may be a human. In some embodiments, the administering comprises pulmonary administration. In some embodiments, the administering comprises inhalation by nebulization. In some embodiments, the administering comprises apical administration. In some embodiments, said subject is human. In some embodiments, said subject exhibits or is determined to exhibit a mutation in CFTR gene. In some embodiments, the mutation is R553X, G542X or F508del, or a combination thereof. In some embodiments, the mutation is R1162X. In some embodiments, the mutation is R553X, G542X, F508del, or R1162X, or a combination thereof.

The methods of the disclosure may be able to treat a subject with cystic fibrosis based on properties of the formulation or compositions. Specifically, the compositions described elsewhere herein may be able to penetrate the mucus associated with cystic fibrosis and thereby deliver the polynucleotides to the cells.

Cells

In some embodiments of any one method described herein, said cell is a lung cell. In some embodiments, said lung cell is a lung airway cell. Example lung airway cells that can be targeted by the delivery of the present application includes but is not limited to basal cell, secretory cell such as goblet cell and club cell, ciliated cell, ionocyte and any combination thereof. In some embodiments of the method, said cell is an airway epithelial cell. In some embodiments, said cell is a bronchial epithelial cell. In some embodiments, said cell is an airway epithelial cell. In some embodiments, said cell is a basal cell characterized by expression of p63 marker. In some embodiments, said cell is an ionocyte characterized by expression of FOXI1 marker. In some embodiments, said cell is undifferentiated. In some embodiments, said cell is differentiated.

Mutation(s)

In some embodiments of any one method described herein, said cell exhibits or is determined to exhibit a mutation in CFTR gene or transcript. In some embodiments, said cell exhibits or is determined to exhibit a mutation in one or more of exons 11-27 of CFTR gene. said cell exhibits or is determined to exhibit a nonsense or frameshift mutation in one or more of exons 11-27 of CFTR gene. In some embodiments, the mutation is located at a position in the CFTR gene at which a change can give rise to a mutant protein having a mutation at F508, e.g., F508del. In some embodiments, the mutation is located at a position in the CFTR gene at which a change can give rise to a mutant protein having a mutation at G542, e.g., G542X, in the CFTR protein, e.g., which corresponds to c.1624G>T in the CFTR gene. In some embodiments, the mutation is located at a position in the CFTR gene at which a change can give rise to a mutant protein having a mutation at R553, e.g., R553X, in the CFTR protein. In some embodiments, the mutation is located at a position in the CFTR gene at which a change can give rise to a mutant protein having a mutation at R1162, e.g., R1162X, in the CFTR protein.

In some embodiments of any one method described herein, said mutation is associated with cystic fibrosis, hereditary emphysema, or chronic obstructive pulmonary disease (COPD).

Methods for Lung Cell Delivery

In some embodiments, provided is a method for targeted pulmonary delivery, such as lung secretory cell or lung basal cell delivery (alternatively, lung secretory and/or basal cell delivery), the method comprising administering to a subject a composition as described herein, thereby yielding a therapeutically effective amount or activity of a synthetic polynucleotide in a lung secretory cell or lung basal cell of the subject. Optionally, the therapeutically effective activity of the synthetic polynucleotide may be determined by measuring a change in a transepithelial ion transport characteristic (e.g., a transepithelial current or voltage) of a lung comprising the lung secretory cell or lung basal cell as compared to that of a reference lung, e.g., in absence of the contacting. The composition may comprise a synthetic polynucleotide (as described herein) assembled with a lipid composition (as described herein). The synthetic polynucleotide may encode a cystic fibrosis transmembrane conductance regulator (CFTR) protein. The lipid composition may comprise an ionizable cationic lipid (as described herein); and a selective organ targeting (SORT) lipid (as described herein) separate from the ionizable cationic lipid. The lung basal cell may be a lung basal stem cell.

In some embodiments, provided is a method for targeted pulmonary delivery, such as lung secretory cell or lung basal cell delivery (alternatively, lung secretory and/or basal cell delivery), the method comprising administering to a subject a composition as described herein, thereby yielding a greater therapeutic amount or activity of a synthetic polynucleotide in a lung secretory cell or lung basal cell of the subject as compared to that in a lung non-secretory cell or lung non-basal cell of the subject. The composition may comprise a synthetic polynucleotide (as described herein) assembled with a lipid composition (as described herein). The synthetic polynucleotide may encode a cystic fibrosis transmembrane conductance regulator (CFTR) protein. The lipid composition may comprise an ionizable cationic lipid (as described herein); and a selective organ targeting (SORT) lipid (as described herein) separate from the ionizable cationic lipid. In some embodiments, the method yields an amount or activity of the synthetic polynucleotide in the lung secretory and/or basal cell that is at least 1.1-, 1.5-, 2-, 2.5-, 3-, 3.5-, 4-, 4.5- or 5-fold greater than that in the lung non-secretory and/or non-basal cell. In some embodiments, the method yields an amount or activity of the synthetic polynucleotide in the lung secretory cell that is at least 1.1-, 1.5-, 2-, 2.5-, 3-, 3.5-, 4-, 4.5- or 5-fold greater than that in the lung non-secretory. In some embodiments, the method yields an amount or activity of the synthetic polynucleotide in the lung basal cell that is at least 1.1-, 1.5-, 2-, 2.5-, 3-, 3.5-, 4-, 4.5- or 5-fold greater than that in the lung non-basal cell. The lung basal cell may be a lung basal stem cell. The lung non-secretory cell may be a lung ciliated cell. The lung non-basal cell may be a lung ciliated cell.

In some embodiments, provided is a method for targeted pulmonary delivery, such as lung secretory cell delivery, the method comprising administering to a subject a composition as described herein, thereby yielding a therapeutically effective amount or activity of a synthetic polynucleotide in a lung secretory cell of the subject. Optionally, the therapeutically effective activity of the synthetic polynucleotide may be determined by measuring a change in a transepithelial ion transport characteristic (e.g., a transepithelial current or voltage) of a lung comprising the lung secretory cell as compared to that of a reference lung, e.g., in absence of the contacting. The composition may comprise a synthetic polynucleotide (as described herein) assembled with a lipid composition (as described herein). The synthetic polynucleotide may encode a cystic fibrosis transmembrane conductance regulator (CFTR) protein. The lipid composition may comprise an ionizable cationic lipid (as described herein); and a selective organ targeting (SORT) lipid separate from the ionizable cationic lipid (as described herein).

In some embodiments, provided is a method for targeted pulmonary delivery, such as lung secretory cell or lung basal cell delivery (alternatively, lung secretory and/or basal cell delivery), the method comprising administering to a subject a composition as described herein, thereby yielding a greater therapeutic amount or activity of a synthetic polynucleotide in a lung secretory cell or lung basal cell of the subject as compared to that in a lung non-secretory cell or lung non-basal cell of the subject. The composition may comprise a synthetic polynucleotide (as described herein) assembled with a lipid composition (as described herein). The synthetic polynucleotide may encode a cystic fibrosis transmembrane conductance regulator (CFTR) protein. The lipid composition may comprise an ionizable cationic lipid (as described herein); and a selective organ targeting (SORT) lipid (as described herein) separate from the ionizable cationic lipid. In some embodiments, the method yields an amount activity of the synthetic polynucleotide in the lung secretory cell that is at least 1.1-, 1.5-, 2-, 2.5-, 3-, 3.5-, 4-, 4.5- or 5-fold greater than that in the lung non-secretory cell. The lung non-secretory cell may be a lung ciliated cell. In some embodiments, the method yields an amount activity of the synthetic polynucleotide in the lung basal cell that is at least 1.1-, 1.5-, 2-, 2.5-, 3-, 3.5-, 4-, 4.5- or 5-fold greater than that in the lung non-basal cell. The lung non-basal cell may be a lung ciliated cell. The lung basal cell may be a lung basal stem cell.

In various embodiments of the method for targeted pulmonary delivery, such as lung secretory cell or lung basal cell delivery (alternatively, lung secretory and/or basal cell delivery), at least about 50%, 55%, or 60% of (e.g., pulmonary) expression of said synthetic polynucleotide is detected or observed in lung secretory cells, lung basal cells, or a combination thereof, e.g., as determined by measuring an amount or activity of the corresponding polypeptide encoded by the synthetic polynucleotide. In various embodiments of the method for targeted pulmonary delivery, such as lung secretory cell or lung basal cell delivery (alternatively, lung secretory and/or basal cell delivery), no more than about 50%, 45%, or 40% of (e.g., pulmonary) expression of said synthetic polynucleotide is detected or observed in lung non-secretory cells, lung non-basal cells, or a combination thereof, e.g., as determined by measuring an amount or activity of the corresponding polypeptide encoded by the synthetic polynucleotide. In various embodiments of the method for targeted pulmonary delivery, such as lung secretory cell or lung basal cell delivery (alternatively, lung secretory and/or basal cell delivery), no more than about 50%, 45%, or 40% of (e.g., pulmonary) expression of said synthetic polynucleotide is in lung ciliated cells, e.g., as determined by measuring an amount or activity of the corresponding polypeptide encoded by the synthetic polynucleotide. In various embodiments, the method for targeted pulmonary delivery, such as lung secretory cell or lung basal cell delivery (alternatively, lung secretory and/or basal cell delivery) yields an amount or activity of said synthetic polynucleotide in lung secretory cell(s) or lung basal cell(s) that is at least 1.1-, 1.5-, or 2-fold greater than that in reference cell(s), which reference cell(s) are neither lung secretory cell(s) nor lung basal cell(s). The reference cell(s) may be lung ciliated cell(s). In various embodiments, the lung non-secretory cell or lung non-basal cell is a lung ciliated cell. The lung basal cell may be a lung basal stem cell. In some embodiments, the method for targeted pulmonary delivery, such as lung secretory cell delivery yields an amount or activity of said synthetic polynucleotide in lung secretory cell(s) that is at least 1.1-, 1.5-, or 2-fold greater than that in lung non-secretory cell(s). In some embodiments, the method for targeted pulmonary delivery, such as lung basal cell delivery yields an amount or activity of said synthetic polynucleotide in lung basal cell(s) that is at least 1.1-, 1.5-, or 2-fold greater than that in lung non-basal cell(s).

In some embodiments, provided is a method for targeted pulmonary delivery, such as lung secretory cell or basal cell delivery, comprising administering to a subject a composition as described herein, thereby yielding a therapeutic amount or activity of the synthetic polynucleotide in at least (about) 5% of lung secretory cells or lung basal cells of the subject. The composition may comprise a synthetic polynucleotide (as described herein) assembled with a lipid composition (as described herein). The synthetic polynucleotide may encode a cystic fibrosis transmembrane conductance regulator (CFTR) protein. The lipid composition may comprise an ionizable cationic lipid (as described herein); and a selective organ targeting (SORT) lipid (as described herein) separate from the ionizable cationic lipid.

In some embodiments of various methods for targeted pulmonary delivery, such as lung secretory cell or lung basal cell delivery, the lung secretory cell or lung basal cell exhibits or is determined to exhibit a mutation in CFTR gene. In some embodiments, the mutation is selected from the group consisting of G542X or F508del. In some embodiments, the mutation is R553X, G542X or F508del, or a combination thereof. In some embodiments, the mutation is R1162X. In some embodiments, the mutation is R553X, G542X, F508del, or R1162X, or a combination thereof.

A therapeutically effective activity of a functional variant of CFTR protein may be determined by measuring a change in a transepithelial ion transport characteristic (e.g., transepithelial current or voltage) of a lung of the subject as compared to that of a reference lung, e.g., prior to the administration.

In some embodiments, provided is a method for targeted pulmonary delivery, such as basal cell delivery of a synthetic polynucleotide that encodes a CFTR protein, comprising contacting a cell composition comprising a plurality of basal cells with a composition that comprises the synthetic polynucleotide assembled with a lipid composition, which lipid composition comprises: (1) an ionizable cationic lipid; and (2) a selective organ targeting (SORT) lipid separate from said ionizable cationic lipid, thereby delivering said synthetic polynucleotide to at least 15% of said plurality of basal cells. In some embodiments, the lipid composition further comprises a zwitterionic lipid or phospholipid. In some embodiments, said cell composition comprises lung basal cells. In some embodiments, said cell composition comprises basal cell, secretory cell such as goblet cell and club cell, ciliated cell, ionocyte and any combination thereof. In some embodiments, said cell composition comprises a first cell of a first CFTR genotype and a second cell of a second CFTR genotype.

In some embodiments, provided is method for targeted pulmonary delivery, such as basal cell-targeted delivery of a synthetic polynucleotide that encodes a CFTR protein, comprising contacting a plurality of cells of a plurality of cell types with a composition that comprises said synthetic polynucleotide as described herein assembled with a lipid composition, which plurality of cells comprise a basal cell and a non-basal cell, wherein said lipid composition comprises: (1) an ionizable cationic lipid; and (2) a selective organ targeting (SORT) lipid separate from said ionizable cationic lipid, thereby delivering said synthetic polynucleotide to said basal cell in a greater amount than that delivered to said non-basal cell. In some embodiments, the lipid composition further comprises a zwitterionic lipid or phospholipid. In some embodiments, said basal cell is a lung basal cell. In some embodiments, said non-basal cell is a lung non-basal cell. In some embodiments, said non-basal cell is a, secretory cell such as goblet cell and club cell, ciliated cell, ionocyte and any combination thereof. In some embodiments, the non-basal cell is a ciliated cell. In some embodiments, said plurality of cells comprise a first cell of a first CFTR genotype and a second cell of a second CFTR genotype.

In some embodiments, the composition can be formulated as any suitable dosage from known in the art. In some embodiments, the composition is formulated in a nanoparticle or a nanocapsule. In some embodiments, the composition is formulated for administration by any suitable route known in the art including, for example, oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections. In some embodiments, said composition is formulated for apical delivery. In some embodiments, said composition is formulated for nebulization. In some embodiments, said composition is an aerosol. In some embodiments, said composition is formulated for intravenous administration.

In some embodiments, the composition can be formulated as any suitable dosage from known in the art. In some embodiments, the composition is formulated in a nanoparticle or a nanocapsule. In some embodiments, the composition is formulated for administration by any suitable route known in the art including, for example, oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections. In some embodiments, said composition is formulated for apical delivery. In some embodiments, said composition is formulated for nebulization. In some embodiments, said composition is formulated for nebulization with a rate usage rate of about 0.1 ml/min to about 1.0 ml/min. In some embodiments, said composition is formulated for nebulization with a rate usage rate of about 0.2 ml/min to about 0.7 ml/min. In some embodiments, said composition is formulated for nebulization with a rate usage rate of about 0.1 ml/min to about 0.5 ml/min. In some embodiments, said composition is formulated for nebulization with a rate usage rate of about 0.5 ml/min to about 1.0 ml/min. In some embodiments, said composition is an aerosol. In some embodiments, the mass median aerodynamic diameter (MMAD) of the aerosols ranges from about 1.0 μm to about 10.0 m, from about 1.0 μm to about 5.0 μm, from about 2.0 μm to about 5.0 μm, or from about 3.0 μm to about 6.0 μm.

List of Embodiments

The following list of embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1. A synthetic polynucleotide encoding a cystic fibrosis transmembrane conductance regulator (CFTR) protein, wherein said synthetic polynucleotide comprises one or more nucleoside analogue(s).

Embodiment 2. The synthetic polynucleotide of Embodiment 1, wherein said synthetic polynucleotide comprises 1-methylpseudouridine.

Embodiment 3. A synthetic polynucleotide encoding a cystic fibrosis transmembrane conductance regulator (CFTR) protein, wherein said synthetic polynucleotide comprises a nucleic acid sequence (e.g., an open reading frame (ORF) sequence) having at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100, 300, 500, 700, 900, or 1,000 bases of a sequence selected from SEQ ID NOs: 1-4 and 23.

Embodiment 4. The synthetic polynucleotide of any one of Embodiment 1-3, wherein said nucleic acid sequence comprises fewer than about 115, 110, 105, 100, 95, or 90 UU or TT dinucleotide Embodiment 5. The synthetic polynucleotide of any one of embodiments 1-4, wherein said nucleic acid sequence comprises at least two synonymous codons encoding arginine.

Embodiment 6. The synthetic polynucleotide of any one of embodiments 1-4, wherein said nucleic acid sequence comprises at least three synonymous codons encoding arginine.

Embodiment 7. The synthetic polynucleotide of any one of embodiments 1-6, wherein no more than about 70%, 65%, 60%, 55%, or 50% of all arginine encoding codons of said nucleic acid sequence is AGA codon.

Embodiment 8. The synthetic polynucleotide of any one of embodiments 1-7, wherein said nucleic acid sequence encodes a polypeptide that comprises an amino acid sequence having at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity over at least 100, 300, 500, 700, 900, or 1,000 contiguous amino acid residues to SEQ ID NO: 5.

Embodiment 9. The synthetic polynucleotide of any one of embodiments 1-8, wherein said synthetic polynucleotide is a messenger ribonucleic acid (mRNA)

Embodiment 10. The synthetic polynucleotide of any one of embodiments 1-9, wherein said synthetic polynucleotide further comprises a 3'- or 5'-noncoding region.

Embodiment 11. The synthetic polynucleotide of embodiment 10, wherein said 3'- or 5'-noncoding region enhances an expression or activity of said CFTR protein encoded by said synthetic polynucleotide within a cell.

Embodiment 12. The synthetic polynucleotide of any one of embodiments 1-11, wherein said synthetic polynucleotide further comprises a 5' cap structure.

Embodiment 13. The synthetic polynucleotide of any one of embodiments 1-12, wherein said 3' noncoding region comprises a poly adenosine tail.

Embodiment 14. The synthetic polynucleotide of embodiment 13, wherein said poly adenosine tail comprises at most 200 adenosines.

Embodiment 15. The synthetic polynucleotide of embodiment 13 or 14, wherein said poly adenosine tail improves a pharmacokinetic characteristic of said synthetic polynucleotide in a cell.

Embodiment 16. The synthetic polynucleotide of embodiment 15, wherein said poly adenosine tail improves a prolonged half-life of said synthetic polynucleotide in a cell.

Embodiment 17. A pharmaceutical composition comprising a synthetic polynucleotide assembled with a lipid composition, which synthetic polynucleotide encodes a cystic fibrosis transmembrane conductance regulator (CFTR) protein, wherein said lipid composition comprises: an ionizable cationic lipid; and a selective organ targeting (SORT) lipid separate from said ionizable cationic lipid.

Embodiment 18. The pharmaceutical composition of embodiment 17, wherein said lipid composition comprises said ionizable cationic lipid at a molar percentage of about 5% to about 30%

Embodiment 19. The pharmaceutical composition of embodiment 17 or 18, wherein a mass or weight ratio of said ionizable cationic lipid to said synthetic polynucleotide is of no more than about 50:1, 40:1, 30:1, 20:1, 15:1 or 10:1

Embodiment 20. The pharmaceutical composition of any one of embodiments 17-19, wherein said SORT lipid is a permanently cationic lipid Embodiment 21. The pharmaceutical composition of any one of embodiments 17-20, wherein said SORT lipid is a second ionizable cationic lipid Embodiment 22. The pharmaceutical composition of embodiment 21, wherein said lipid composition comprises said SORT lipid at a molar percentage of about 5% to about 65%

Embodiment 23. The pharmaceutical composition of embodiment 21, wherein said lipid composition comprises said SORT lipid at a molar percentage of about 5% to about 30%

Embodiment 24. The pharmaceutical composition of any one of embodiments 17-23, wherein said lipid composition further comprises a zwitterionic lipid (e.g., a phospholipid)

Embodiment 25. The pharmaceutical composition of embodiment 24, wherein said lipid composition comprises said zwitterionic lipid at a molar percentage of about 5% to about 25%

Embodiment 26. The pharmaceutical composition of embodiment 24, wherein a molar ratio of said zwitterionic lipid to said synthetic polynucleotide is of no more than about 50:1, 40:1, 30:1, or 20:1

Embodiment 27. The pharmaceutical composition of any one of embodiments 17-26, wherein said lipid composition further comprises a steroid or steroid derivative Embodiment 28. The pharmaceutical composition of embodiment 27, wherein said lipid composition comprises said steroid or steroid derivative at a molar percentage of about 15% to about 46%

Embodiment 29. The pharmaceutical composition of any one of embodiments 17-28, wherein said lipid composition further comprises a polymer-conjugated lipid (e.g., poly(ethylene glycol) (PEG)-conjugated lipid).

Embodiment 30. The pharmaceutical composition of embodiment 29, wherein said lipid composition comprises said polymer-conjugated lipid at a molar percentage of about 0.5% to about 10%, or about 1% to about 10%, or about 2% to about 10%.

Embodiment 31. The pharmaceutical composition of any one of embodiments 17-30, wherein a molar ratio of nitrogen in said lipid composition to phosphate in said synthetic polynucleotide (N/P ratio) is of no more than about 50:1, 40:1, 30:1, or 20:1

Embodiment 32. The pharmaceutical composition of embodiment 31, wherein said N/P ratio is from about 5:1 to about 30:1.

Embodiment 33. The pharmaceutical composition of any one of embodiments 17-32, wherein a mass or weight ratio of said synthetic polynucleotide to total lipids of said lipid composition is no more than about 1:20, 1:50, or 1:100.

Embodiment 34. The pharmaceutical composition of any one of embodiments 17-33, wherein said SORT lipid comprises a permanently positively charged moiety (e.g., a quaternary ammonium ion).

Embodiment 35. The pharmaceutical composition of embodiment 34, wherein said SORT lipid comprises a counterion.

Embodiment 36. The pharmaceutical composition of any one of embodiments 17-35, wherein said SORT lipid is a phosphocholine lipid (e.g., saturated or unsaturated).

Embodiment 37. The pharmaceutical composition of any one of embodiments 36, wherein said SORT lipid is an ethylphosphocholine.

Embodiment 38. The pharmaceutical composition of any one of embodiments 17-37, wherein said SORT lipid comprises a headgroup having a structural formula:

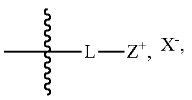

wherein L is a (e.g., biodegradable) linker; $Z^+$ is positively charged moiety (e.g., a quaternary ammonium ion); and $X^-$ is a counterion.

Embodiment 39. The pharmaceutical composition of embodiment 38, wherein said SORT lipid has a structural formula:

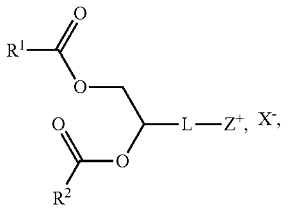

wherein $R^1$ and $R^2$ are each independently an optionally substituted $C_6$-$C_{24}$ alkyl, or an optionally substituted $C_6$-$C_{24}$ alkenyl.

Embodiment 40. The pharmaceutical composition of embodiment 38, wherein said SORT lipid has a structural formula:

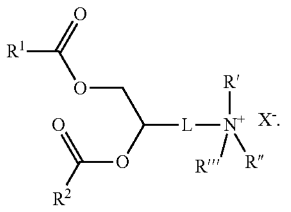

Embodiment 41. The pharmaceutical composition of embodiment 40, wherein L is

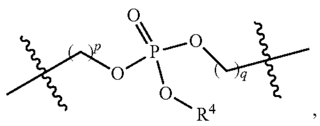

, wherein:

p and q are each independently 1, 2, or 3; and $R^4$ is an optionally substituted $C_1$-$C_6$ alkyl.

Embodiment 42. The pharmaceutical composition of embodiment 38, wherein said SORT lipid has a structural formula:

(IA)

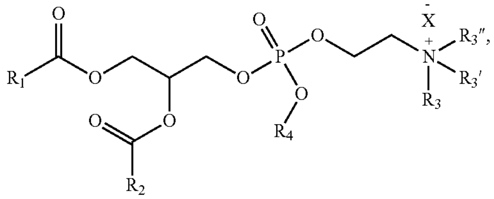

wherein:

$R_1$ and $R_2$ are each independently alkyl$_{(C8\text{-}C24)}$, alkenyl$_{(C8\text{-}C24)}$, or a substituted version of either group;

$R_3$, $R_{3'}$, and $R_3''$ are each independently alkyl$_{(C\leq 6)}$ or substituted alkyl$_{(C\leq 6)}$;

$R_4$ is alkyl$_{(C\leq 6)}$ or substituted alkyl$_{(C\leq 6)}$; and $X^-$ is a monovalent anion.

Embodiment 43. The pharmaceutical composition of any one of embodiments 17-35, wherein said SORT lipid has a structural formula:

(S-I')

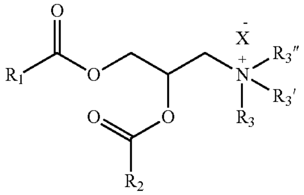

wherein:

$R_1$ and $R_2$ are each independently alkyl$_{(C8\text{-}C24)}$, alkenyl$_{(C8\text{-}C24)}$, or a substituted version of either group;

$R_3$, $R_{3'}$, and $R_3''$ are each independently alkyl$_{(C\leq 6)}$ or substituted alkyl$_{(C\leq 6)}$;

$X^-$ is a monovalent anion.

Embodiment 44. The pharmaceutical composition of any one of embodiments 17-35, wherein said SORT lipid has a structural formula:

(S-II')

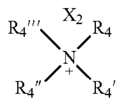

wherein:

$R_4$ and $R_{4'}$ are each independently alkyl$_{(C6\text{-}C24)}$, alkenyl$_{(C6\text{-}C24)}$, or a substituted version of either group;

$R_4$" is alkyl$_{(C\le24)}$, alkenyl$_{(C\le24)}$, or a substituted version of either group;

$R_{4'}$" is alkyl$_{(C1\text{-}C8)}$, alkenyl$_{(C2\text{-}C8)}$, or a substituted version of either group; and $X_2$ is a monovalent anion.

Embodiment 45. The pharmaceutical composition of any one of embodiments 17-35, wherein said SORT lipid has a structural formula:

(S-III)

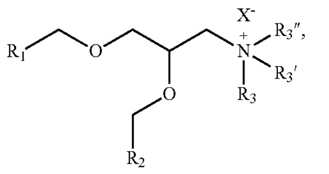

wherein:

$R_1$ and $R_2$ are each independently alkyl$_{(C8\text{-}C24)}$, alkenyl$_{(C8\text{-}C24)}$, or a substituted version of either group;

$R_3$, $R_{3'}$, and $R_3$" are each independently alkyl$_{(C\le6)}$ or substituted alkyl$_{(C\le6)}$; and $X^-$ is a monovalent anion.

Embodiment 46. The pharmaceutical composition of any one of embodiments 17-35, wherein said SORT lipid has a structural formula:

(S-IV)

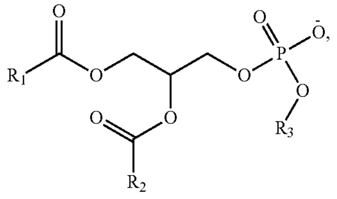

wherein:

$R_1$ and $R_2$ are each independently alkyl$_{(C8\text{-}C24)}$, alkenyl$_{(C8\text{-}C24)}$, or a substituted version of either group;

$R_3$ is hydrogen, alkyl$_{(C\le6)}$ or substituted alkyl$_{(C\le6)}$, or —$Y_1$—$R_4$, wherein:

$Y_1$ is alkanediyl$_{(C\le6)}$ or substituted alkanediyl$_{(C\le6)}$; and $R_4$ is acyloxy$_{(C\le8\text{-}24)}$ or substituted acyloxy$_{(C\le8\text{-}24)}$.

Embodiment 47. The pharmaceutical composition of any one of embodiments 17-46, wherein said pharmaceutical composition is an aerosol composition.

Embodiment 48. The pharmaceutical composition of embodiment 45, wherein said aerosol composition has a droplet size from 0.5 micron (μm) to 10 μm.

Embodiment 49. The pharmaceutical composition of embodiment 45, wherein said aerosol composition has a median droplet size from 0.5 μm to 10 μm.

Embodiment 50. The pharmaceutical composition of embodiment 45, wherein said aerosol composition has an average droplet size from 0.5 μm to 10 μm.

Embodiment 51. The pharmaceutical composition of any one of embodiments 17-50, wherein said pharmaceutical composition is formulated for aerosol administration Embodiment 52. The pharmaceutical composition of any one of embodiments 17-51, wherein said pharmaceutical composition is formulated for apical delivery.

Embodiment 53. The pharmaceutical composition of any one of embodiments 17-52, wherein said pharmaceutical composition is formulated for nebulization.

Embodiment 54. A method for enhancing an expression or activity of cystic fibrosis transmembrane conductance regulator (CFTR) protein in a cell, the method comprising:

contacting said cell with a composition comprising a synthetic polynucleotide assembled with a lipid composition, wherein said synthetic polynucleotide encodes a CFTR protein; and wherein said lipid composition comprises:

an ionizable cationic lipid; and a selective organ targeting (SORT) lipid separate from said ionizable cationic lipid, thereby yielding a therapeutically effective amount or activity of a functional variant of CFTR protein in said cell at least 24 hours after contacting, optionally wherein said therapeutically effective activity of said functional variant of CFTR protein is determined by measuring a change in a transepithelial ion transport characteristic of a plurality of cells comprising said cell as compared to that of a reference plurality of cells in absence of said contacting.

Embodiment 55. The method of embodiment 54, wherein said contacting is repeated

Embodiment 56. The method of embodiment 55, wherein said contacting is at least once a week Embodiment 57. The method of embodiment 55, wherein said contacting is at least twice a week Embodiment 58. The method of any one of embodiments 54-57, wherein the method yields a therapeutically effective amount or activity of a functional variant of CFTR protein in said cell at least 24 hours after each contacting Embodiment 59. The method of any one of embodiments 54-58, wherein said contacting is a first contacting, and wherein the method comprises a second contacting, optionally, performed at least 1, 2, or 3 day(s) after said first contacting Embodiment 60. The method of embodiment 59, further comprising a third contacting, optionally wherein said third contacting is performed at least 1, 2, or 3 day(s) after said second contacting Embodiment 61. The method of embodiment 59, wherein the method yields a therapeutically effective amount or activity of a functional variant of CFTR protein in said cell at least 24 hours after said second contacting Embodiment 62. The method of embodiment 60, wherein the method yields a therapeutically effective amount or activity of a functional variant of CFTR protein in said cell at least 24 hours after said third contacting Embodiment 63. The method of any one of embodiments 54-62, wherein said contacting comprises administering to a subject said composition comprising said synthetic polynucleotide assembled with said lipid composition Embodiment 64. The method of embodiment 63, wherein said subject is a mammal.

Embodiment 65. The method of embodiment 63, wherein said subject is a human.

Embodiment 66. The method of any one of embodiments 63-65, wherein said administering comprises inhalation by nebulization.

Embodiment 67. The method of any one of embodiments 54-66, wherein said composition in each contacting is identical Embodiment 68. The method of any one of embodiments 54-67, wherein said cell is a lung airway cell.

Embodiment 69. The method of embodiment 68, wherein said cell is a lung secretory cell Embodiment 70. The method of embodiment 68 or 69, wherein said cell is a bronchial epithelial cell Embodiment 71. The method of any one of embodiments 54-70, wherein said cell is undifferentiated.

Embodiment 72. The method of any one of embodiments 54-70, wherein said cell is differentiated.

Embodiment 73. The method of any one of embodiments 54-72, wherein said cell is derived from said subject.

Embodiment 74. The method of any one of embodiments 54-73, wherein said contacting is in vivo.

Embodiment 75. The method of any one of embodiments 54-73, wherein said contacting is in vitro.

Embodiment 76. The method of any one of embodiments 54-73, wherein said contacting is ex vivo.

Embodiment 77. The method of any one of embodiments 54-76, wherein said functional variant of CFTR protein is a wild-type CFTR protein Embodiment 78. The method of any one of embodiments 54-77, wherein said functional variant of CFTR protein is a full-length CFTR protein Embodiment 79. The method of any one of embodiments 54-78, wherein said therapeutically effective activity of said functional variant of CFTR protein corresponds to a transepithelial current of at least about 5 micro-Ampere (μA), e.g., as determined in an in vitro assay.

Embodiment 80. The method of embodiment 79, wherein said therapeutically effective activity of said functional variant of CFTR protein corresponds to a transepithelial current from about 5 micro-Ampere (μA) to about 30 μA.

Embodiment 81. The method of any one of embodiments 54-80, wherein said therapeutically effective activity of said functional variant of CFTR protein corresponds to a transepithelial current of at least about 2 micro-Ampere (μA) per squared centimeter per minute ($\mu A \cdot cm^{-2} \cdot min^{-1}$), e.g., as determined in an in vitro assay.

Embodiment 82. The method of embodiment 81, wherein said therapeutically effective activity of said functional variant of CFTR protein corresponds to a transepithelial current from about 2 micro-Ampere (μA) per squared centimeter per minute ($\mu A \cdot cm^{-2} \cdot min^{-1}$) to about 20 $\mu A \cdot cm^{-2}\ min^{-1}$.

Embodiment 83. The method of any one of embodiments 54-82, wherein the method increases an amount or activity of said functional variant of CFTR protein in said cell (e.g., by at least about 1.1-fold) relative to a corresponding control (e.g., that of a corresponding cell absent said contacting).

Embodiment 84. The method of any one of embodiments 54-83, wherein the method enhances (e.g., chloride) ion transport in said cell (e.g., by at least about 1.1-fold) relative to a corresponding control (e.g., that of a corresponding cell absent said contacting).

Embodiment 85. The method of any one of embodiments 54-84, wherein said subject exhibits or is determined to exhibit a mutation in a cystic fibrosis transmembrane conductance regulator (CFTR) gene.

Embodiment 86. The method of embodiment 85, wherein said mutation is a loss-of-function mutation.

Embodiment 87. The method of embodiment 85 or, wherein said mutation is a nonsense or frameshift mutation.

Embodiment 88. The method of any one of embodiments 85-87, wherein said mutation is in one or more of exons 11-27 of CFTR gene.

Embodiment 89. The method of any one of embodiments 85-88, wherein said mutation is R553X, G542X, F508del, or R1162X, or a combination thereof; for example, said mutation is G542X or F508del.

Embodiment 90. A method for lung secretory cell or lung basal cell delivery, comprising administering to a subject a composition comprising a synthetic polynucleotide assembled with a lipid composition, which synthetic polynucleotide encodes a cystic fibrosis transmembrane conductance regulator (CFTR) protein, wherein said lipid composition comprises:

an ionizable cationic lipid; and a selective organ targeting (SORT) lipid separate from said ionizable cationic lipid, thereby yielding a therapeutically effective amount or activity of said synthetic polynucleotide in a lung secretory cell of said subject, optionally wherein said therapeutically effective activity of said synthetic polynucleotide is determined by measuring a change in a transepithelial ion transport characteristic of a lung comprising said lung secretory cell or lung basal cell as compared to that of a reference lung in absence of said contacting.

Embodiment 91. A method for lung secretory cell or lung basal cell delivery, comprising administering to a subject a composition comprising a synthetic polynucleotide assembled with a lipid composition, which synthetic polynucleotide encodes a cystic fibrosis transmembrane conductance regulator (CFTR) protein, wherein said lipid composition comprises:

an ionizable cationic lipid; and a selective organ targeting (SORT) lipid separate from said ionizable cationic lipid, thereby yielding a greater therapeutic amount or activity of said synthetic polynucleotide in a lung secretory cell or lung basal cell of said subject as compared to that in a lung non-secretory cell or non basal cell of said subject.

Embodiment 92. The method of embodiment 91, wherein the method is characterized in that: (i) at least about 50%, 55%, or 60% of (e.g., pulmonary) expression of said synthetic polynucleotide is detected in lung secretory cells, lung basal cells, or a combination thereof; or (ii) no more than about 50%, 45%, or 40% of (e.g., pulmonary) expression of said synthetic polynucleotide is detected in lung non-secretory cells, lung non-basal cells, or a combination thereof.

Embodiment 93. The method of embodiment 91 or 92, wherein said lung non-secretory cell is a lung ciliated cell Embodiment 94. The method of any one of embodiments 91-93, wherein said lung non-secretory cell is a lung basal cell Embodiment 95. A method for lung secretory cell delivery, comprising administering to a subject a composition comprising a synthetic polynucleotide assembled with a lipid composition, which synthetic polynucleotide encodes a cystic fibrosis transmembrane conductance regulator (CFTR) protein, wherein said lipid composition comprises:

an ionizable cationic lipid; and a selective organ targeting (SORT) lipid separate from said ionizable cationic lipid, thereby yielding a therapeutic amount or activity of said synthetic polynucleotide in at least 5% of lung secretory cells of said subject.

Embodiment 96. The method of embodiment 95, wherein said administering comprises administering to a lung of said subject said composition comprising said synthetic polynucleotide assembled with said lipid composition.

Embodiment 97. The method of embodiment 95 or 96, wherein said lung secretory cell is a club cell or a goblet cell.

Embodiment 98. A method for treating a subject having or suspected of having a cystic fibrosis transmembrane conductance regulator (CFTR)-associated condition, the method comprising administering to said subject a pharmaceutical composition of any one of embodiments 17-53 and 101-151.

Embodiment 99. The method of embodiment 98, wherein said CFTR-associated condition is cystic fibrosis, hereditary emphysema, or chronic obstructive pulmonary disease (COPD).

Embodiment 100. The method of embodiment 98 or 99, wherein said administering comprises local administration (e.g., nebulization).

Embodiment 101. The composition of any one of Embodiments 17-53, wherein said SORT lipid is selected from those set forth in Table 8, or pharmaceutically acceptable salts thereof, or a subset of the lipids and the pharmaceutically acceptable salts thereof.

Embodiment 102. The composition of any one of Embodiments 17-53 and 101, wherein the ionizable cationic lipid is a dendrimer or dendron of a generation (g) having a structural formula:

(X)

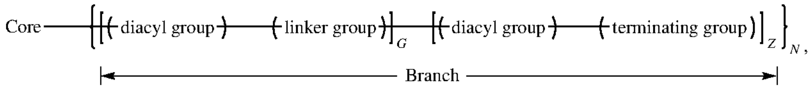

or a pharmaceutically acceptable salt thereof, wherein:

(a) the core comprises a structural formula ($X_{Core}$):

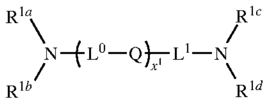

($X_{Core}$), wherein:

Q is independently at each occurrence a covalent bond, —O—, —S—, —$NR^2$—, or —$CR^{3a}R^{3b}$—;

$R^2$ is independently at each occurrence $R^{1g}$ or —$L^2$—$NR^{1e}R^{1f}$;

$R^{3a}$ and $R^{3b}$ are each independently at each occurrence hydrogen or an optionally substituted (e.g., $C_1$-$C_6$, such as $C_1$-$C_3$) alkyl;

$R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen, or an optionally substituted (e.g., $C_1$-$C_{12}$) alkyl;

$L^0$, $L^1$, and $L^2$ are each independently at each occurrence selected from a covalent bond, (e.g., $C_1$-$C_{12}$, such as $C_1$-$C_6$ or $C_1$-$C_3$) alkylene, (e.g., $C_1$-$C_{12}$, such as $C_1$-$C_8$ or $C_1$-$C_6$) heteroalkylene (e.g., $C_2$-$C_8$ alkyleneoxide, such as oligo(ethyleneoxide)), [(e.g., $C_1$-$C_6$) alkylene]-[(e.g., $C_4$-$C_6$) heterocycloalkyl]-[(e.g., $C_1$-$C_6$) alkylene], [(e.g., $C_1$-$C_6$) alkylene]-(arylene)-[(e.g., $C_1$-$C_6$) alkylene] (e.g., [(e.g., $C_1$-$C_6$) alkylene]-phenylene-[(e.g., $C_1$-$C_6$) alkylene]), (e.g., $C_4$-$C_6$) heterocycloalkyl, and arylene (e.g., phenylene); or, alternatively, part of $L^1$ form a (e.g., $C_4$-$C_6$) heterocycloalkyl (e.g., containing one or two nitrogen atoms and, optionally, an additional heteroatom selected from oxygen and sulfur) with one of $R^{1c}$ and $R^{id}$; and $x^1$ is 0, 1, 2, 3, 4, 5, or 6; and (b) each branch of the plurality (N) of branches independently comprises a structural formula ($X_{Branch}$):

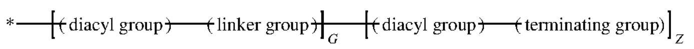

($X_{Branch}$), wherein:

indicates a point of attachment of the branch to the core;

g is 1, 2, 3, or 4;

$$Z = 2^{(g-1)};$$

G=0, when g=1; or $G=\Sigma_{i=0}^{i=g-2} 2^i$, when g≠1;

(c) each diacyl group independently comprises a structural formula

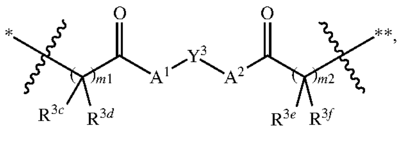

wherein:

indicates a point of attachment of the diacyl group at the proximal end thereof;

* indicates a point of attachment of the diacyl group at the distal end thereof;

$Y^3$ is independently at each occurrence an optionally substituted (e.g., $C_1$-$C_{12}$); alkylene, an optionally substituted (e.g., $C_1$-$C_{12}$) alkenylene, or an optionally substituted (e.g., $C_1$-$C_{12}$) arenylene;

$A^1$ and $A^2$ are each independently at each occurrence —O—, —S—, or —$NR^4$—, wherein:

$R^4$ is hydrogen or optionally substituted (e.g., $C_1$-$C_6$) alkyl;

$m^1$ and $m^2$ are each independently at each occurrence 1, 2, or 3; and $R^{3c}$, $R^{3d}$, $R^{3e}$, and $R^{3f}$ are each independently at each occurrence hydrogen or an optionally substituted (e.g., $C_1$-$C_8$) alkyl; and (d) each linker group independently comprises a structural formula

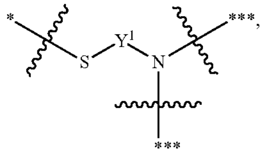

wherein:

* indicates a point of attachment of the linker to a proximal diacyl group;

** indicates a point of attachment of the linker to a distal diacyl group; and $Y_1$ is independently at each occurrence an optionally substituted (e.g., $C_1$-$C_{12}$) alkylene, an optionally substituted (e.g., $C_1$-$C_{12}$) alkenylene, or an optionally substituted (e.g., $C_1$-$C_{12}$) arenylene; and (e) each terminating group is independently selected from optionally substituted (e.g., $C_1$-$C_{18}$, such as $C_4$-$C_{18}$) alkylthiol, and optionally substituted (e.g., $C_1$-$C_{18}$, such as $C_4$-$C_{18}$) alkenylthiol.

Embodiment 103. The composition of Embodiment 102, wherein $x^1$ is 0, 1, 2, or 3.

Embodiment 104. The composition of Embodiment 102 or 103, wherein $R^{1a}$, $R^{1b}$, $R^{1c}$, $R^{1d}$, $R^{1e}$, $R^{1f}$, and $R^{1g}$ (if present) are each independently at each occurrence a point of connection to a branch (e.g., as indicated by *), hydrogen, or $C_1$-$C_{12}$ alkyl (e.g., $C_1$-$C_8$ alkyl, such as $C_1$-$C_6$ alkyl or $C_1$-$C_3$ alkyl), wherein the alkyl moiety is optionally substituted with one or more substituents each independently selected from —OH, $C_4$-$C_8$ (e.g., $C_4$-$C_6$) heterocycloalkyl (e.g., piperidinyl (e.g.,

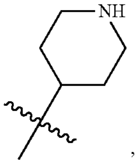

, or

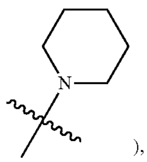

),

N—($C_1$-$C_3$ alkyl)-piperidinyl (e.g.,

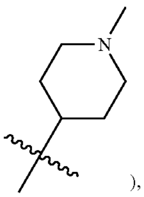 [SMILES: *C1CCN(C)CC1]

), piperazinyl (e.g.,

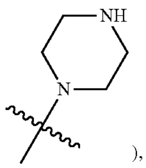 [SMILES: *N1CCNCC1]

),

N—($C_1$-$C_3$ alkyl)-piperadizinyl (e.g.,

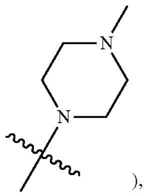 [SMILES: *N1CCN(C)CC1]

), morpholinyl (e.g.,

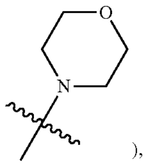 [SMILES: *N1CCOCC1]

),

N-pyrrolidinyl (e.g.,

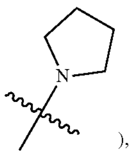

), pyrrolidinyl (e.g.,

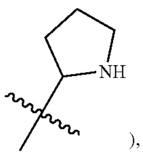 [SMILES: *C1CCCN1]

), or N—($C_1$-$C_3$ alkyl)-pyrrolidinyl (e.g.,

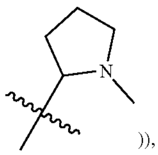 [SMILES: *C1CCCN1C]

)), (e.g., $C_6$-$C_{10}$) aryl, and $C_3$-$C_5$ heteroaryl (e.g., imidazolyl (e.g.,

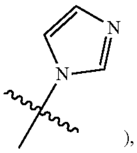 [SMILES: *n1ccnc1]

), or pyridinyl (e.g.,

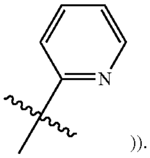 [SMILES: *c1ccccn1]

)).

Embodiment 105. The composition of Embodiment 104, wherein $R^{1a}$, $R^{1b}$, $R^{1c}$, $R^{1d}$, $R^{1e}$, $R^{1f}$, and $R_{1f}$ (if present) are each independently at each occurrence a point of connection to a branch (e.g., as indicated by *), hydrogen, or $C_1$-$C_{12}$ alkyl (e.g., $C_1$-$C_8$ alkyl, such as $C_1$-$C_6$ alkyl or $C_1$-$C_3$ alkyl), wherein the alkyl moiety is optionally substituted with one substituent —OH.

Embodiment 106. The composition of any one of Embodiments 102-105, wherein $R^{3a}$ and $R^{3b}$ are each independently at each occurrence hydrogen.

Embodiment 107. The composition of any one of Embodiments 102-106, wherein the plurality (N) of branches comprises at least 3 (e.g., at least 4, or at least 5) branches.

Embodiment 108. The composition of any one of Embodiments 102-107, wherein g=1; G=0; and Z=1.

Embodiment 109. The composition of Embodiment 108, wherein each branch of the plurality of branches comprises a structural formula

*—(diacyl group)—(terminating group).

Embodiment 110. The composition of any one of Embodiments 102-107, wherein g=2; G=1; and Z=2.

Embodiment 111. The composition of Embodiment 110, wherein each branch of the plurality of branches comprises a structural formula

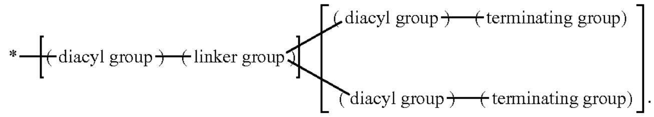

.

Embodiment 112. The composition of any one of Embodiments 102-111, wherein the core comprises a structural formula:

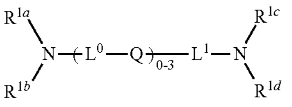

(e.g.,

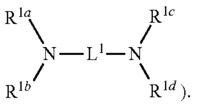

Embodiment 113. The composition of any one of Embodiments 102-111, wherein the core comprises a structural formula:

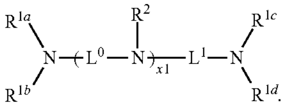

Embodiment 114. The composition of Embodiment 113, wherein the core comprises a structural formula:

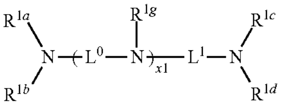

(e.g.,

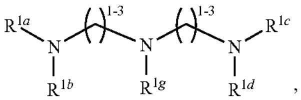

,

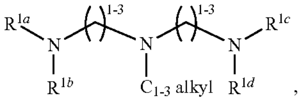

,

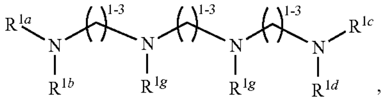

, or

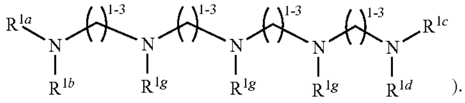

).

Embodiment 115. The composition of Embodiment 113, wherein the core comprises a structural formula:

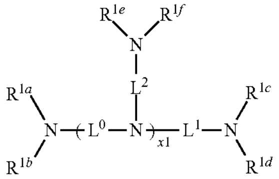

(e.g.,

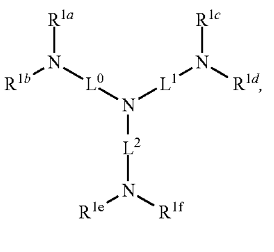

such as

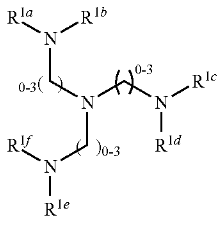

or

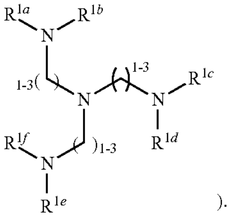

).

Embodiment 116. The composition of any one of Embodiments 102-111, wherein the core comprises a structural formula:

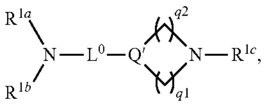

wherein Q' is —$NR^2$— or —$CR^{3a}R^{3b}$—; $q^1$ and $q^2$ are each independently 1 or 2.

Embodiment 117. The composition of Embodiment 116, wherein the core comprises a structural formula:

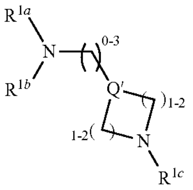

or

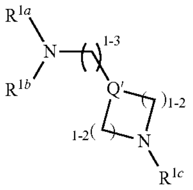

(e.g.,

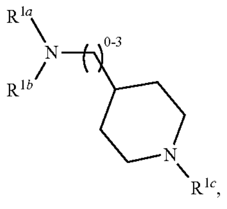

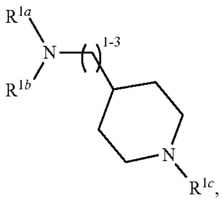

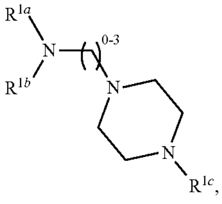

or

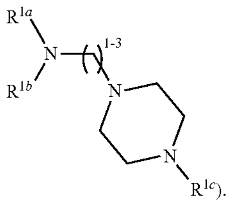

Embodiment 118. The composition of any one of Embodiments 102-111, wherein the core comprises a structural formula

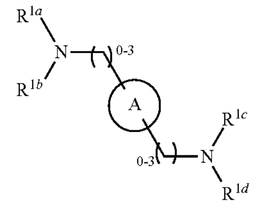

or

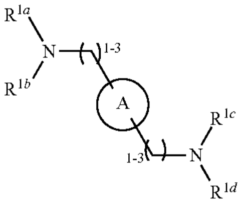

(e.g.,

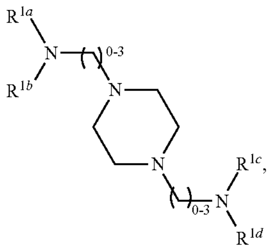

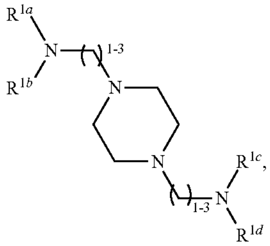

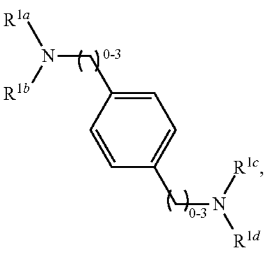

or

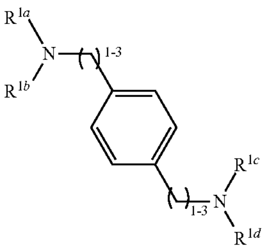

), wherein ring A is an optionally substituted aryl or an optionally substituted (e.g., $C_3$-$C_{12}$, such as $C_3$-$C_5$) heteroaryl.

Embodiment 119. The composition of any one of Embodiments 102-111, wherein the core comprises has a structural formula

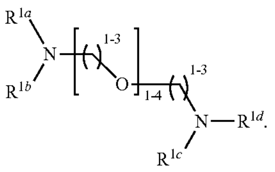
Embodiment 120. The composition of any one of Embodiments 102-111, wherein the core is selected from those set forth in Table 3 or a subset thereof.
Embodiment 121. The composition of any one of Embodiments 102-111, wherein the core comprises a structural formula selected from the group consisting of:
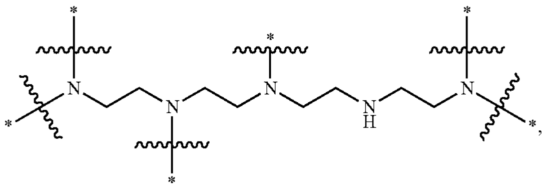
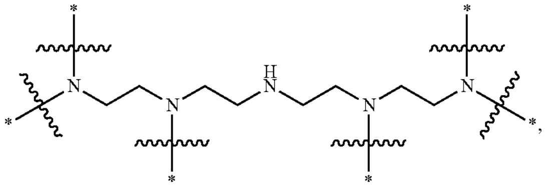
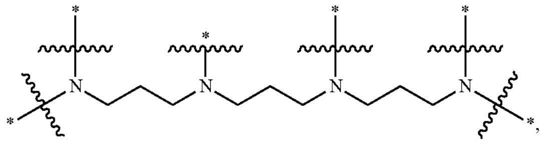
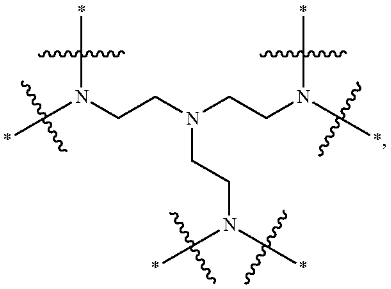
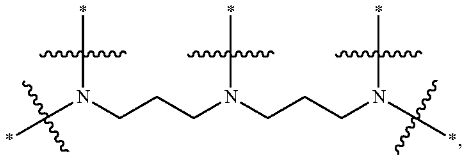
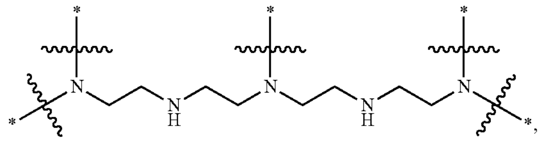
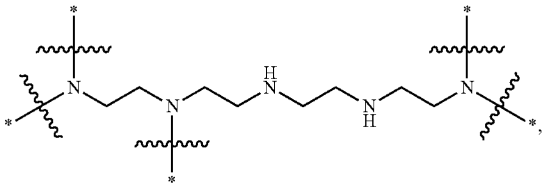
-continued
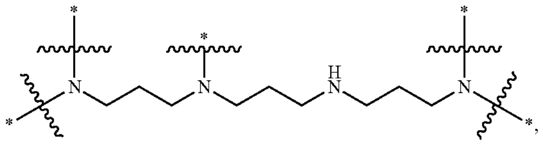
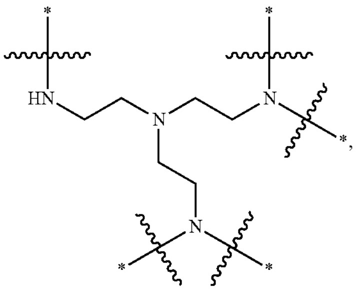
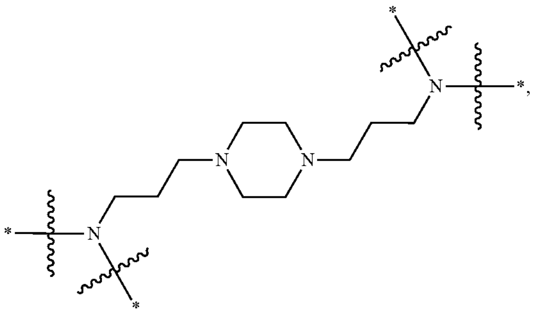
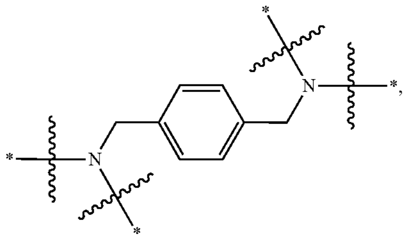
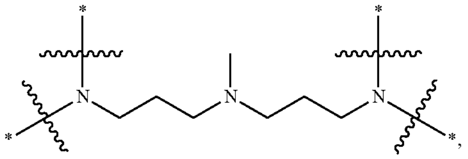
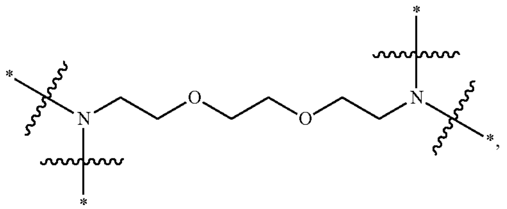
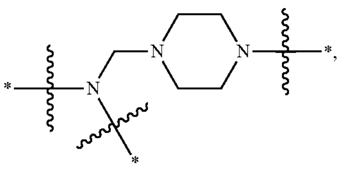
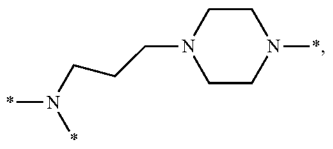

-continued

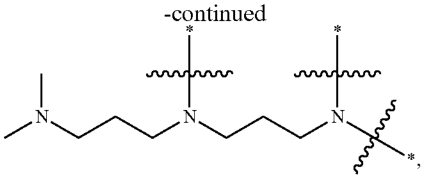

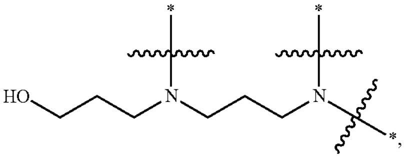

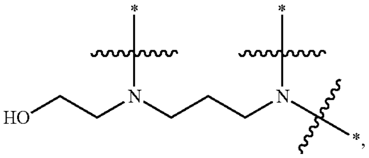

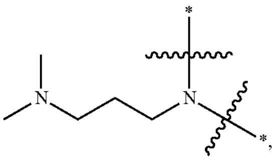

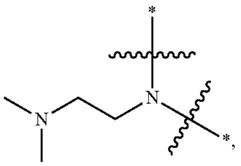

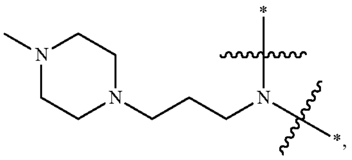

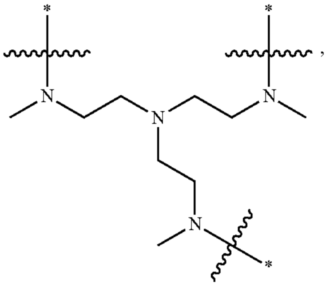

and pharmaceutically acceptable salts thereof, wherein * indicates a point of attachment of the core to a branch of the plurality of branches.

Embodiment 122. The composition of any one of Embodiments 102-111, wherein the core comprises a structural formula selected from the group consisting of:

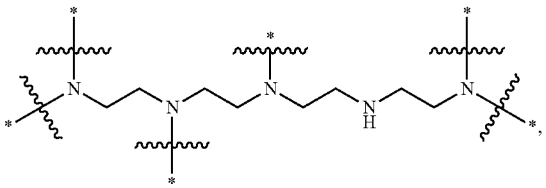

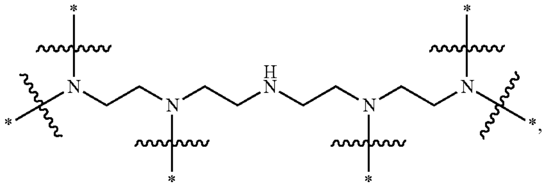

-continued

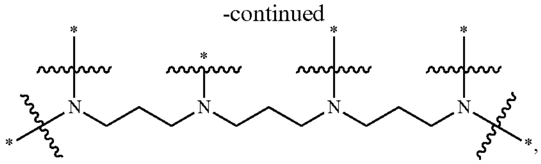

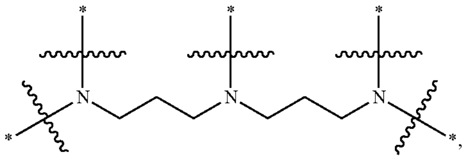

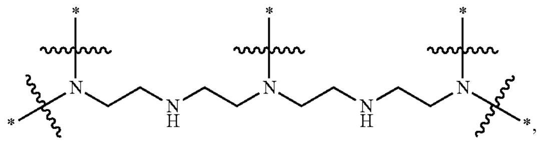

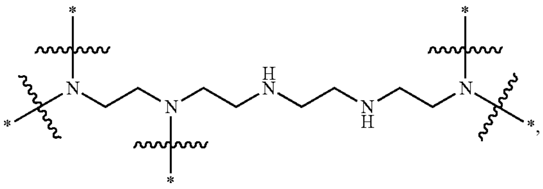

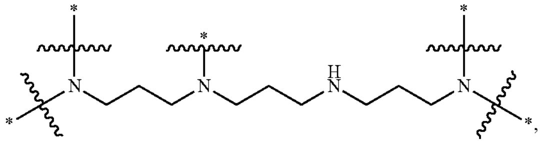

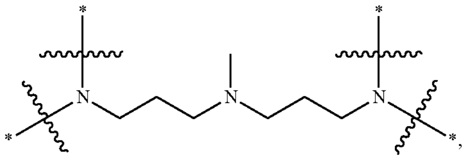

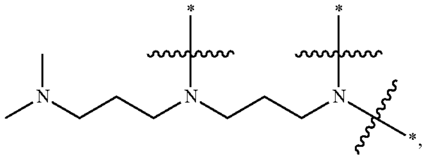

and pharmaceutically acceptable salts thereof, wherein * indicates a point of attachment of the core to a branch of the plurality of branches.

Embodiment 123. The composition of any one of Embodiments 102-111, wherein the core has the structure

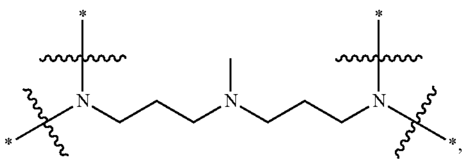

wherein * indicates a point of attachment of the core to a branch of the plurality of branches or H.

Embodiment 124. The composition of Embodiment 123, wherein at least 2 branches are attached to the core.

Embodiment 125. The composition of Embodiment 123, wherein at least 3 branches are attached to the core.

Embodiment 126. The composition of Embodiment 123, wherein at least 4 branches are attached to the core.

Embodiment 127. The composition of any one of Embodiments 102-111, wherein the core has the structure

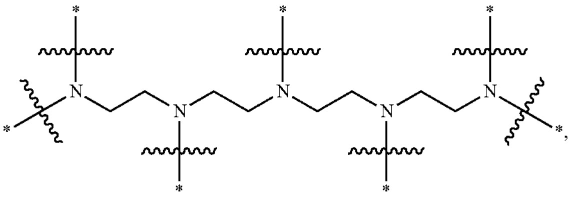
, wherein * indicates a point of attachment of the core to a branch of the plurality of branches or H.

Embodiment 128. The composition of Embodiment 127, wherein at least 4 branches are attached to the core.

Embodiment 129. The composition of Embodiment 127, wherein at least 5 branches are attached to the core.

Embodiment 130. The composition of Embodiment 127, wherein at least 6 branches are attached to the core.

Embodiment 131. The composition of any one of Embodiments 102-130, wherein $A^1$ is —O— or —NH—.

Embodiment 132. The composition of Embodiment 131, wherein $A^1$ is —O—.

Embodiment 133. The composition of any one of Embodiments 102-132, wherein $A^2$ is —O— or —NH—.

Embodiment 134. The composition of any Embodiment 133, wherein $A^2$ is —O—.

Embodiment 135. The composition of any one of Embodiments 102-134, wherein $Y^3$ is $C_1$-$C_{12}$ (e.g., $C_1$-$C_6$, such as $C_1$-$C_3$) alkylene.

Embodiment 136. The composition of any one of Embodiments 102-135, wherein the diacyl group independently at each occurrence comprises a structural formula

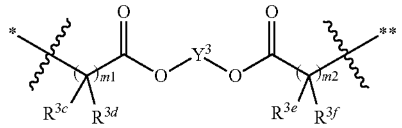

(e.g.,

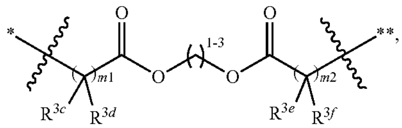
, such as

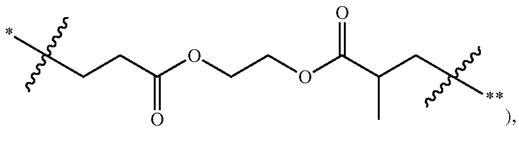
), optionally wherein $R^{3c}$, $R^{3d}$, $R^{3e}$, and $R^{3f}$ are each independently at each occurrence hydrogen or $C_1$-$C_3$ alkyl.

Embodiment 137. The composition of any one of Embodiments 102-136, wherein $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$) alkyleneoxide (e.g., oligo(ethyleneoxide), such as —$(CH_2CH_2O)_{1-4}$—$(CH_2CH_2)$—), [($C_1$-$C_4$) alkylene]-[($C_4$-$C_6$) heterocycloalkyl]-[($C_1$-$C_4$) alkylene] (e.g.,

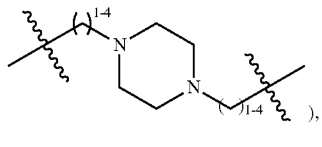
), and [($C_1$-$C_4$) alkylene]-phenylene-[($C_1$-$C_4$) alkylene] (e.g.,

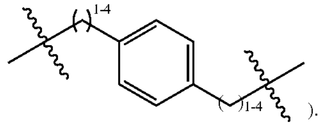
).

Embodiment 138. The composition of Embodiment 137, wherein $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$—($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-.

Embodiment 139. The composition of Embodiment 137, wherein $L^0$, $L^1$, and $L^2$ are each independently at each occurrence $C_1$-$C_6$ alkylene (e.g., $C_1$-$C_3$ alkylene).

Embodiment 140. The composition of Embodiment 137, wherein $L^0$, $L^1$, and $L^2$ are each independently at each occurrence $C_2$-$C_{12}$ (e.g., $C_2$-$C_8$) alkyleneoxide (e.g., —($C_1$-$C_3$ alkylene-O)$_{1-4}$—($C_1$-$C_3$ alkylene)).

Embodiment 141. The composition of Embodiment 137, wherein $L^0$, $L^1$, and $L^2$ are each independently at each occurrence selected from [($C_1$-$C_4$) alkylene]-[($C_4$-$C_6$) heterocycloalkyl]-[($C_1$-$C_4$) alkylene] (e.g., —($C_1$-$C_3$ alkylene)-phenylene-($C_1$-$C_3$ alkylene)-) and [($C_1$-$C_4$) alkylene]-[($C_4$-$C_6$) heterocycloalkyl]-[($C_1$-$C_4$) alkylene] (e.g., —($C_1$-$C_3$ alkylene)-piperazinyl-($C_1$-$C_3$ alkylene)-).

Embodiment 142. The composition of any one of Embodiments 102-141, wherein each terminating group is independently $C_1$-$C_{18}$ (e.g., $C_4$-$C_{18}$) alkenylthiol or $C_1$-$C_{18}$ (e.g., $C_4$-$C_{18}$) alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as

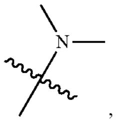
,
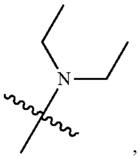
,
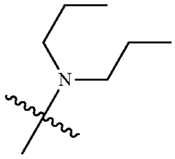
,

-continued

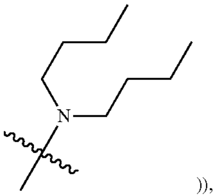
)), $C_4$-$C_6$ N-heterocycloalkyl (e.g., N-pyrrolidinyl ( 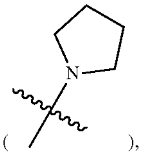 ), N-piperidinyl ( 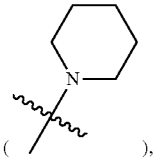 ), N-azepanyl ( 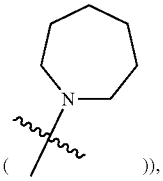 )), —OH, —C(O)OH, —C(O)N($C_1$-$C_3$ alkyl)-($C_1$-$C_6$ alkylene)-($C_1$-$C_{12}$ alkylamino (e.g., mono- or di-alkylamino)) (e.g.,

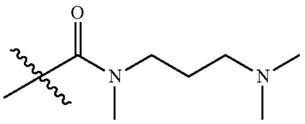
),

—C(O)N($C_1$-$C_3$ alkyl)-($C_1$-$C_6$ alkylene)-($C_4$-$C_6$ N-heterocycloalkyl) (e.g.,

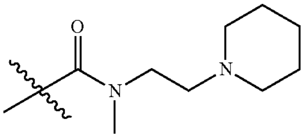
),

—C(O)—($C_1$-$C_{12}$ alkylamino (e.g., mono- or di-alkylamino)), and —C(O)—($C_4$-$C_6$ N-heterocycloalkyl) (e.g.,

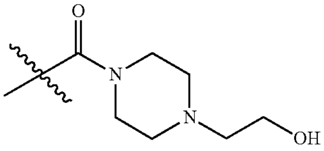
), wherein the $C_4$-$C_6$ N-heterocycloalkyl moiety of any of the preceding substituents is optionally substituted with $C_1$-$C_3$ alkyl or $C_1$-$C_3$ hydroxyalkyl.

Embodiment 143. The composition of Embodiment 142, wherein each terminating group is independently $C_1$-$C_{18}$ (e.g., $C_4$-$C_{18}$) alkylthiol, wherein the alkyl moiety is optionally substituted with one or more (e.g., one) substituents each independently selected from $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as $—NHCH_2CH_2CH_2CH_3$) or $C_1$-$C_8$ di-alkylamino (such as

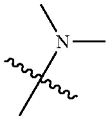
,
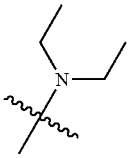
,
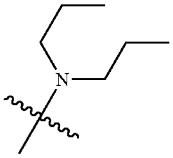
,
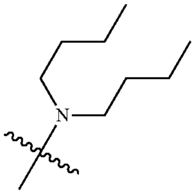
)), $C_4$-$C_6$ N-heterocycloalkyl (e.g., N-pyrrolidinyl ( 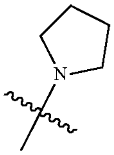 ), N-piperidinyl ( 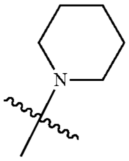 ), N-azepanyl ( 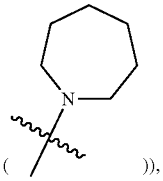 )), —OH, —C(O)OH, —C(O)N($C_1$-$C_3$ alkyl)-($C_1$-$C_6$ alkylene)-($C_1$-$C_{12}$ alkylamino (e.g., mono- or di-alkylamino)) (e.g.,

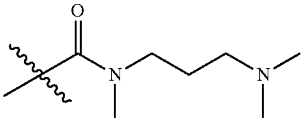 ),

—C(O)N($C_1$-$C_3$ alkyl)-($C_1$-$C_6$ alkylene)-($C_4$-$C_6$ N-heterocycloalkyl) (e.g.,

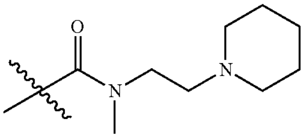 ), and —C(O)—($C_4$-$C_6$ N-heterocycloalkyl) (e.g.,

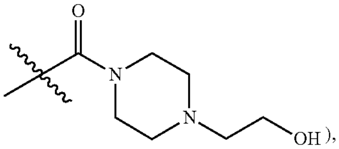 [SMILES: *C(=O)N1CCN(CCO)CC1] ), wherein the $C_4$-$C_6$ N-heterocycloalkyl moiety of any of the preceding substituents is optionally substituted with $C_1$-$C_3$ alkyl or $C_1$-$C_3$ hydroxyalkyl.

Embodiment 144. The composition of Embodiment 143, wherein each terminating group is independently $C_1$-$C_{18}$ (e.g., $C_4$-$C_{18}$) alkylthiol, wherein the alkyl moiety is optionally substituted with one substituent —OH.

Embodiment 145. The composition of Embodiment 143, wherein each terminating group is independently $C_1$-$C_{18}$ (e.g., $C_4$-$C_{18}$) alkylthiol, wherein the alkyl moiety is optionally substituted with one substituent selected from $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as

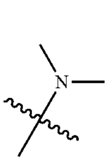 , 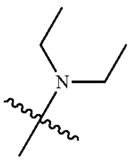 , 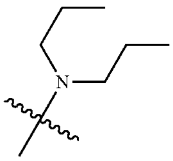 ,

-continued

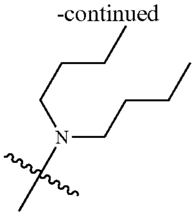 ))

and $C_4$-$C_6$ N-heterocycloalkyl (e.g., N-pyrrolidinyl ( 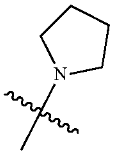 ),

N-piperidinyl ( 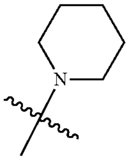 ),

N-azepanyl ( 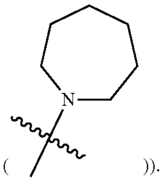 )).

Embodiment 146. The composition of Embodiment 142, wherein each terminating group is independently $C_1$-$C_{18}$ (e.g., $C_4$-$C_{18}$) alkenylthiol or $C_1$-$C_{18}$ (e.g., $C_4$-$C_{18}$) alkylthiol.

Embodiment 147. The composition of Embodiment 146, wherein each terminating group is independently $C_1$-$C_{18}$ (e.g., $C_4$-$C_{18}$) alkylthiol.

Embodiment 148. The composition of Embodiment 147, wherein each terminating group is independently selected from the group consisting of:

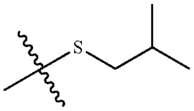 , 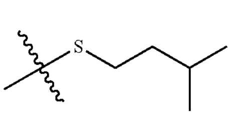 ,

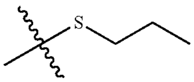 , 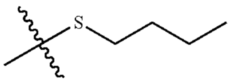 ,

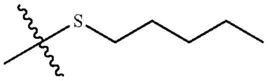 ,

-continued

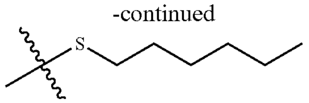 ,

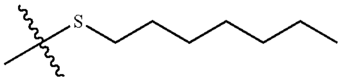 ,

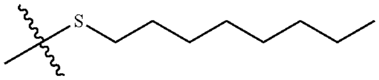 ,

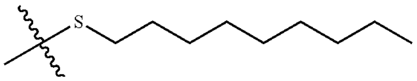 ,

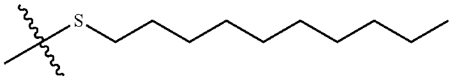 ,

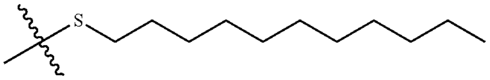 ,

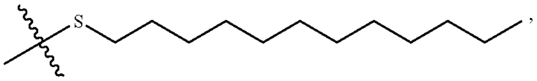 ,

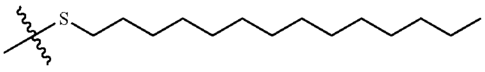 , and

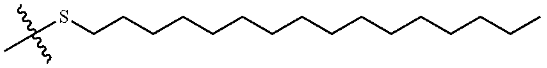 .

Embodiment 149. The composition of any one of Embodiments 102-141, wherein each terminating group is independently selected from those set forth in Table 5 or a subset thereof.

Embodiment 150. The composition of any one of Embodiments 17-53 and 101, wherein the ionizable cationic lipid is selected from those set forth in Table 6, or pharmaceutically acceptable salts thereof, or a subset of the lipids and the pharmaceutically acceptable salts thereof.

Embodiment 151. The composition of any one of Embodiments 17-53 and 101, wherein the ionizable cationic lipid is selected from those set forth in Table 6 or Table 7, or pharmaceutically acceptable salts thereof, or a subset of the lipids and the pharmaceutically acceptable salts thereof.

Embodiment 101. The method of any one of Embodiments 54-97, wherein the composition is according to any one of Embodiments 17-53 and 101-151

EXAMPLES

Example 1: Preparation of DOTAP or DODAP Modified Lipid Nanoparticles

Lipid nanoparticles (LNPs) are the most efficacious carrier class for in vivo nucleic acid delivery. Historically, effective LNPs are composed of 4 components: an ionizable cationic lipid, zwitterionic phospholipid, cholesterol, and lipid poly(ethylene glycol) (PEG). However, these LNPs result in only general delivery of nucleic acids, rather than organ or tissue targeted delivery. LNPs administered by IV typically deliver RNAs only to the liver. Therefore, new formulations of LNPs were sought in an effort to provide targeted nucleic acid delivery.

Figure 2:
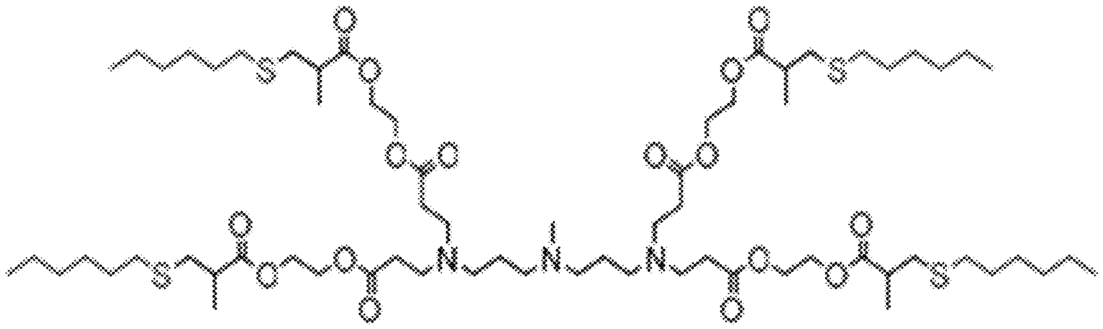
FIG. 2 shows the chemical structures of example dendrimer lipids.
Figure 2:
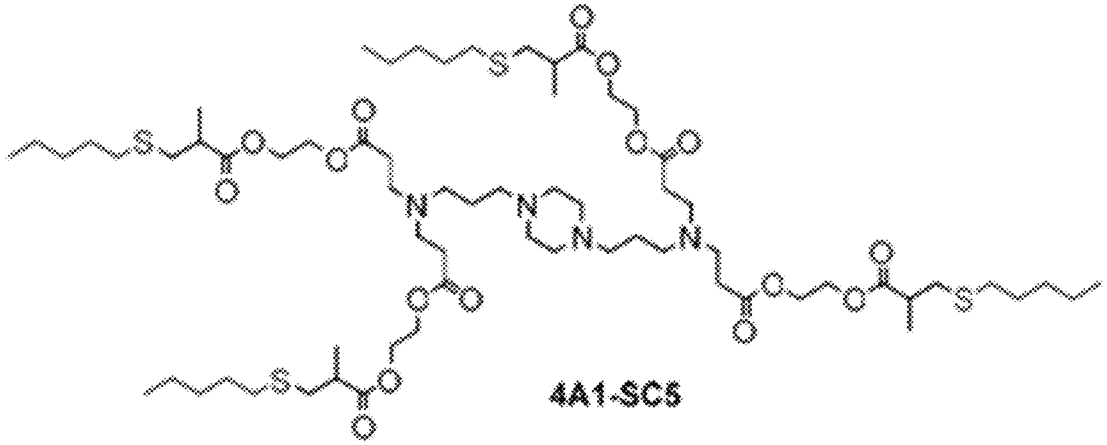
Figure 2:
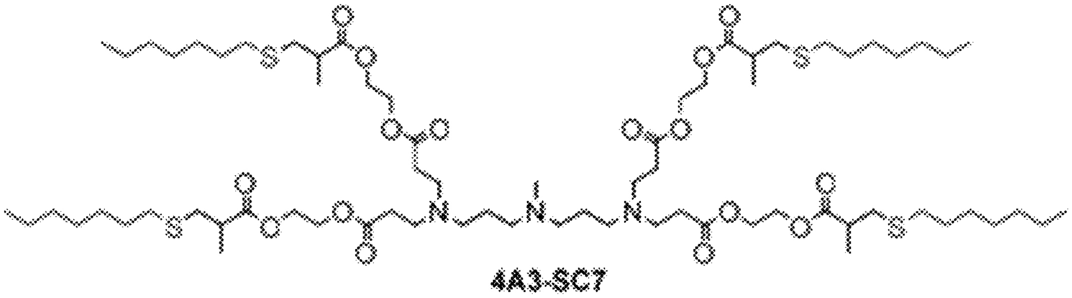
Figure 2:
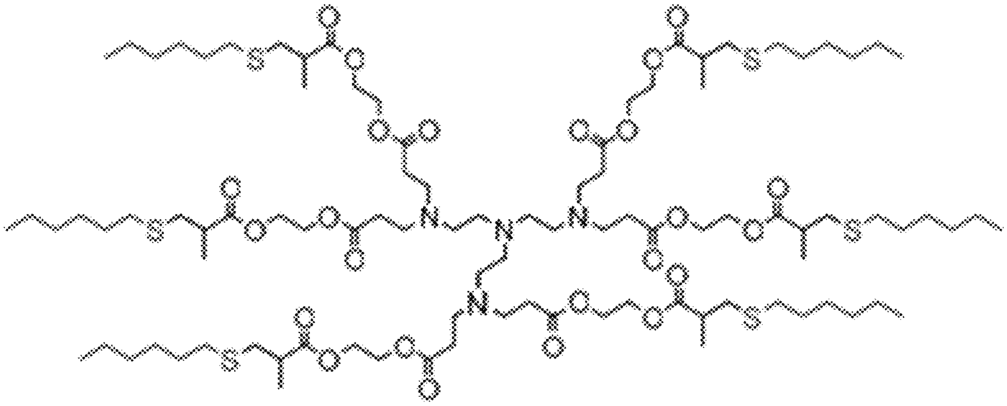
Figure 2:
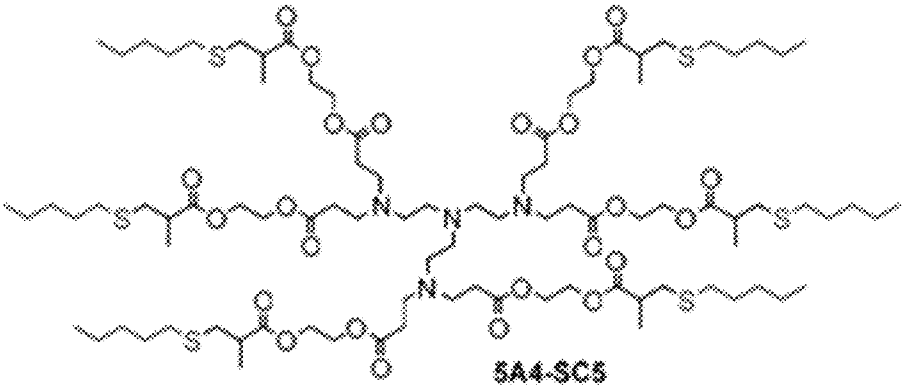
Figure 2:
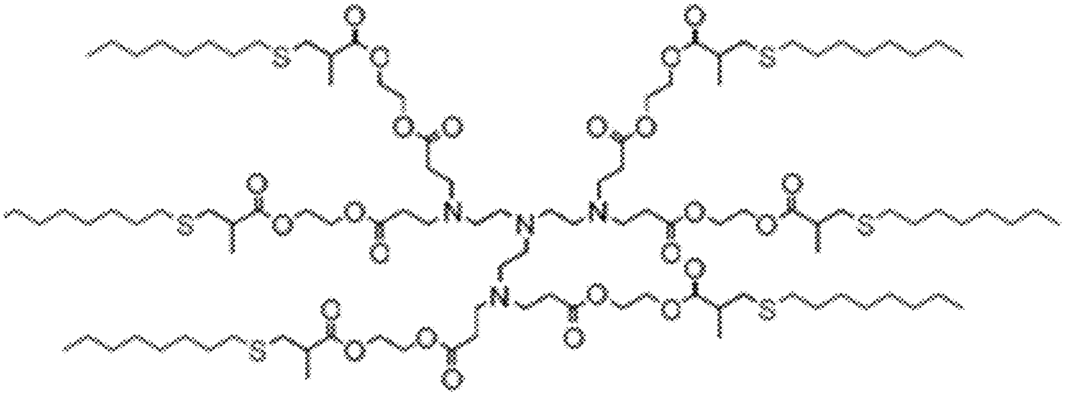
Figure 2:
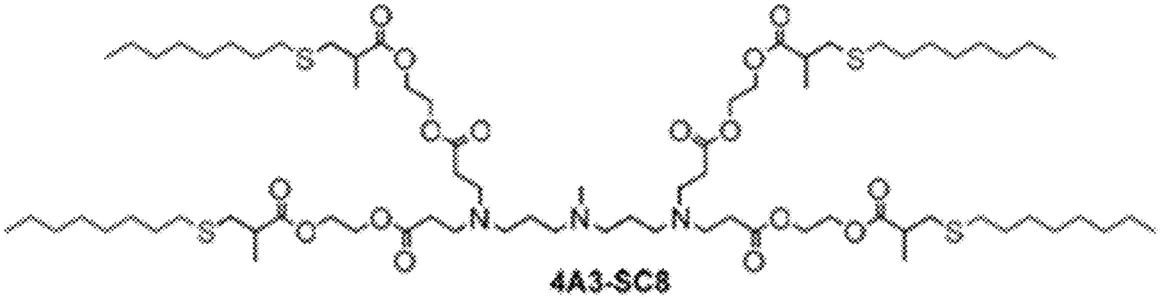
Figure 2:
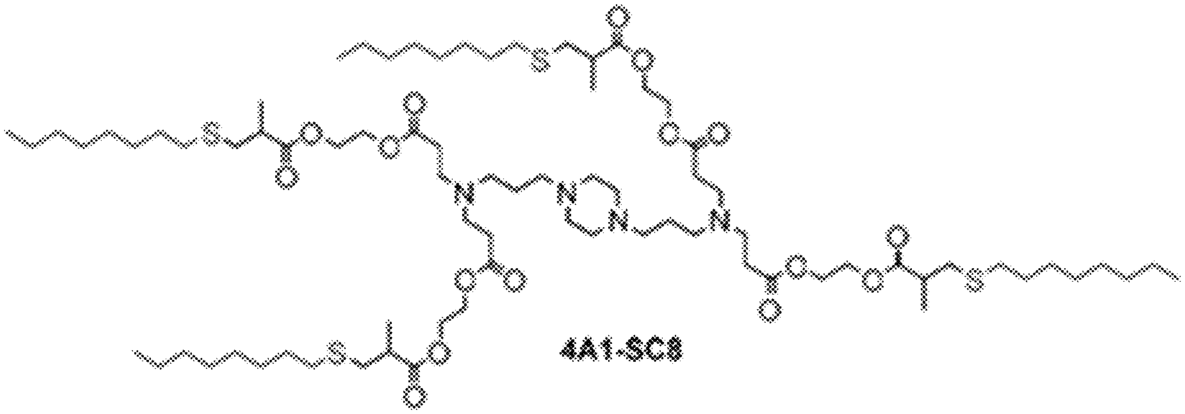
Figure 2:
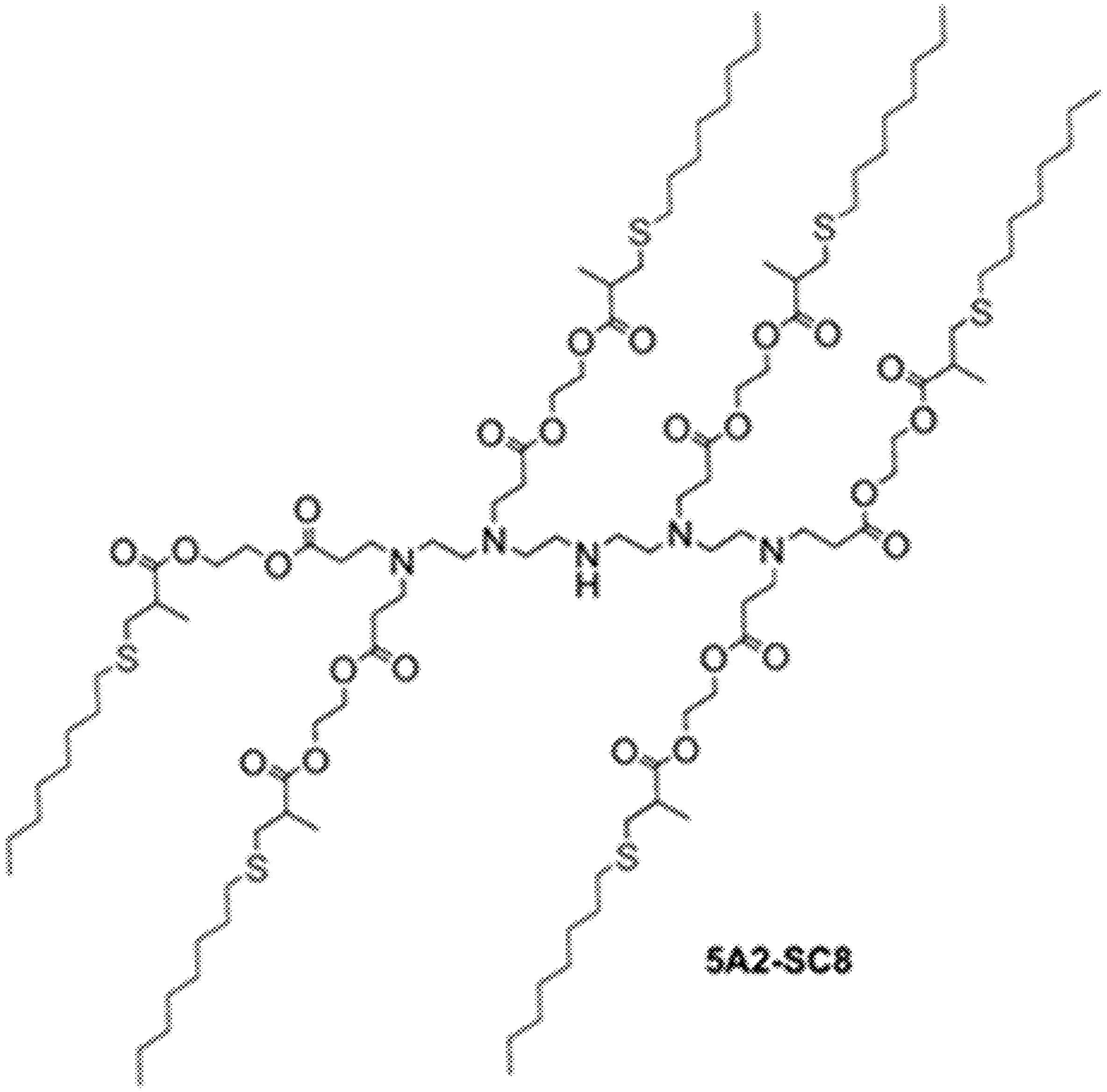

The four canonical types of lipids were mixed in a 15:15:30:3 molar ratio, with or without the addition of a permanently cationic lipid. Briefly, LNPs were prepared by mixing a dendrimer lipid (ionizable cationic), DOPE (zwitterionic), cholesterol, DMG-PEG, and DOTAP (permanently cationic). Alternatively DOTAP can be substituted for DODAP to generate a LNP comprising DODAP. The structure of DOTAP and DODAP are shown in FIG. 1. Various dendrimer lipids that may be used are shown in FIG. 2.

For preparation of the LNP formulation, a dendrimer lipid, DOPE, Cholesterol and DMG-PEG were dissolved in ethanol at desired molar ratios. The mRNA was dissolved in citrate buffer (10 mM, pH 4.0). The mRNA was then diluted into the lipids solution to achieve a weight ratio of 40:1 (total lipids:mRNA) by rapidly mixing the mRNA into the lipids solution at a volume ratio of 3:1 (mRNA:lipids, v/v). This solution was then incubated for 10 min at room temperature. For formation of DOTAP modified LNP formulations, mRNA was dissolved in 1×PBS or citrate buffer (10 mM, pH 4.0), and mixed rapidly into ethanol containing 5A2-SC8, DOPE, Cholesterol, DMG-PEG and DOTAP, fixing the weight ratio of 40:1 (total lipids:mRNA) and volume ratio of 3:1 (mRNA:lipids). Formulations are named X % DOTAP Y (or X % DODAP Y) where X represents the DOTAP (or DODAP) molar percentage in total lipids, and Y represents the type of dendrimer lipid. Alternatively, formulation may be named Y X % DOTAP or Y X % DODAP where X represents the DOTAP (or DODAP) molar percentage in total lipids, and Y represents the type of dendrimer lipid.

Example 2: SORT LNP Stability

LNPs were tested for stability. 5A2-SC8 20% DODAP ("Liver-SORT) and 5A2-SC8 50% DOTAP ("Lung-SORT") were generated using either a microfluidic mixing method or a cross/tee mixing method. The different LNP formulations were characterized by size, polydispersity index (PDI) and zeta-potential, as assessed by dynamic light scattering, 3 separate times for each formulation. The characteristics of the LNPs are show in Table 9.

TABLE 9

SORT LNP characteristics

| | Size (nm) | PDI | Zeta (mV) | Encapsulation Efficiency (%) |
|---|---|---|---|---|
| Lung-SORT - microfluidic | 82.3 | 0.10 | 3.0 | 100 |
| Lung-SORT - cross/tee mixing | 78.1 | 0.09 | 2.2 | 100 |
| Liver-SORT - microfluidic | 59.1 | 0.10 | −2.3 | 97 |
| Liver-SORT - cross/tee mixing | 60.0 | 0.11 | −30 | 96 |

Figure 6:
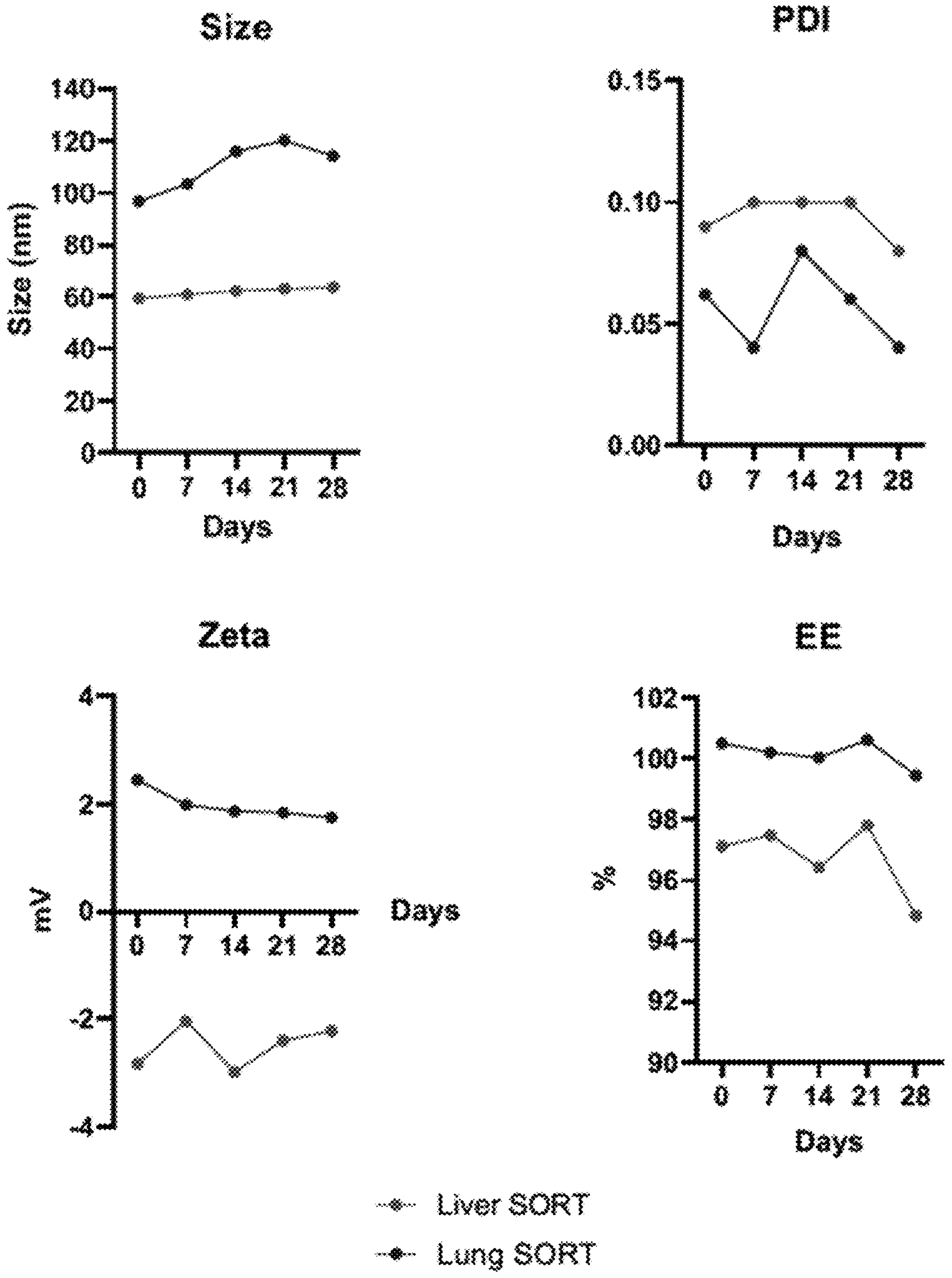
FIG. 6 illustrates the stability and general characteristics of various LNP compositions.

The encapsulation efficiency was tested using a Ribogreen RNA assay (Zhao et al., 2016). Briefly, mRNA was encapsulated with >95% efficiency in LNPs when the mRNA was dissolved in acidic buffer (10 mM citrate, pH 4). The characteristics were observed over 28 days for the two types of LNPs (5A2-SC8 20% DODAP ("Liver-SORT") and 5A2-SC8 50% DOTAP ("Lung-SORT")). FIG. 6 shows the changes of the characteristics of the LNP over the course of 28 days.

Figure 7:
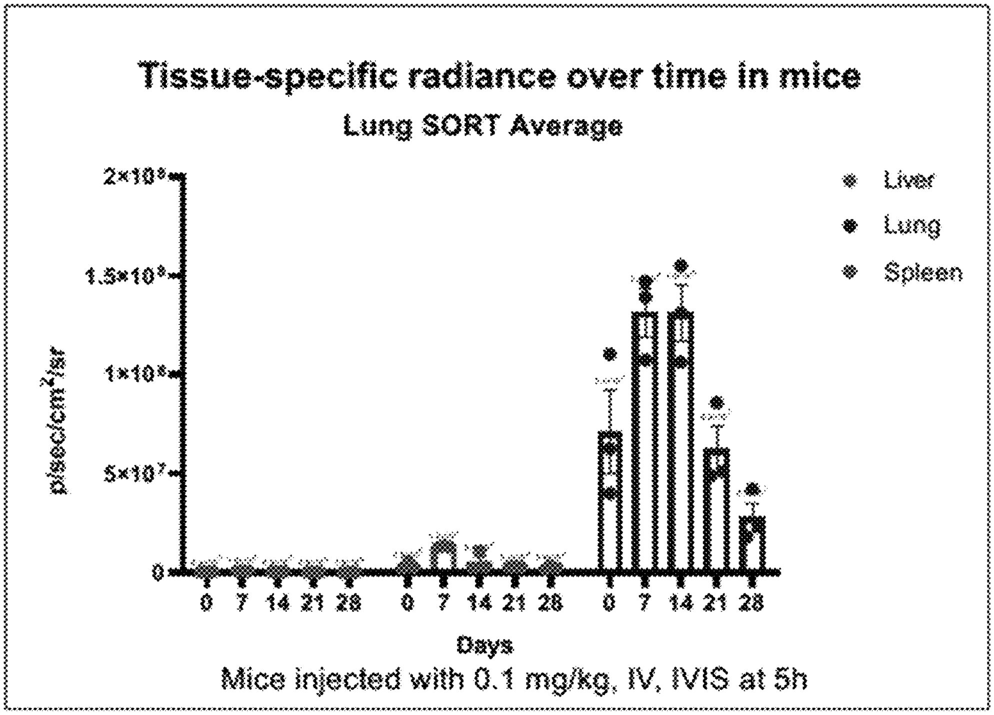
FIG. 7 shows a chart of tissue specific radiance over time in a mouse of an LNP composition (e.g., 5A2-SC8 DOTAP).
Figure 8:
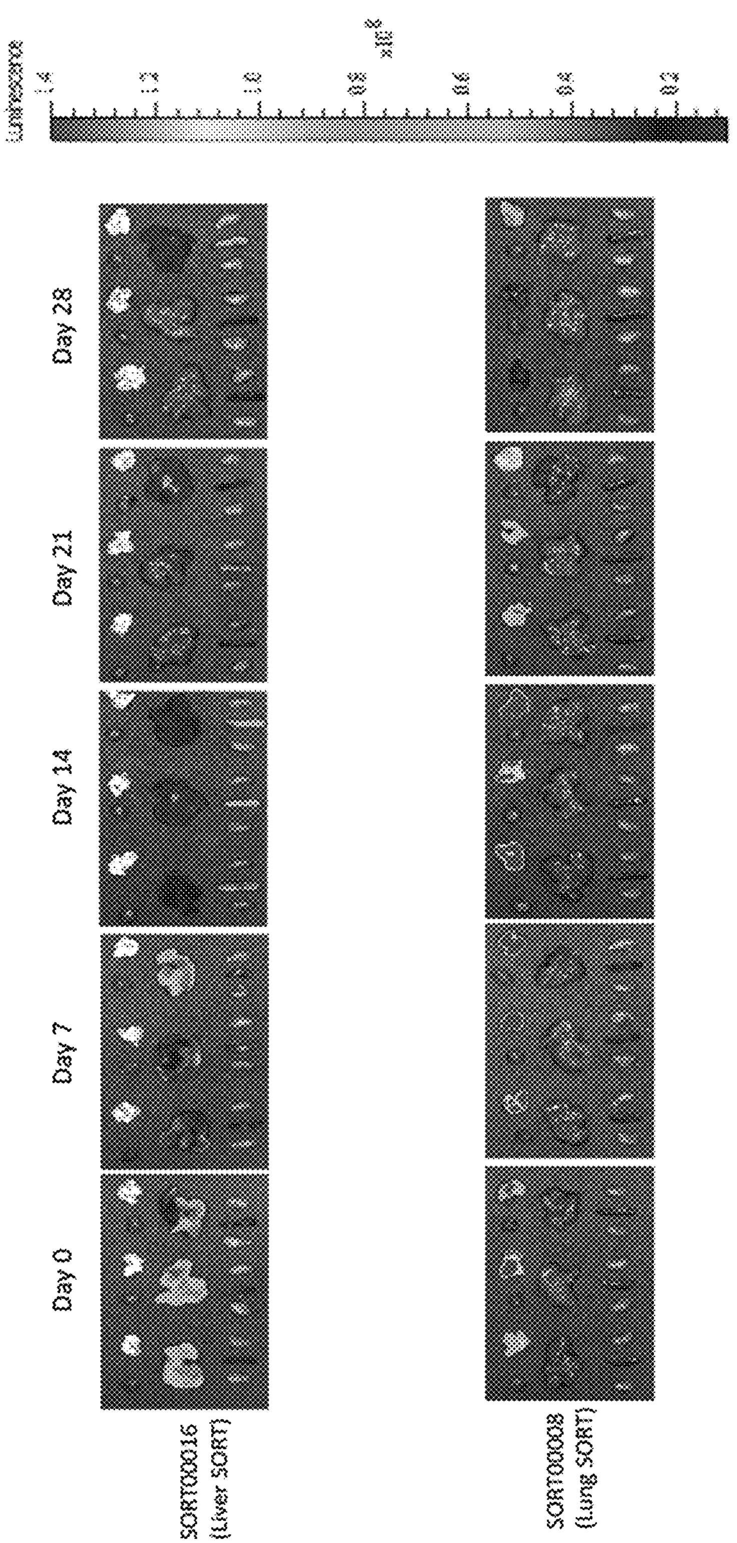
FIG. 8 shows images of tissue specific radiance over time in a mouse of an LNP composition (e.g., 5A2-SC8 DOTAP).

In addition, to the measure of the stability of the LNPs in solution, the stability of the LNPs and resulting mRNA expression was observed in mice. Briefly, mice were injected intravenously with 0.1 mg/kg and observed in vivo. Luciferin was added 5 hrs after injection and visualized. As shown in FIG. 7, the Lung-SORT LNP generated tissue specific radiance in the lungs which remained high even after 14 days with a slight decay in signal by the $21^{st}$ and $28^{th}$ day. FIG. 8 shows images of the organs of the mouse at specific times periods after being treated with Lung-SORT or Liver-SORT.

Example 3: Expression of TR (Tomato Red) mRNA in Different Cell Types

Figure 3:
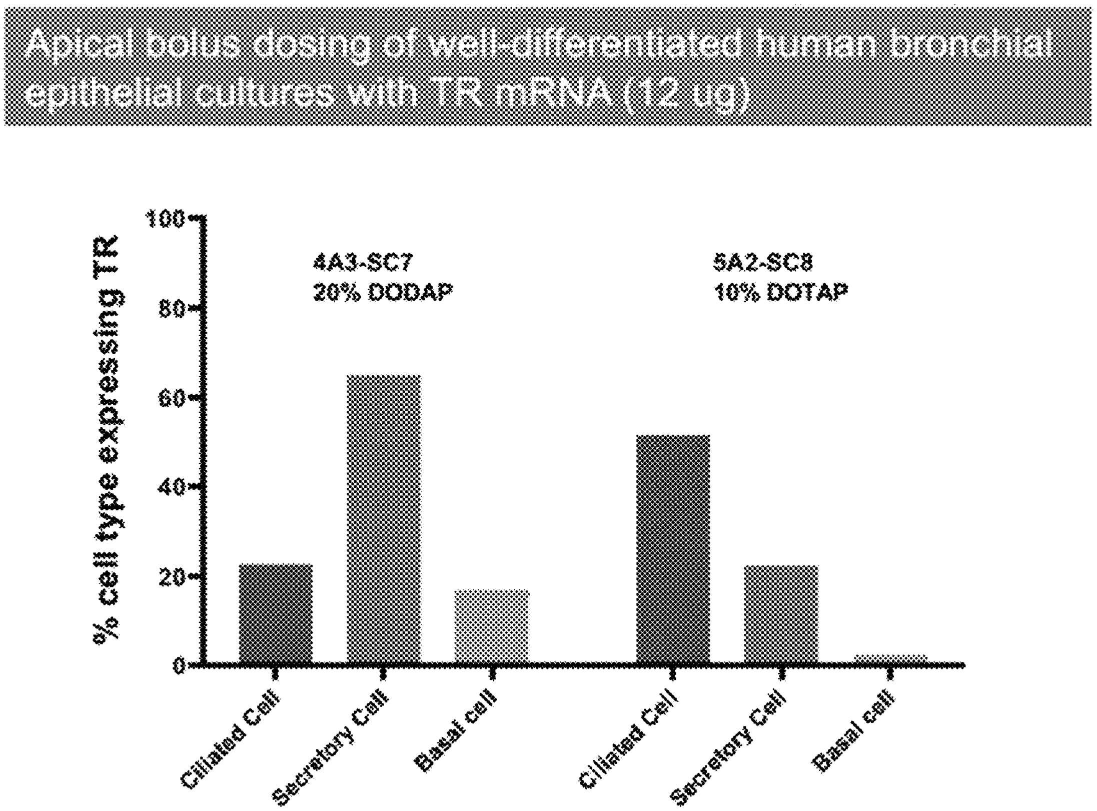
FIG. 3 shows a chart of cells type and expression levels of a delivered mRNA using different compositions of LNP.
Figure 3:
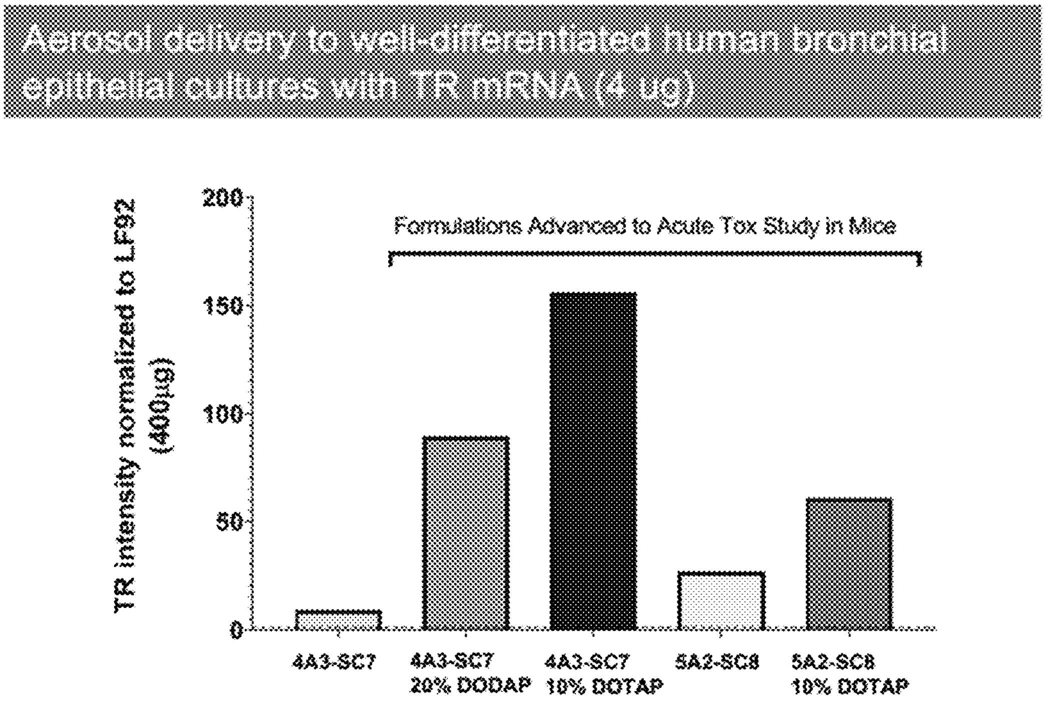

Expression of TR (Tomato Red) mRNA in different cell types in hBE cultures (human bronchial epithelial cultures) was analyzed. TR mRNA was loaded into either 20% DODAP 4A3-SC7 LNP or 10% DOTAP 5A2-SC8 LNPs and delivered into well-differentiated human bronchial epithelial cultures using apical bolus dosing (upper panel) or aerosol delivery (bottom panel). TR protein expression in various cell-types was observed and the percent of TR positive cells in different cell-type was plotted. As shown in the top panel of FIG. 3, the 20% DODAP 4A3-SC7 LNPs preferentially caused secretory cells to express TR, while 10% DOTAP 5A2-SC8 LNPs cause the ciliated cells to preferentially express TR. This preferential delivery may allow a treatment delivered to the lungs to preferentially affect a specific cell type in the lungs. The TR mRNA was also loaded into LNPs without the SORT lipid (e.g. DODAP or DOTAP) to identify how the DODAP or DOTAP affected the potency. As shown in the bottom panel of FIG. 3, the LNPs comprising DOTAP or DODAP showed increased TR expression compared to their corresponding LNP without DOTAP or DODAP.

Figure 4:
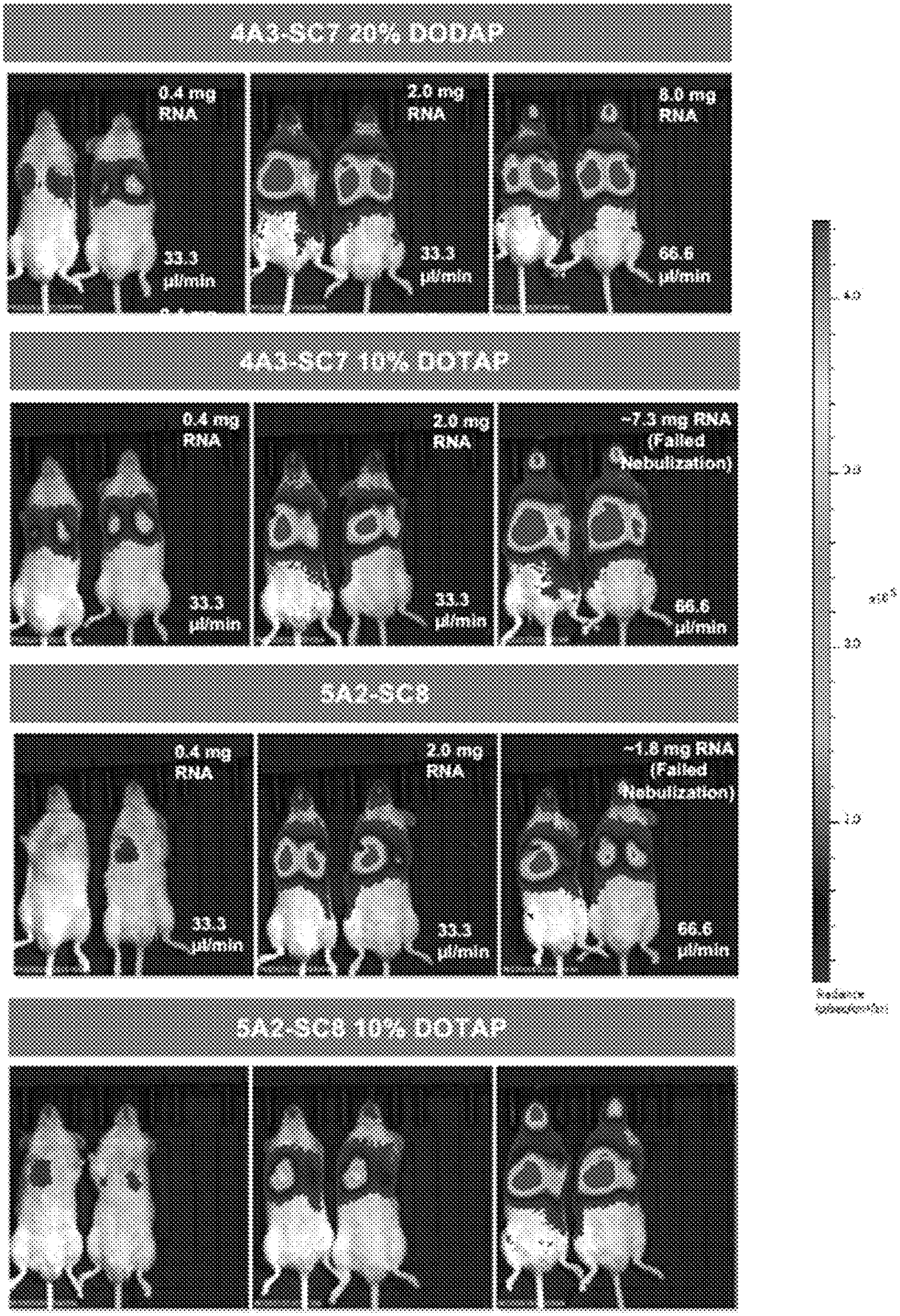
FIG. 4 illustrates images using in vivo imaging of bioluminescence of a mouse after inhaled aerosol delivery of a reporter Luc mRNA/LNP using multiple compositions of LNP.

Example 4: Luciferase Activity and Histopathology from LNPs Delivered Via Inhaled Aerosol Luc mRNA was loaded into a number of LNPs including LNPs comprising a SORT lipid and a dendrimer. LNPs of 4A3-SC7 20% DODAP, 4A3-SC7 10% DODAP, 5A2-SC8, and 5A2-SC8 10% DOTAP were generated and loaded with Luc mRNA. 0.4/2/8 mg of LNP-formulated Luc2 mRNA (1 mg/ml) was delivered into a pie chamber by nebulization (Aerogen solo), with an estimated (not measured) per mouse delivered dose of 0.01, 0.06 or 0.22 mg/kg. The mice were 7 week old B6 male albino mice. Luciferin was administered to the mice 5 hrs after delivery of the LNPs. The luciferase activity was detected as a measure of delivery to the target. FIG. 4 shows the distribution and expression of the luciferase in the mice demonstrating the expression was successful and delivery of the LNPs may be performed using inhaled aerosol delivery.

Example 5: Toxicity of EPC Containing LNPs

Figure 5:
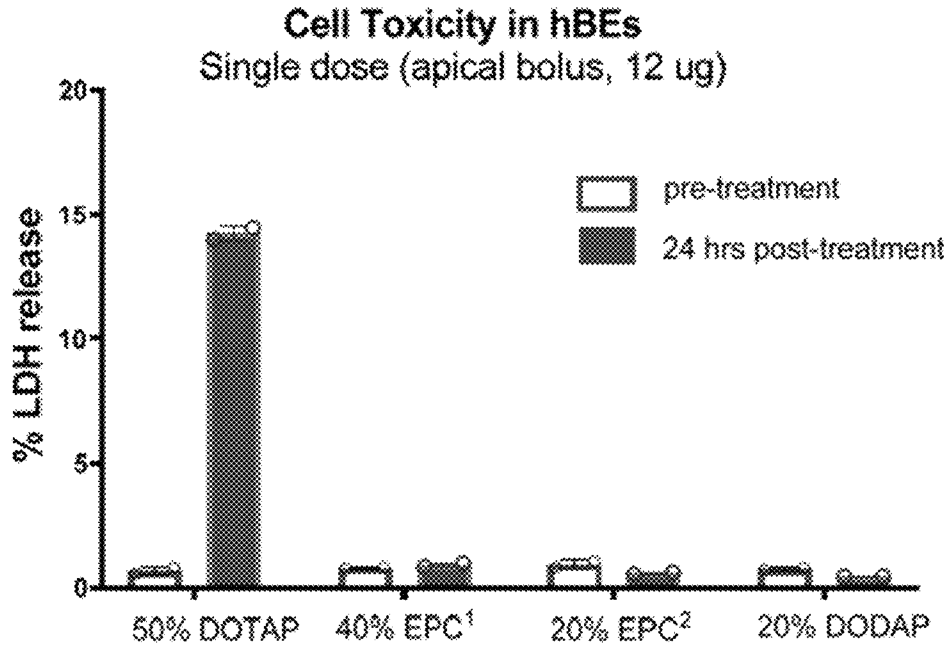
FIG. 5 shows a chart regarding cell toxicity of various LNP compositions in human bronchial epithelial (hBE) cells.

LNPs comprising ethylphosphocholine (EPC) in place of DOTAP or DODAP were tested for toxicity by using apical bolus dosing on human bronchial epithelial cells. The % of lactate dehydrogenase (LDH) that was released was used as a metric of cellular death and indicative of the toxicity of the LNP. The release of LDH was detected prior to treatment (pre-treatment) and 24 post treatment. As shown in FIG. 5, the treatment of 50% DOTAP LNP resulted in an ~15% LDH release whereas EPC didn't show a significant % LDH release. Importantly, DOTAP and EPC have a similar quaternary amine moiety, indicating that the activity for cell targeting may be similar, but that EPC is considerably less toxic.

Figure 9A:
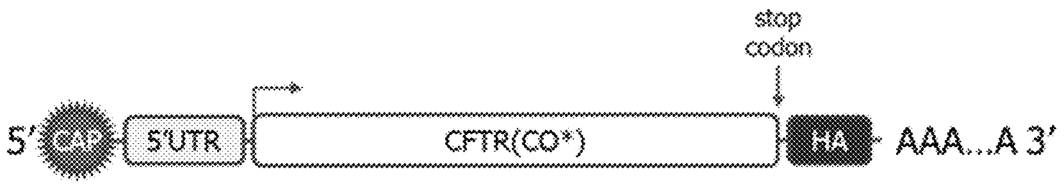
FIG. 9A illustrates a structural design of CFTR mRNA described in the present application.

Example 6: Optimization of CFTR mRNA mRNA sequences of CFTR mRNA were optimized before production. Briefly, wild type sequence was firstly subject to optimization according to % codon-usage, elimination of UU and UA hydrolysis hotspots, elimination of U-containing codons other than TAC and TTC, and elimination of unwanted or accidental restriction to obtain a codon optimized ORF. The example structure of CFTR mRNA is as shown in FIG. 9A. A variation of Kozak sequence AUGC was used to maintain the wild-type amino acid composition. Second residue after N-terminal Met is Gln (coded by CAG). ORF sequence including SEQ ID NO. 1. was placed after Kozak sequence, followed by polyA.

Figure 9B:
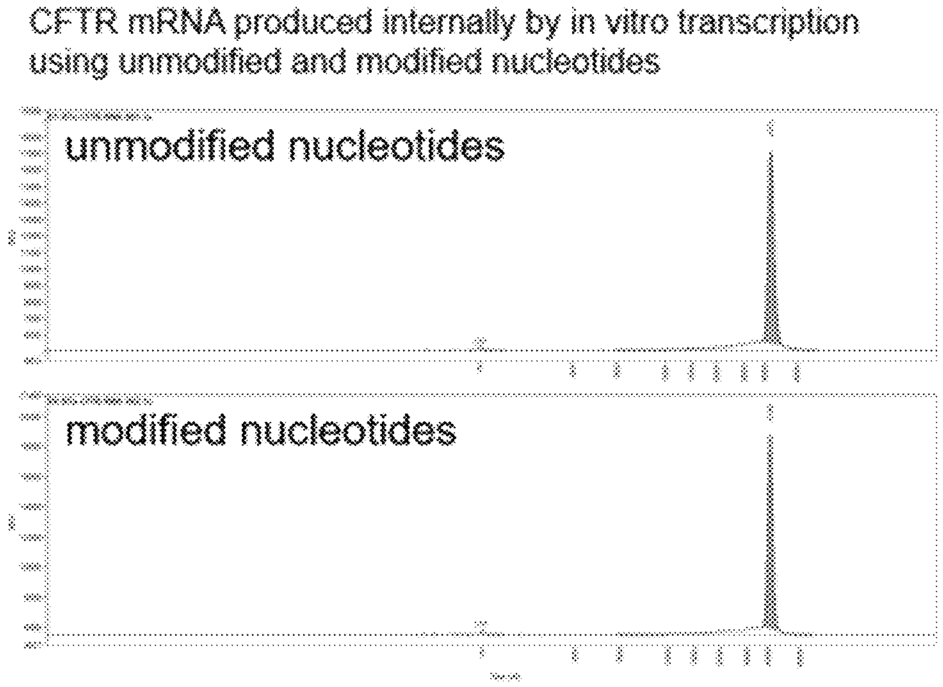
FIG. 9B illustrates production of CFTR mRNA described in the present application.

DNA corresponding to the gene of CFTR was synthesized at GenScript. pUC57/CFTR was digested with BstBI (the ORF for CFTR is codon optimized). Standard in vitro transcription procedure was used for RNA production utilizing either unmodified or modified nucleotides. Capping reaction was carried out using Vaccinia Virus capping system and cap 2'-O-methyl transferase. Full Length CFTR mRNA was further subjected to fragment analysis, as shown in FIG. 9B and demonstrated the synthesis of full length CFTR mRNA with unmodified or modified nucleotides. Additional routine QC parameters tested include concentration, sterility, mRNA function, residual plasmid and bacterial DNA, dsRNA, and endotoxin.

Example 7: Dose-Dependent Expression of CFTR Protein in FRT Cells

Figure 10A:
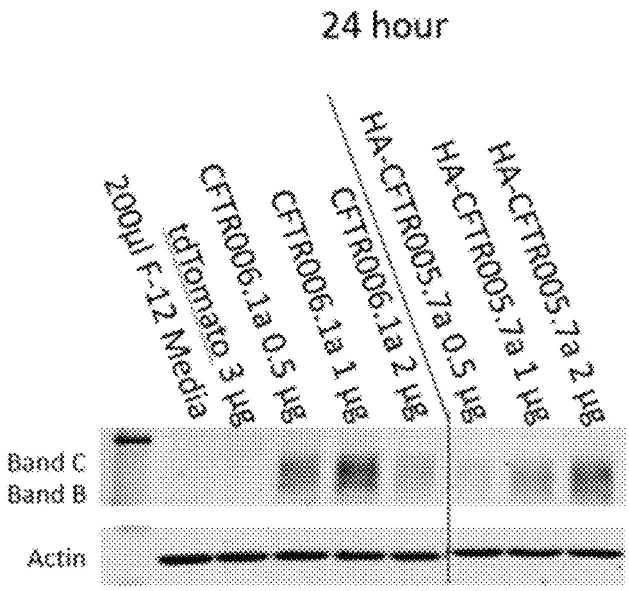
FIG. 10A-10B illustrate dose-dependent expression of CFTR protein in FRT cells.
Figure 10B:
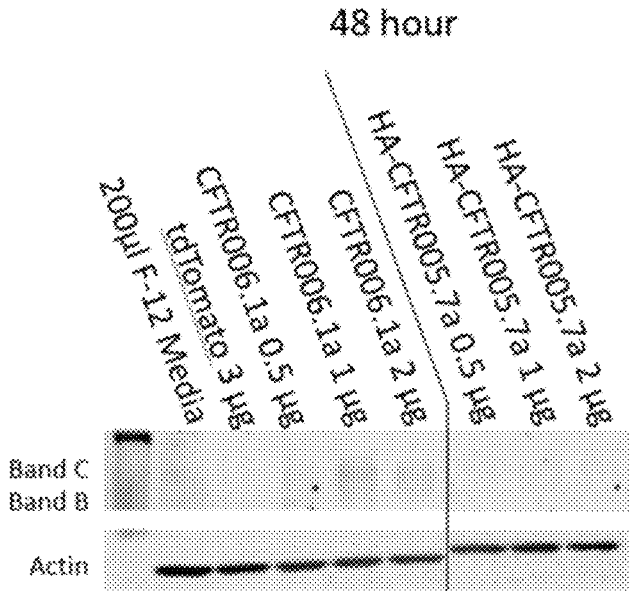

Briefly, CFTR mRNAs of the present application were transfected into FRT cells. As shown in FIGS. 10A and 10B, transfection of CFTR mRNAs induced CFTR protein expression in FRTs. The FRT cells were lysed and the lysate was collected. Gel electrophoresis was performed on the lysate samples and subsequently Western blotted with anti-CFTR. Both HA-tagged CFTR and untagged CFTR mRNAs produced detectable protein, with more detectable protein from the untagged mRNA. CFTR expression was observed to be higher at 24 h vs. 48 h post transfection.

Figure 11A:
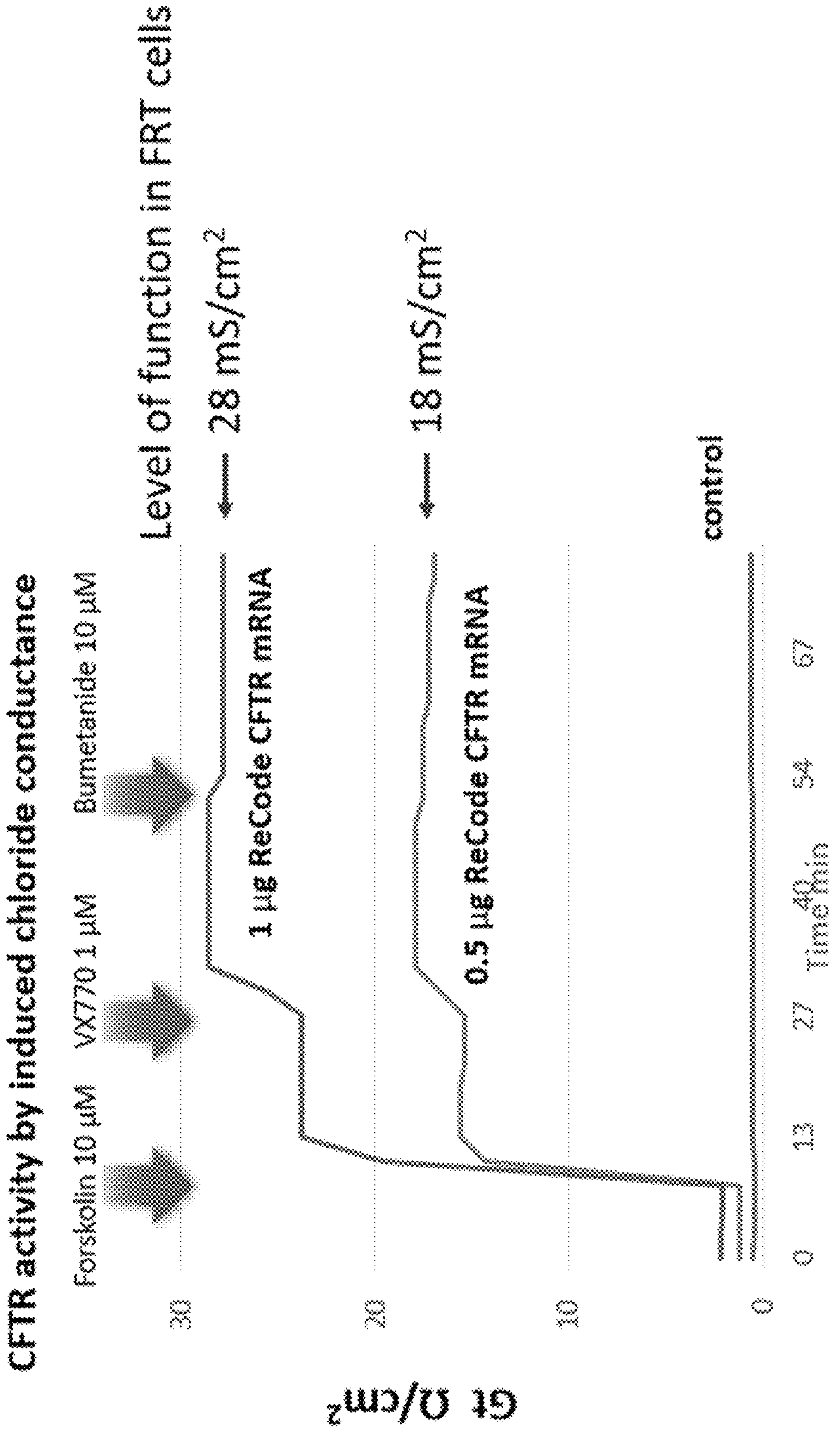
FIG. 11A illustrates activity of CFTR in FRT cells.
Figure 11B:
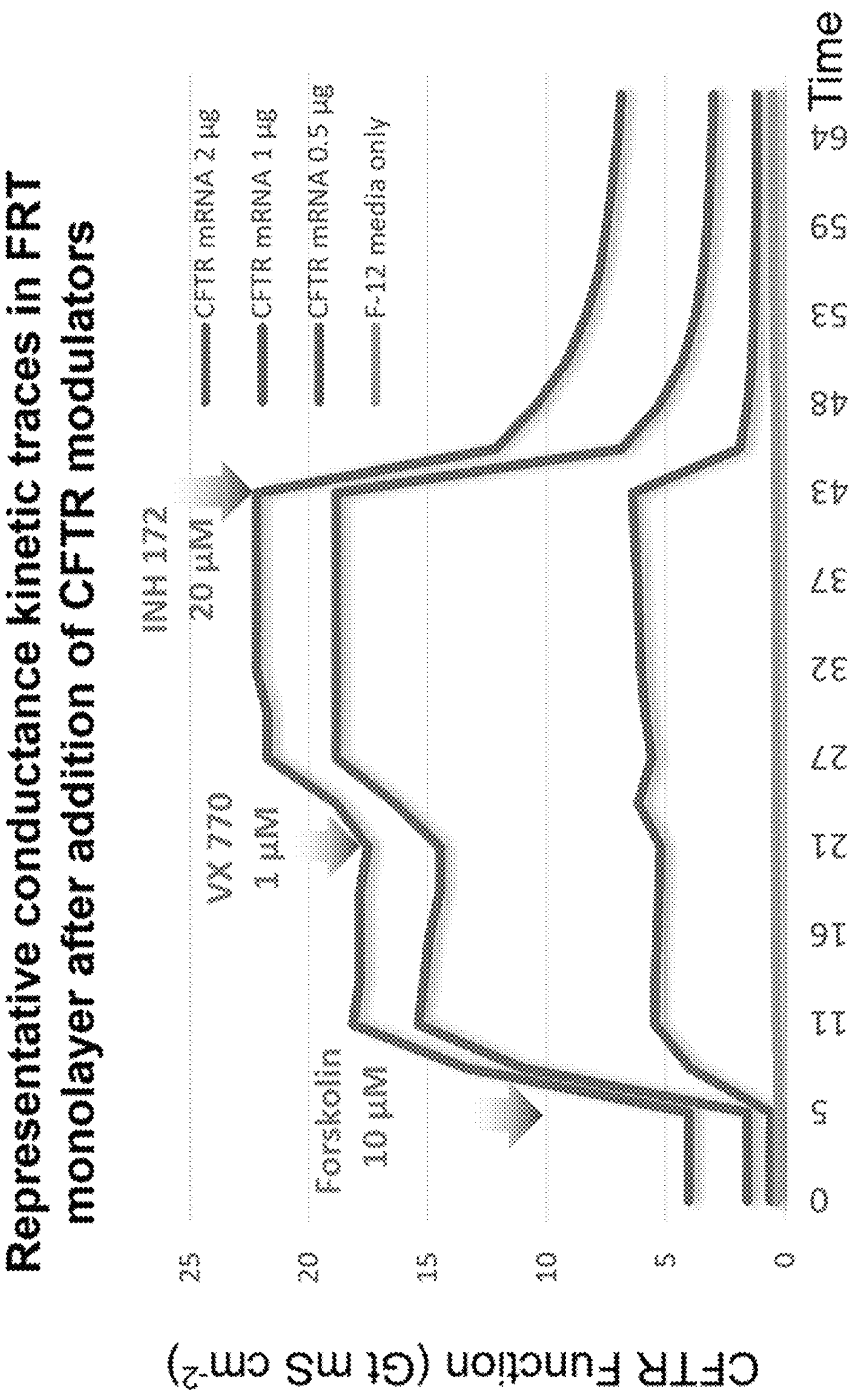
FIG. 11B-11C show that does-dependent CFTR function was observed with CFTR mRNA described herein in FRT cells.
Figure 11C:
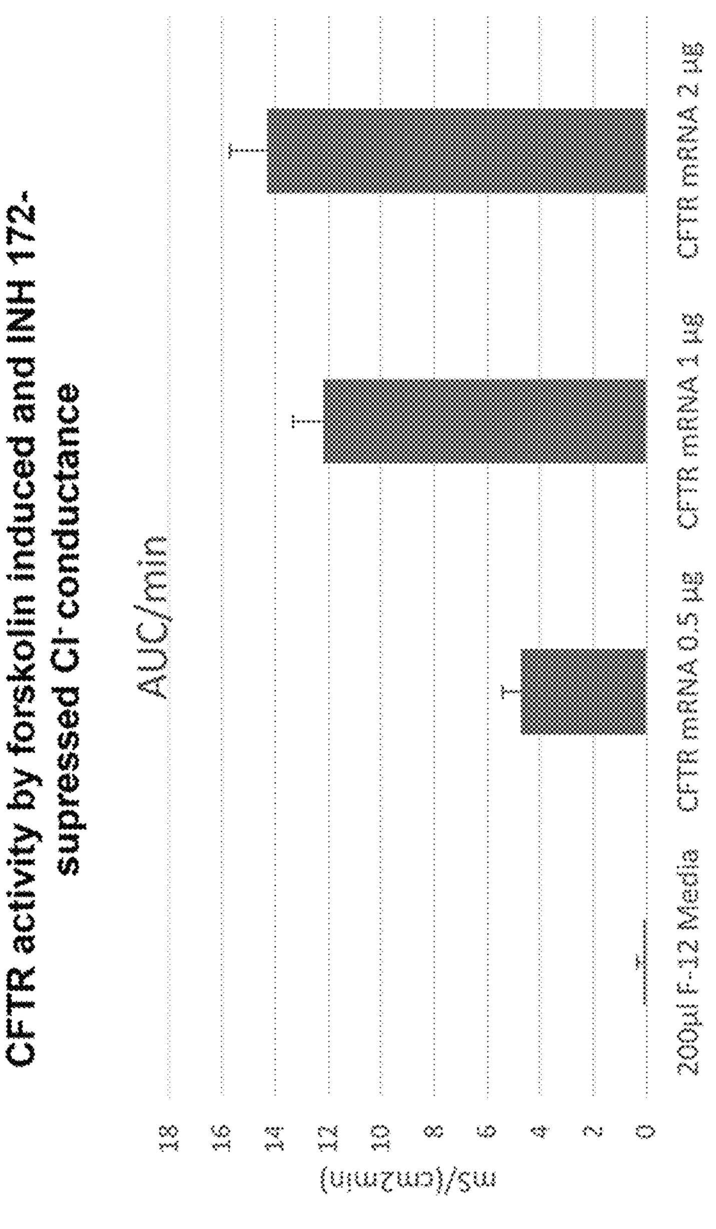

The functional expression of CFTR mRNAs was assessed in Fisher Rat Thyroid (FRT) cell lines using TransEpithelial Current Clamp with 24 electrode manifold (TECC24) and 24 well plates with permeable membrane support inserts Transwell® (Corning). The FRT cells were seeded on the porous membrane and grown until confluence before transfection. Lipofectamine 2000 was used as an optimal reagent for FRT transfection. 24 hours after transfection FRT plates were placed on thermostabilized (36° C.) platforms and transepithelial resistance (Rt) values were measured with ~1 min acquisition interval upon robot-assisted or manual transitions of the electrode manifold between cell-populated and reference plates filled with assay buffer. The FRT assay sequence includes baseline reading interval (~8 min), 10 μM Forskolin-induced CFTR activation interval (~10 min), 1 μM VX-770-induced CFTR potentiation interval (~10 min), and 20 μM INH-172-induced CFTR inhibition interval (~10 min). The FRT conductance traces [Gt=1/(Rt-50), mS/cm] were reconstructed vs. time. The Forskolin/VX-770-mediated responses were calculated as an Area Under the Gt Curve (Gt AUC) for time points between Forskolin and NIH-172 addition. This AUC calculation was performed after baseline subtraction calculated as a slop line between the initial baseline Gt timepoint and a plateau Gt timepoint acquired after apparent complete CFTR inhibition (FIG. 11A, dashed line). The changes in the Gt/min corresponding to CFTR-mediated alteration of Cl— flux across FRT layer extrapolated as the CFTR functional activity were statistically compared for different mRNA designs. As example in FIG. 11, the parental FRT cells were tested with the TECC24 conductance assay after treatment with two concentrations of CFTR mRNA, with 1 μg of mRNA resulting in the Forskolin-induced conductance of ~28 mS/$cm^2$ and 0.5 μg of mRNA resulting in the conductance of ~7 mS/$cm^2$ demonstrating the ReCode mRNA-mediated functional expression of CFTR protein. FIG. 11B and FIG. 11C show an example experiment of dose-dependent CFTR function observed with optimized CFTR mRNA in FRT cells. FIG. 11B shows a representative conductance kinetic traces in FRT monolayer after addition of CFTR modulators. 5 day-old confluent FRT cells grown on TransWell® permeable support were transfected with optimized mRNAs using Lipofectamine 2000. MTECC24 assay of the transepithelial conductance was performed 1 day after transfection with one dose of optimized CFTR mRNA. FIG. 11C shows CFTR activity by forskolin induced and INH 172-suppressed Cl— conductance: mRNA dose dependent transepithelial conductance (Gt) responses: bars are Gt area under the curve (AUC) per min between forskolin addition and Inhibitor-172 addition time points.

Example 8: Delivery of Reporter mRNA into Fully Differentiated hBE Cells

Figure 12:
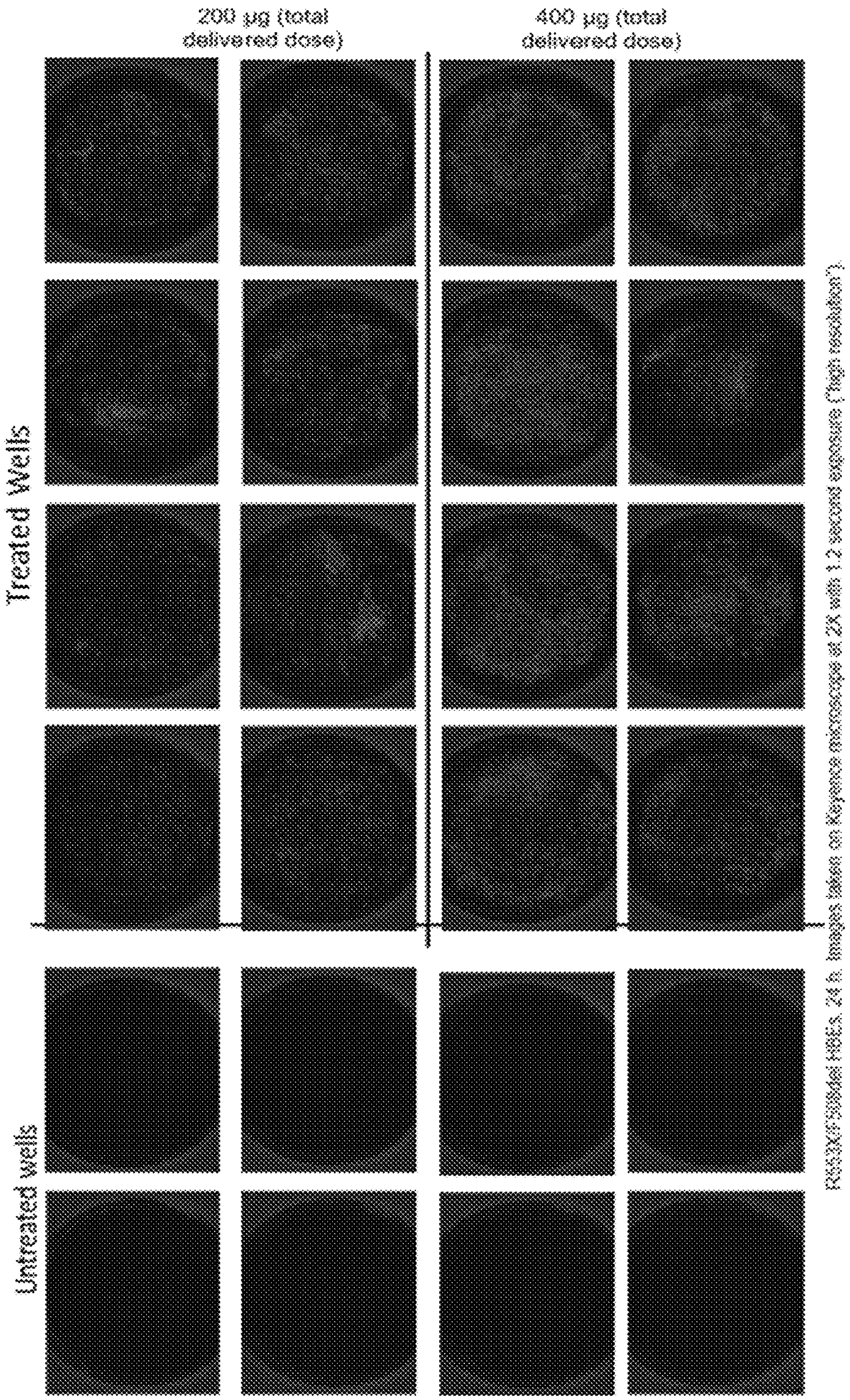
FIG. 12 illustrates delivery of reporter mRNA into fully differentiated hBE cells.

Expression of TR (Tomato Red) mRNA in fully differentiated hBE cells was analyzed. Briefly, hBE cells were plated in 24 well plate and allowed to proliferate. LNPs comprising Tomato Red mRNA were nebulized onto the 24-well plate by placing the plate into an enclosed chamber and allowing the nebulized LNPs to settle onto the hBE cells. As shown in FIG. 12, the untreated wells did not show any signal, whereas the wells treated with nebulized LNPs were observed to comprise cells with Tomato Red expression. Two different delivered doses were tested, with increased expression observed after the 400-μg dose compared to treatment with 200-μg dose.

Figure 13B:
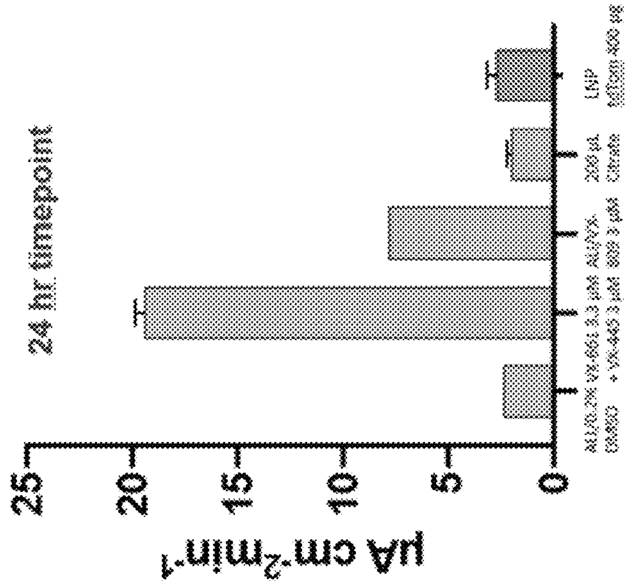
FIG. 13A-13C show resistance and response of hBE cells to reference compounds and CFTR mRNA formulation of the present application w/tdTomato mRNA.
Figure 13C:
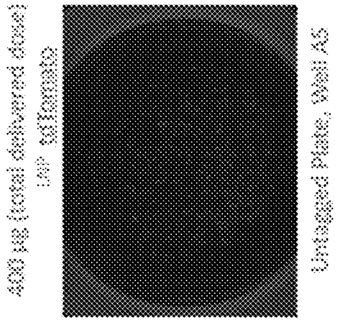
Figure 13A:
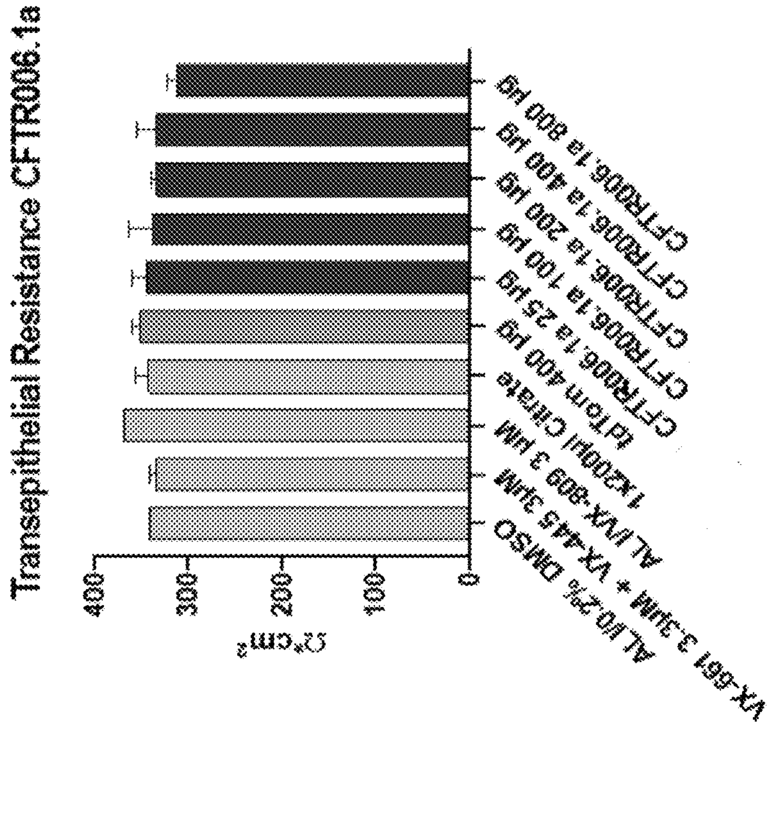

Example 9. Transepithelial Resistance and Equivalent Transepithelial Current Assay in hBE Cells to Validate Cellular Tolerability and CFTR Rescue Efficacy of Selected Pharmacological Compounds and CFTR mRNA/LNP Formulations of the Present Application Transepithelial resistance (Rt) of human Bronchial Epithelia (hBE) cells grown on permeable support in 24 well Transwell® plate and differentiated/polarized against apical air-liquid interface (ALI) was used to assess the tolerability of human bronchial epithelia to mRNA/LNP formulations of the present application. The reduction of baseline Rt>50% is considered significant, corresponding to obstruction of the barrier epithelial function. As shown in FIG. 13A, LNPs encapsulated Tomato Red reporter mRNA and CFTR mRNA induces no significant loss of Rt vs. vehicle, suggesting good tolerability of human bronchial epithelia to the ReCode mRNA/LNP formulations. As expected, hBE treated with TR reporter mRNA LNPs showed no detectable Forskolin induced current (FIG. 13B) despite strong TR protein expression (red fluorescent signal FIG. 13C). The results revealed that TR reporter LNPs can be used as positive transfection control along with CFTR therapeutics used as a positive control of CFTR activity in hBE.

Figure 14B:
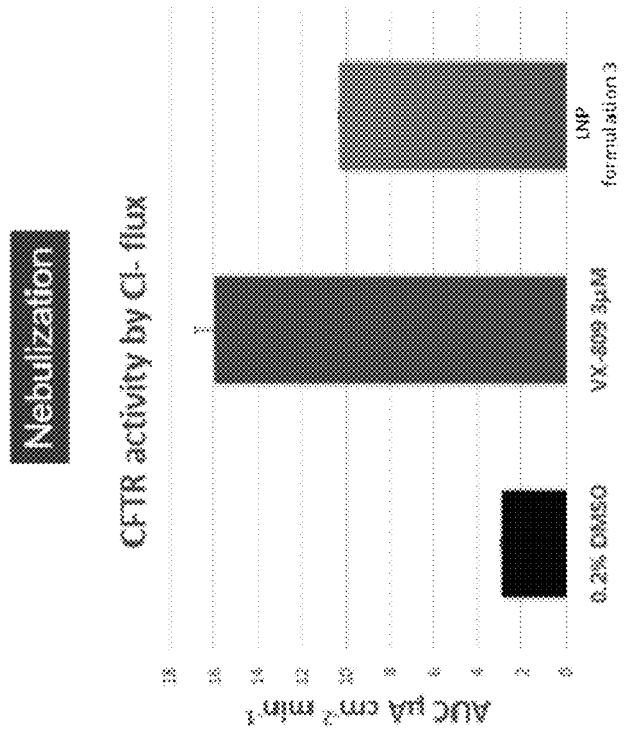
FIG. 14A-14B illustrates restoration of CFTR function in fully differentiated F508del/F508del hBEs by CFTR mRNA formulation of the present application.
Figure 14A:
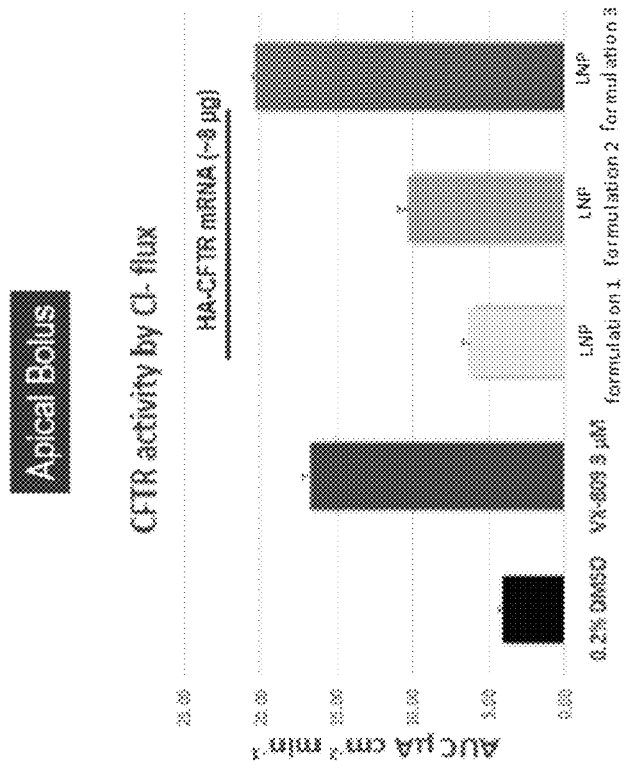

Example 10. Compensation of F508del/F508del CFTR Mutation by CFTR mRNA LNP Formulations of the Present Application in Differentiated Primary hBE Cells from a F508del/F508del Subject ReCode CFTR mRNA-encapsulated LNPs showed significant rescue of CFTR in the F508del/F508del CFTR hBE model. Briefly, CFTR mRNA was encapsulated with different LNP compositions and delivered to F508del/F508del hBE cells as apical liquid bolus or apical exposure of ALI hBE to nebulized LNPs aerosol. The hBE cell isolated from a cystic fibrosis patient with F508del/F508del genotype at passage 3 were seeded on 24 wells Transwell® plates and airlifted after 96 hours. Cells grown following a 3 days/week feeding routine with Vertex ALI media. After 5 weeks hBE cell culture were considered fully differentiated, polarized, and to be ready for the TECC24 functional assay. 4 days prior to treatment mucus was washed from the apical side of the hBE culture with 3 mM DTT in PBS. 24 hours before treatment cells were washed with PBS, additionally washed with PBS on the treatment day, treated apically with liquid bolus or VitroCell nebulized formulations, and tested after 24 or 24+n24 hour $CO_2$ incubation as planned. The TECC 24 assay was performed similarly as described for FRT cells, except for different pharmacological agents needed to suppress large $Na^+$ conductance and record small isolate CFTR mediated $Cl^-$ current typical for hBE. Specifically, the hBE assay sequence includes background current/resistance recording interval (~8 min), baseline $Cl^-$ current recording interval (~8 min) after inhibition of $Na^+$ conductance with 6 μM Benzamil, 10 μM Forskolin+1 μM VX-770 induced CFTR activation interval (~15 min), and 20 μM Bumetanide induced $Cl^-$ current inhibition interval (~10 min). The hBE transepithelial equivalent current traces [Ieq=Vt/(Rt-50), μA/cm] were reconstructed vs. time. The Forskolin/VX-770-induced $Cl^-$ current responses were calculated as an Area Under the Ieq Curve (Ieq AUC) for time points between Forskolin/VX770 and NIH-172 addition. The Ieq AUC/min values were statistically validated and compared across experimental samples. As shown in FIG. 14A, the apical bolus treatment with the LNPs comprising HA-CFTR mRNA 5A2-SC8 and DOTAP formulation recovered forskolin-dependent $Cl^-$ current. in F508del/F508del hBEs, suggestion rescue of CFTR function equal or better in comparison to a positive pharmacological control (VX-809). The treatment of F508del/F508del hBEs with apical aerosol of VitroCell-nebulized also recovered CFTR activity.

Figure 15A:
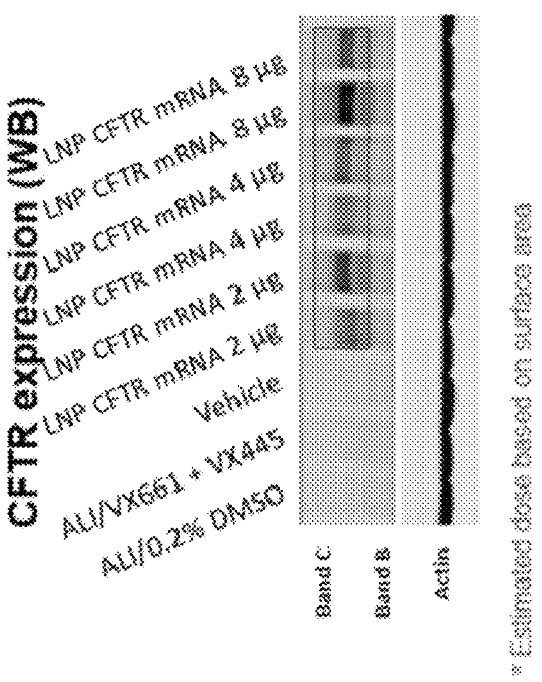
FIG. 15A-15B illustrates restoration of CFTR function in R553X/F508del hBEs by CFTR mRNA formulation of the present application.
Figure 15B:
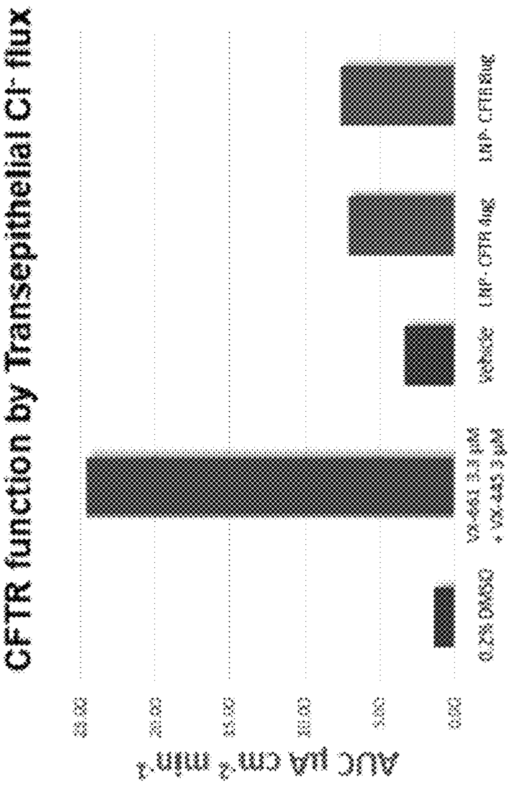

Example 11. Restoration of CFTR Function in CFTR Mutant hBEs on with CFTR mRNA Formulation of the Present Application ReCode CFTR mRNA encapsulated LNPs were validated to rescue of CFTR function in CFTR mutant (such as R553X/F508del) hBE. Briefly, CFTR mRNA was assembled with different LNP compositions and delivered to CFTR mutant (such as R553X/F508del) hBE cells following similar protocol as described for F508del/F508del hBE above. As shown, in FIG. 15A, delivery of the HA-CFTR mRNA via nebulization using LNPs (comprising 4A3-SC7 and DODAP) yielded expression of CFTR in the cells. As shown in FIG. 15B, delivery of the composition comprising CFTR mRNA via nebulization was also shown to be effective at rescuing function.

Figure 16B:
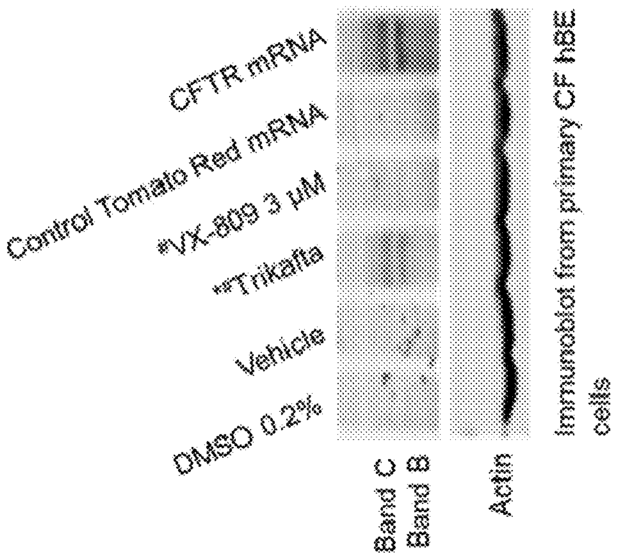
FIG. 16A-16B illustrates single dose aerosol treatment with CFTR mRNA LNPS described herein rescuing CFTR function in in primary CF hBE cells.
Figure 16A:
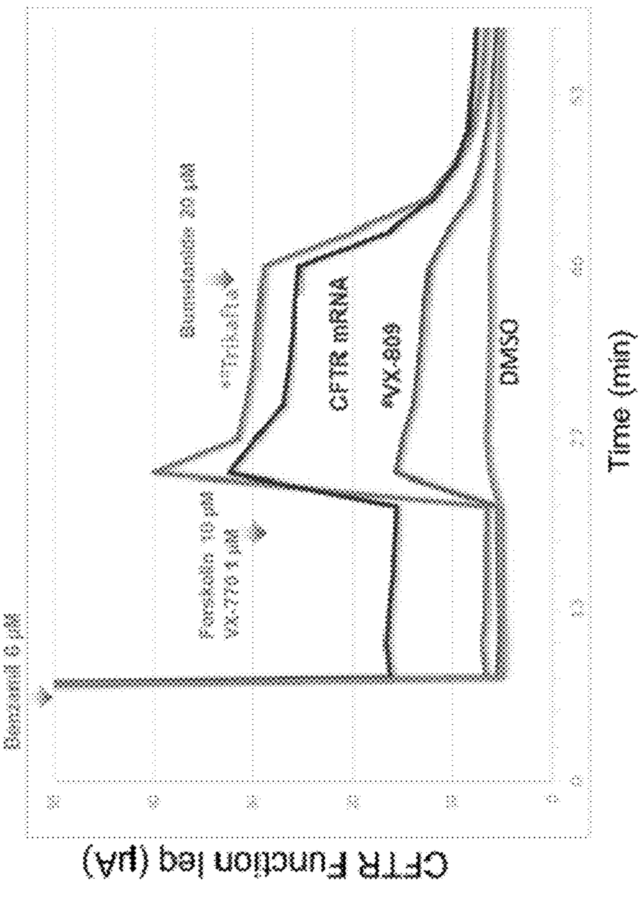

Example 12. Compensation of G542X/F508del CFTR Mutation by CFTR mRNA LNP Formulations of the Present Application in Differentiated Primary hBE Cells from a G542X/F508del Subject ReCode CFTR mRNA encapsulated LNPs showed significant rescue of CFTR in the G542X/F508del CFTR hBE model. Briefly, CFTR mRNA was encapsulated with different LNP compositions and delivered to G542X/F508del hBE cells as apical liquid bolus or apical exposure of ALI hBE to nebulized LNPs aerosol. The hBE cells isolated from a cystic fibrosis patient with G542X/F508del genotype at passage 3 were seeded on 24 wells Transwell® plates and airlifted after 96 hours. Cells grown following a 3 days/week feeding routine with Vertex ALI media. After 5 weeks hBE cell culture were considered as fully differentiated, polarized, and to be ready for the TECC24 functional assay. 4 days prior to treatment mucus was washed from the apical side of the hBE culture with 3 mM DTT in PBS. 24 hours before treatment cells were washed with PBS, additionally washed with PBS on the treatment day, treated apically with liquid bolus or VitroCell nebulized formulations, and tested after 24 or 24+n24 12-, 24-, 48-, 72-, or 96-hour $CO2$ incubation post-treatment time points. Specifically, the hBE assay sequence includes background (initial) current/resistance recording interval (~8 min), baseline $Cl^-$ current recording interval (~8 min after inhibition of $Na^+$ conductance with 6 μM Benzamil), 10 μM Forskolin+1 μM VX-770 induced CFTR activation interval (~15 min), and 20 μM Bumetanide induced $Cl^-$ current inhibition interval (~10 min). The hBE transepithelial equivalent current traces [Ieq=Vt/(Rt-50), μA/cm] were reconstructed vs. time. The Forskolin/VX-770-induced $Cl^-$ current responses were calculated as an Area Under the Ieq Curve (Ieq AUC) for time points between Forskolin/VX-770 and NIH-172 addition. The Ieq AUC/min values were statistically validated and compared across experimental samples. As shown in FIG. 16A, the apical bolus treatment with the LNPs comprising CFTR mRNA recovered forskolin-dependent $Cl^-$ current in G542X/F508del hBEs, suggesting rescue of CFTR function equal or better in comparison to a positive pharmacological control (VX-809 and Trikafta). Also shown in FIG. 16A are representative traces of Forskolin-induced and Bumetanide-suppressed $Cl^-$ current in ΔF508-HBE grown and ALI on Transwell® permeable support. The MTECC24 assay was performed 1 day posttreatment with single dose aerosolized CFTR mRNA LNP, VX-809 and Trikafta equivalent. FIG. 16B shows relative CFTR functional activity shown as equivalent current AUC/min. FIG. 16C shows initial transepithelial resistance as a relative reference of treatment toxicity. FIG. 16D shows a protein blot for CFTR and demonstrates that CFTR protein is successfully produced in the CFTR mRNA treated cells is produced in similar or larger amounts than the positive pharmacological controls, cells treated with Lumacaftor (3 μM VX-809) or Trikafta (3.3 μM VX-661+3 μM VX-445 and 1 μM VX-770 added with Forskolin).

Figure 17A:
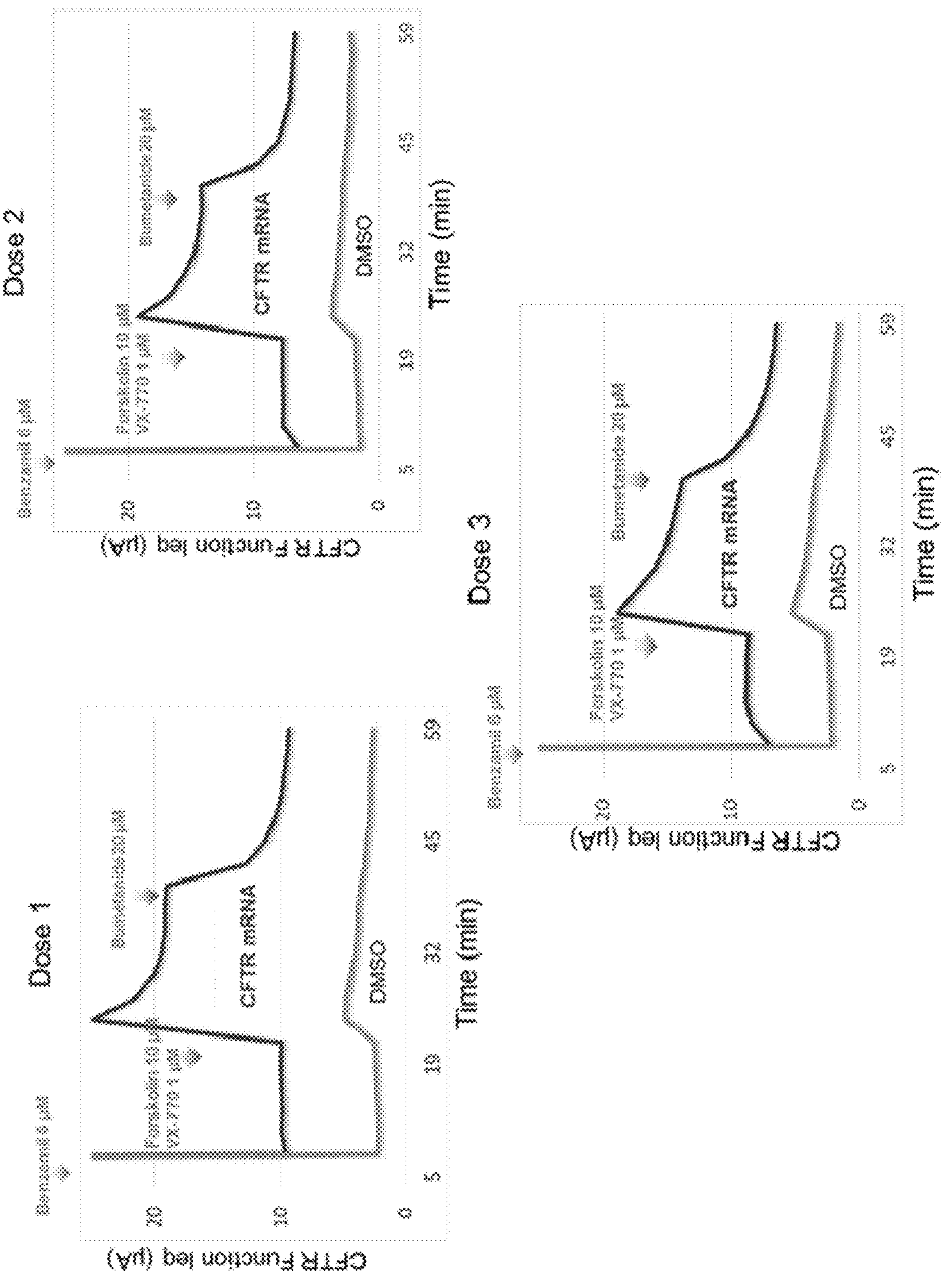
FIG. 17A-17B show repeat administration of the CFTR mRNA LNP formulation based on a twice weekly dosing schedule. Using a similar protocol to determine the CFTR function, the repeated administration showed CFTR function after each dose.
Figure 17B:
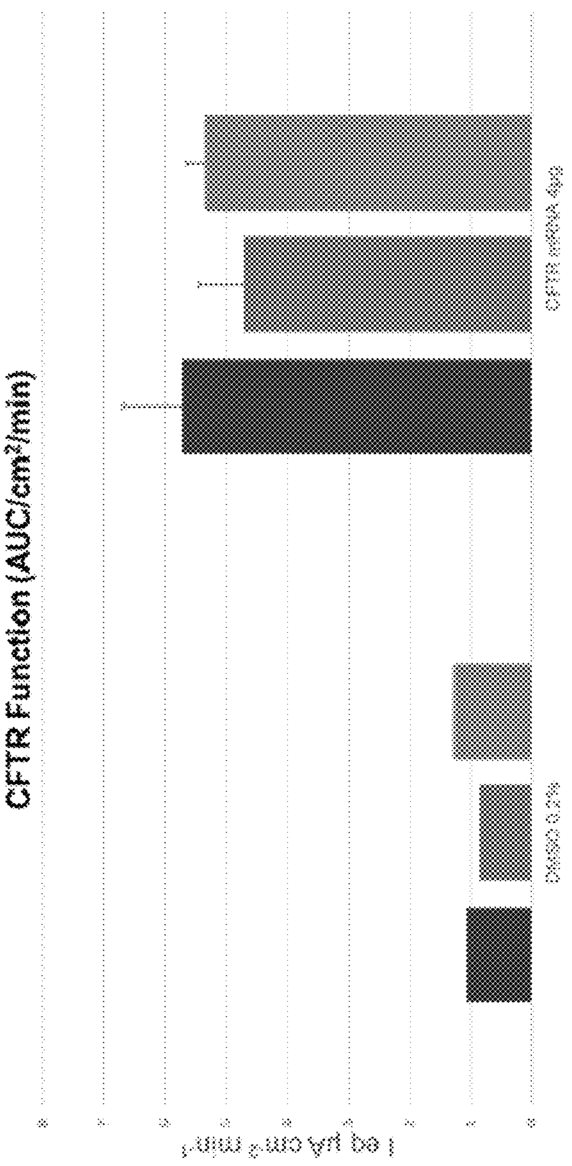

In a similar assay, the CFTR mRNA LNP formulations were repeatedly administered based on a twice a week dosing schedule. Using a similar protocol to determine the CFTR function, the repeated administrations showed CFTR function after each dose. FIGS. 17A and 17B show that each dose was able to generate improved CFTR function over a negative control.

Example 13. mRNA Delivery to Specific Lung Cells

Figure 18:
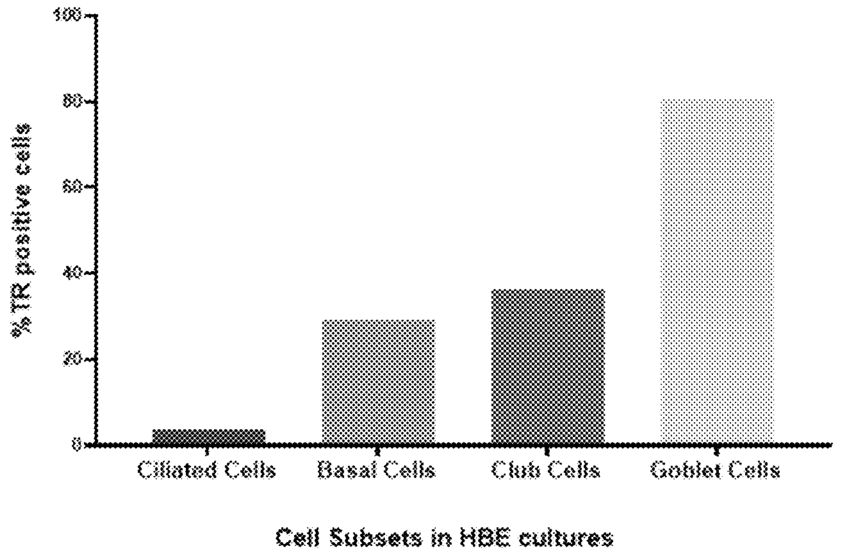
FIG. 18 shows transfection of hBE cells with report mRNA reveals formulation-specific cell tropism signatures. Top graphs shows that well-differentiated human hBE cells were treated once with RTX0001 formulated Td Tomato mRNA (4 mg) using Vitrocell nebulization. % positive cells were determined by colocalization with the indicated markers. As used herein, "RTX001" refers to an example lipid composition tested herein. RTX0001 was a 5-component lipid composition comprising about 19.05% 4A3-SC7 (ionizable cationic lipid), about 20% DODAP (SORT lipid), about 19.05% DOPE, about 38.9% cholesterol, and about 3.81% DMG-PEG (PEG conjugated lipid), wherein each lipid component is defined as mol % of the total lipid composition.

Expression of TR (Tomato Red) mRNA in different cell types in hBE cultures (human bronchial epithelial cultures) was analyzed. TR mRNA was loaded in LNPs and delivered into well-differentiated human bronchial epithelial cultures using apical bolus dosing (upper panel) or aerosol delivery (bottom panel). TR protein expression in various cell-types was observed and the percent of TR positive cells in different cell-types was plotted. As shown in the top panel of FIG. 18, TR expression was observed strongly in goblet cells, with less expression in basal and club cells, and minimal expression in ciliated cells. FIG. 18 also shows that well-differentiated human hBE cells were treated once with RTX0001 formulated Td Tomato mRNA (4 mg) using Vitrocell nebulization. % positive cells were determined by co-localization with the indicated markers. This demonstrates that the LNP formulations can be selectively delivered to specific selected lung cell types for delivery.

Example 14. Detection of CFTR mRNA Delivery to a Subject

A subject having or suspected of having cystic fibrosis is given a treatment by administering a composition as described elsewhere herein. The subject is monitored at regular intervals for expression of CFTR in the lungs. A sample of lung tissue from the subject is taken comprising ciliated cells of the lung. The cells are harvested and prepared for RNA isolation. cDNA is produced from the RNA using a first strand synthesis kit and random hexamer. qPCR reactions are run using a set of forward and reverse primers and a fluorescent probe, specific to CFTR and a second set specific to a control or housekeeping gene for expression normalization. Expression of CFTR is detected using a fluorescent readout corresponding the CFTR probe.

Example 15. Clinical Trials on Human Subjects

ReCode CFTR mRNA encapsulated LNPs are administered to human subjects having cystic fibrosis for maximum tolerated dose, dose limiting toxicity, and safety through single ascending dose (SAD) and multiple ascending dose (MAD) studies. The SAD and MAD studies are tested on human subjects over a 3-month period. Additionally, long term extension study of tolerability and toxicity is tested in subjects in open-label extension studies (OLE). The OLE studies are tested on human subjects over 9 months. In the SAD, MAD, and OLE studies, cohorts of human subjects are tested with either a low dosage of the ReCode CFTR mRNA encapsulated LNPs, high dosage of the ReCode CFTR mRNA encapsulated LNPs, or a placebo. Further, the absolute change in percent of FEV1 of the human subjects are compared before the administration of the ReCode CFTR mRNA encapsulated LNPs and after treatment to evaluate therapeutic efficacy. An overview of the study is shown in FIG. 19.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A pharmaceutical composition comprising a synthetic polynucleotide assembled with a lipid composition, wherein said synthetic polynucleotide encodes a cystic fibrosis transmembrane conductance regulator (CFTR) protein that comprises a nucleic acid sequence having at least about 98% sequence identity to SEQ ID NO: 4, wherein said lipid composition comprises an ionizable cationic lipid at a molar percentage of about 5% to about 30%;

a selective organ targeting (SORT) lipid separate from said ionizable cationic lipid at a molar percentage of about 5% to about 30%;

a phospholipid at a molar percentage of about 5% to about 25%;

a steroid or steroid derivative at a molar percentage of about 15% to about 46%; and a polymer-conjugated lipid at a molar percentage of about 0.5% to about 10%.

2. The pharmaceutical composition of claim 1, wherein said synthetic polynucleotide is a messenger ribonucleic acid (mRNA).

3. The pharmaceutical composition of claim 1, wherein said synthetic polynucleotide comprises 1-methylpseudouridine.

4. The pharmaceutical composition of claim 1, wherein said synthetic polynucleotide further comprises a 3'- or 5'-noncoding region.

5. The pharmaceutical composition of claim 4, wherein said synthetic polynucleotide further comprises a 5' cap structure.

6. The pharmaceutical composition of claim 5, wherein the 5' cap structure comprises a nucleic acid sequence having at least about 90% sequence identity to SEQ ID NO: 6.

7. The pharmaceutical composition of claim 5, wherein the 5' cap structure comprises a nucleic acid sequence according to SEQ ID NO: 6.

8. The pharmaceutical composition of claim 4, wherein said 3'-noncoding region comprises a poly adenosine tail.

9. The pharmaceutical composition of claim 8, wherein said poly adenosine tail comprises at most 200 adenosines.

10. The pharmaceutical composition of claim 4, wherein said 3'- or 5'-noncoding region enhances an expression or activity of said CFTR protein encoded by said synthetic polynucleotide within a cell.

11. The pharmaceutical composition of claim 1, wherein said pharmaceutical composition is an aerosol composition.

12. The pharmaceutical composition of claim 11, wherein the droplet size of the aerosol droplets in said aerosol composition is from 0.5 μm to 10 μm.

13. The pharmaceutical composition of claim 11, wherein the median droplet size of the aerosol droplets in said aerosol composition is from 0.5 μm to 10 μm.

14. The pharmaceutical composition of claim 11, wherein the average droplet size of the aerosol droplets in said aerosol composition is from 0.5 μm to 10 μm.

15. The pharmaceutical composition of claim 1, wherein said pharmaceutical composition is formulated for apical delivery.

16. The pharmaceutical composition of claim 1, wherein said pharmaceutical composition is formulated for nebulization.

17. The pharmaceutical composition of claim 1, wherein said lipid composition comprises
- an ionizable cationic lipid at a molar percentage of about 10% to about 25%;
- a selective organ targeting (SORT) lipid separate from said ionizable cationic lipid at a molar percentage of about 10% to about 30%;
- a phospholipid at a molar percentage of about 5% to about 25%;
- a steroid or steroid derivative at a molar percentage of about 15% to about 46%; and
- a polymer-conjugated lipid at a molar percentage of about 3% to about 5%.

18. The pharmaceutical composition of claim 17, wherein the polymer-conjugated lipid comprises a poly(ethylene glycol) (PEG)-conjugated lipid.

19. The pharmaceutical composition of claim 17, wherein the polymer-conjugated lipid is 1,2-dimyristoyl-sn-glycero-methoxypolyethylene glycol.

20. The pharmaceutical composition of claim 1, wherein said lipid composition comprises
- 4A3-SC7 at a molar percentage of about 10% to about 25%;
- 1,2-Dioleoyl-3-dimethylammonium-propane (DODAP) at a molar percentage of about 10% to about 30%;
- dioleoylphosphatidylethanolamine (DOPE) at a molar percentage of about 5% to about 25%;
- cholesterol at a molar percentage of about 15% to about 46%; and
- DMG-PEG at a molar percentage of about 3% to about 5%.

21. The pharmaceutical composition of claim 1, wherein said lipid composition comprises
- 4A3-SC7 at a molar percentage of about 15%;
- 1,2-Dioleoyl-3-dimethylammonium-propane (DODAP) at a molar percentage of about 16%;
- dioleoylphosphatidylethanolamine (DOPE) at a molar percentage of about 22%;
- cholesterol at a molar percentage of about 44%; and
- DMG-PEG at a molar percentage of about 3%.

22. The pharmaceutical composition of claim 1,
wherein said synthetic polynucleotide comprises a nucleic acid sequence having at least about 98% sequence identity to SEQ ID NO: 4, and
wherein said lipid composition comprises
- 4A3-SC7 at a molar percentage of about 15%;
- 1,2-Dioleoyl-3-dimethylammonium-propane (DODAP) at a molar percentage of about 16%;
- dioleoylphosphatidylethanolamine (DOPE) at a molar percentage of about 22%;
- cholesterol at a molar percentage of about 44%; and
- DMG-PEG at a molar percentage of about 3%.

23. The pharmaceutical composition of claim 1,
wherein said synthetic polynucleotide comprises a nucleic acid sequence according to SEQ ID NO: 4, and
wherein said lipid composition comprises
- 4A3-SC7 at a molar percentage of about 15%;
- 1,2-Dioleoyl-3-dimethylammonium-propane (DODAP) at a molar percentage of about 16%;
- dioleoylphosphatidylethanolamine (DOPE) at a molar percentage of about 22%;
- cholesterol at a molar percentage of about 44%; and
- DMG-PEG at a molar percentage of about 3%.

24. The pharmaceutical composition of claim 1, wherein the polymer-conjugated lipid comprises a poly(ethylene glycol) (PEG)-conjugated lipid.

25. The pharmaceutical composition of claim 1, wherein the polymer-conjugated lipid is a 1,2-dimyristoyl-sn-glycero-methoxypolyethylene glycol.

26. The pharmaceutical composition of claim 1, wherein the ionizable cationic lipid is a compound having the structural formula:

Core-Repeating Unit-Terminating Group (D-I), or a pharmaceutically acceptable salt thereof, wherein:

the core is linked to two to six repeating units by removing two to six hydrogen atoms from the core and replacing the hydrogen atoms with the repeating units; wherein:

the core has the formula:

(D-IV)

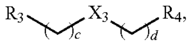

wherein, in Formula (D-IV):

$X_3$ is —$NR_6$—, —O—, or optionally substituted alkylaminodiyl$_{(c\leq 8)}$; wherein $R_6$ is hydrogen, alkyl$_{(c\leq 8)}$, or substituted alkyl$_{(c\leq 8)}$, $R_3$ and $R_4$ are each independently amino, optionally substituted alkylamino$_{(c\leq 12)}$, or optionally substituted dialkylamino$_{(c\leq 12)}$;

wherein:

c and d are each independently 1, 2, 3, 4, 5, or 6;

the repeating unit comprises a degradable diacyl group of the formula:

(D-VII)

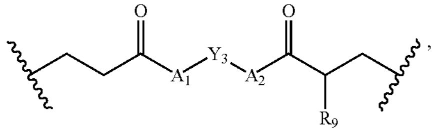

wherein, in Formula (D-VII):

$A_1$ and $A_2$ are each independently —O—;

$Y_3$ is —$CH_2CH_2$—; and $R_9$ is —$CH_3$; and the terminating group has the formula:

(D-VIII)

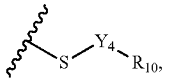

wherein, in Formula (D-VIII):

$Y_4$ is alkanediyl$_{(C\leq 18)}$ or an alkanediyl$_{(C\leq 18)}$; and $R_{10}$ is hydrogen.

27. The pharmaceutical composition of claim 1, wherein the ionizable cationic lipid is:

(4A3-SC7)

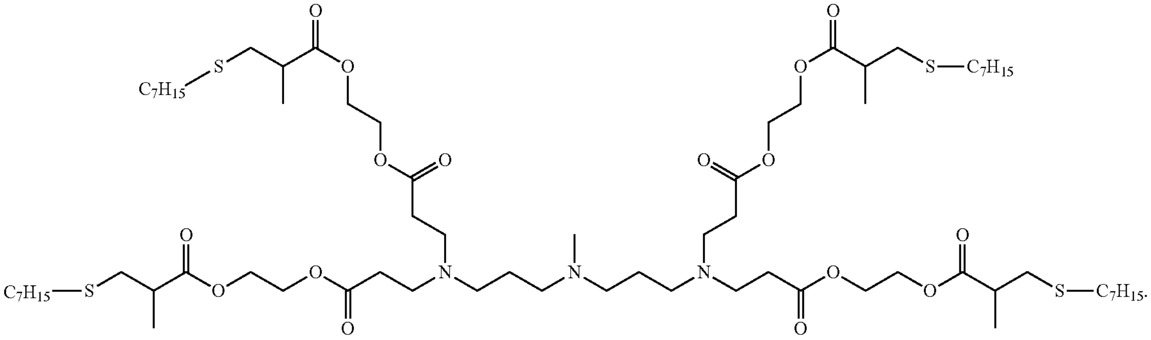

28. The pharmaceutical composition of claim 1, wherein the SORT lipid is 1,2-Dioleoyl-3-dimethylammonium-propane (DODAP).

29. The pharmaceutical composition of claim 1, wherein the SORT lipid is selected from 1,2-dimyristoyl-3-trimethylammonium-propane (14:0 TAP), 1,2-dipalmitoyl-3-trimethylammonium-propane (16:0 TAP), 1,2-stearoyl-3-trimethylammonium-propane (18:0 TAP), and 1,2-Dioleoyl-3-trimethylammonium-propane (DOTAP).

30. The pharmaceutical composition of claim 1, wherein the SORT lipid is selected from 1,2-dilauroyl-sn-glycero-3-ethylphosphocholine (12:0 EPC), 1,2-Dioleoyl-sn-glycero-3-ethylphosphocholine (14:0 EPC), 1,2-dimyristoleoyl-sn-glycero-3-ethylphosphocholine (14:1 EPC), 1,2-dipalmitoyl-sn-glycero-3-ethylphosphocholine (16:0 EPC), 1,2-distearoyl-sn-glycero-3-ethylphosphocholine (18:0 EPC), 1,2-dioleoyl-sn-glycero-3-ethylphosphocholine (18:1 EPC), and 1-palmitoyl-2-oleoyl-sn-glycero-3-ethylphosphocholine (16:0-18:1 EPC).

* * * * *